US010465187B2

(12) United States Patent
Khalil et al.

(10) Patent No.: US 10,465,187 B2
(45) Date of Patent: Nov. 5, 2019

(54) INTEGRATED SYSTEM FOR PROGRAMMABLE DNA METHYLATION

(71) Applicant: Trustees of Boston University, Boston, MA (US)

(72) Inventors: Ahmad S. Khalil, Lexington, MA (US); Albert J. Keung, Raleigh, NC (US); Minhee Park, Boston, MA (US)

(73) Assignee: Trustees of Boston University, Boston, MA (US)

( * ) Notice: Subject to any disclaimer, the term of this patent is extended or adjusted under 35 U.S.C. 154(b) by 13 days.

(21) Appl. No.: 15/889,368

(22) Filed: Feb. 6, 2018

(65) Prior Publication Data
US 2018/0245075 A1 Aug. 30, 2018

Related U.S. Application Data

(60) Provisional application No. 62/454,984, filed on Feb. 6, 2017.

(51) Int. Cl.
| C12N 15/11 | (2006.01) |
| C12N 9/10  | (2006.01) |
| C12N 9/22  | (2006.01) |
| C12N 15/10 | (2006.01) |
| C12N 15/63 | (2006.01) |

(52) U.S. Cl.
CPC ............ *C12N 15/11* (2013.01); *C12N 9/1007* (2013.01); *C12N 9/22* (2013.01); *C12N 15/102* (2013.01); *C12N 15/63* (2013.01); *C12Y 201/01* (2013.01); *C12Y 301/21003* (2013.01); *C07K 2319/81* (2013.01); *C12N 2310/20* (2017.05)

(58) Field of Classification Search
CPC ...... C12N 15/11; C12N 15/63; C12N 15/102; C12N 9/22; C12N 9/1007; C12N 2310/20; C12Y 301/21003; C12Y 201/01; C07K 2319/81
See application file for complete search history.

(56) References Cited

U.S. PATENT DOCUMENTS

| 2003/0212455 A1 | 11/2003 | Van Steensel |
| 2012/0003630 A1 | 1/2012 | Collins et al. |
| 2015/0267263 A1 | 9/2015 | Rehli |
| 2016/0272963 A1 | 9/2016 | Forsyth |

OTHER PUBLICATIONS

Witkowski et al., Biochemistry 38:11643-11650, 1999.*
Tang et al., Phil Trans R Soc B 368:20120318, 1-10, 2013.*
Seffemick et al., J. Bacteriol. 183(8):2405-2410, 2001.*
Branden et al., Introduction to Protein Structure, Garland Publishing Inc., New York, p. 247, 1991.*
Sadowski et al., Current Opinion in Structural Biology 19:357-362, 2009.*
Keung et al., "Chromatin regulation at the frontier of synthetic biology", Nat Rev Genet 16(3) 159-171 (2015).
Mierzejewska et al., "Structural basis of the methylation specificity of R.DpnI", Nucleic Acids Res 42(13) 8745-8754 (2014).
Al-Sady et al., "Division of labor between the chromodomains of HP1 and Suv39 methylase enables coordination of heterochromatin spread", Mol Cell 51(1) 80-91 (2013).
Bintu et al., "Dynamics of epigenetic regulation at the single-cell leveld", Science 351(6274) 720-724 (2016).
"Coffin et al., ""*Escherichia coli* DNA Adenine Methyltransferase:The Structural Basis of Processive Catalysis and Indirect Read-Out""", The Journal of Biological Chemistry 284; 18390-18400 (2009)."
Frieda et al., "Synthetic recording and in situ readout of lineage information in single cells", Nature 541; 107-11 (2017).
Gardner et al., "OPERating on chromatin, a colorful language where context matters", J Mol Biol 409(1) 36-46 (2011).
Hathaway et al., "Dynamics and Memory of Heterochromatin in Living Cells", Cell 149(7) 1447-1460 (2012).
Haynes et al., "Synthetic Reversal of Epigenetic Silencing", The Journal of Biological Chemistry 286; 27176-27182 (2011).
Heyn et al., "An Adenine Code for DNA: A Second Life for N6-Methyladenine", Cell 161(4) 710-713 (2015).
Hodges et al., "Dynamics of inherently bounded histone modification domains", PNAS 109(33) 13296-13301 (2012).
Horton et al., "Structure and Substrate Recognition of the *Escherichia coli* DNA Adenine Methyltransferase", JMB 358(2) 559-570 (2006).
Keung et al., "Using targeted chromatin regulators to engineer combinatorial and spatial transcriptional regulation", Cell 158(1) 110-120 (2014).
Kind et al., "Genome-wide maps of nuclear lamina interactions in single human cells", Cell 163(1) 134-147 (2015).
Kind et al., "Single-Cell Dynamics of Genome-Nuclear Lamina Interactions", Cell 153(1) 178-192 (2013).
Lachner et al., "Methylation of histone H3 lysine 9 creates a binding site for HP1 proteins", Nature 410; 116-120 (2001).
Lee et al., "The Language of Histone Crosstalk", Cell 142(5) 682-685 (2010).
Liang et al., "Engineering the ABA Plant Stress Pathway for Regulation of Induced Proximity", Sci Signal 4(164) rs2 (2011).

(Continued)

*Primary Examiner* — Delia M Ramirez
(74) *Attorney, Agent, or Firm* — Nixon Peabody LLP; Ronald I. Eisenstein

(57) ABSTRACT

Provided herein are engineered systems and methods for establishing DNA adenine methylation at specific genomic locations and using DNA adenine methylation as an artificial chemical "handle" on the genome. These systems and methods allow for placing the handle on specific genomic locations as well as molecular technologies to bind, spatially spread, and maintain the handle. The systems described herein comprise, in some embodiments, three functional modules that mediate m6A operations: (1) a synthetic initiator module to place m6A at specific genomic sites; (2) a synthetic readout module to program m6A recognition and m6A-dependent transcriptional logic; and (3) propagation module that implements "read-write," a mechanism proposed to underlie chromatin spreading and epigenetic maintenance across cellular systems.

27 Claims, 22 Drawing Sheets
(22 of 22 Drawing Sheet(s) Filed in Color)

Specification includes a Sequence Listing.

(56) References Cited

OTHER PUBLICATIONS

Lim et al., "Phosphotyrosine Signaling: Evolving a New Cellular Communication System", Cell 142(5) 661-667 (2010).
Maier et al., "Design of synthetic epigenetic circuits featuring memory effects and reversible switching based on DNA methylation", Nature Communications 8; 15336 (2017).
O'Brown et al., "N6-methyladenine: a conserved and dynamic DNA mark", Adv Exp Med Biol 945: 213-246 (2016).
Ragunathan et al., "Epigenetic inheritance uncoupled from sequence-specific recruitment", Science 348(6230) 1258699 (2015).
Slusarczyk et al., "Foundations for the design and implementation of synthetic genetic circuits", Nature Reviews Genetics 13; 406-420 (2012).
Van Steensel et al., "Identification of in vivo DNA targets of chromatin proteins using tethered Dam methyltransferase", Nat Biotechnol 18; 424-428 (2000).
Vogel et al., "Detection of in vivo protein-DNA interactions using DamID in mammalian cells", Nature Protocols 2; 1467-1478 (2007).

\* cited by examiner

INTEGRATED SYSTEM FOR PROGRAMMABLE DNA METHYLATION

CROSS-REFERENCE TO RELATED APPLICATIONS

This application claims benefit under 35 U.S.C. § 119(e) of U.S provisional application No. 62/454,984, filed on Feb. 6, 2017, the content of which is incorporated herein by reference in its entirety.

GOVERNMENT SUPPORT

This invention was made with Government Support under Contract No. W911NF-11-2-0056 awarded by the Department of Defense, and Contract No. CCF-1522074 awarded by the National Science Foundation. The Government has certain rights in the invention.

SEQUENCE LISTING

The instant application contains a Sequence Listing which has been submitted electronically in ASCII format and is hereby incorporated by reference in its entirety. Said ASCII copy, created on May 15, 2018, is named 701586-088242-US_SL.txt and is 160,337 bytes in size.

TECHNICAL FIELD

The present invention relates generally to compositions and methods for modulating the epigenetic states.

BACKGROUND OF THE INVENTION

Technologies that provide new ways to manipulate the genome and epigenome of cells can have considerable impact in medicine and biotechnology. Such technologies can be used to correct genetic diseases or be used to endow agricultural organisms with desirable qualities, such as drought and pest tolerance.

Current technologies enable the editing of small segments of the genome and epigenome, for example, a segment that covers one gene. These technologies are also static and often silenced or shut off over time leading to the loss of beneficial effects, especially when the effect is to regulate the activity of a gene.

SUMMARY OF THE INVENTION

The engineered systems and methods thereof described herein provide novel molecular technologies for establishing DNA adenine methylation at specific genomic locations and using DNA adenine methylation as an artificial chemical "handle" on the genome. These systems and methods allow for placing the handle on specific genomic locations as well as molecular technologies to bind, spatially spread, and maintain the handle. The technologies described herein provide numerous advantages over existing methods, including: (i) efficiency and stability by permitting efficient and temporally stable regulation of the genome over large genomic regions using a minimal number of constructs; (ii) broad functionality by mimicking the "binding-and-writing" spreading mechanism of mammalian cells but using a modification that is very rare in human and other eukaryotic cells, namely methylation of adenine in DNA, thereby making it broadly operational across eukaryotic cells and organisms; and (iii) allowing for delayed and/or sequential logic where the extra- or intra-cellular signal that activates the expression of the writer protein is required prior to the signal that turns on the reader-effector protein in order to impart the intended functionality to the gene of interest.

Provided herein, in some aspects, are engineered DNA methylation systems comprising: a reporter module, such as a synthetic reporter module, comprising a nucleic acid sequence encoding one or more DNA binding domain target sites, one or more GATC nucleic acid sequences, a promoter nucleic acid sequence, and a nucleic acid sequence encoding an output protein molecule; a writer module or synthetic initiator module comprising a promoter sequence operably linked to a nucleic acid sequence encoding a writer fusion protein comprising: a DNA binding protein or domain thereof and a mutant DNA adenine methyltransferase;

a reader-effector module or synthetic readout module comprising a promoter sequence operably linked to a nucleic acid sequence encoding a reader-effector fusion protein comprising: of a methyl-adenine DNA binding domain, such as a methyl-adenine DNA binding domain of DpnI endonuclease, and one or more transcriptional effector domains; and a reader-writer module or synthetic read-write module comprising a promoter sequence operably linked to a nucleic acid sequence encoding a reader-writer fusion protein comprising: a mutant DNA adenine methyltransferase and a methyl-adenine DNA binding domain, such as a methyl-adenine DNA binding domain of DpnI endonuclease.

In some aspects, provided herein, are engineered DNA methylation systems comprising: a reporter module, such as a synthetic reporter module, comprising a nucleic acid sequence encoding one or more DNA binding domain target sites, one or more GATC nucleic acid sequences, a promoter nucleic acid sequence, and a nucleic acid sequence encoding an output protein molecule;

a writer module or synthetic initiator module comprising a promoter sequence operably linked to a nucleic acid sequence encoding a writer fusion protein comprising: a DNA binding protein or domain thereof and a mutant DNA adenine methyltransferase, wherein the writer module binds the one or more DNA binding domain target sites and methylate adenines (A) of the one or more GATC nucleic acid sequences of the synthetic reporter module, thereby initiating adenine methylation;

a reader-effector module or synthetic readout module comprising a promoter sequence operably linked to a nucleic acid sequence encoding a reader-effector fusion protein comprising methyl-adenine DNA binding domain, such as a methyl-adenine DNA binding domain of DpnI endonuclease, and one or more transcriptional effector domains, wherein the reader-effector module recognizes methylated adenines and can recruit one or more regulatory factors to the synthetic reporter module; and a reader-writer module or synthetic read-write module comprising a promoter sequence operably linked to a nucleic acid sequence encoding a reader-writer fusion protein comprising: a mutant DNA adenine methyltransferase and a methyl-adenine DNA binding domain, such as a methyl-adenine DNA binding domain of DpnI endonuclease, wherein the reader-writer fusion protein propagates the adenine methylation initiated by the writer fusion protein module.

In some embodiments of these aspects and all such aspects described herein, the one or more DNA binding domain target sites of the reporter module are zinc finger DNA binding domain target sites.

In some embodiments of these aspects and all such aspects described herein, the zinc finger DNA binding domain target site comprises SEQ ID NO: 1.

In some embodiments of these aspects and all such aspects described herein, the one or more DNA binding domain target sites of the reporter module are CRISPR DNA binding domain target sites.

In some embodiments of these aspects and all such aspects described herein, the one or more CRISPR DNA binding domain target sites comprise a sequence complementary or identical to SEQ ID NO: 36 or SEQ ID NOs: 37.

In some embodiments of these aspects and all such aspects described herein, the reporter module comprises nucleic acid sequences encoding at least one DNA binding domain target sites.

In some embodiments of these aspects and all such aspects described herein, the reporter module comprises at least one GATC nucleic acid sequence. In some embodiments of these aspects and all such aspects described herein, the reporter module comprises at least two GATC nucleic acid sequences.

In some embodiments of these aspects and all such aspects described herein, the reporter module comprises a spacer nucleic acid sequence between the one or more GATC nucleic acid sequences.

In some embodiments of these aspects and all such aspects described herein, the spacer sequence is at least 20 bp.

In some embodiments of these aspects and all such aspects described herein, the nucleic acid sequence encoding a mutant DNA adenine methyltransferase of the writer fusion protein encodes any one of SEQ ID NOs: 12-31.

In some embodiments of these aspects and all such aspects described herein, the nucleic acid sequence encoding the DNA binding protein or domain thereof of the writer fusion protein encodes a zinc finger binding protein or domain thereof.

In some embodiments of these aspects and all such aspects described herein, the zinc finger binding protein or domain thereof comprises SEQ ID NO: 9.

In some embodiments of these aspects and all such aspects described herein, the nucleic acid sequence encoding the DNA binding protein or domain thereof of the writer fusion protein encodes a deactivated Cas protein or domain thereof, and wherein the system further comprises a guide module comprising a promoter sequence operably linked to a target sequence and a sequence encoding a guide RNA.

In some embodiments of these aspects and all such aspects described herein, the Cas protein or domain thereof comprises SEQ ID NO: 10.

In some embodiments of these aspects and all such aspects described herein, the sequence encoding a guide RNA comprises SEQ ID NO: 45.

In some embodiments of these aspects and all such aspects described herein, the target sequence comprises SEQ ID NO: 36 or SEQ ID NO: 37.

In some embodiments of these aspects and all such aspects described herein, the nucleic acid sequence encoding the writer fusion protein comprises a nuclear export signal.

In some embodiments of these aspects and all such aspects described herein, the writer fusion protein further comprises a linker sequence between the DNA binding protein or domain thereof and the mutant DNA adenine methyltransferase.

In some embodiments of these aspects and all such aspects described herein, the nucleic acid sequence encoding the methyl-adenine DNA binding domain of DpnI endonuclease of the reader-effector fusion protein encodes SEQ ID NO: 40.

In some embodiments of these aspects and all such aspects described herein, the at least one of the one or more transcriptional effector domains of the reader-effector fusion protein is a repressive transcriptional domain. In some embodiments of these aspects and all such aspects described herein, the at least one of the one or more transcriptional effector domains of the reader-effector fusion protein is an activating transcriptional domain.

In some embodiments of these aspects and all such aspects described herein, the nucleic acid sequence encoding a mutant DNA adenine methyltransferase of the reader-writer fusion protein encodes any one of SEQ ID NOs: 12-31.

In some embodiments of these aspects and all such aspects described herein, the nucleic acid sequence encoding the methyl-adenine DNA binding domain of DpnI endonuclease of the reader-writer fusion protein encodes SEQ ID NO: 40.

In some aspects, provided herein are one or more vectors for modulating adenine methylation status of a target sequence comprising any of the engineered DNA methylation systems or component modules described herein.

In some aspects, provided herein are cells comprising any of the engineered DNA methylation systems or component modules described herein.

In some embodiments of these aspects and all such aspects described herein, at least the reporter module of the engineered DNA methylation system is integrated at a target genomic locus of the cell. In some embodiments of these aspects and all such aspects described herein, all four modules are integrated at a target genomic locus of the cell.

In some aspects, provided herein are methods of modulating adenine methylation status of a target sequence comprising introducing any of the engineered DNA methylation systems described herein or one or more vectors comprising any of the engineered DNA methylation systems or component modules described herein into a cell or artificial cell.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIG. 8A shows defining three functional modules of common chromatin operations: (1) Initiate: "initiators" establish defined patterns of chromatin modifications at sequence-specific sites; (2) Read Out: modifications are recognized by reader proteins and used to mediate transcriptional changes; (3) Propagate: modifications are propagated in the absence of an initial stimulus by read-write mechanisms. FIG. 8B shows a design of a synthetic initiator module (synI) for sequence-specific, de novo placement of m6A in the human genome. synI is a fusion of a Dam (DNA adenine methyltransferase) writer domain and an engineered zinc finger protein (ZF), which specifically binds a 20-bp synthetic binding sequence (BS). synI nucleates m6A marks at designer reporters integrated into 293FT cells. For these experiments, stable cell lines harboring the singly-integrated Clustered Reporter were used, with ZF BS and GATC arrays upstream of a pMinCMV driving expression of destabilized GFP (d2EGFP), as the background strain. FIG. 8C shows screening Dam mutants to identify synI factors that specifically place m6A at target sites. Quantification of m6A enrichment at target reporter locus (red) and off-target, GATC-containing endogenous loci (grey shades) by transfected synI constructs composed of different Dam mutants. Off-target loci were chosen to represent different chromosomal locations. To obtain m6A enrichment, fraction methylation at a single GATC site in the locus of interest was measured using an m6A-qPCR assay, and normalized to basal methylation induced by Dam not fused to the ZF (see Methods, FIGS. 12, 23A-23C). (n=3; error bars, SD). Alanine mutagenesis of the residues predicted to make non-specific contact with the flanking DNA phosphate groups is aimed at lowering the intrinsic affinity of Dam for GATC, thus making the enzyme's activity more dependent on the ZF DNA binding activity. In particular, the mutant N132A showed ~11-fold enrichment in methylation at the target site while keeping low methylation level at off-target sites. FIG. 8D demonstrates expression of synI has minimal effect on the transcriptome. Correlation of transcriptome from RNA-seq measurements for reporter cells transfected with synI vs. empty plasmid. Correlation coefficient of endogenous genes between samples was calculated using $\log_2$ transformed expression values. mRNA corresponding to synI is labeled. The data are representative of two biological replicates.

FIG. 9A shows an exemplary design of a synthetic readout module (synR). synR is a fusion of an m6A reader domain (RD, binding domain of DpnI (aa146-254)) and a transcriptional effector domain (ED). m6A established by the synI module are specifically recognized by synR, which in turn regulates transcriptional activity of a reporter gene. For these experiments, stable cell lines harboring a singly-integrated Interspersed Reporter were used, with intermixed ZF BS and GATC sites upstream of a promoter (pMinCMV for activation or pCMV for repression), as the background strains. FIG. 9B shows engineering m6A-mediated transcriptional activation. Top: Schematic of the synRVP64 module, a fusion of DpnI binding domain and VP64 transcriptional activation domain, which drives activation of a reporter gene via m6A recognition. Bottom: GFP fluorescence intensity, measured by flow cytometry, for cells transfected with indicated combinations of synI and synRVP64 expression constructs, or a direct ZF-VP64 construct. Bottom left shows fold change of geometric mean GFP intensity normalized to the −/− condition (n=3; error bars, SD); bottom right shows raw flow cytometry distributions. As shown in the data, the combination of synI and synRVP64 led to ~30-fold activation of GFP (and 80% of population being GFP activated) from the genomically integrated Reporter cell line. FIG. 9C shows engineering m6A-mediated transcriptional repression. It was investigated whether a mechanism of adenine methylation-based effector recruitment could be used to silence a strong, full length CMV promoter on an integrated reporter. Top: Schematic of the synRKRAB module, a fusion of the DpnI binding domain and KRAB transcriptional repressive domain, which drives repression of a reporter gene via m6A recognition. Bottom: GFP fluorescence intensity, measured by flow cytometry, for cells transfected with indicated combinations of synI and synRKRAB expression constructs, or a direct ZF-KRAB construct.

FIG. 10A shows design of a synthetic read-write module (synRW) for propagating m6A modifications over a domain. synRW is a fusion of an m6A RD (DpnI binding domain) and a Dam writer domain (Dam mutant). synRW is designed to recognize pre-existing m6A and catalyze methylation of nearby GATC motifs, creating local reinforcement and spreading of m6A to larger domains. For these experiments, Clustered Reporter cell lines were used, with pMinCMV driving expression of d2EGFP, as the background strain. FIG. 10B shows screening synRW candidates for nucleation-dependent propagation. Top: Schematic of the "spatial propagation screen" design. A library of synRW constructs was screened for the ability to activate a distal reporter gene in cells with an inducible initiator module (+synI$^{IND}$, GFP High), but not in cells lacking the initiator (−synI$^{IND}$, GFP Low). Bottom left: The synRW module library featuring different promoter strengths and Dam writer mutants. Each member of the synRW library was individually transfected into reporter lines stably expressing synR$^{VP64}$, either with (+synI$^{IND}$) or without (−synI$^{IND}$) stable expression of synI$^{IND}$. Bottom right: Screen results. Heat map of % GFP activated cells, quantified by flow cytometry 4 days following transfection of synRW (with continuous 200 μM ABA induction of synI$^{IND}$). Hierarchical clustering analysis based on similarity in % GFP activated cells is shown. FIG. 10C shows a summary and modeling of a spatial propagation screen. Quantitative metrics to score propagation propensity were defined for synRW library candidates: "expt. spreading score" (red; n=3, error bars, SD) is the difference between % GFP activated cells with and without synI$^{IND}$ measured from the experimental screen; "model spreading score" (mean±SD) is the difference between model-computed m6A density at promoter-proximal sites with and without synI (see FIGS. 19A-19C). Shades of red correspond to Dam writer mutants: WT, single mutants, double mutants (dark to light, respectively). FIG. 10D shows m6A profiles measured across the GATC array and over time for cells stably expressing the three-module "propagation circuit" (purple) or circuits lacking either synRW (grey) or synI$^{IND}$ (black). Cells were continuously induced with 200 μM ABA. Model simulations are shown in insets (with bZF=10, bDpnI=100, see FIGS. 19A-19C). (n=3; error bars, SD).

FIG. 11A shows a schematic depicting ON (+ABA) and OFF (−ABA) states using an inducible ZF-VP64$^{IND}$ regulator (top) and the two-module m6A system (synI$^{IND}$/synR$^{VP64}$, bottom). Addition of ABA mediates dimerization to form an active ZF-VP64$^{IND}$ (top) or synI$^{IND}$ initiator (bottom). Removal of ABA allows analysis of deactivation dynamics and epigenetic memory. For these experiments, Interspersed Reporter cell lines were used, with pMinCMV driving expression of d2EGFP, as the background strain. FIG. 11B shows activation/deactivation dynamics for the inducible ZF-VP64$^{IND}$ (grey) vs. the two-module m6A system (green) in response to a transient (3 day) ABA pulse. The percentage of GFP activated cells was quantified by flow cytometry (see FIG. 17E). Dots are data points (n=3; error bars, SD); lines represent sigmoidal curve fits to ON phase and exponential fits with time delay to OFF phase. FIG. 11C shows maintenance of m6A (top) and transcriptional state (bottom) by inhibiting DNA replication. Cells stably expressing the two-module m6A system were induced with a 3 day ABA pulse, then ABA was washed out and cells were maintained in media with or without 5 μg/mL APC. Fraction methylation and percentage of GFP activated cells were quantified at the indicated time points following ABA washout. (n=3; error bars, SD). FIG. 11D shows epigenetic memory induced by the three-module propagation circuit. Deactivation dynamics following transient (2 hr) ABA pulse for cells stably expressing: three-module propagation circuit (purple), the circuit lacking synRW (green), and the circuit with a reader-defective synR$^{NT}$W (light purple), or cells stably expressing ZF-VP64$^{IND}$ (grey). Also plotted are cells stably expressing the two-module system continuously induced with 200 μM ABA (grey, dotted line). The percentage of GFP activated cells was quantified by flow cytometry. Dots are data points (n=3; error bars, SD); lines represent exponential fits to OFF phase. FIG. 11E shows an exemplary model for engineering transcriptional states with different durations and memory using synthetic m6A operations. Simple TF recruitment induces transient transcriptional states (top). Placing m6A marks facilitates passive, cell-division coupled persistence of the induced transcriptional state (middle). Propagation by adding a synRW module promotes long-term epigenetic memory (bottom).

FIG. 12 discloses "5×GS" as SEQ ID NO: 92, "6×GS" as SEQ ID NO: 93 and "10×GS" as SEQ ID NO: 91.

FIG. 23A shows a schematic of a m6A-qPCR assay for quantifying adenine methylation frequency at the Clustered Reporter. GATC sites in the Clustered Reporter are flanked by unique 20-bp barcode spacers (colored bars), allowing single GATC site resolution in methylation levels. Genomic DNA is isolated and digested with DpnII, then intact GATC sites are qPCR amplified using primers (colored arrows) unique to the barcodes (see Methods). Sequences containing unmethylated GATC are cut by DpnII yielding no PCR product, while methylated sequences are protected from digestion yielding a PCR product proportional to the methylation frequency. FIG. 13B shows an overview of digestion treatments and PCR sites used to quantify methylation frequency at GATC site(s) of interest with m6A-qPCR assay. Methylation frequency is calculated as the fraction of DNA that is resistant to DpnII digestion (see Methods). FIG. 13C shows validation of the m6A-qPCR assay for quantifying methylated DNA. Episomal reporter plasmid was transformed and propagated in either dam$^-$ (Dam−, K12 ER2925) or dam$^+$(Dam+, TOP10) *E. coli*. Plasmids were then isolated and treated with either DpnI or DpnII. Left: Digested plasmids were run on a 1% agarose gel, confirming that plasmid derived from Dam+ is fully adenine-methylated (cut by DpnI, protected from DpnII digestion) while plasmid derived from Dam− is unmethylated. Right: Quantification of fraction methylation of the two plasmids as measured by the m6A-qPCR assay. (n=3; error bars, SD).

FIG. 14A shows "basal" adenine methylation levels for a library of synI$^{NT}$ factors, non-targeting factors composed of a fusion of mCherry and Dam writer allele. Fraction methylation was measured using m6A-qPCR at a single GATC site proximal to the ZF BS array in the singly integrated Clustered Reporter (6$^{th}$ site, 140 bp downstream from end of ZF array). (n=3; error bars, SD). FIG. 14B shows "targeted" adenine methylation levels for a library of synI factors, targeting factors composed of a fusion of sequence-specific ZF and Dam writer allele. (n=3; error bars, SD). FIG. 14C shows distribution of targeted (synI) vs. basal (synI$^{NT}$) adenine methylation levels for Dam writer mutants. Diagonal line represents no enrichment in ZF sequence-specific methylation over "background" methylation. Dam N132A and WT are marked in red and black, respectively. (n=3; error bars, SD). FIG. 14D shows lowering expression levels and using Dam mutants leads to lower adenine methylation levels genome-wide. Cells were transfected with the indicated constructs: Interspersed Reporter only, ZF-VP64 constitutively expressed from pUBC, synI$^{NT}$ (Dam WT) constitutively expressed from a strong promoter (pCLPIT with no Dox induction), synI$^{NT}$ (Dam WT) constitutively expressed from a weak promoter (pMinCMV), and synI$^{NT}$ (Dam N132A) constitutively expressed from a weak promoter (pMinCMV). Genomic DNA (gDNA) was isolated 2 days following transfection, digested with or without DpnII, run out on an agarose gel (top), and the bands used to quantify total fraction methylated DNA (bottom). Undigested bands appearing at the top of each lane in DpnII-treated samples represent methylated (protected) gDNA, while methylated gDNA fragments that are digested by DpnII appear as a smear (from ~0.3-2 kb). Total fraction methylated gDNA is calculated as undigested gDNA in DpnII-treated samples normalized by total gDNA.

FIG. 15A shows a volcano plot generated from differential transcript (DEseq2) analysis of RNA-seq measurements for cells transiently transfected with synI (N132A, constitutive expression) vs. empty plasmid (see also FIG. 8D). Only one transcript showed significant enrichment based on differential expression>$\log_2$ 1.5 and FDR<0.01 (LIF, red point). No evidence was found for the presence of a near match (having <6-bp mismatch) to the ZF BS in genomic sequences 1-kb upstream and downstream of LIF, indicating that the changes observed are due to a small level of noise in RNA-seq measurements. The data represent two independent biological replicates for each condition. FIG. 15B shows correlation of transcriptome from RNA-seq measurements of synI-expressing sample replicates. Correlation coefficient is 0.98, calculated using $\log_2$ transformed expression values. FIG. 15C shows cell cycle is not affected by expression of synI. Flow cytometry plots of Interspersed Reporter cell lines stably expressing a small molecule inducible synI (uninduced=−synI, induced with 200 μM ABA=+synI; see also FIG. 17E), labeled with EdU-Pacific Blue to analyze DNA replication and FxCycle Far Red to quantify DNA content. Cell percentages in different phases of the cell cycle are quantified. FIG. 15D shows cell viability is not affected by expression of synI. Quantification of Trypan Blue dye exclusion for Interspersed Reporter cell lines (grey) and Interspersed Reporter cell lines stably expressing small molecule inducible synI (uninduced=−synI, induced with 200 μM ABA=+synI; see also FIG. 17E).

FIG. 16A shows methylation levels quantified by m6A-qPCR for Clustered Reporter cell lines transfected with indicated combinations of synI and synR$^{VP64}$ expression constructs. (n=3; error bars, SD). FIG. 16B shows m6A-mediated transcriptional activation of episomal reporter. synI and synR$^{VP64}$ expression constructs (or direct ZF-VP64 fusion) were co-transfected into cells along with an Interspersed pMinCMV Reporter plasmid (pMP472) in the combinations shown. GFP fluorescence intensity, measured by flow cytometry, was normalized to the −/− condition to obtain GFP fold change. (n=3; error bars, SD). FIG. 16C shows m6A-mediated transcriptional repression of episomal reporter. Left: synI and synR$^{KRAB}$ expression constructs (or direct ZF-KRAB fusion) were co-transfected into cells along with an Interspersed pCMV Reporter plasmid (pMP506) in the combinations shown, and GFP fluorescence assayed by flow cytometry. Right: Identical experiment but replacing KRAB with the Hp1α chromo shadow domain (CSD). (n=3; error bars, SD). FIG. 16D shows m6A-mediated transcriptional repression with synI and synR$^{HP1}$ modules. GFP fluorescence intensity, measured by flow cytometry, for Interspersed Reporter cell lines (with pMinCMV) transfected with indicated combinations of synI and synR$^{VP64}$ expression constructs (or a direct ZF-HP1α (CSD) fusion). (n=3; error bars, SD). FIG. 16E shows GATC sites are required for transcriptional regulation by synI and synR modules. An Interspersed pMinCMV Reporter lacking GATC sites was generated by replacing the 14 GATC motifs with 4-bp random sequences (NNNN, blue boxes). synI and synR$^{VP64}$ expression constructs (or direct ZF-VP64 fusion) were co-transfected into cells along with the GATC-lacking reporter plasmid in the combinations shown. (n=3; error bars, SD). FIG. 16F shows m6A-mediated transcriptional activation by synI and synR$^{VP64}$ modules is highly specific genome-wide. Correlation of transcriptome from RNA-seq measurements of Interspersed Reporter cell lines co-transfected with either two-module m6A system (synI and synR$^{VP64}$, blue) or ZF-VP64 (orange) vs. reporter cells transfected with empty plasmid. mRNAs corresponding to synI, synR$^{VP64}$, ZF-VP64, and GFP are labeled.

FIG. 17A shows a schematic of the synthetic inducible initiator, synI$^{IND}$, which uses abscisic acid (ABA)-induced dimerization to provide temporal control over m6A initiation. In this scheme, the ZF and Dam (N132A) writer domain are fused to ABI1 and PYL1 domains, respectively, and co-expressed from a bicistronic cassette. Upon addition of ABA, the two halves are reconstituted and localize to the ZF BS array. FIG. 17B shows dose-dependent activation of episomal reporter. Cells were co-transfected with Interspersed pMinCMV Reporter and synI$^{IDN}$/synR$^{VP64}$ expression constructs. GFP fluorescence intensity was measured by flow cytometry 2 days after ABA induction, and normalized to reporter only-transfected cells to obtain GFP fold change. (n=3; error bars, SD). FIG. 17C shows dynamic range of activation of episomal reporter. Cells were co-transfected with Interspersed pMinCMV Reporter and indicated combinations of synI$^{IND}$ and synR$^{VP64}$ expression constructs. Values indicate GFP fold change over reporter only control. +ABA=200 µM ABA. (n=3; error bars, SD). FIG. 17D shows time course of activation of episomal reporter. Cells were co-transfected with Interspersed pMinCMV Reporter and synI$^{IND}$ and synR$^{VP64}$ expression constructs, and GFP fluorescence measured at indicated time points. Values indicate GFP fold change over reporter only control. (n=3; error bars, SD). FIG. 17E shows quantifying percentage of GFP activated cells induced by the two-module m6A system (synI$^{IND}$/synR$^{VP64}$). Flow cytometry GFP fluorescence distributions for Interspersed Reporter cell lines stably expressing the two-module synI$^{IND}$/synR$^{VP64}$ system (+synI$^{IND}$) or only synR$^{VP64}$ (−synI$^{IND}$) with 200 µM ABA induction. The threshold for GFP activated cells is indicated. FIG. 17F shows deactivation dynamics of a reporter gene following transient induction of synI$^{IND}$. Interspersed Reporter cell lines stably expressing synI$^{IND}$ and synR$^{VP64}$ were used. Duration of synI$^{IND}$ recruitment was varied by administering ABA pulses of different length. The percentage of GFP activated cells was quantified by flow cytometry over 7 days after ABA washout. (n=3; error bars, SD).

FIG. 18A shows representative flow cytometry plots of a circuit candidate from the spatial propagation screen (see FIG. 10B). The percentage of GFP activated cells for a given synRW candidate is quantified in cells with (+synI$^{IND}$) and without (−synI$^{IND}$) stable expression of the initiator module. FIG. 18A shows m6A-mediated transcriptional regulation by the two-module (synI/synR) system is insensitive to synR expression level. Left: Relative expression levels for a weak (pMinCMV) and strong (pUBC) promoter, assayed by measuring GFP expression from plasmid-transfected cells. GFP fluorescence intensity, measured by flow cytometry, was normalized to dark cells to obtain GFP fold change. (n=3; error bars, SD). Right: m6A-mediated activation by two-module (synI/synR$^{VP64}$) system, where synR$^{VP64}$ is expressed at different levels. Interspersed reporter lines were co-transfected with synI and synR$^{VP64}$, driven by either weak pMinCMV or strong pUBC, and the percentage of GFP activated cells was quantified by flow cytometry. (n=3; error bars, SD).

FIG. 19A shows a lattice model of chromatin spreading dynamics. In this model, a synthetic promoter is represented by a one-dimensional array of 63 GATC sites (index j), each of which can be in one of two states: unmethylated ($I_j$=0), and methylated ($I_j$=1). The dynamics are controlled by four reactions: (1) Basal (non-targeted) methylation governed by rates $k_{synI\_act}$ (for synI) and $k_{synRW\_act}$ (for synRW); (2) Sequence-specific nucleation proximal to the ZF BS array at a rate $b_{ZF} \cdot k_{synI\_act}$; (3) If nearest neighbor site is methylated, reader-mediated writing occurs at a rate $b_{DpnI} \cdot k_{synRW\_act}$; (4) Turnover of the modification from any methylated GATC site at a constant rate $k_{turn}$. FIG. 19B shows model parameterization of m6A nucleation by synI. Model profiles of steady-state targeted vs. basal methylation by synI for different values of $b_{ZF}$ (colored lines), overlaid onto the experimentally determined values for the Dam mutant library (see FIG. 14C) synI (Dam N132A) is described well with $b_{ZF}$=10. FIG. 19C shows computational workflow for simulating and quantifying spatial spreading. Mean m6A density at reporter-proximal sites (15 downstream sites, j=49-63) is computed after simulating synRW reactions for a range of $k_{synRW\_act}$ and $b_{DpnI}$ values). To obtain a "model spreading score" (analogous to expt. spreading score used in screen (FIG. 10B)), the difference (Δ) in mean m6A density for simulations with and without synI was computed. FIG. 19D shows a summary of spatial propagation screen results. The "expt. spreading score" is a quantitative metric used to score propagation propensity for the synRW library candidates. This is plotted for all library members as a function of Dam basal methylation activity. Three synRW constructs representing different levels of writer (methylation) activity are highlighted: 1) Low=Dam (R95A, Y119A); 2) Intermediate=Dam (R95A); 3) High=Dam (WT). (n=3; error bars, SD). Data are fitted with a log-normal distribution. FIG. 19E shows a summary of spatial propagation simulation results. The "model spreading score" is a quantitative metric used to score propagation propensity for the simulated synRW library candidates. Model-generated profiles of "model spreading score" (Δ mean m6A density) are plotted as a function of Dam basal methylation activity. Simulation results are shown for three different parameter values of $b_{DpnI}$ (reader-mediated writing specificity multiplier), and the three representative synRW constructs (low, intermediate, high Dam writer activity) are highlighted. FIG. 19F shows spatial propagation-mediated reporter activation in Clustered Reporter cells (stably expressing synI$^{IND}$/synR$^{VP64}$), transfected with one of three synRW constructs (low, intermediate, and high Dam writer activity). Percentage of GFP activated cells was quantified as previously described. Cells were continuously induced with 200 µM ABA. (n=3; error bars, SD). FIG. 19G shows m6A profiles measured across the GATC array in Clustered Reporter cells (stably expressing synI$^{IND}$/synR$^{VP64}$), transfected with one of three synRW constructs (low, intermediate, and high Dam writer activity). Cells were continuously induced with 200 µM ABA. (n=3; error bars, SD). Model simulation results are shown in insets with $b_{ZF}$=10, $b_{DpnI}$=100, $k_{synRW\_act}$=1.1•10$^{-4}$ (left), 3.4•10$^{-4}$ (middle), and 1.4•10$^{-3}$ hr$^{-1}$ (right).

FIG. 20A shows spatial propagation-mediated reporter activation in cells stably expressing the three-module "propagation circuit", featuring variant synRW constructs. Cells were continuously induced with 200 µM ABA. synR$^{NT}$W is a control construct in which the DpnI reader domain was replaced with non-binding mCherry. Percentage of GFP activated cells was quantified as previously described. (n=3; error bars, SD). FIGS. 20B-20C show m6A profiles measured across the GATC array and over time for cells stably expressing indicated combinations of propagation circuit components. Cells were continuously induced with 200 µM ABA. (n=3; error bars, SD).

FIG. 21A shows using Aphidicolin treatment to inhibit DNA replication in cells. Flow cytometry plots of Interspersed Reporter cells (stably expressing synI$^{IND}$/synR$^{VP64}$) that were either control-treated (−APC, top) or treated with the DNA replication inhibitor Aphidicolin (+APC, bottom) (see Methods). DNA replication was monitored with 5-ethynyl-2'-deoxyuridine (EdU) Pacific Blue, which is incorporated into newly synthesized DNA. Cells were also stained with FxCycle Far Red to measure DNA content. FIG. 21B shows maintenance of the m6A-mediated transcriptional state by the synRW module. Cells stably expressing the propagation circuit were induced with a 3 day ABA pulse, then ABA was washed out and cells were maintained in media with or without 5 µg/mL APC. (n=3; error bars, SD). FIG. 21C shows m6A establishment by synI$^{IND}$ is required for GFP activation and epigenetic memory. Cells stably expressing either the three-module propagation circuit (+synI$^{IND}$) or the circuit lacking an initiator module (−synI$^{IND}$) were induced with a 2 hr ABA pulse, and the percentage of GFP activated cells were quantified at the indicated time points following ABA washout. Curves represent exponential fits. (n=3; error bars, SD). FIG. 21D shows cells expressing the three-module propagation circuit are actively dividing and transmitting the epigenetic state. Flow cytometry plots of cells stably expressing either the propagation circuit (+synRW) or the circuit lacking synRW (−synRW), labeled with Cell-Trace Far Red to trace cell divisions across time following a 3 day ABA pulse. Dashed line represents cutoff for percentage of GFP activated cells, showing that GFP+state is transmitted to progeny in cellular populations expressing the propagation circuit. FIG. 21E shows maintenance and loss of GFP activated state by variant synRW constructs. Cells stably expressing propagation circuits featuring different, indicated synRW constructs were induced with a 2 hr ABA pulse, and the fraction of GFP activated cells were quantified for up to 20 days. ZF-VP64$^{IND}$ indicates cells stably expressing an inducible ZF-VP64 (FIG. 11A), in place of the propagation circuit. synR$^{NT}$W are control constructs in which the DpnI reader domain in synRW was replaced with non-binding mCherry. Curves represent exponential fits. (n=3; error bars, SD).

DETAILED DESCRIPTION

Technologies to edit and regulate the genome and epigenome have proliferated in the past decade. For example, zinc fingers (ZFs), transcription activator like effectors (TALEs), and CRISPR/Cas9 proteins have enabled the targeting of specific DNA sequences in the genome. Fusing such DNA-targeting proteins with other protein domains can recruit diverse functionalities to specific genomic regions. These capabilities have been exploited to cleave and edit genomic sequences, activate and repress genes, and alter epigenomic states. In all of these cases, the effector protein domain containing the desired (epi)genomic editing functionality, is directly recruited to a genomic location defined by the DNA targeting protein.

However, there are situations where one might want the same functionality to be active at an adjacent location or an adjacent gene. This could be to communicate information in cis, or as a more efficient way to regulate sets of commonly-regulated genes. To achieve this type of regulation using existing technologies, the effector protein domain would need to be fused to another DNA-targeting protein, or set of proteins, with binding specificity at the new location. This would become onerous and it is technically prohibitive to express large numbers of DNA-targeting proteins.

Natural systems bypass spatial restrictions through specialized spreading mechanisms on chromatin. Heterochromatin is a naturally occurring and representative structure that spans several kilobases of the genome. It achieves this delocalized "footprint" through a "binding-and-writing" mechanism. A chemical modification of DNA or of nucleosomal protein complexes bound to DNA serves as a binding site for protein complexes. These complexes also have the catalytic activity necessary to place the same chemical modification on an adjacent DNA location or an adjacent nucleosome. This mechanism uses the natural array of nucleosome proteins on DNA to "hop-and-spread" a chemical modification across the genome.

The engineered systems and methods described herein mimic and replicate this spreading mechanism, but utilize a modification that is very rare in human and other eukaryotic cells, namely methylation of adenine in DNA. This modification has been previously used in a technique called DamID, analogous to chromatin immunoprecipitation. It has also been used to label all chromatin close to the nuclear lamina and then to recruit an activator to the lamina resulting in migration of chromatin towards the nucleoplasm.

As described herein, the engineered systems and methods can nucleate adenine methylation in specific locations in the genome and then recruit transcriptional regulators through binding of the methylation to both activate and repress nearby genes. Furthermore, these technologies can be used to spread regulation over longer distances, and provide a self-reinforcing mechanism to maintain gene regulation over long periods of time.

Figure 1:
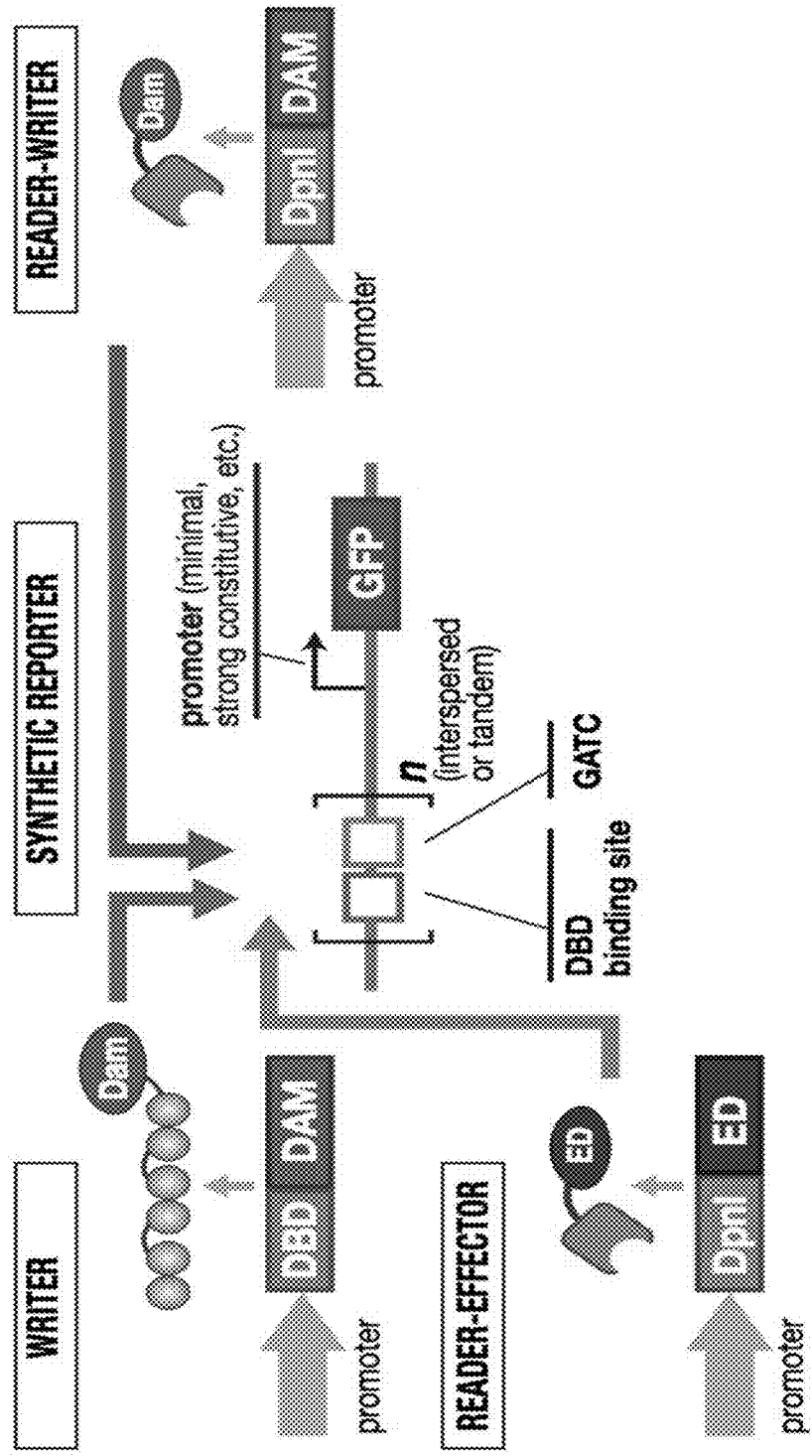
FIG. 1 depicts an overview schematic of an embodiment of the system design.
Figure 2:
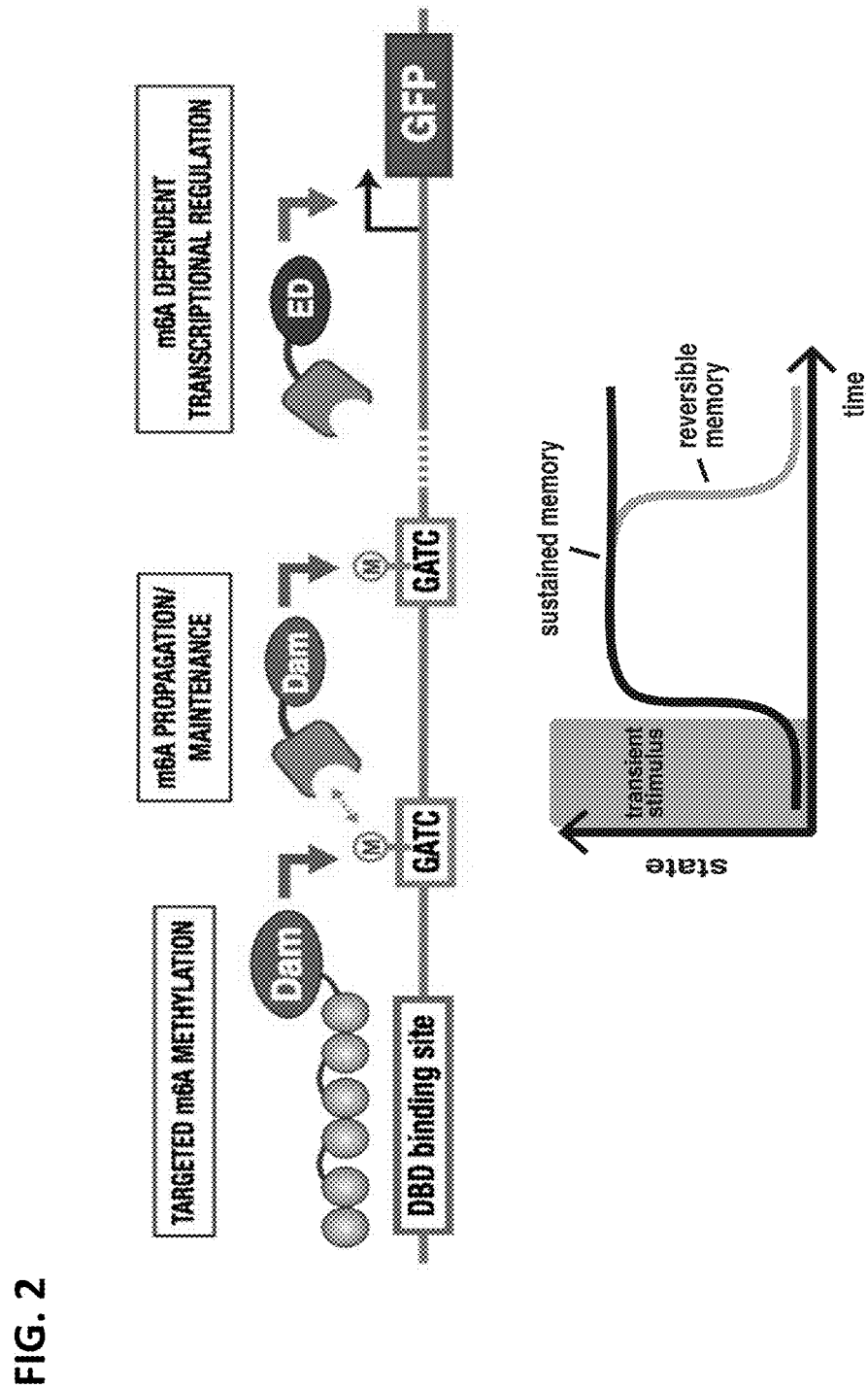
FIG. 2 depicts a schematic illustrating the mechanism of one embodiment of the system.
Figure 3:
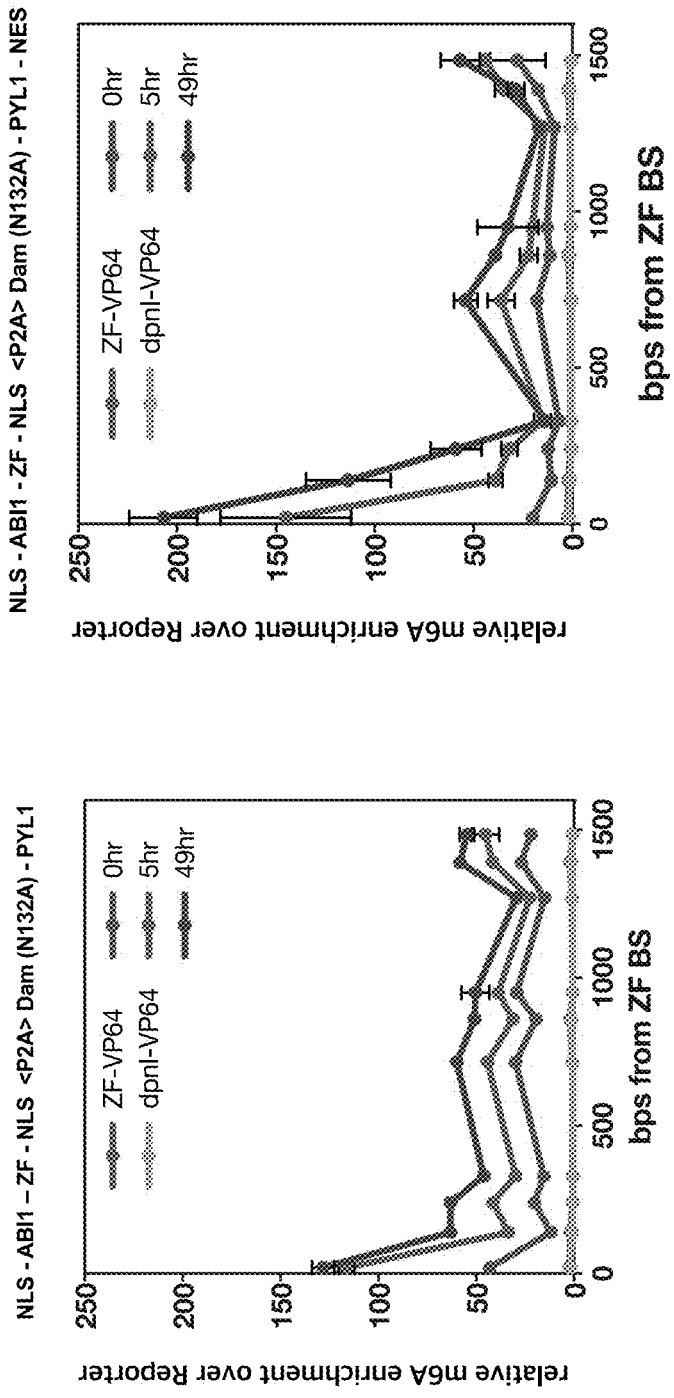
FIG. 3 shows data using a transiently transfected [5XZF_63XGATC] min CMV promoter (1.5-kb; 20-bps spacer) reporter, and probing of the spatial footprint of m6A upon transient induction of Writers (using the ABA-inducible Writer constructs). This was performed by inducing cells with ABA for 0 hr (green), 5 hr (blue), and 49 hr (red), and subsequently using the m6A-qPCR assay and a "barcoded" reporter to measure methylation frequencies across the length of the reporter. Significant enrichment of m6A at the ZF DBD nucleation site was observed, along with a concomitant decrease in methylation along the length of the reporter. Additionally, the profiles showed a dependency on the temporal duration of Writer induction, whereby longer recruitment of the Writer generally resulted in higher levels of m6A. As negative controls, the corresponding m6A footprints for ZF-VP64 (grey) and DpnI-VP64 (pink) were measured, in place of inducible Writers, and no enrichment of m6A across the entire reporter was observed.
Figure 4:
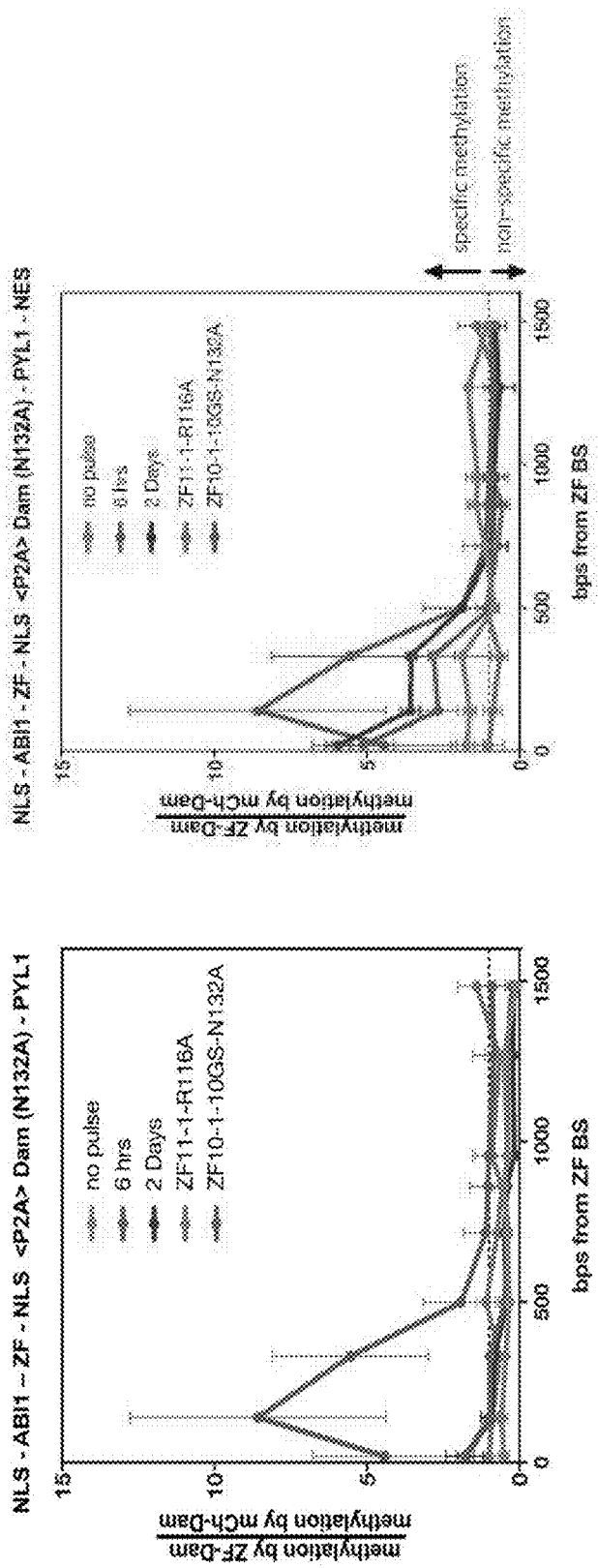
FIG. 4 shows data from probing the spatial footprint of m6A upon transient induction of Writers (using the ABA-inducible Writer constructs or constitutive expression of minCMV-ZF10-1-Dam (N132A) Writer construct) into integrated reporter cell line ([5XZF_63XGATC] min CMV promoter (1.5-kb; 20-bps spacer); AAVS1 locus; HEK cells). This was performed by inducing cells with ABA for 0 hour (light blue), 6 hours (medium blue), and 2 days (dark blue), followed by the m6A-qPCR assay. For ABA inducible Writer with NES (minCMV-NLS-ABI1-ZF10-1-<P2A>-Dam (N132A)-PYL1-NES), significant specific (i.e., % methylation by Writer with ZF DBD over % methylation by Writer with mCh is greater than 1) enrichment of m6A at the ZF DBD nucleation site was observed, with a concomitant decrease in methylation along the length of the reporter. Additionally, the profiles showed a similar dependency on the temporal duration of Writer induction as in transiently transfected reporter assay. However, for ABA inducible Writer with no NES (minCMV-NLS-ABI1-ZF10-1-<P2A>-Dam (N132A)-PYL1), any specific enrichment of m6A at any site along the length of the reporter was not observed. This piece of data supports that actively localizing Dam protein with nuclear export signal (NES) to the cytoplasm in the absence of ABA is much more effective than passive cytoplasmic localization with no NES in minimizing the basal non-targeted activity of Dam (N132A). As a negative control, the corresponding m6A footprints for ZF11-1-Dam (R116A) (grey), which has non-cognate ZF, was measured and no specific enrichment of m6A across the entire reporter was observed. For comparison, the corresponding m6A footprints for constitutively expressed direct fusion Writer (minCMV-ZF10-1-Dam (N132A)) was also measured, in place of inducible Writers, and again significant specific enrichment near the ZF nucleation site and a concomitant decrease in methylation along the length of the reporter was observed.
Figure 5:
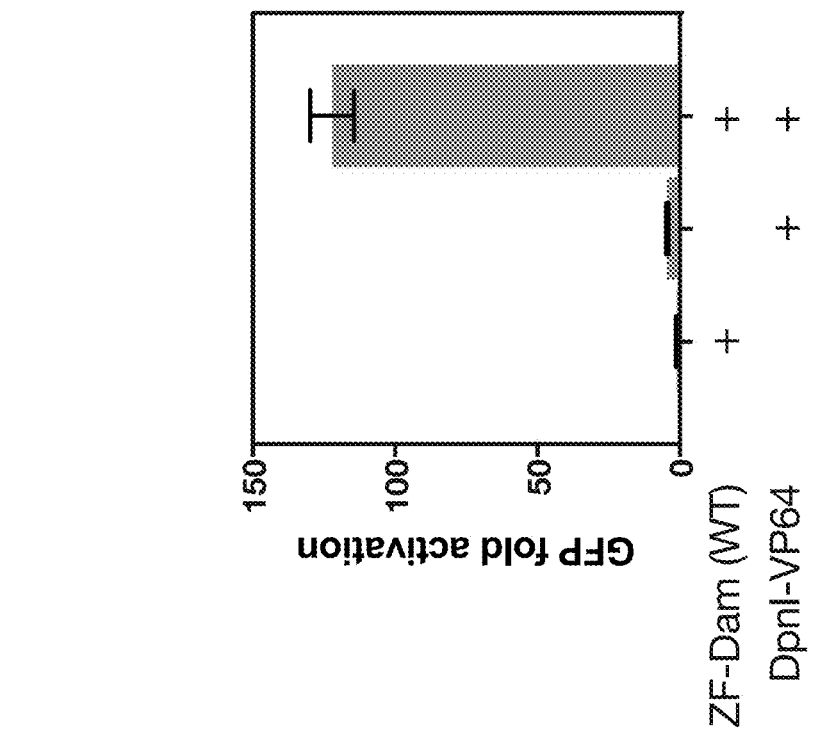
FIG. 5 shows trans-activation of GFP on plasmid reporter by a combination of Writer (ZF-Dam (WT)) and Reader-Effector (DpnI-VP64). Reporter plasmid was co-transfected with Writer and Reader-Effector constructs, and single-cell GFP levels were measured with flow cytometry two days post-transfection. The data shows fold-change of GFP over the basal (reporter only) level. Co-transfection of both the Writer and Reader-Effector constructs resulted in greater than 100-fold increase in GFP, as compared with negative controls (Writer only, Reader-Effector only). Specific constructs corresponding to the data below were: Reporter: [8XZF_14XGATC_interspersed] minimal CMV promoter; Writer: minCMV-ZF10-1-Dam (WT); and Reader-Effector: UBC-NLS-DpnI DBD-VP64.
Figure 6:
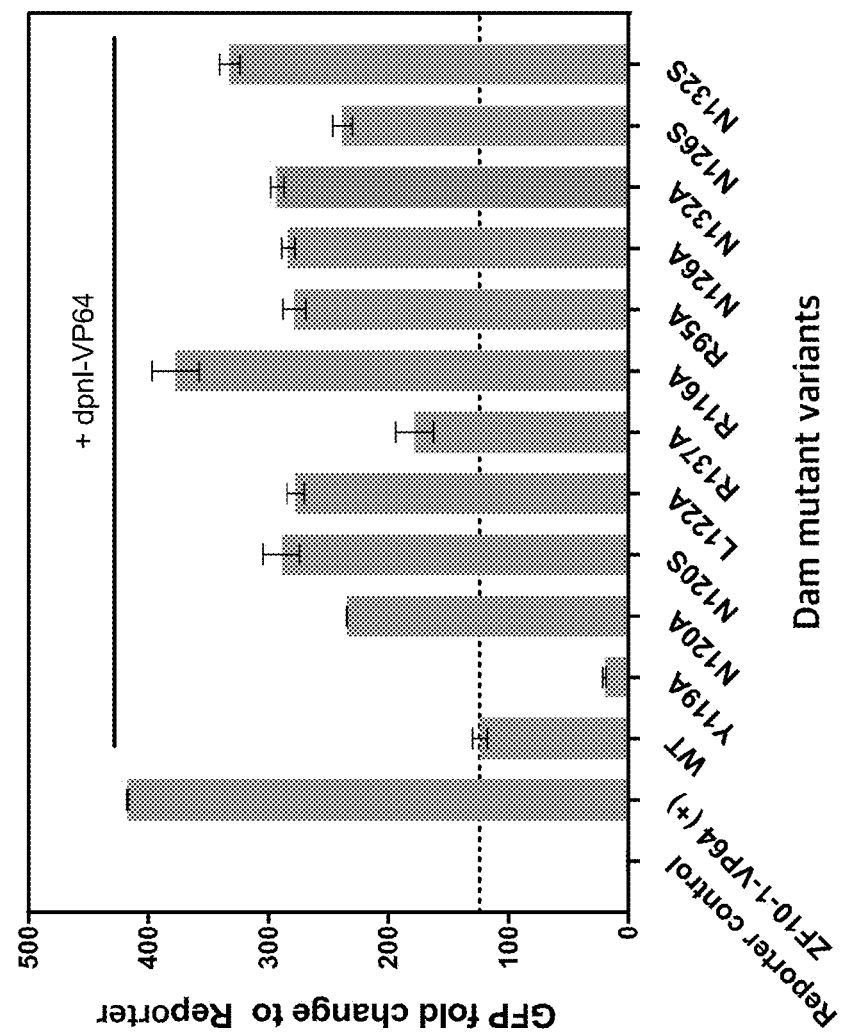
FIG. 6 shows enhanced trans-activation of GFP on plasmid reporter by a combination of Writer (ZF-Dam mutants) and Reader-Effector (DpnI-VP64). Writers incorporating the Dam mutants that were found to have more specific adenine methylation at target sites were tested. As shown, Writers incorporating mutant Dam (with exception for Y199A and R137A) led to an additional 3-4 fold increase in GFP trans-activation compared with Writers using wild type Dam.
Figure 7:
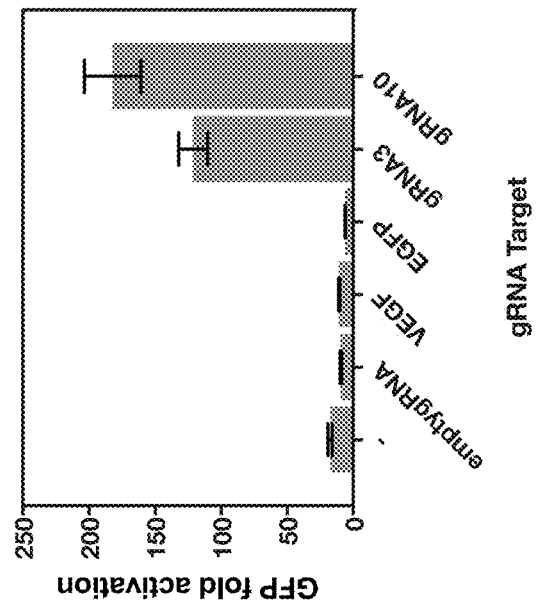
FIG. 7 shows trans-activation of GFP on plasmid reporter by combination of Writer (dCas9-Dam (N132A)) and Reader-Effector (DpnI-VP64). Writers that use an alternative DNA targeting platform were next tested. Specifically, the ability of dCas9-Dam Writers to drive adenine methylation-based transcriptional activation of reporters was tested. As shown, dCas9-Dam Writers that are recruited to the reporter target DBD sites (via gRNA3 or gRNA10) led to greater than 100-fold increase in GFP levels as compared with negative control (no gRNA, empty gRNA, and non-specific gRNAs target the VEGF-A gene or EGFP). Specific constructs corresponding to the data below were: Reporter: [8XZF_14XGATC_interspersed] minimal CMV promoter: Writer: minCMV-dCas9-NLS-Dam (N132A); gRNA: U6 promoter-gRNA, and Reader-Effector: UBC-NLS-DpnI DBD-VP64.
Figure 12:
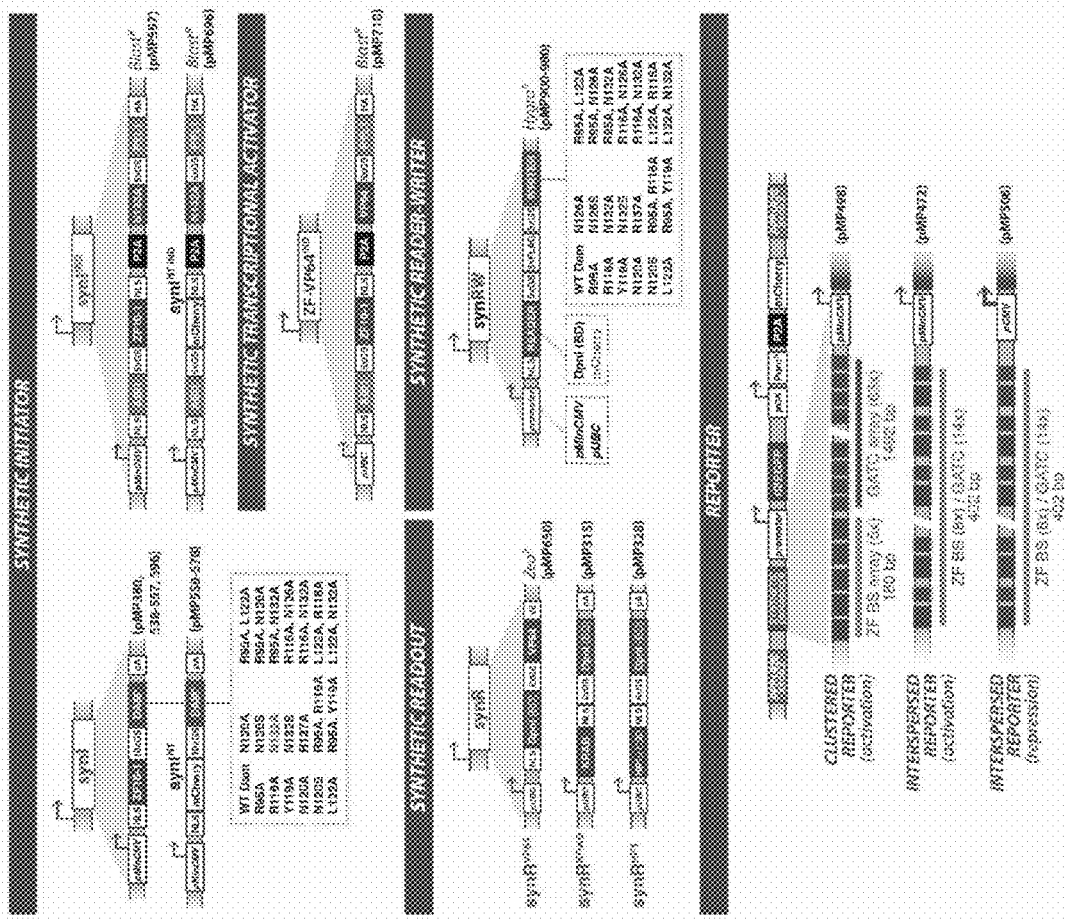
FIG. 12 shows an overview of genetic components and constructs. Synthetic molecular components and corresponding plasmid constructs (pMPXXX, listed in Table 1) are indicated. Plasmid constructs for synI$^{IND}$, synR, synRW and ZF-VP64$^{IND}$, listed with resistance markers, indicate constructs used for lentiviral integration of cells. Reporter constructs were singly-integrated into the AAVS1 (PPP1R2C) locus using CRISPR/Cas9 (see Methods). Stable cell lines derived from combinations of these constructs are listed in Table 2. NLS, SV40 nuclear localization sequence; FLAG, epitope tag; GS, glycine-serine linker; ZF10-1, engineered zinc finger (ZF) designed to bind synthetic 20-bp nucleotide sequence (BS=cGGCGTAGCCGATGTCGCGc (SEQ ID NO: 1)); DAM*, E. coli DNA adenine methyltransferase (Dam) mutants (mutants denoted in red dashed box); DpnI (BD), DpnI binding domain (aa 146-254); VP64, tetramer of Herpes simplex VP16 transcriptional activation domain; KRAB, human Krüppel associated box; HP1α CSD, human Hp1α chromo shadow domain; d2EGFP, EGFP destabilized with degradation domain (fusion with aa 422-461 of mouse ornithine decarboxylase); pCMV, CMV promoter; pMinCMV, minimal CMV promoter; pUBC, human ubiquitin C promoter; pGK, human phosphoglycerate kinase promoter; P2A, porcine teschovirus-1 2A ribosome skipping peptide; ABI1, ABA insensitive 1 complementary surfaces (aa 126-423); PYL1, PYR1-like complementary surfaces (aa 33-209); HA, epitope tag; Blast$^R$ Blasticidin resistance; Hygro$^R$, Hygromycin resistance; Puro$^R$, Puromycin resistance; Zeo$^R$, Zeocin resistance.

Accordingly, provided herein, in some aspects, are engineered, modular, targeted and programmable DNA methylation systems, termed herein as "engineered DNA methylation systems." A depiction of an exemplary embodiment of such a system and component modules are shown at FIG. 1 and FIG. 12. Such systems comprise, in part, a "synthetic reporter" module, a "Writer" module, a "reader-effector" module, and a "reader-writer" module, as those terms are defined herein.

A "reporter module" or "reporter module" used in the engineered DNA methylation systems described herein refers to one or more transiently delivered, genome-integrated DNA sequences, and/or endogenous site/locus comprising arrays of DNA-binding domain (DBD) sites, e.g., Zinc Finger (ZFs) or CRISPR/dCas9, and GATC sequences, which act as a methylation target, placed upstream of a promoter (e.g., minimal CMV or full length CMV promoter)

driving the expression of an output protein molecule, such as a reporter molecule (e.g., EGFP) or other genes. In some embodiments of the systems described herein, a reporter module can comprise an endogenous site or locus to be used with the remaining modules. In some embodiments of the systems described herein, a reporter module is a synthetic reporter module.

As used herein, a "writer module," "synthetic initiator module," or "synI" used in the engineered DNA methylation systems described herein refer to sequences encoding fusions of programmable DNA binding proteins (e.g., a ZF or dCas9) to metazoan, particularly human, codon optimized, mutant versions of E. coli DNA adenine methyltransferase (Dam).

As used herein, a "reader-effector module," "synthetic readout module," or "synR" used in the engineered DNA methylation systems described herein refers to sequences encoding fusions of the methyl-adenine DNA binding domain, such as the methyl-adenine DNA binding domain of DpnI endonuclease, to one or more transcriptional effector domains (EDs), such as, for example, transcriptionally activating or repressive domains.

As used herein, a "reader-writer module," "synthetic read-write module," or "synRW" used in the engineered DNA methylation systems described herein refers to sequences encoding fusions of Dam mutants and the methyl-adenine DNA binding domain of DpnI endonuclease.

As described herein, embodiments of the engineered DNA methylation systems work according to the following mechanism. Briefly, a Writer protein is recruited to target DBD sites (via, for example, a ZF or CRISPR/dCas9), thereby catalyzing the specific and selective methylation of adenines at nearby GATC motifs (within the target locus). Reader-Writer proteins specifically recognize adenine-methylated Gm6ATC sequences, but not unmethylated GATC, via a DpnI methyl-adenine DNA binding domain or modified version thereof. Reader-writer proteins catalyze methylation on adjacent adenines, thereby propagating the chemical modification over longer DNA/genomic distances and sustaining the modifications over time periods beyond when the Writer protein is removed. Reader-Effector proteins specifically recognize adenine-methylated Gm6ATC and recruit transcriptional and other regulatory functions to the locus to drive transcriptional and epigenetic regulation of genes.

Details of various embodiments of the different modules making up the engineered DNA methylation systems described herein and methods thereof are provided herein below. Sequences for the exemplary constructs for the various modules described herein include both DNA sequences as well as amino acid sequences encoding the protein(s) expressed by the modules. As understood by one of ordinary skill in the art, any suitable codon encoding the amino acids of such protein sequences can be used in generating similar constructs for the modules described herein.

Reporter Modules

As described herein, reporter module constructs with methylation targets of various architectures were designed and developed for the reporter module of the engineered DNA methylation modular systems described herein. These reporter module constructs comprise transiently delivered, genome-integrated DNA sequences, and/or endogenous site(s)/loci that comprise arrays of one or more DBD binding sites and one or more GATC sequences (i.e., methylation targets) placed upstream of a promoter sequence, such as, for example, a minimal CMV or full length CMV promoter, that drives the expression of an output product, such as reporter gene(s) (e.g., EGFP). All reporter module constructs described herein were first developed and characterized as transient transfection plasmids and later stably integrated into the human HEK293 genome at a single locus, using, in some embodiments, CRISPR-Cas9 targeting the AAVS1 locus.

In some embodiments of the engineered DNA methylation systems described herein, a reporter module or endogenous sequence/locus comprises a nucleic acid sequence encoding at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least twenty, at least 25, or more, DNA binding domain target sites or sequences.

In some embodiments of the engineered DNA methylation systems described herein, a reporter module or endogenous sequence/locus comprises at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least twenty . . . at least 63 . . . at least 77 . . . at least 100, or more, GATC nucleic acid sequences.

In some embodiments of the engineered DNA methylation systems described herein, distances between DBD target sites, such as ZF binding sites, and GATC sites of the reporter module can range from about 3 bp to about 500 bp, from about 3 bp to about 450 bp, from about 3 bp to about 400 bp, from about 3 bps to about 375 bp, from about 3 bps to about 350 bp, from about 3 bps to about 300 bp, from about 3 bps to about 250 bp, from about 3 bp to about 200 bp, from about 3 bp to about 150 bp, from about 3 bp to about 100 bp, from about 3 bps to about 50 bp, from about 3 bps to about 20 bp, and from about 3 bps to about 25 bp. In some embodiments of the engineered DNA methylation systems described herein, distances between DBD binding sites, such as ZF binding sites, and GATC sites of the reporter module can range from about 3 bps to about 379 bp.

In some embodiments of the engineered DNA methylation systems described herein, a DNA binding domain target site is a DNA sequence that can be bound by a zinc finger (ZF) binding domain expressed by the writer protein. In other words, in some embodiments, a DNA binding domain target site can be bound by a writer fusion protein comprising a zinc finger binding domain.

An exemplary DNA binding domain target site sequence that can be bound by a zinc finger (ZF) binding domain is: cGGCGTAGCCGATGTCGCGc (SEQ ID NO: 1)

In some embodiments of the engineered DNA methylation systems described herein, a DNA binding domain target site is a CRISPR (Clustered Regularly Interspaced Short Palindromic Repeats) DNA sequence that can be bound by a deactivated Cas protein or DNA binding domain thereof expressed by the writer module. In other words, in some embodiments, a DNA binding domain target site can be bound by a writer fusion comprising a deactivated Cas protein or DNA binding domain thereof.

An exemplary DNA binding domain target site sequence that can be bound by a deactivated Cas protein or DNA binding domain thereof is a sequence identical or complementary to any of the guide sequences of SEQ ID NOs: 36 or 37.

The reporter designs or modules include various embodiments having different arrangements and combinations of DBD and GATC sites placed upstream of various promoters, as described herein. One embodiment of a reporter module, termed herein as "8XZF_14XGATC_interspersed" (Interspersed Reported) or SEQ ID NO: 3, comprises 8 ZF binding sites interspersed with 14 GATC sites. This embodiment of an interspersed reporter module was designed to enable a ZF-Dam Writer protein to methylate all or as many GATC sites as possible. The DBD and GATC arrays are placed upstream of promoter sequences driving the expression of reporter genes. In general, a minimal CMV promoter (minCMV) was used to test and enable selective transcriptional activation, while full length CMV promoter was used to test and enable selective transcriptional repression. All reporter constructs described herein were propagated, amplified, and purified from a Dam/Dcm *E. coli* strain (K12 ER2925) before delivery into mammalian cells. The sequence of the "8XZF_14XGATC_interspersed" reporter module having a minimal CMV promoter or SEQ ID NO: 3 is, where ZF binding site (bold)|GATC (bold and underlined)|minCMV promoter (italicized)|Kozak (bold and italicized)|spacer|Restriction Site (underlined and italicized):

<u>GTCGAC</u>gaacGGCGTAGCCGATGTCGCGccctttccacGATCatgtgccG

GCGTAGCCGATGTCGCGcagtaataccaccactgcgaccctaGATCggaG

ATCcaattaGATCcatGATCcgaaacGGCGTAGCCGATGTCGCGcgtgt cgcacgtatcacttGATCggcaaaGGCGTAGCCGATGTCGCGcttgctt cctcGGCGTAGCCGATGTCGCGcgaggtaGATCaggccacGGCGTAGCC GATGTCGCGcttgcgctgcctaGATCatcgttggcGGCGTAGCCGATGT CGCGcacaGATCgaGATCtttggtcGGCGTAGCCGATGTCGCGctccata gtgagttctGATCgtgtcacggctagccgatgtcgcgctagGATCgagGA TCatctctGATCtgttttagg<u>ACTAGT</u>taggcgtgtacggtgggaggcct atataagcagagctcgtttagtgaaccgtcagatcgcctgga<u>ACGCGT</u>ac <u>cggtgt</u>*GCCACC*.

The sequence of the "8XZF_14XGATC_interspersed" reporter module having a full-length CMV promoter or SEQ ID NO: 4 is, where ZF binding site (bold)|GATC (bold and underlined)|full length CMV promoter (italicized)|Kozak (bold and italicized)|spacer Restriction Site (underlined and italicized):

<u>GTCGAC</u>gaacGGCGTAGCCGATGTCGCGccctttccacGATCatgtgccG

GCGTAGCCGATGTCGCGcagtaataccaccactgcgaccctaGATCggaG

ATCcaattaGATCcatGATCcgaaacGGCGTAGCCGATGTCGCGcgtgt cgcacgtatcacttGATCggcaaaGGCGTAGCCGATGTCGCGcttgctt cctcGGCGTAGCCGATGTCGCGcgaggtaGATCaggccacGGCGTAGCC GATGTCGCGcttgcgctgcctaGATCatcgttggcGGCGTAGCCGATGT CGCGcacaGATCgaGATCtttggtcGGCGTAGCCGATGTCGCGctccata gtgagttctGATCgtgtcacggctagccgatgtcgcgctagGATCgagGA TCatctctGATCtgttttagg<u>ACTAGT</u>*GCATGCGCGTTGACATTGATTAT*

*TGACTAGTTATTAATAGTAATCAATTACGGGGTCATTAGTTCATAGCCCA*

*TATATGGAGTTCCGCGTTACATAACTTACGGTAAATGGCCCGCCTGGCTG*

*ACCGCCCAACGACCCCCGCCCATTGACGTCAATAATGACGTATGTTCCCA*

-continued

*TAGTAACGCCAATAGGGACTTTCCATTGACGTCAATGGGTGGAGTATTTA*

*CGGTAAACTGCCCACTTGGCAGTACATCAAGTGTATCATATGCCAAGTAC*

*GCCCCCTATTGACGTCAATGACGGTAAATGGCCCGCCTGGCATTATGCCC*

*AGTACATGACCTTATGGGACTTTCCTACTTGGCAGTACATCTACGTATTA*

*GTCATCGCTATTACCATGGTGATGCGGTTTTGGCAGTACATCAATGGGCG*

*TGGATAGCGGTTTGACTCACGGGGATTTCCAAGTCTCCACCCCATTGACG*

*TCAATGGGAGTTTGTTTTGGCACCAAAATCAACGGGACTTTCCAAAATGT*

*CGTAACAACTCCGCCCCATTGACGCAAATGGGCGGTAGGCGTGTACGGTG*

*GGAGGTCTATATAAGCAGAGCTCTCTGGCTAACTAGAGAACCCACTGCTT*

*ACTGGCTTATCGAAATTAATACGACTCACTATAGGGAGACCCAAGCTG*<u>AC</u>

<u>GCGT</u>accggt*GCCACC*

To study and engineer propagation or spreading of adenine methylation by the engineered DNA methylation systems described herein, provided herein are embodiments of second-generation reporter modules that have separable, rather than interspersed, DBD sites and GATC sites. More specifically, in some embodiments, reporter modules with a single, well-defined "nucleation" site (e.g., 5xDBD sites) upstream of GATC arrays, termed herein as "clustered reporter modules," rather than DBD sites that are interspersed with GATC sites, were used. Reporter modules with variable length (longer) domains of repeated GATC arrays were also examined, in some embodiments. These domains were designed to be sufficiently long such that expression of a Writer protein alone does not lead to methylation of the entire GATC array, surpassing the intrinsic processivity of Dam. Exemplary GATC array domain lengths tested include 1.5 kb and 4.1 kb, in some embodiments of the reporter modules described herein.

In addition, in some embodiments, reporter modules with unique, "barcoded" spacer sequences (e.g., minimum 20 bp) between adjacent GATC sites were deigned. This was designed to enable unique qPCR primer sets to amplify each individual GATC site, in order to generate m6A footprints with single GATC site resolution. (Neutral spacer sequences, orthogonal to sequences in the human genome, were generated using freely-available software available on the world wide web at r2odna.com). Spacer lengths were generally guided by nucleosome units, i.e., the length of DNA sequence packaged in a nucleosome, and included 20-bp, 50-bp, 212-bp, and 800-bp spacer lengths.

Accordingly, in some embodiments, a reporter module comprises a spacer nucleic acid sequence between two or more GATC nucleic acid sequences. In some such embodiments, the spacer sequence is at least 20 bp, at least 25 bp, at least 30 bp, at least 35 bp, at least 40 bp, at least 45 bp, at least 50 bp, at least 55 bp, at least 60 bp, at least 65 bp, at least 70 bp, at least 75 bp, at least 80 bp, at least 85 bp, at least 90 bp, at least 95 bp, at least 100 bp, at least 200 bp . . . at least 212 bp . . . at least 300 bp, at least 400 bp, at least 500 bp, at least 600 bp, at least 700 bp, at least 800 bp, at least 900 bp, at least 1000 bp, or more.

The sequence of the "5XZF_63XGATC" reporter module having a minimal CMV promoter (1.5-kb; 20-bps spacer) or SEQ ID NO: 5 is, where ZF binding site (bold)|GATC (bold and underlined)|min CMV promoter (italicized)|Kozak (bold and italicized)|spacer|Restriction Site (underlined and italicized):

*caattg*GAAAAGTGCCACCTGGGTCGACcGGCGTAGCCGATGTCGCGcAA
CCACCAGTAAGTATCTCAcGGCGTAGCCGATGTCGCGcCAGTAAAGGCTT
CTCTACACcGGCGTAGCCGATGTCGCGcCTCCTTCGGGATAAAATCTCc**G
GCGTAGCCGATGTCGCGcAGTGTGGTAGACTATCTCTGcGGCGTAGCCGA
TGTCGCGcTAAAGGCTTACTGAGCACTAgatc**GAAGTTGTCTCTGAATCA
CAgatcGTTACGATACTTTACACGGTgatcGTGGTATTGTTGTGACACTA
gatcAGATAGGGTGTGATTGGTTAgatcAATCGTTGCGTAATCTACAAga
tcTATTTCTCCAACTTTCGCAAgatcCTTTCTGAGTAAGTAGCACCgatc
TCTGGAGGATAATCTCAGTCgatcGATAATAAACCTGGCTCCTGgatcGA
TTACTGAGGATACGCTTCgatcGTTTCCAACTACTGGCTTTAgatcGAGA
TTCGTAAAGGCTGATgatcGAACTTTCTCTGCGTCTATTgatcCCTGAA
GACCTATTGCTTACgatcAATAATACTATCGGGCGAGAgatcAGTAGGTG
AGGATTACACAAgatcCGAATCTCTGGCTTCAATAAgatcTGTGGTTATT
ACTCAGGGATgatcGGCGAAACAATCTTCTCTATgatcCGATTGCGAGAT
ACTATTGTgatcCAGTGTGCCAATAAGTTTTCgatcAAATAATACTGTGC
CAGAGCgatcAGGATAACACCCTGTGAATAgatcATCAGACAGTCGGATT
CTATgatcGAAAGTCTGAGCGATTTACTgatcAGCGACAACTATTTACTG
ACgatcATCAACGATAGAGGTGAGATgatcTAAACCGATACGGGTAACTA
gatcCCTTCTGTATTTCTACTGGCgatcATCCACCAATACCTGAGTTA**ga
tcGAATCAGCCTTTACAGTAGGgatcCAGTCCTACTATCACCAGATgatc**
GCTCTCAGTTTCTATTTCGTgatcACAGTAGTGAGAACCAGTTAgatcAT
AAGTGTTGATACCTCCCAgatcCTCTGAAATAGGCAGTTACCgatcCAGG
GCTTACAATAGAACTCgatcTACACCACAATAGAAGGGATgatcGATACT
ATTCCGAGGATTGCgatcCTTATTGCTACCAGGAACTCgatcCTGGAATA
AGAAGGTGCTACgatcCGAGAATCACGATAGTAAGGgatcAGCACGATTC
TCCTTTTATCgatcAACTTTCCTATTACCAACGGgatcTGAAGAATAGA
TTTCCTGCGgatcTATTTTCCGTCGTAACTCAGgatcGAATAAGAATCGC
TCTGGTTgatcGCTTTATCACTGGGTAAGAGgatcAGTTGAATACTGTGG
GTAGAgatcGAGTAAAACCCGTTCACTTAgatcCTCTCAATAACCGATAG
ACGgatcTTTATTCAACCTTCTGCGAAgatcGCTTTTACCAGTCCTGATA
GgatcGAAACAGAACCGAAAATCAGgatcGGAGGCTATTGCTACTCTAT**g
atcTGATACTCAATCGTCAGGTAgatcAAATAGTCCGTAAGTAGGCTgat
cCCAGTTGAATAGTAAGAGCCgatcTACTCAACTGGTGGGATAATgatc**T
TTTATTGAGTTCAGCCGAAgatcGGATAAACTTCTACCAGCAGgatcTAT
CCGTGATTATCTGGACAgatcACTAGT*taggcgtgtacggtgggaggcct
atataagcagagctcgtttagtgaaccgtcagatcgcctgga*ACGCGT*ac
cggt*gccacc*

The sequence of the "5XZF_77XGATC" reporter module having a minimal CMV promoter (4.1-kb; 50-bps spacer) or SEQ ID NO: 6 is, where ZF binding site (bold) GATC (bold and underlined)|min CMV promoter (italicized)|Kozak (bold and italicized)|spacer|Restriction Site (underlined and italicized):

*caattg*GAAAAGTGCCACCTGGGTCGACcGGCGTAGCCGATGTCGCGcAA
CCACCAGTAAGTATCTCAcGGCGTAGCCGATGTCGCGcCAGTAAAGGCTT
CTCTACACcGGCGTAGCCGATGTCGCGcCTCCTTCGGGATAAAATCTCc**G
GCGTAGCCGATGTCGCGcAGTGTGGTAGACTATCTCTGcGGCGTAGCCGA
TGTCGCGc**TAAAGGCTTACTGAGCACTA*gctagc*gatcATTCTGTGGATT
CAATACCAGCGAGATTTAGACGGAGGCTCACTTTTACAgatcATCCCTTG
TAGAGTATTTGAGATAACCGCTAACTGATAGGACTTTCCGAGgatcTAAG
CGAGGTTATTACCACAAAACGATAGATTCTGGCTACTTGACTGCTGgatc
TTTCAGATTTTCGTTTACAAGACGCCGTTCAACAGTGGAAGAGTATCGCA
gatcCTCAAGCAGTAAAACGACGAGTATTCTATTGGAGCCTTCTTAGTGC
CTATgatcGTCTGACAGTAAAGGGATTTCCTAAGATTCAACCGCAGTTTG
TTCTACAGGgatcGCAAACTCCTTAGCCGTGGTTCTACAATAGGTCTTCG
TAAAATAATCGGAgatcAGGTGCCTTTAGAAGTCACTGAGACGATTGTTT
ATTACTCCACTACGAAGgatcGAATAAATAGGGTCTCACTGTGTAATCAG
ATACGAACTCCGCTTCCTTTGgatcTATTCACCCTATTTCTTCAGTTGAG
GAGTCACGCAGCAAAGTTACAAGGAgatcTTCTGCGTCTATTTTGGATAC
GGAAACTTGAATCTCAGGCGACTAAGCAAgatcATAGGAGTAACTGTTCA
CACGCTGATACACAATCGTTTAGGTCTGTCACTgatcAGCACGGATTCTG
ATAAACGACTATTTGGCTGGACCTGTCTACAAGTAATgatcTAACGGGAG
GCAGTAACAATCTCACTACGACTTTATTTTAGACCGAGGTTgatcAAGTC
AACGGCTATTTCTTGGGATTACCGAGATAAACTACTGTGTCCTACgatcT
ATTAGTAACCTTCTTCAGGGCGAAAGTATTCACCACACGGGTAAGTTCT**g
atc**CTCCCTTCCAGTTGTAAGACGCAAGTATTATTTTAGGTGATAGGACG
ACAgatcTTGAGTTCTTGGATAGTGCGTTCCGTCCTACGACAACCAGATT
GAAAATAgatcACACCGTAGCGTTCTTGCTCAAAGGAAACAACTTCTATT
GGGTAACTGTAgatcACCGACGCTTAGAATAGAGTTCCTACCCTGATTAG
TTTGAAAGTATCGCTgatcAAGCCCACGAAAGGTCACCGTTTTGTCTGTA
AATAGTAAGTCTTGAGTCAgatcGGCTCAAACCTATCCAAGTGTAGTATC
AGGAGATTCTATTATTCAGTGGCgatcATTCTTGAGGCGGTCTAAATAAA
ACTTGGCTTACCTTCGCAACGAGTATCgatcTACTAAATCAAAGTGTCTG
AAAGGGCGTGAATCTCCCAGTTGGTTACCTAgatcGTTGGGTAACGCCGA
TTTAGTAGAAAACACCTTTGAACCTATTGACTCAGgatcACAAAGCGTAG
AAAATCAGTAGGGTTTATCCTTGGTAGTCTTCCTCCAGTgatcCACGAGG
CTTGTGTTGTATTGACTTTATCCGTAGACAGCAAAATCACCAAgatcATC
AGATAACCTCCCAGAATAAACCGATTGGTGTTCCGTTCGTGGTAATA**gat
c**ATTACCTAAGCGTCTAACTTGCGACTACAGCAGTGACTCTATTGAGATT
GgatcCTTTAGGGCAAACTGTGATAGCAATCCGCTGTTAGTCAAATCTAC
GCTTAgatcGCTGAACCACAGTATTTGTTTTAGAAGGAAGTAAGCCTATC
TGGCAACTCgatcACACTTACTTGGAACTATTTTCAAACGATACGACTGA
TAACGCTGGGTGCgatcGTGGTCCTCAAATCTTCTCGTGCCGTAGTGATA
ATAAGCAGCAAACAATAgatcCGTCGTTCAGTTGGATAACAGCGAAAAGT -continued TTGATACCCTCTCAGATTGTA*gatc*TGTCCTGACTCTGAATACCGTCTGT GAAATAACTGTTTGTAAGCGAACGA*gatc*GCGGAATCTGTAAAAGGGAGT CCAATAATACGCTATCCTGTTCTACTTAG*gatc*GAGTAGAGTTATCCCTT AGACTGTATCTTCACCCGTAGGCAAAGTATTGA*gatc*CCACGGGATTACT AAACCTGATTTGTTGCCGAAGAGATACTTGTGATAAC*gatc*ATCTCACTA TTGGTCAAGGAAGAGTAGAGCACTTTCTCCCGTAACGATTT*gatc*ATTGC GTCAGCGTTGGCTCTCGGTTATTACTATTGAAACAAGGACCTAAA*gatc*A TACCTGGGAGAACGATTTTAGTGACTTATTTACGCTATCAGCCCTACGA*g
atc*ATCAATCCTTAGGGTGCGAAGTCAGTTTGTCTTATTCCAGCGATACA GAA*gatc*TTATCGTAGATTTCCGACACCTGAGACTGTGAAGACCCACTTT GAGTAAT*gatc*TTTAGAAAGTTGACAAGGCTGTATTTTGCTGAATCCAGA CCCTGACTCCA*gatc*TGCCTCGTAACGGCTTGGTCTTAGTCAATCTGAAC CGATAGTAAAATACA*gatc*TTCCAACTGCTTCAAAAGTAATCTATCAAGG TGGTTCTGTGGGCTAAACG*gatc*TTCACCTATTAGACAGTGTCGTCAGT AGTCGGTAAGATAAAGTAACCTC*gatc*CTCTACTGTGTAAATCGTAACAA TAAACGGGCTGGTGTGGCTATCCAAAT*gatc*TGCCTATCCTCCCTTGTTG GAAATCACTAAAACTGAGTAAGAGTCGGAAT*gatc*AGTGTCGGCTTCTTA TTCCTCGCAACCGTCAGAGTAAAACAGTAGTATTA*gatc*GTTGAGCCAAA TAACTGACTCGGAATAGAGGTTTTACGCCTAATACTGCT*gatc*CAATAGG TGAGGGTCCTTATCGGAAAATCGTCGCAAAACTTACTCTTAGT*gatc*ATT TCAACAGTATCGGTTAGCAACTACCTACGCCAGTGTAAGGATTTTCG*gat
c*AGTAAGATTTGTTTAGTTGACACTGCGAGTCTATTTCCCTCCAAGAAGG C*gatc*TAGAATCGTTGAAACCTGTGGCTAAAATAGTTGTGCGTAATCCCT TCCGA*gatc*GAAGAAGTTCCCTACGAGTTACGCTGCCTTTATTAGAGATT ACCCTTGAA*gatc*AAGAGATTATTGATTTGCTATTTTGTGACACCGAAAG TCCACCTGGCACG*gatc*TCGGCTCACTACAGATTGATAATAACGACTAAG GTAAACTCTTCGGGTCT*gatc*GTCACTGTTACAACTAATAAAATAGGTGG ACGACTCCCTTGAATCTGTGC*gatc*GTTTCAGGGCAACGGTTCAACACTT ACAAGGTATCTGTGCTAATCAATCT*gatc*GAGACAATCGCTGTATTAGAT AAACCGTGTAGTTGAATCAGTTACCTCCC*gatc*AGGCTTTACACAATAGA CTTAGATTAGCAACTCTTACGGGATTCCTGGAC*gatc*ATTACCCTGATAC GACCTGGATAACAAGGCTAAATAAGTGGTGTCTCTTC*gatc*TTGTGATTC GTGTAAAACTATCCTGAAGAGCACCGTTCCTCCAAAAGTAG*gatc*TACCG TTTTATCCTTAGAAGCAGAGGTTAGTTCACGAGCAAGCGTCAAAT*gatc*A ACTATTAGAGGATTGTGCCTACACTTTATTTGACTCAGCCAGCAGCGAT*g
atc*CAGCCGTTTCCCGTCCTCAATAGTTAGAAGATTTAGGTAATAAGCGA AGT*gatc*TAAAATCTATTAGCAATCGTAAGTCCCTTTGAGGAGACCTTCT ACCGTGG*gatc*AACGAACTTCTAACTCTACCGTAAGGTCAAACCAGTGTA TTGTGGCTGAT*gatc*TAAACCCAAGAGGGACCGTGATTATTCTGTATTAC CTGTTAGCAAGTAGC*gatc*TTCTCTGGTTACAAAAGTGAGTGCCTTACCT -continued CGTCAGGAATAAACACAGT*gatc*CAAAATAATAGAGGCTTGGAGATTCCT GTGAAAAGTCCTACTCGGTCTTC*gatc*TTGCGAAGAATAATCTGTCTAAA GTCCGAACTGCTGAAACTCGTGTTACG*gatc*TGTTACCACGCTATTTGTC TTGTGAAAGCCAGTCCGAGAATCGTTAGAAA*gatc*TTCGCAGGATTCTAC AGTTTCCGTGTTCTCGGCAAATAGCAATAAAAGGT*gatc*GCTTCAAACAC GGAGAACTACGATTTCCTCAGGCTATTTATTACAGGGTA*gatc*TATCCGT GATTATCTGGACA*ACTAGT*taggcgtgtacggtgggaggcctatataagc agagctcgtttagtgaaccgtcagatcgcctgga*ACGCGT*accggt
gccacc The sequence of the "5XZF_20XGATC" reporter module having a minimal CMV promoter (4.1-kb; 212-bps spacer) or SEQ ID NO: 7 is, where ZF binding site (bold)|GATC (bold and underlined)|min CMV promoter (italicized)|Kozak (bold and italicized)|spacer|Restriction Site (underlined and italicized):

*caattg*GAAAAGTGCCACCTGGGTCGACcGGCGTAGCCGATGTCGCGcAA

CCACCAGTAAGTATCTCAcGGCGTAGCCGATGTCGCGcCAGTAAAGGCTT

CTCTACACcGGCGTAGCCGATGTCGCGcCTCCTTCGGGATAAAATCTCcG

GCGTAGCCGATGTCGCGcAGTGTGGTAGACTATCTCTGc**GGCGTAGCCGA

TGTCGCGcTAAAGGCTTACTGAGCACTA*gctagcgatc*ATTCTGTGGATT

CAATACCAGCGAGATTTAGACGGAGGCTCACTTTTACAagtaATCCCTTG

TAGAGTATTTGAGATAACCGCTAACTGATAGGACTTTCCGAGcgtaTAAG

CGAGGTTATTACCACAAAACGATAGATTCTGGCTACTTGACTGCTGgcat

TTTCAGATTTTCGTTTACAAGACGCCGTTCAACAGTGGAAGAGTATCGCA

*gatc*CTCAAGCAGTAAAACGACGAGTATTCTATTGGAGCCTTCTTAGTGC

CTATggtcGTCTGACAGTAAAGGGATTTCCTAAGATTCAACCGCAGTTTG

TTCTACAGacacGCAAACTCCTTAGCCGTGGTTCTACAATAGGTCTTCGT

AAAATAATCGGAacagAGGTGCCTTTAGAAGTCACTGAGACGATTGTTTA

TTACTCCACTACGAAG*gatc*GAATAAATAGGGTCTCACTGTGTAATCAGA

TACGAACTCCGCTTCCTTTGtagaTATTCACCCTATTTCTTCAGTTGAGG

AGTCACGCAGCAAAGTTACAAGGAatgcTTCTGCGTCTATTTTGGATACG

GAAACTTGAATCTCAGGCGACTAAGCAAatccATAGGAGTAACTGTTCAC

ACGCTGATACACAATCGTTTAGGTCTGTCACT*gatc*AGCACGGATTCTGA

TAAACGACTATTTGGCTGGACCTGTCTACAAGTAATaagtTAACGGGAGG

CAGTAACAATCTCACTACGACTTTATTTTAGACCGAGGTTtctaAAGTCA

ACGGCTATTTCTTGGGATTACCGAGATAAACTACTGTGTCCTACatggTA

TTAGTAACCTTCTTCAGGGCGAAAGTATTCACCACACGGGTAAGTTCT*ga
tc*CTCCCTTCCAGTTGTAAGACGCAAGTATTATTTTAGGTGATAGGACGA

CAcgatTTGAGTTCTTGGATAGTGCGTTCCGTCCTACGACAACCAGATTG

AAAAATgtgACACCGTAGCGTTCTTGCTCAAAGGAAACAACTTCTATTG

GGTAACTGTAgatgACCGACGCTTAGAATAGAGTTCCTACCCTGATTAGT

TTGAAAGTATCGCT*gatc*AAGCCCACGAAAGGTCACCGTTTTGTCTGTAA

-continued

ATAGTAAGTCTTGAGTCAggcaGGCTCAAACCTATCCAAGTGTAGTATCA

GGAGATTCTATTATTCAGTGGCttgtATTCTTGAGGCGGTCTAAATAAAA

CTTGGCTTACCTTCGCAACGAGTATCtacaTACTAAATCAAAGTGTCTGA

AAGGGCGTGAATCTCCCAGTTGGTTACCTAgatcGTTGGGTAACGCCGAT

TTAGTAGAAAACACCTTTGAACCTATTGACTCAGtaccACAAAGCGTAGA

AAATCAGTAGGGTTTATCCTTGGTAGTCTTCCTCCAGTtgctCACGAGGC

TTGTGTTGTATTGACTTTATCCGTAGACAGCAAAATCACCAAgaatATCA

GATAACCTCCCAGAATAAACCGATTGGTGTTCCGTTCGTGGTAATAgatc

ATTACCTAAGCGTCTAACTTGCGACTACAGCAGTGACTCTATTGAGATTG agtgCTTTAGGGCAAACTGTGATAGCAATCCGCTGTTAGTCAAATCTACG CTTAgcgaGCTGAACCACAGTATTTGTTTTAGAAGGAAGTAAGCCTATCT GGCAACTCtatgACACTTACTTGGAACTATTTTCAAACGATACGACTGAT AACGCTGGGTGCgatcGTGGTCCTCAAATCTTCTCGTGCCGTAGTGATAA TAAGCAGCAAACAATAgcgtCGTCGTTCAGTTGGATAACAGCGAAAAGTT TGATACCCTCTCAGATTGTAgtgaTGTCCTGACTCTGAATACCGTCTGTG AAATAACTGTTTGTAAGCGAACGAgctcGCGGAATCTGTAAAAGGGAGTC CAATAATACGCTATCCTGTTCTACTTAGgatcGAGTAGAGTTATCCCTTA GACTGTATCTTCACCCGTAGGCAAAGTATTGAcagtCCACGGGATTACTA AACCTGATTTGTTGCCGAAGAGATACTTGTGATAACtgctATCTCACTAT TGGTCAAGGAAGAGTAGAGCACTTTCTCCCGTAACGATTTtcagATTGCG TCAGCGTTGGCTCTCGGTTATTACTATTGAAACAAGGACCTAAAgatcAT ACCTGGGAGAACGATTTTAGTGACTTATTTACGCTATCAGCCCTACGAca caATCAATCCTTAGGGTGCGAAGTCAGTTTGTCTTATTCCAGCGATACAG AAtgcaTTATCGTAGATTTCCGACACCTGAGACTGTGAAGACCCACTTTG AGTAATagtaTTTAGAAAGTTGACAAGGCTGTATTTTGCTGAATCCGAC CCTGACTCCAgatcTGCCTCGTAACGGCTTGGTCTTAGTCAATCTGAACC GATAGTAAAATACAgtcgTTCCAACTGCTTCAAAAGTAATCTATCAAGGT GGTTCTGTGGGCTAAACGattgTTCACCTATTAGAGCAGTGTCGTCAGTA GTCGGTAAGATAAAGTAACCTCgtcaCTCTACTGTGTAAATCGTAACAAT AAACGGGCTGGTGTGGCTATCCAAATgatcTGCCTATCCTCCCTTGTTGG AAATCACTAAAACTGAGTAAGAGTCGGAATccgaAGTGTCGGCTTCTTAT TCCTCGCAACCGTCAGAGTAAAACAGTAGTATTAgtgaGTTGAGCCAAAT AACTGACTCGGAATAGAGGTTTTACGCCTAATACTGCTgcgtCAATAGGT GAGGGTCCTTATCGGAAAATCGTCGCAAAACTTACTCTTAGTgatcATTT CAACAGTATCGGTTAGCAACTACCTACGCCAGTGTAAGGATTTTCGgaca

AGTAAGATTTGTTTAGTTGACACTGCGAGTCTATTTCCCTCCAAGAAGGC gaacTAGAATCGTTGAAACCTGTGGCTAAAATAGTTGTGCGTAATCCCTT CCGAccatGAAGAAGTTCCCTACGAGTTACGCTGCCTTTATTAGAGATTA CCCTTGAAgatcAAGAGATTATTGATTTGCTATTTTGTGACACCGAAAGT CCACCTGGCACGttccTCGGCTCACTACAGATTGATAATAACGACTAAGG TAAACTCTTCGGGTCTtagtGTCACTGTTACAACTAATAAAATAGGTGGA -continued CGACTCCCTTGAATCTGTGCccatGTTTTCAGGGCAACGGTTCAACACTTA CAAGGTATCTGTGCTAATCAATCTgatcGAGACAATCGCTGTATTAGATA AACCGTGTAGTTGAATCAGTTACCTCCCccgaAGGCTTTACACAATAGAC TTAGATTAGCAACTCTTACGGGATTCCTGGACtcgtATTACCCTGATACG ACCTGGATAACAAGGCTAAATAAGTGGTGTCTCTTCacatTTGTGATTCG TGTAAAACTATCCTGAAGAGCACCGTTCCTCCAAAAGTAGgatcTACCGT TTTATCCTTAGAAGCAGAGGTTAGTTCACGAGCAAGCGTCAAATgttcAA CTATTAGAGGATTGTGCCTACACTTTATTTGACTCAGCCAGCAGCGATac tcCAGCCGTTTCCCGTCCTCAATAGTTAGAAGATTTAGGTAATAAGCGAA GTatgaTAAAATCTATTAGCAATCGTAAGTCCCTTTGAGGAGACCTTCTA CCGTGGgatcAACGAACTTCTAACTCTACCGTAAGGTCAAACCAGTGTAT TGTGGCTGATacctTAAACCCAAGAGGGACCGTGATTATTCTGTATTACC TGTTAGCAAGTAGCtaagTTCTCTGGTTACAAAAGTGAGTGCCTTACCTC GTCAGGAATAAACACAGTgaacCAAAATAATAGAGGCTTGGAGATTCCTG TGAAAAGTCCTACTCGGTCTTCgatcTTGCGAAGAATAATCTGTCTAAAG TCCGAACTGCTGAAACTCGTGTTACGcacaTGTTACCACGCTATTTGTCT TGTGAAAGCCAGTCCGAGAATCGTTAGAAAagagTTCGCAGGATTCTACA GTTTCCGTGTTCTCGGCAAATAGCAATAAAAGGTtttccGCTTCAAACACG GAGAACTACGATTTCCTCAGGCTATTTATTACAGGGTAgatcTATCCGTG ATTATCTGGACA<u>*ACTAGT*</u>taggcgtgtacggtgggaggcctatataagca gagctcgtttagtgaaccgtcagatcgcctgga<u>*ACGCGT*</u>accggtgccacc

The sequence of the "5XZF_6XGATC" reporter module having a minimal CMV promoter (4.1-kb; 800-bps spacer) or SEQ ID NO: 8 is, where ZF binding site (bold)|GATC (bold and underlined)|min CMV promoter (italicized)|Kozak (bold and italicized)|spacer|Restriction Site (underlined mid italicized):

<u>*caattg*</u>GAAAAGTGCCACCTGGGTCGACcGGCGTAGCCGATGTCGCGcAA

CCACCAGTAAGTATCTCAcGGCGTAGCCGATGTCGCGcCAGTAAAGGCTT

CTCTACACcGGCGTAGCCGATGTCGCGcCTCCTTCGGGATAAAATCTCcG

GCGTAGCCGATGTCGCGcAGTGTGGTAGACTATCTCTGcGGCGTAGCCGA

TGTCGCGcTAAAGGCTTACTGAGCACTA*gctagcgatc*ATTCTGTGGATT

CAATACCAGCGAGATTTAGACGGAGGCTCACTTTTACAagtaATCCCTTG

TAGAGTATTTGAGATAACCGCTAACTGATAGGACTTTCCGAGcgtaTAAG

CGAGGTTATTACCACAAAACGATAGATTCTGGCTACTTGACTGCTGgcat

TTTCAGATTTTCGTTTACAAGACGCCGTTCAACAGTGGAAGAGTATCGCA tgcaCTCAAGCAGTAAAACGACGAGTATTCTATTGGAGCCTTCTTAGTGC CTATggtcGTCTGACAGTAAAGGGATTTCCTAAGATTCAACCGCAGTTTG TTCTACAGacacGCAAACTCCTTAGCCGTGGTTCTACAATAGGTCTTCGT AAAATAATCGGAacagAGGGTGCCTTTAGAAGTCACTGAGACGATTGTTTA TTACTCCACTACGAAGcttgGAATAAAATAGGGTCTCACTGTGTAATCAGA

```
TACGAACTCCGCTTCCTTTGtagaTATTCACCCTATTTCTTCAGTTGAGG
AGTCACGCAGCAAAGTTACAAGGAatgcTTCTGCGTCTATTTTGGATACG
GAAACTTGAATCTCAGGCGACTAAGCAAatccATAGGAGTAACTGTTCAC
ACGCTGATACACAATCGTTTAGGTCTGTCACTaggaAGCACGGATTCTGA
TAAACGACTATTTGGCTGGACCTGTCTACAAGTAATaagtTAACGGGAGG
CAGTAACAATCTCACTACGACTTTATTTTAGACCGAGGTTtctaAAGTCA
ACGGCTATTTCTTGGGATTACCGAGATAAACTACTGTGTCCTACgatcTA
TTAGTAACCTTCTTCAGGGCGAAAGTATTCACCACACGGGTAAGTTCTct
tcCTCCCTTCCAGTTGTAAGACGCAAGTATTATTTTAGGTGATAGGACGA
CAcgatTTGAGTTCTTGGATAGTGCGTTCCGTCCTACGACAACCAGATTG
AAAATAtgtgACACCGTAGCGTTCTTGCTCAAAGGAAACAACTTCTATTG
GGTAACTGTAgatgACCGACGCTTAGAATAGAGTTCCTACCCTGATTAGT
TTGAAAGTATCGCTgtagAAGCCCACGAAAGGTCACCGTTTTGTCTGTAA
ATAGTAAGTCTTGAGTCAggcaGGCTCAAACCTATCCAAGTGTAGTATCA
GGAGATTCTATTATTCAGTGGCttgtATTCTTGAGGCGGTCTAAATAAAA
CTTGGCTTACCTTCGCAACGAGTATCtacaTACTAAATCAAAGTGTCTGA
AAGGGCGTGAATCTCCCAGTTGGTTACCTAgatgGTTGGGTAACGCCGAT
TTAGTAGAAAACACCTTTGAACCTATTGACTCAGtaccACAAAGCGTAGA
AAATCAGTAGGGTTTATCCTTGGTAGTCTTCCTCCAGTtgctCACGAGGC
TTGTGTTGTATTGACTTTATCCGTAGACAGCAAAATCACCAAgaatATCA
GATAACCTCCCAGAATAAACCGATTGGTGTTCCGTTCGTGGTAATAttgc
ATTACCTAAGCGTCTAACTTGCGACTACAGCAGTGACTCTATTGAGATTG
agtgCTTTAGGGCAAACTGTGATAGCAATCCGCTGTTAGTCAAATCTACG
CTTAgatcGCTGAACCACAGTATTTGTTTTAGAAGGAAGTAAGCCTATCT
GGCAACTCtatgACACTTACTTGGAACTATTTTCAAACGATACGACTGAT
AACGCTGGGTGCgcgaGTGGTCCTCAAATCTTCTCGTGCCGTAGTGATAA
TAAGCAGCAAACAATAgcgtCGTCGTTCAGTTGGATAACAGCGAAAAGTT
TGATACCCTCTCAGATTGTAgtgaTGTCCTGACTCTGAATACCGTCTGTG
AAATAACTGTTTGTAAGCGAACGAgctcGCGGAATCTGTAAAAGGGAGTC
CAATAATACGCTATCCTGTTCTACTTAGtggtGAGTAGAGTTATCCCTTA
GACTGTATCTTCACCCGTAGGCAAAGTATTGAcagtCCACGGGATTACTA
AACCTGATTTGTTGCCGAAGAGATACTTGTGATAACtgctATCTCACTAT
TGGTCAAGGAAGAGTAGAGCACTTTCTCCCGTAACGATTTtcagATTGCG
TCAGCGTTGGCTCTCGGTTATTACTATTGAAACAAGGACCTAAAatggAT
ACCTGGGAGAACGATTTTAGTGACTTATTTACGCTATCAGCCCTACGAca
caATCAATCCTTAGGGTGCGAAGTCAGTTTGTCTTATTCCAGCGATACAG
AAtgcaTTATCGTAGATTTCCGACACCTGAGACTGTGAAGACCCACTTTG
AGTAATagtaTTTAGAAAGTTGACAAGGCTGTATTTTGCTGAATCCAGAC
CCTGACTCCAaagcTGCCTCGTAACGGCTTGGTCTTAGTCAATCTGAACC
GATAGTAAAATACAgatcTTCCAACTGCTTCAAAAGTAATCTATCAAGGT
GGTTCTGTGGGCTAAACGattgTTCACCTATTAGAGCAGTGTCGTCAGTA
GTCGGTAAGATAAAGTAACCTCgtcaCTCTACTGTGTAAATCGTAACAAT
AAACGGGCTGGTGTGGCTATCCAAATgtcgTGCCTATCCTCCCTTGTTGG
AAATCACTAAAACTGAGTAAGAGTCGGAATccgaAGTGTCGGCTTCTTAT
TCCTCGCAACCGTCAGAGTAAAACAGTAGTATTAgtgaGTTGAGCCAAAT
AACTGACTCGGAATAGAGGTTTTACGCCTAATACTGCTgcgtCAATAGGT
GAGGGTCCTTATCGGAAAATCGTCGCAAAACTTACTCTTAGTagcaATTT
CAACAGTATCGGTTAGCAACTACCTACGCCAGTGTAAGGATTTTCGgaca
AGTAAGATTTGTTTAGTTGACACTGCGAGTCTATTTCCCTCCAAGAAGGC
gaacTAGAATCGTTGAAACCTGTGGCTAAAATAGTTGTGCGTAATCCCTT
CCGAccatGAAGAAGTTCCCTACGAGTTACGCTGCCTTTATTAGAGATTA
CCCTTGAAtccaAAGAGATTATTGATTTGCTATTTTGTGACACCGAAAGT
CCACCTGGCACGttccTCGGCTCACTACAGATTGATAATAACGACTAAGG
TAAACTCTTCGGGTCTtagtGTCACTGTTACAACTAATAAAATAGGTGGA
CGACTCCCTTGAATCTGTGCccatGTTTCAGGGCAACGGTTCAACACTTA
CAAGGTATCTGTGCTAATCAATCTgatcGAGACAATCGCTGTATTAGATA
AACCGTGTAGTTGAATCAGTTACCTCCCccgaAGGCTTTACACAATAGAC
TTAGATTAGCAACTCTTACGGGATTCCTGGACtcgtATTACCCTGATACG
ACCTGGATAACAAGGCTAAATAAGTGGTGTCTCTTCacatTTGTGATTCG
TGTAAAACTATCCTGAAGAGCACCGTTCCTCCAAAAGTAGccaaTACCGT
TTTATCCTTAGAAGCAGAGGTTAGTTCACGAGCAAGCGTCAAATgttcAA
CTATTAGAGGATTGTGCCTACACTTTATTTGACTCAGCCAGCAGCGATac
tcCAGCCGTTTCCCGTCCTCAATAGTTAGAAGATTTAGGTAATAAGCGAA
GTatgaTAAAATCTATTAGCAATCGTAAGTCCCTTTGAGGAGACCTTCTA
CCGTGGcacaAACGAACTTCTAACTCTACCGTAAGGTCAAACCAGTGTAT
TGTGGCTGATacctTAAACCCAAGAGGGACCGTGATTATTCTGTATTACC
TGTTAGCAAGTAGCtaagTTCTCTGGTTACAAAAGTGAGTGCCTTACCTC
GTCAGGAATAAACACAGTgaacCAAAATAATAGAGGCTTGGAGATTCCTG
TGAAAAGTCCTACTCGGTCTTCcgtaTTGCGAAGAATAATCTGTCTAAAG
TCCGAACTGCTGAAACTCGTGTTACGcacaTGTTACCACGCTATTTGTCT
TGTGAAAGCCAGTCCGAGAATCGTTAGAAAagagTTCGCAGGATTCTACA
GTTTCCGTGTTCTCGGCAAATAGCAATAAAAGGTgatcGCTTCAAACACG
GAGAACTACGATTTCCTCAGGCTATTTATTACAGGGTAttccTATCCGTG
ATTATCTGGACAACTAGTtaggcgtgtacggtgggaggcctatataagca
gagctcgtttagtgaaccgtcagatcgcctggaACGCGTaccggtgccacc
```

A variety of target genes and output products are provided for use in the reporter modules of the systems and methods described herein. As used herein, "output products" refer to gene products that can be used in the synthetic reporter modules described herein. A sequence encoding for an output product can be used to mark the state of the cell comprising an engineered DNA methylation system upon receiving a particular input. Such output products can be used as an indicator of the methylation status of a cell. Representative output products for the engineered DNA methylation systems described herein include, without limitation, reporter proteins, transcriptional repressors, transcriptional activators, selection markers, enzymes, receptor proteins, ligand proteins, RNAs, ribo es, short-hairpin RNAs and recombinases. Sequences encoding such output products that can be used in conjunction with the systems described herein are known in the art.

In some embodiments of the aspects described herein, the output protein molecule is a "reporter" or "reporter molecule." As used herein, a reporter refers to a protein that can be used to measure gene expression and generally produce a measurable signal such as fluorescence, luminescence or color. The presence of a reporter in a cell or organism is readily observed. For example, fluorescent proteins (e.g., green fluorescent protein (GFP), red fluorescent protein such as mCherry) cause a cell to fluoresce when excited with light of a particular wavelength, luciferases cause a cell to catalyze a reaction that produces light, and enzymes such as β-galactosidase convert a substrate to a colored product. Reporters for use in accordance with the systems described herein include any reporter described herein or known to one of ordinary skill in the art and sequences encoding the same.

There are several different ways to measure or quantify a reporter depending on the particular reporter and what kind of characterization data is desired. In some embodiments, microscopy can be a useful technique for obtaining both spatial and temporal information on reporter activity, particularly at the single cell level. In some embodiments, flow cytometers can be used for measuring the distribution in reporter activity across a large population of cells. In some embodiments, plate readers can be used for taking population average measurements of many different samples over time. In some embodiments, instruments that combine such various functions can be used, such as multiplex plate readers designed for flow cytometers, and combination microscopy and flow cytometric instruments.

Examples of sequences and genes encoding fluorescent proteins that can be used in accordance with the invention include, without limitation, those proteins provided in U.S. Patent Application No. 2012/0003630 (see Table 59), incorporated herein by reference in its entirety.

Examples of UV fluorescent proteins useful as reporter proteins include, but are not limited to, Sirius. Examples of blue fluorescent proteins include, but are not limited to, Azurite, EBFP2, mKalama1, mTagBFP2, and tagBFP. Examples of cyan fluorescent proteins include, but are not limited to, ECFP, Cerulean, mCerulean3, SCFP3A, CyPet, mTurquoise, mTurquoise2, TagCFP, Mtfp1, monomeric Midoriishi-Cyan, and Aquamarine. Examples of green fluorescent proteins include, but are not limited to, TurboGFP, TagGFP2, mUKG, Superfolder GFP, Emerald, EGFP, Monomeric Azami Green, mWasabi, Clover, and mNeonGreen. Examples of yellow fluorescent proteins include, but are not limited to, TagYFP, EYFP, Topaz, Venus, SYFP2, Citrine, Ypet, IanRFP-ΔS83, and mPapaya1. Examples of orange fluorescent proteins include, but are not limited to, Monomeric Kusabira-Orange, mOrange, mOrange2, mKOK, and Mko2. Examples of red fluorescent proteins include, but are not limited to, TagRFP, TagRFP-T, mRuby, mRuby2, mTangerine, mApple, mStrawberry, FusionRed, mCherry, and mNectarine. Examples of far red fluorescent proteins include, but are not limited to, mKate2, HcRedTandem, mPlum, mRaspberry, mNeptune, NirFP, TagRFP657, TagRFP675, and mCardinal. Examples of near IR fluorescent proteins include, but are not limited to, iFP1.4, iRFP713 (iRFP), iRFP670, iRFP682, iRFP702, iRFP720, and iFP2.0. Examples of sapphire-type fluorescent proteins include, but are not limited to, Sapphire, T-Sapphire, and mAmetrine. Examples of long Stokes shift fluorescent proteins include, but are not limited to, mKeima Red, mBeRFP, LSS-mKate2, LSS-mKate1, and LSSmOrange.

Luciferases can also be used as reporter molecules, as cells tend to have little to no background luminescence in the absence of a luciferase. Luminescence can be readily quantified using a plate reader or luminescence counter. Examples of genes encoding luciferases for that can be used in the systems described herein include, without limitation, dmMyD88-linker-Rluc, dmMyD88-linker-Rluc-linker-PEST191, Renilla luciferase, and firefly luciferase (from *Photinus pyralis*).

Enzymes that produce colored substrates ("colorimetric enzymes") can also be used as reporter molecules. Enzymatic products can be quantified using spectrophotometers or other instruments that can take absorbance measurements including plate readers. Like luciferases, enzymes such as β-galactosidase can be used for measuring low levels of gene expression because they tend to amplify low signals. Examples of genes encoding colorimetric enzymes that can be used in accordance with the systems described herein include, without limitation, lacZ alpha fragment, lacZ (encoding beta-galactosidase, full-length), and xylE.

Writer or Synthetic Initiator Modules

As described herein, synthetic Writer fusion protein modules, also referred to herein as synthetic initiator modules, were designed and developed that are capable of selectively establishing adenine methylation at GATCs at target locations on transient plasmids or genomic DNA sequences in human cells. These Writer fusion proteins comprise fusions of engineered, programmable DNA binding proteins or domains thereof and human codon optimized, mutant versions of *E. coli* DNA adenine methyltransferase (Dam). Accordingly, the writer protein modules described herein comprise, in part, a nucleic acid sequence encoding a DNA binding protein or domain thereof, which can bind to the one or more DNA binding domain target site nucleic acid sequences on the synthetic reporter module, fused to a mutant version of *E. coli* DNA adenine methyltransferase (Dam).

Accordingly, to allow for highly targeted and selective methylation, several key design strategies were developed in constructing the synthetic Writer fusion protein modules comprising mutant versions of *E. coli* Dam. In some embodiments of the engineered DNA methylation systems described herein, a mutant Dam enzyme was fused to high affinity engineered DNA binding proteins that target desired 18-20 bp sequences. This was demonstrated using two different DNA targeting technologies.

Specifically, in some embodiments, engineered six-finger ZF arrays that recognize 18-20 bp sequences were used. The Writer fusion protein constructs, in some embodiments, used a ZF array (ZF10-1) with a target sequence: cGGCGTAGC-CGATGTCGCGc (SEQ ID NO: 1). In some embodiments, the CRISPR/dCas9 system was used in the writer fusion protein constructs using a catalytically dead, i.e., "deactivated," dCas9 protein and a gRNA (guide RNA) that targeted a desired 20 bp sequence. As shown herein, use of CRISPR/dCas9 enables an alternative, highly flexible DNA targeting platform with the capability to rapidly target GATC sequences within endogenous genes and genomic locations.

Further, in some embodiments of the engineered DNA methylation systems described herein, Writer fusion proteins can be expressed at low expression levels, either using, in some embodiments, weak constitutive promoters (e.g., a crippled minimal CMV promoter, minCMV) or, in other embodiments, inducible expression systems.

In some embodiments of the engineered DNA methylation systems described herein, a DNA binding protein or domain thereof is a zinc finger domain.

In some embodiments, the one or more DNA binding domains comprise three zinc-finger domains to target a total 9 base pair region of DNA. In some embodiments, the number of zinc-finger domains is at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or more zinc finger domains that can target the one or more DNA binding domain target sites on the reporter module.

An exemplary amino acid sequence encoding a zinc finger binding protein or domain thereof for use as a DNA binding protein or domain thereof in the writer fusions proteins described herein is: SRPGERPFQCRICMRNFSRRHGL-DRHTRTHTGEKPFQCRICMRNFSDHSSLKRHLRTH-TGSQKPF QCRICMRNFSVRHNLTRHLRTHTGEKP-FQCRICMRNFSDHSNLSRHLKTHTGSQKPFQCRICMRN FSQRSSLVRHLRTHTGEKPFQCRICMRNFSES-GHLKRHLRTHLRGS (SEQ ID NO: 9).

In some embodiments of the engineered DNA methylation systems described herein, a DNA binding protein or domain thereof is a deactivated Cas enzyme or domain thereof.

CRISPR (Clustered Regularly Interspaced Short Palindromic Repeats) is an acronym for DNA loci that contain multiple, short, direct repetitions of base sequences. CRISPRs are often associated with cas genes which code for proteins that perform various functions related to CRISPRs. The CRISPR/Cas system functions as a prokaryotic immune system by conferring resistance to exogenous genetic elements such as plasmids and phages thereby imparting for a form of acquired immunity. Endogenous CRISPR spacers recognize and silence exogenous genetic elements in a manner similar to RNAi in eukaryotic organisms. In embodiments of the engineered systems and methods thereof described herein, the CRISPR/Cas-mediated genome modulating composition refers to elements of a CRISPR system needed to carry out CRISPR/Cas-mediated genome modulation in a mammalian subject for use with the systems and methods described herein. As discussed herein, CRISPR/Cas-mediated genome editing compositions typically include one or more nucleic acids encoding a crRNA, a tracrRNA (or chimeric thereof also referred to a guide RNA or single guide RNA) and a deactivated Cas enzyme, such as, for example, a deactivated Cas9. The CRISPR/Cas-mediated genome modulating composition can optionally include a donor polynucleotide that can be recombined into the target cell's genome at or adjacent to the target site (e.g., the site of single or double strand break induced by the Cas9).

The CRISPR/Cas system has been adapted for use as gene editing (silencing, enhancing or changing specific genes) for use in eukaryotes (see, for example, Cong, Science, 15:339 (6121):819-823 (2013) and Jinek, et al., iScience, 337 (6096):816-21 (2012)). By transfecting a cell with the required elements including a cas gene and specifically designed CRISPRs, an organism's genome can be cut and modified at any desired location. Methods of preparing compositions for use in genome editing and genome modulation using the CRISPR/Cas systems are described in detail in WO 2013/176772 and WO 2014/018423, which are specifically incorporated by reference herein in their entireties.

The engineered systems and methods thereof disclosed herein are suitable for use with numerous variations on the CRISPR/Cas system.

In general, in embodiments of the engineered systems and methods thereof disclosed herein, a CRISPR system is characterized by elements that promote the formation of a CRISPR complex at the site of a DNA binding domain target site (also known as a protospacer in the context of an endogenous CRISPR system). In the context of formation of a CRISPR complex, "DNA binding domain target site" refers to a sequence to which a guide sequence is designed to have complementarity, where hybridization between a DNA binding domain target site and a guide sequence promotes the formation of a CRISPR complex.

There are many resources available for helping practitioners determine suitable DNA binding domain target sites. For example, numerous public resources, including a bioinformatically generated list of about 190,000 potential sgRNAs, targeting more than 40% of human exons, are available to aid practitioners in selecting DNA binding domain target site and designing the associate sgRNA to bind at the site. See also, on the worldwide web at crispr.u-psud.fr/, a tool designed to help scientists find CRISPR targeting sites in a wide range of species and generate the appropriate crRNA sequence.

In some embodiments of the engineered systems and methods thereof disclosed herein, a DNA binding protein or domain thereof is a natural or genetically modified CRISPR enzyme, such as a enzymatically inactive or deactived Cas protein, or a DNA binding domain thereof. Non-limiting examples of Cas proteins include Cas1, Cas1B, Cas2, Cas3, Cas4, Cas5, Cash, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified and engineered versions thereof.

In some embodiments of the engineered systems and methods thereof disclosed herein, a a CRISPR enzyme that is used as a DNA binding protein or domain thereof is mutated with respect to a corresponding wild-type enzyme such that the mutated CRISPR or domain thereof lacks the ability to cleave a nucleic acid sequence containing a DNA binding domain target site. For example, in some embodiments, a D10A mutation is combined with one or more of H840A, N854A, or N863A mutations to produce a Cas9 enzyme substantially lacking all DNA cleavage activity, i.e., a "deactivated Cas protein."

In some embodiments of the engineered systems and methods thereof disclosed herein, a coding sequence encoding a deactivated CRISPR enzyme or domain thereof is codon optimized for expression in particular cells, such as eukaryotic cells. The eukaryotic cells can be those of or derived from a particular organism, such as a mammal, including but not limited to human, mouse, rat, rabbit, dog, or non-human primate. In general, codon optimization refers to a process of modifying a nucleic acid sequence for enhanced expression in the host cells of interest by replacing at least one codon (e.g., about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules.

The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database", and these tables can be adapted in a number of ways. See Nakamura, Y., et al., Nucl. Acids Res., 28:292 (2000). Computer algorithms for codon optimizing a particular sequence for expression in a particular host cell, for example Gene Forge (Aptagen; Jacobus, Pa.), are also available. In some embodiments, one or more codons (e.g., 1, 2, 3, 4, 5, 10, 15, 20, 25, 50, or more, or all codons) in a sequence encoding a CRISPR enzyme correspond to the most frequently used codon for a particular amino acid.

In some embodiments of the engineered systems and methods thereof disclosed herein, where a writer module comprises a CRISPR enzyme or domain thereof, one or more nuclear localization sequences (NLSs) are used. When more than one NLS is present, each may be selected independently of the others, such that a single NLS may be present in more than one copy and/or in combination with one or more other NLSs present in one or more copies. In general, the one or more NLSs are of sufficient strength to drive accumulation of the CRISPR enzyme or domain thereof in a detectable amount in the nucleus of a eukaryotic cell. In general, strength of nuclear localization activity can derive from the number of NLSs in the CRISPR enzyme, the particular NLS(s) used, or a combination of these factors.

Detection of accumulation in the nucleus may be performed by any suitable technique. For example, a detectable marker may be fused to the CRISPR enzyme, such that location within a cell may be visualized, such as in combination with a means for detecting the location of the nucleus (e.g., a stain specific for the nucleus such as DAPI). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of CRISPR complex formation (e.g., assay for DNA cleavage or mutation at the target sequence, or assay for altered gene expression activity affected by CRISPR complex formation and/or CRISPR enzyme activity), as compared to a control no exposed to the CRISPR enzyme or complex, or exposed to a CRISPR enzyme lacking the one or more NLSs.

In some embodiments, one or more of the elements of a CRISPR system used in the engineered methylations systems described herein are under the control of an inducible promoter, which can include inducible Cas, such as Cas9.

An exemplary amino acid sequence encoding a catalytically inactive Cas enzyme or domain thereof for use as a DNA binding protein or domain thereof in the writer fusions proteins described herein is:

(SEQ ID NO: 10)
MDKKYSIGLAIGTNSVGWAVITDEYKVPSKKFKVLGNTDRHSIKKNLIGA

LLFDSGETAEATRLKRTARRRYTRRKNRICYLQEIFSNEMAKVDDSFFHR

LEESFLVEEDKKHERHPIFGNIVDEVAYHEKYPTIYHLRKKLVDSTDKAD

-continued

LRLIYLALAHMIKFRGHFLIEGDLNPDNSDVDKLFIQLVQTYNQLFEENP

INASGVDAKAILSARLSKSRRLENLIAQLPGEKKNGLFGNLIALSLGLTP

NFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLR

KQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDK

NLPNEKVLPKHSLLYEYFTVYNELTKVKYVTEGMRKPAFLSGEQKKAIVD

LLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQ

LKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHP

VENTQLQNEKLYLYYLQNGRDMYVDQELDINRLSDYDVDAIVPQSFLKDD

SIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLI

REVKVITLKSKLVSDFRKDFQFYKVREINNYHHAHDAYLNAVVGTALIKK

YPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEV

QTGGFSKESILPKRNSDKLIARKKDWDPKKYGGFDSPTVAYSVLVVAKVE

KGKSKKLKSVKELLGITIMERSSFEKNPIDFLEAKGYKEVKKDLIIKLPK

YSLFELENGRKRMLASAGELQKGNELALPSKYVNFLYLASHYEKLKGSPE

DNEQKQLFVEQHKHYLDEIIEQISEFSKRVILADANLDKVLSAYNKHRDK

PIREQAENIIHLFTLTNLGAPAAFKYFDTTIDRKRYTSTKEVLDATLIHQ

SITGLYETRIDLSQLGGD.

The wild type Dam molecule possesses intrinsic affinity for GATC sequences, and is a highly active and processive enzyme. However, expression of wild type Dam leads to uncontrolled and global methylation of adenines at all GATC sequences. Accordingly, mutations in Dam were introduced at residues predicted to mediate nonspecific interactions with flanking phosphate groups on DNA, in order to lower the intrinsic affinity of Dam for GATC sequences for use in the writer fusion proteins described herein. An exemplary specific Dam mutant (N132A) was selected as a particularly effective and specific methylase in the context of the Writer fusion for use in some embodiments, as described herein.

The protein reference sequence for wild-type Dam enzyme is:

(SEQ ID NO: 11)
KKNRAFLKWAGGKYPLLDDIKRHLPKGECLVEPFVGAGSVFLNTDFSRYI

LADINSDLISLYNIVKMRTDEYVQAARELFVPETNCAEVYYQFREEFNKS

QDPFRRAVLFLYLNRYGYNGLCRYNLRGEFNVPFGRYKKPYFPEAELYHF

AEKAQNAFFYCESYADSMARADDASVVYCDPPYAPLSATANFTAYHTNSF

The protein sequence encoding a Y119A Dam mutant enzyme is:

(SEQ ID NO: 12)
KKNRAFLKWAGGKYPLLDDIKRHLPKGECLVEPFVGAGSVFLNTDFSRYI
LADINSDLISLYNIVKMRTDEYVQAARELFVPETNCAEVYYQFREEFNKS
QDPFRRAVLFLYLNRYGANGLCRYNLRGEFNVPFGRYKKPYFPEAELYHF
AEKAQNAFFYCESYADSMARADDASVVYCDPPYAPLSATANFTAYHTNSF
TLEQQAHLAEIAEGLVERHIPVLISNHDTMLTREWYQRAKLHVVKVRRSI
SSNGGTRKKVDELLALYKPGVVSPAKK.

The protein sequence encoding a N120A Dam mutant enzyme is:

(SEQ ID NO: 13)
KKNRAFLKWAGGKYPLLDDIKRHLPKGECLVEPFVGAGSVFLNTDFSRYI
LADINSDLISLYNIVKMRTDEYVQAARELFVPETNCAEVYYQFREEFNKS
QDPFRRAVLFLYLNRYGYAGLCRYNLRGEFNVPFGRYKKPYFPEAELYHF
AEKAQNAFFYCESYADSMARADDASVVYCDPPYAPLSATANFTAYHTNSF
TLEQQAHLAEIAEGLVERHIPVLISNHDTMLTREWYQRAKLHVVKVRRSI
SSNGGTRKKVDELLALYKPGVVSPAKK.

The protein sequence encoding a N120S Dam mutant enzyme is:

(SEQ ID NO: 14)
KKNRAFLKWAGGKYPLLDDIKRHLPKGECLVEPFVGAGSVFLNTDFSRYI
LADINSDLISLYNIVKMRTDEYVQAARELFVPETNCAEVYYQFREEFNKS
QDPFRRAVLFLYLNRYGYSGLCRYNLRGEFNVPFGRYKKPYFPEAELYHF
AEKAQNAFFYCESYADSMARADDASVVYCDPPYAPLSATANFTAYHTNSF
TLEQQAHLAEIAEGLVERHIPVLISNHDTMLTREWYQRAKLHVVKVRRSI
SSNGGTRKKVDELLALYKPGVVSPAKK.

The protein sequence encoding a L122A Dam mutant enzyme is:

(SEQ ID NO: 15)
KKNRAFLKWAGGKYPLLDDIKRHLPKGECLVEPFVGAGSVFLNTDFSRYI
LADINSDLISLYNIVKMRTDEYVQAARELFVPETNCAEVYYQFREEFNKS
QDPFRRAVLFLYLNRYGYNGACRYNLRGEFNVPFGRYKKPYFPEAELYHF
AEKAQNAFFYCESYADSMARADDASVVYCDPPYAPLSATANFTAYHTNSF
TLEQQAHLAEIAEGLVERHIPVLISNHDTMLTREWYQRAKLHVVKVRRSI
SSNGGTRKKVDELLALYKPGVVSPAKK.

The protein sequence encoding a R137A Dam mutant enzyme is:

(SEQ ID NO: 16)
KKNRAFLKWAGGKYPLLDDIKRHLPKGECLVEPFVGAGSVFLNTDFSRYI
LADINSDLISLYNIVKMRTDEYVQAARELFVPETNCAEVYYQFREEFNKS
QDPFRRAVLFLYLNRYGYNGLCRYNLRGEFNVPFGAYKKPYFPEAELYHF
AEKAQNAFFYCESYADSMARADDASVVYCDPPYAPLSATANFTAYHTNSF
TLEQQAHLAEIAEGLVERHIPVLISNHDTMLTREWYQRAKLHVVKVRRSI
SSNGGTRKKVDELLALYKPGVVSPAKK.

The protein sequence encoding a R116A Dam mutant enzyme is:

(SEQ ID NO: 17)
KKNRAFLKWAGGKYPLLDDIKRHLPKGECLVEPFVGAGSVFLNTDFSRYI
LADINSDLISLYNIVKMRTDEYVQAARELFVPETNCAEVYYQFREEFNKS
QDPFRRAVLFLYLNAYGYNGLCRYNLRGEFNVPFGRYKKPYFPEAELYHF
AEKAQNAFFYCESYADSMARADDASVVYCDPPYAPLSATANFTAYHTNSF
TLEQQAHLAEIAEGLVERHIPVLISNHDTMLTREWYQRAKLHVVKVRRSI
SSNGGTRKKVDELLALYKPGVVSPAKK.

The protein sequence encoding a R95A Dam mutant enzyme is:

(SEQ ID NO: 18)
KKNRAFLKWAGGKYPLLDDIKRHLPKGECLVEPFVGAGSVFLNTDFSRYI
LADINSDLISLYNIVKMRTDEYVQAARELFVPETNCAEVYYQFAEEFNKS
QDPFRRAVLFLYLNRYGYNGLCRYNLRGEFNVPFGRYKKPYFPEAELYHF
AEKAQNAFFYCESYADSMARADDASVVYCDPPYAPLSATANFTAYHTNSF
TLEQQAHLAEIAEGLVERHIPVLISNHDTMLTREWYQRAKLHVVKVRRSI
SSNGGTRKKVDELLALYKPGVVSPAKK.

The protein sequence encoding a N126A Dam mutant enzyme is:

(SEQ ID NO: 19)
KKNRAFLKWAGGKYPLLDDIKRHLPKGECLVEPFVGAGSVFLNTDFSRYI
LADINSDLISLYNIVKMRTDEYVQAARELFVPETNCAEVYYQFREEFNKS
QDPFRRAVLFLYLNRYGYNGLCRYALRGEFNVPFGRYKKPYFPEAELYHF
AEKAQNAFFYCESYADSMARADDASVVYCDPPYAPLSATANFTAYHTNSF
TLEQQAHLAEIAEGLVERHIPVLISNHDTMLTREWYQRAKLHVVKVRRSI
SSNGGTRKKVDELLALYKPGVVSPAKK.

The protein sequence encoding a N132A Dam mutant enzyme is:

(SEQ ID NO: 20)
KKNRAFLKWAGGKYPLLDDIKRHLPKGECLVEPFVGAGSVFLNTDFSRYI
LADINSDLISLYNIVKMRTDEYVQAARELFVPETNCAEVYYQFREEFNKS
QDPFRRAVLFLYLNRYGYNGLCRYNLRGEFAVPFGRYKKPYFPEAELYHF

The protein sequence encoding a N126S Dam mutant enzyme is:

(SEQ ID NO: 21)
KKNRAFLKWAGGKYPLLDDIKRHLPKGECLVEPFVGAGSVFLNTDFSRYI
LADINSDLISLYNIVKMRTDEYVQAARELFVPETNCAEVYYQFREEFNKS
QDPFRRAVLFLYLNRYGYNGLCRYSLRGEFNVPFGRYKKPYFPEAELYHF
AEKAQNAFFYCESYADSMARADDASVVYCDPPYAPLSATANFTAYHTNSF
TLEQQAHLAEIAEGLVERHIPVLISNHDTMLTREWYQRAKLHVVKVRRSI
SSNGGTRKKVDELLALYKPGVVSPAKK.

The protein sequence encoding a N132S Dam mutant enzyme is:

(SEQ ID NO: 22)
KKNRAFLKWAGGKYPLLDDIKRHLPKGECLVEPFVGAGSVFLNTDFSRYI
LADINSDLISLYNIVKMRTDEYVQAARELFVPETNCAEVYYQFREEFNKS
QDPFRRAVLFLYLNRYGYNGLCRYNLRGEFSVPFGRYKKPYFPEAELYHF
AEKAQNAFFYCESYADSMARADDASVVYCDPPYAPLSATANFTAYHTNSF
TLEQQAHLAEIAEGLVERHIPVLISNHDTMLTREWYQRAKLHVVKVRRSI
SSNGGTRKKVDELLALYKPGVVSPAKK.

The Protein seauence encoding a R95A-N126A Dam mutant enzyme is:

(SEQ ID NO: 23)
KKNRAFLKWAGGKYPLLDDIKRHLPKGECLVEPFVGAGSVFLNTDFSRYI
LADINSDLISLYNIVKMRTDEYVQAARELFVPETNCAEVYYQFAEEFNKS
QDPFRRAVLFLYLNRYGYNGLCRYALRGEFNVPFGRYKKPYFPEAELYHF
AEKAQNAFFYCESYADSMARADDASVVCDPPYAPLSATANFTAYHTNSFT
LEQQAHLAEIAEGLVERHIPVLISNHDTMLTREWYQRAKLHVVKVRRSIS
NGGTRKKVDELLALYKPGVVSPAKK.

The protein sequence encoding a R95A-R116A Dam mutant enzyme is:

(SEQ ID NO: 24)
KKNRAFLKWAGGKYPLLDDIKRHLPKGECLVEPFVGAGSVFLNTDFSRYI
LADINSDLISLYNIVKMRTDEYVQAARELFVPETNCAEVYYQFAEEFNKS
QDPFRRAVLFLYLNAYGYNGLCRYNLRGEFNVPFGRYKKPYFPEAELYHF
AEKAQNAFFYCESYADSMARADDASVVYCDPPYAPLSATANFTAYHTNSF
TLEQQAHLAEIAEGLVERHIPVLISNHDTMLTREWYQRAKLHVVKVRRSI
SSNGGTRKKVDELLALYKPGVVSPAKK.

The protein sequence encoding a R95A-N132A Dam mutant enzyme is:

(SEQ ID NO: 25)
KKNRAFLKWAGGKYPLLDDIKRHLPKGECLVEPFVGAGSVFLNTDFSRYI
LADINSDLISLYNIVKMRTDEYVQAARELFVPETNCAEVYYQFAEEFNKS
QDPFRRAVLFLYLNRYGYNGLCRYNLRGEFAVPFGRYKKPYFPEAELYHF
AEKAQNAFFYCESYADSMARADDASVVYCDPPYAPLSATANFTAYHTNSF
TLEQQAHLAEIAEGLVERHIPVLISNHDTMLTREWYQRAKLHVVKVRRSI
SSNGGTRKKVDELLALYKPGVVSPAKK.

The protein sequence encoding a R95A-L122A Dam mutant enzyme is:

(SEQ ID NO: 26)
KKNRAFLKWAGGKYPLLDDIKRHLPKGECLVEPFVGAGSVFLNTDFSRYI
LADINSDLISLYNIVKMRTDEYVQAARELFVPETNCAEVYYQFAEEFNKS
QDPFRRAVLFLYLNRYGYNGACRYNLRGEFNVPFGRYKKPYFPEAELYHF
AEKAQNAFFYCESYADSMARADDASVVYCDPPYAPLSATANFTAYHTNSF
TLEQQAHLAEIAEGLVERHIPVLISNHDTMLTREWYQRAKLHVVKVRRSI
SSNGGTRKKVDELLALYKPGVVSPAKK.

The protein sequence encoding a R95A-Y119A Dam mutant enzyme is:

(SEQ ID NO: 27)
KKNRAFLKWAGGKYPLLDDIKRHLPKGECLVEPFVGAGSVFLNTDFSRYI
LADINSDLISLYNIVKMRTDEYVQAARELFVPETNCAEVYYQFAEEFNKS
QDPFRRAVLFLYLNRYGANGLCRYNLRGEFNVPFGRYKKPYFPEAELYHF
AEKAQNAFFYCESYADSMARADDASVVYCDPPYAPLSATANFTAYHTNSF
TLEQQAHLAEIAEGLVERHIPVLISNHDTMLTREWYQRAKLHVVKVRRSI
SSNGGTRKKVDELLALYKPGVVSPAKK.

The protein sequence encoding a L122A-R116A Dam mutant enzyme is:

(SEQ ID NO: 28)
KKNRAFLKWAGGKYPLLDDIKRHLPKGECLVEPFVGAGSVFLNTDFSRYI
LADINSDLISLYNIVKMRTDEYVQAARELFVPETNCAEVYYQFREEFNKS
QDPFRRAVLFLYLNAYGYNGACRYNLRGEFNVPFGRYKKPYFPEAELYHF
AEKAQNAFFYCESYADSMARADDASVVYCDPPYAPLSATANFTAYHTNSF
TLEQQAHLAEIAEGLVERHIPVLISNHDTMLTREWYQRAKLHVVKVRRSI
SSNGGTRKKVDELLALYKPGVVSPAKK.

The protein sequence encoding a L122A-N132A Dam mutant enzyme is:

(SEQ ID NO: 29)
KKNRAFLKWAGGKYPLLDDIKRHLPKGECLVEPFVGAGSVFLNTDFSRYI
LADINSDLISLYNIVKMRTDEYVQAARELFVPETNCAEVYYQFREEFNKS
QDPFRRAVLFLYLNRYGYNGACRYNLRGEFAVPFGRYKKPYFPEAELYHF

-continued

AEKAQNAFFYCESYADSMARADDASVVYCDPPYAPLSATANFTAYHTNSF
TLEQQAHLAEIAEGLVERHIPVLISNHDTMLTREWYQRAKLHVVKVRRSI
SSNGGTRKKVDELLALYKPGVVSPAKK.

The protein seauence encoding a R116A-N126A Dam mutant enzyme is:

(SEQ ID NO: 30)
KKNRAFLKWAGGKYPLLDDIKRHLPKGECLVEPFVGAGSVFLNTDFSRYI
LADINSDLISLYNIVKMRTDEYVQAARELFVPETNCAEVYYQFREEFNKS
QDPFRRAVLFLYLNAYGYNGLCRYALRGEFNVPFGRYKKPYFPEAELYHF
AEKAQNAFFYCESYADSMARADDASVVYCDPPYAPLSATANFTAYHTNSF
TLEQQAHLAEIAEGLVERHIPVLISNHDTMLTREWYQRAKLHVVKVRRSI
SSNGGTRKKVDELLALYKPGVVSPAKK.

The protein sequence encoding a R116A-N132A Dam mutant enzyme is:

(SEQ ID NO: 31)
KKNRAFLKWAGGKYPLLDDIKRHLPKGECLVEPFVGAGSVFLNTDFSRYI
LADINSDLISLYNIVKMRTDEYVQAARELFVPETNCAEVYYQFREEFNKS
QDPFRRAVLFLYLNAYGYNGLCRYNLRGEFAVPFGRYKKPYFPEAELYHF
AEKAQNAFFYCESYADSMARADDASVVYCDPPYAPLSATANFTAYHTNSF
TLEQQAHLAEIAEGLVERHIPVLISNHDTMLTREWYQRAKLHVVKVRRSI
SSNGGTRKKVDELLALYKPGVVSPAKK.

The sequence of the "minCMV-NLS-ZF10-1-Dam (WT)" writer module or SEQ ID NOs: 32 and 94 are, where minCMV promoter (italicized)|Kozak (bold and italicized) |Nuclear Localization Sequence (underlined)|ZF (SEQ ID NO: 9, bold)|Dam (SEQ ID NO: 11, WT) (bold and underlined)|linker taggcgtgtacggtgggaggcctatataagcagagctcgtttagtgaacc
gtcagatcgcctggaACGCGTttaattaaGCC*gccacc*MFE<u>PKKKRKV</u>FE
GTASSRPGERPFQCRICMRNFSRRHGLDRHTRTHTGEKPFQCRICMRNFS
DHSSLKRHLRTHTGSQKPFQCRICMRNFSVRHNLTRHLRTHTGEKPFQCR
ICMRNFSDHSNLSRHLKTHTGSQKPFQCRICMRNFSQRSSLVRHLRTHTG
EKPFQCRICMRNFSESGHLKRHLRTHLRGSTCR<u>KKNRAFLKWAGGKYPLL</u>
<u>DDIKRHLPKGECLVEPFVGAGSVFLNTDFSRYILADINSDLISLYNIVKM</u>
<u>RTDEYVQAARELFVPETNCAEVYYQFREEFNKSQDPFRRAVLFLYLNRYG</u>
<u>YNGLCRYNLRGEFNVPFGRYKKPYFPEAELYHFAEKAQNAFFYCESYADS</u>
<u>MARADDASVVYCDPPYAPLSATANFTAYHTNSFTLEQQAHLAEIAEGLVE</u>
<u>RHIPVLISNHDTMLTREWYQRAKLHVVKVRRSISSNGGTRKKVDELLALY</u>
<u>KPGVVSPAKK</u>*

The sequence of the "minCMV-NLS-ZF10-1-Dam (N132A)" writer module or SEQ ID NOs: 33 and 46 are, where minCMV promoter (italicized)|Kozak (bold and italicized)|Nuclear Localization Sequence (underlined)|ZF (SEQ ID NO: 9, bold)|Dam (N132A) (bold and underlined) linker taggcgtgtacggtgggaggcctatataagcagagctcgtttagtgaacc
gtcagatcgcctggaACGCGTttaattaaGCC*gccacc*MFE<u>PKKKRKV</u>FE
GTASSRPGERPFQCRICMRNFSRRHGLDRHTRTHTGEKPFQCRICMRNFS
DHSSLKRHLRTHTGSQKPFQCRICMRNFSVRHNLTRHLRTHTGEKPFQCR
ICMRNFSDHSNLSRHLKTHTGSQKPFQCRICMRNFSQRSSLVRHLRTHTG
EKPFQCRICMRNFSESGHLKRHLRTHLRGSTCR<u>KKNRAFLKWAGGKYPLL</u>
<u>DDIKRHLPKGECLVEPFVGAGSVFLNTDFSRYILADINSDLISLYNIVKM</u>
<u>RTDEYVQAARELFVPETNCAEVYYQFREEFNKSQDPFRRAVLFLYLNRYG</u>
<u>YNGLCRYNLRGEFAVPFGRYKKPYFPEAELYHFAEKAQNAFFYCESYADS</u>
<u>MARADDASVVYCDPPYAPLSATANFTAYHTNSFTLEQQAHLAEIAEGLVE</u>
<u>RHIPVLISNHDTMLTREWYQRAKLHVVKVRRSISSNGGTRKKVDELLALY</u>
<u>KPGVVSPAKK</u>*

The sequence of the "minCMV-dcas9-NLS-Dam (N132A)" writer module or SEQ ID NOs: 34 and 47 are, where minCMV promoter (italicized)|Kozak (bold and italicized)|NLS 3× FLAG (underlined)|dCas9 (SEQ ID NO: 10, bold)|Dam (N132A) (bold and underlined)|linker taggcgtgtacggtgggaggcctatataagcagagctcgtttagtgaacc
gtcagatcgcctggaACGCGTttaattaa*gccacc*MDKKYSIGLAIGTNS
VGWAVITDEYKVPSKKFKVLGNTDRHSIKKNLIGALLFDSGETAEATRLK
RTARRRYTRRKNRICYLQEIFSNEMAKVDDSFFHRLEESFLVEEDKKHER
HPIFGNIVDEVAYHEKYPTIYHLRKKLVDSTDKADLRLIYLALAHMIKFR
GHFLIEGDLNPDNSDVDKLFIQLVQTYNQLFEENPINASGVDAKAILSAR
LSKSRRLENLIAQLPGEKKNGLFGNLIALSLGLTPNFKSNFDLAEDAKLQ
LSKDTYDDDLDNLLAQIGDQYADLFLAAKNLSDAILLSDILRVNTEITKA
PLSASMIKRYDEHHQDLTLLKALVRQQLPEKYKEIFFDQSKNGYAGYIDG
GASQEEFYKFIKPILEKMDGTEELLVKLNREDLLRKQRTFDNGSIPHQIH
LGELHAILRRQEDFYPFLKDNREKIEKILTFRIPYYVGPLARGNSRFAWM
TRKSEETITPWNFEEVVDKGASAQSFIERMTNFDKNLPNEKVLPKHSLLY
EYFTVYNELTKVKYVTEGMRKPAFLSGEQKKAIVDLLFKTNRKVTVKQLK
EDYFKKIECFDSVEISGVEDRFNASLGTYHDLLKIIKDKDFLDNEENEDI
LEDIVLTLTLFEDREMIEERLKTYAHLFDDKVMKQLKRRRYTGWGRLSRK
LINGIRDKQSGKTILDFLKSDGFANRNFMQLIHDDSLTFKEDIQKAQVSG
QGDSLHEHIANLAGSPAIKKGILQTVKVVDELVKVMGRHKPENIVIEMAR
ENQTTQKGQKNSRERMKRIEEGIKELGSQILKEHPVENTQLQNEKLYLYY
LQNGRDMYVDQELDINRLSDYDVDAIVPQSFLKDDSIDNKVLTRSDKNRG
KSDNVPSEEVVKKMKNYWRQLLNAKLITQRKFDNLTKAERGGLSELDKAG
FIKRQLVETRQITKHVAQILDSRMNTKYDENDKLIREVKVITLKSKLVSD
FRKDFQFYKVREINNYHHAHDAYLNAVVGTALIKKYPKLESEFVYGDYKV -continued
```
YDVRKMIAKSEQEIGKATAKYFFYSNIMNFFKTEITLANGEIRKRPLIET

NGETGEIVWDKGRDFATVRKVLSMPQVNIVKKTEVQTGGFSKESILPKRN

SDKLIARKKDWDPKKYGGFDSPTVAYSVLVVAKVEKGKSKKLKSVKELLG

ITIMERSSFEKNPIDFLEAKGYKEVKKDLIIKLPKYSLFELENGRKRMLA

SAGELQKGNELALPSKYVNFLYLASHYEKLKGSPEDNEQKQLFVEQHKHY

LDEIIEQISEFSKRVILADANLDKVLSAYNKHRDKPIREQAENIIHLFTL

TNLGAPAAFKYFDTTIDRKRYTSTKEVLDATLIHQSITGLYETRIDLSQL

GGDGSPKKKRKVSSDYKDHDGDYKDHDIDYKDDDDKAAGGGGSGGELSSG

NSNANSRGPSFSSGLVPLSLRGSHACRKKNRAFLKWAGGKYPLLDDIKRH

LPKGECLVEPFVGAGSVFLNTDFSRYILADINSDLISLYNIVKMRTDEYV

QAARELFVPETNCAEVYYQFREEFNKSQDPFRRAVLFLYLNRYGYNGLCR

YNLRGEFAVPFGRYKKPYFPEAELYHFAEKAQNAFFYCESYADSMARADD

ASVVYCDPPYAPLSATANFTAYHTNSFTLEQQAHLAEIAEGLVERHIPVL

ISNHDTMLTREWYQRAKLHVVKVRRSISSNGGTRKKVDELLALYKPGVVS

PAKK*
```

The sequence of the "U6 promoter-gRNA" target sequence module or SEQ ID NOs: 35 and 45 are, where U6 promoter (italicized)|gRNA (underlined)|target sequence (bold)|linker

```
tgtacaaaaaagcaggctttaaaggaaccaattcagtcgactggatccgg taccaaggtcgggcaggaagagggcctatttcccatgattccttcatatt tgcatatacgatacaaggctgttagagagataattagaattaatttgact gtaaacacaaagatattagtacaaaatacgtgacgtagaaagtaataatt tcttgggtagtttgcagttttaaaattatgttttaaaatggactatcata tgcttaccgtaacttgaaagtatttcgatttcttggctttatatatcttg tggaaaggacgaaacaccgg[TARGET sequence]

gttttagagctagaaatagcaagttaaaataaggctagtccgttatcaac ttgaaaaagtggcaccgagtcggtgcttttttt
```

Exemplary target sequences used in the modules described herein include: gRNA3: acgcgcgacatcggctacgc (SEQ ID NO: 36) and gRNA10: cggctagccgatgtcgcgct (SEQ ID NO: 37).

In addition to constitutively expressed Writer protein modules, inducible Writer modules using protein domains from the plant abscisic acid (ABA) stress response pathway were also developed. The Writer modules were split into DBD and Dam protein halves, and the subcellular localization of these halves was controlled using the chemically induced proximity (CIP) partners, PYL1 and ABI1, which dimerize in the presence of ABA. Specifically, ZF proteins were fused to ABI1, and Dam (N132A) to PYL1. Additionally, to minimize the basal activity of Dam (N132A), it was ensured that it was localized to the cytoplasm in the absence of ABA by 1) not fusing a nuclear localization signal to Dam or 2) fusing a nuclear export signal to Dam.

Accordingly, the sequence of the "minCMV-NLS-ABI1-ZF10-1-NLS-<P2A>-Dam (N132A)-PYL1" writer module or SEQ ID NOs: 38 and 48 are, where minCMV promoter (italicized)|Kozak (bold and italicized)|Nuclear Localization Sequence (underlined)|ABI1 (bold)|ZF (bold and underlined)|P2A (italicized and underlined)|Dam (N132A) (bold, italicized, and underlined)|linker|PYL1 (double underline):

```
taggcgtgtacggtgggaggcctatataagcagagctcgtttagtgaacc gtcagatcgcctggaACGCGTttaattaaGCCgccaccMFEPKKKRKVFE

TSVPLYGFTSICGRRPEMEAAVSTIPRFLQSSSGSMLDGRFDPQSAAHFF

GVYDGHGGSQVANYCRERMHLALAEEIAKEKPMLCDGDTWLEKWKKALFN

SFLRVDSEIESVAPETVGSTSVVAVVFPSHIFVANCGDSRAVLCRGKTAL

PLSVDHKPDREDEAARIEAAGGKVIQWNGARVFGVLAMSRSIGDRYLKPS

IIPDPEVTAVKRVKEDDCLILASDGVWDVMTDEEACEMARKRILLWHKKN

AVAGDASLLADERRKEGKDPAAMSAAEYLSKLAIQRGSKDNISVVVVDLK

GGSGGSRPGERPFQCRICMRNFSRRHGLDRHTRTHTGEKPFQCRICMRNF

SDHSSLKRHLRTHTGSQKPFQCRICMRNFSVRHNLTRHLRTHTGEKPFQC

RICMRNFSDHSNLSRHLKTHTGSQKPFQCRICMRNFSQRSSLVRHLRTHT

GEKPFQCRICMRNFSESGHLKRHLRTHLRGSPKKKRKVTCRGSGATNFSL

LKQAGDVEENPGPGHHKKNRAFLKWAGGKYPLLDDIKRHL

PKGECLVEPFVGAGSVFLNTDFSRYILADINSDLISLYNIVKMRTD
EYVQAARELFVPETNCAEVY

YQFREEFNKSQDPFRRAVLFLYINRYGYNGLCRYNLRGEFAVPF
GRYKKPYFPEAELYHFAEKA

QNAFFYCESYADSMARADDASVVYCDPPYAPLSATANFTAYHTN
SFTLEQQAHLAEIAEGLVER

HIPVLISNHDTMLTREWYQRAKLHVVKVRRSISSNGGTRKKVDEL
LALYKPGVVSPAKK

GGGSGQLTQDEFTQLSQSIAEFHTYQLGNGRCSSLLAQRIHAPPETVWSV

VRRFDRPQIYKHFIKSCNVSEDFEMRVGCTRDVNVISGLPANTSRERLDL

LDDDRRVTGFSITGGEHRLRNYKSVTTVHRFEKEEEEERIWTVVLESYVV

DVPEGNSEEDTRLFADTVIRLNLQKLASITEAMN*
```

The sequence of the "minCMV-NLS-ABI1-ZF10-1-<P2A>-Dam (N132A)-PYL1-NES" writer module or SEQ ID NOs: 39 and 49 are, where minCMV promoter (italicized)|Kozak (bold and italicized)|Nuclear Localization Sequence (underlined)|ABI1 (bold)|ZF (bold and underlined) P2A (italicized and underlined)|Dam (N132A) (bold, italicized, and underlined)|linker|PYL1 (double underline) |Nuclear Export Signal (grey shading):

```
taggcgtgtacggtgggaggcctatataagcagagctcgtttagtgaaccgtcagatcgcctggaACGCGTttaattaaGCCgccacc

MFEPKKKRKVFETSVPLYGFTSICGRRPEMEAAVSTIPRFLQSSSGSMLDGRFDPQSAAHFFG

VYDGHGGSQVANYCRERMHLALAEEIAKEKPMLCDGDTWLEKWKKALFNSFLRVDSEIE

SVAPETVGSTSVVAVVFPSHIFVANCGDSRAVLCRGKTALPLSVDHKPDREDEAARIEAAGG
```

-continued

KVIQWNGARVFGVLAMSRSIGDRYLKPSIIPDPEVTAVKRVKEDDCLILASDGVWDVMTDE

EACEMARKRILLWHKKNAVAGDASLLADERRKEGKDPAAMSAAEYLSKLAIQRGSKDNIS

VVVVDLKGGSGGSRPGERPFOCRICMRNFSRRHGLDRHTRTHTGEKPFOCRICMRNFSDHS

SLKRHLRTHTGSOKPFOCRICMRNFSVRHNLTRHLRTHTGEKPFOCRICMRNFSDHSNLSR

HLKTHTGSOKPFOCRICMRNFSORSSLVRHLRTHTGEKPFOCRICMRNFSESGHLKRHLRT

HLRGSPKKKRKVTCR*GSGATNFSLLKQAGDVEENPGPGHH*KKNRAFLKWAGGKYPLLDDIKRHL*

*PKGECLVEPFVGAGSVFLNTDFSRYILADINSDLISLYNIVKMRTDEYVQAARELFVPETNCAEVY*

*YQFREEFNKSQDPFRRAVLFLYLNRYGYNGLCRYNLRGEFAVPFGRYKKPYFPEAELYHFAEKA*

*QNAFFYCESYADSMARADDASVVYCDPPYAPLSATANFTAYHTNSFTLEQQAHLAEIAEGLVER*

*HIPVLISNHDTMLTREWYQRAKLHVVKVRRSISSNGGTRKKVDELLALYKPGVVSPAKKGGGSG*

QL*TQDEFTQLSQSIAEFHTYQLGNGRCSSLLAQRIHAPPETVWSVVRRFDRPQIYKHFIKSCNVSE*

*DFEMRVGCTRDVNVISGLPANTSRERLDLLDDDRRVTGFSITGGEHRLRNYKSVTTVHRFEKEEE*

*EERIWTVVLESYVVDVPEGNSEEDTRLFADTVIRLNLQKLASITEAMN*CLNIQQQLGQITLENLQ

ME*

Reader-Effector or Synthetic Readout Modules

Also provided herein are engineered reader-effector modules, also referred to herein as synthetic readout modules, and constructs encoding the same. Embodiments of reader-effector fusion protein modules were designed and engineered by fusing the methyl-adenine binding domain of the DpnI endonuclease to transcriptional effector domains (e.g., transcriptionally activating or repressive domains). Specifically, in some embodiments, a C-terminal fragment (aa146-254) of DpnI, which harbors a Gm6ATC-binding domain but not the endonuclease catalytic domain, was used. This domain has high affinity for fully-methylated GATC sequences, as opposed to unmethylated or hemimethylated GATC sequences (Kind et al., Cell, 2013). A human codon optimized version of this DpnI truncation was fused to a variety of transcriptional effector domains, including, for example, 1) VP64 (activating), 2) KRAB (repressive), and 3) the HP1 alpha chromoshadow domain (repressive). These Reader-Effector proteins were expressed from the UBC promoter.

A variety of transcriptional effectors and domains thereof can be used in the reader-effector modules of the systems and methods described herein. Transcriptional effectors or regulators either activate or repress transcription from cognate, operably linked promoters. Transcriptional activators typically bind nearby to transcriptional promoters and recruit RNA polymerase to directly initiate transcription. Repressors bind to transcriptional promoters and either sterically hinder transcriptional initiation by RNA polymerase or recruit other repressor proteins and machinery that collectively function to establish a repressive chromatin state. Other transcriptional regulators serve as either an activator or a repressor depending on where they bind and cellular conditions. Transcriptional effectors for use with the systems and methods described herein include any transcriptional effector described herein or known to one of ordinary skill in the art. Examples of genes encoding transcriptional effectors that can be used with the systems and methods described herein include, without limitation, those effectors provided in U.S. Patent Application No. 2012/0003630, incorporated herein by reference.

An exemplary amino acid sequence encoding a methyl-adenine binding domain of the DpnI endonuclease fragment, but not the endonuclease catalytic domain, for use in the reader-effector fusion proteins described herein is: SQVPSKGRIFLVQDGQVRDPEKVTKEFKQGLFLRKS SLS SRGWTIEILNCIDKIEGSEFTLEDMYRF ESDLKNIFVKNNHIKEKIRQQLQILRDKEIIEFKGRG-KYRKL (SEQ ID NO: 40).

The sequence of the "UBC-NLS-DpnI DBD-VP64" reader-effector module or SEQ ID NOs: 41 and 50 are, where UBC promoter (italicized)|Kozak (bold and italicized)|Nuclear Localization Sequence (underlined)|DpnI DBD (bold)|VP64 (bold and underlined)|linker:

```
gcgccgggttttggcgcctcccgcgggcgcccccctcctcacggcgagcg
ctgccacgtcagacgaagggcgcaggagcgttcctgatccttccgcccgg
acgctcaggacagcggcccgctgctcataagactcggccttagaacccca
gtatcagcagaaggacattttaggacgggacttgggtgactctagggcac
tggttttctttccagagagcggaacaggcgaggaaaagtagtcccttctc
ggcgattctgcggagggatctccgtgggcggtgaacgccgatgattata
taaggacgcgccgggtgtggcacagctagttccgtcgcagccgggatttg
ggtcgcggttcttgtttgtggatcgctgtgatcgtcacttggtgagttgc
gggctgctgggctggccggggctttcgtggccgccgggccgctcggtggg
acgaagcgtgtggagagaccgccaagggctgtagtctgggtccgcgagc
aaggttgccctgaactgggggttgggggagcgcacaaaatggcggctgt
tcccgagtcttgaatggaagacgcttgtaaggcgggctgtgaggtcgttg
aaacaaggtgggggcatggtgggcggcaagaacccaaggtcttgaggcc
```

-continued
```
ttcgctaatgcgggaaagctcttattcgggtgagatgggctggggcacca
tctgggaccctgacgtgaagtttgtcactgactggagaactcggtttg
tcgtctggttgcgggggcggcagttatgcggtgccgttgggcagtgcacc
cgtacctttgggagcgcgcgcctcgtcgtgtcgtgacgtcacccgttctg
ttggcttataatgcagggtggggccacctgccggtaggtgtgcggtaggc
ttttctccgtcgcaggacgcagggttcgggcctagggtaggctctcctga
atcgacaggcgccggacctctggtgaggggagggataagtgaggcgtcag
tttctttggtcggttttatgtacctatcttcttaagtagctgaagctccg
gttttgaactatgcgctcggggttggcgagtgtgttttgtgaagttttt
aggcacctttgaaatgtaatcatttgggtcaatatgtaattttcagtgt
tagactagtaaagcttctgcaggtcgactctagaaaattgtccgctaaat
tctggccgttttggcttttttgttagacaggatccccgggtaccgt
gccacc
MVNPKKKRKVVNLESQVPSKGRIFLVQDGQVRDPEKVTKEFKQGLF
LRKSSLSSRGWTIEILNCIDKIEGSEFTLEDMYRFESDLKNIFVKNNHIK
EKIRQQLQILRDKEHEFKGRGKYRKLFEGGGGSGRADALDDFDLDMLGSD
ALDDFDLDMLGSDALDDFDLDMLGSDALDDFDLDML*
```

The sequence of the "UBC-KRAB-NLS-DpnI DBD-VP64" reader-effector module or SEQ ID NOs: 42 and 51 are, where UBC promoter (italicized)|Kozak (bold and italicized)|Nuclear Localization Sequence (underlined)|DpnI DBD (bold)|KRAB domain (bold and underlined)|linker:

```
gcgccgggttttggcgcctcccgcgggcgccccctcctcacggcgagcg
ctgccacgtcagacgaagggcgcagcgagcgtcctgatccttccgcccgg
acgctcaggacagcggcccgctgctcataagactcggccttagaaccca
gtatcagcagaaggacatttaggacgggacttgggtgactctagggcac
tggttttctttccagagagcggaacaggcgaggaaaagtagtcccttctc
ggcgattctgcggagggatctccgtgggcggtgaacgccgatgattata
taaggacgcgccgggtgtggcacagctagttccgtcgcagccgggatttg
ggtcgcggttcttgtttgtggatcgctgtgatcgtcacttggtgagtagc
gggctgctgggctggccgggctttcgtggccgccgggccgctcggtggg
acggaagcgtgtggagagaccgccaagggctgtagtctgggtccgcgagc
aaggttgccctgaactgggggttgggggagcgcacaaaatggcggctgt
tcccgagtcttgaatggaagacgcttgtaaggcgggctgtgaggtcgttg
aaacaaggtgggggcatggtgggcggcaagaacccaaggtcttgaggcc
ttcgctaatgcgggaaagctcttattcgggtgagatgggctggggcacca
tctgggaccctgacgtgaagtttgtcactgactggagaactcggtttgt
cgtctgttgcgggggcggcagttatgcggtgccgttgggcagtgcaccc
gtacctttgggagcgcgcgcctcgtcgtgtcgtgacgtcacccgttct
gttggcttataatgcagggtggggccacctgccggtaggtgtgcggtagg
cttttctccgtcgcaggacgcagggttcgggcctagggtaggctctcctg
aatcgacaggcgccggacctctggtgaggggagggataagtgaggcgtca
```

-continued
```
gttctttggtcggttttatgtacctatcttcttaagtagctgaagctcc
ggttttgaactatgcgctcggggttggcgagtgtgttttgtgaagttttt
taggcacctttgaaatgtaatcatttgggtcaatatgtaattttcagtg
ttagactagtaaattgtccgctaaattctggccgttttggcttttttgt
tagacACGCGTttaattaaGCCgccaccMDAKSLTAWSRTLVTFKDVFVD
FTREEWKLLDTAQQILYRNVMLENYKNLVSLGYQLTKPDVILRLEKGEEP
WLVEREIHQETHPDSETAFEIKSSVPKKKRKVLEGGGGSGTCRSQVPSKG
RIFLVQDGQVRDPEKVTKEFKQGLFLRKSSLSSRGWTIEILNCIDKIEGS
EFTLEDMYRFESDLKNIFVKNNHIKEKIRQQLQILRDKEIIEFKGRGKYR
KL*
```

The sequence of the "UBC-HP1alpha-NLS-DpnI DBD" reader-effector module or SEQ ID NOs: 43 and 52 are, where UBC promoter (italicized)|Kozak (bold and italicized)|Nuclear Localization Sequence (underlined)|DpnI DBD (bold)|HP1 alpha cs domain (bold and underlined)|linker:

```
gcgccgggttttggcgcctcccgcgggcgccccctcctcacggcgagcg
ctgccacgtcagacgaagggcgcagcgagcgtcctgatccttccgcccgg
acgctcaggacagcggcccgctgctcataagactcggccttagaaccca
gtatcagcagaaggacatttaggacgggacttgggtgactctagggcac
tggttttctttccagagagcggaacaggcgaggaaaagtagtcccttctc
ggcgattctgcggagggatctccgtgggcggtgaacgccgatgattata
taaggacgcgccgggtgtggcacagctagttccgtcgcagccgggatttg
ggtcgcggttcttgtttgtggatcgctgtgatcgtcacttggtgagtagc
gggctgctgggctggccgggctttcgtggccgccgggccgctcggtggg
acggaagcgtgtggagagaccgccaagggctgtagtctgggtccgcgagc
aaggttgccctgaactgggggttgggggagcgcacaaaatggcggctgt
tcccgagtcttgaatggaagacgcttgtaaggcgggctgtgaggtcgttg
aaacaaggtgggggcatggtgggcggcaagaacccaaggtcttgaggcc
ttcgctaatgcgggaaagctcttattcgggtgagatgggctggggcacca
tctgggaccctgacgtgaagtttgtcactgactggagaactcggtttgt
cgtctgttgcgggggcggcagttatgcggtgccgttgggcagtgcaccc
gtacctttgggagcgcgcgcctcgtcgtgtcgtgacgtcacccgttctg
ttggcttataatgcagggtggggccacctgccggtaggtgtgcggtaggc
ttttctccgtcgcaggacgcagggttcgggcctagggtaggctctcctga
atcgacaggcgccggacctctggtgaggggagggataagtgaggcgtcag
tttctttggtcggttttatgtacctatcttcttaagtagctgaagctccg
gttttgaactatgcgctcggggttggcgagtgtgttttgtgaagttttt
aggcacctttgaaatgtaatcatttgggtcaatatgtaattttcagtgt
tagactagtaaattgtccgctaaattctggccgttttggcttttttgtt
agacACGCGTttaattaaGCCgccaccKKREQSNDIARGFERGLEPEKII
GATDSCGDLMFLMKWKDTDEADLVLAKEANVKCPQIVIAFYEERLTWHAY
```

-continued

PEDAENKEKASPKKKRKVLEGGGGSGTCRSQVPSKGRIFLVQDGQVRDPE

KVTKEFKQGLFLRKSSLSSRGWTIEILNCIDKIEGSEFTLEDMYRFESDL

KNIFVKNNHIKEKIRQQLQILRDKEIIEFKGRGKYRKL*

Reader-Writer or Synthetic Read-Write Modules

Also provided herein are engineered reader-writer modules, also referred to herein as synthetic read-write modules, and constructs encoding the same. Embodiments of reader-writer fusion protein modules were designed and engineered by fusing the DpnI methyl-adenine binding domain and mutant Dam proteins. These synthetic reader-writer proteins are capable of recognizing/binding methylated GATC sequences and, in turn, catalyzing adenine methylation at adenines on adjacent/nearby GATC sequences to propagate and sustain the chemical modifications for use in the engineered DNA methylation systems described herein.

Exemplary mutant Dam enzymes for use in the reader-writer fusion proteins include any of the sequences provided herein as SEQ ID NOs: 12-31. An exemplary DpnI methyl-adenine binding domain is provided herein as SEQ ID NO: 40.

The sequence of the "UBC-DpnI DBD-Dam (R95A)" reader-writer module or SEQ ID NOs: 44 and 53 are, where UBC promoter (italicized)|Kozak (bold and italicized) |Nuclear Localization Sequence (underlined)|DpnI DBD (bold)|Dam (R95A) (bold and underlined)|linker:

*gcgccgggttttggcgcctcccgcgggcgccccctcctcacggcgagcg*

*ctgccacgtcagacgaagggcgcagcgagcgtcctgatccttccgcccgg*

*acgctcaggacagcggcccgctgctcataagactcggccttagaacccca*

*gtatcagcagaaggacattttaggacgggacttgggtgactctagggcac*

*tggattttctttccagagagcggaacaggcgaggaaaagtagtcccttct*

*cggcgattctgcggagggatctccgtggggcggtgaacgccgatgattat*

*ataaggacgcgccgggtgtggcacagctagttccgtcgcagccgggattt*

*gggtcgcggttcagtttgtggatcgctgtgatcgtcacttggtgagtagc*

*gggctgctgggctggccggggctttcgtggccgccgggccgctcggtggg*

*acggaagcgtgtggagagaccgccaagggctgtagtctgggtccgcgagc*

*aaggagccctgaactgggggttggggggagcgcacaaaatggcggctgtt*

*cccgagtcttgaatggaagacgcttgtaaggcgggctgtgaggtcgttga*

*aacaaggtgggggcatggtgggcggcaagaacccaaggtcttgaggcct*

*tcgctaatgcgggaaagctcttattcgggtgagatgggctggggcaccat*

*ctggggaccctgacgtgaagtttgtcactgactggagaactcggtttgtc*

*gtctgttgcgggggcggcagttatggcggtgccgttgggcagtgcacccg*

*taccatgggagcgcgcccctcgtcgtgtcgtgacgtcacccgttctgtt*

*ggcttataatgcagggtggggccacctgccggtaggtgtgcggtaggctt*

*ttctccgtcgcaggacgcagggttcgggcctagggtaggctctcctgaat*

*cgacaggcgccggacctctggtgaggggagggataagtgaggcgtcagtt*

*tctttggtcggttttatgtacctatcttcttaagtagctgaagctccggt*

*tttgaactatgcgctcggggttggcgagtgtgttttgtgaagttttttag*

-continued

*gcaccttttgaaatgtaatcatttgggtcaatatgtaattttcagtgtta*

*gactagtaaattgtccgctaaattctggccgttttggcttttttgttag* acACGCGTttaattaaGCC*gccacc*MFE<u>PKKKRKV</u>FEGTASSQVPSKGRI

FLVQDGQVRDPEKVTKEFKQGLFLRKSSLSSRGWTIEILNCIDKIEGSEF

TLEDMYRFESDLKNIFVKNNHIKEKIRQQLQILRDKEHEFKGRGKYRKLT

CR<u>KKNRAFLKWAGGKYPLLDDIKRHLPKGECLVEPFVGAGSVFLNTDFSR</u>

<u>YILADINSDLISLYNIVKMRTDEYVQAARELFVPETNCAEVYYQFAEEFN</u>

<u>KSQDPFRRAVLFLYLNRYGYNGLCRYNLRGEFNVPFGRYKKPYFPEAELY</u>

<u>HFAEKAQNAFFYCESYADSMARADDASVVYCDPPYAPLSATANFTAYHTN</u>

<u>SFTLEQQAHLAEIAEGLVERHIPVLISNHDTMLTREWYQRAKLHVVKVRR</u>

<u>SISSNGGTRKKVDELLALYKPGVVSPAKK</u>*

Component Parts for Use with the Modules and Engineered DNA Methylation Systems

Promoters and promoter sequences are required for use of the various modules and components of the engineered DNA methylation systems described herein. The term "promoter," as used herein, refers to any nucleic acid sequence that regulates the expression of another nucleic acid sequence by driving transcription of the nucleic acid sequence, which can be a heterologous target gene encoding a protein or an RNA. Promoters can be constitutive, inducible, repressible, tissue-specific, or any combination thereof. A promoter is a control region of a nucleic acid sequence at which initiation and rate of transcription of the remainder of a nucleic acid sequence are controlled. A promoter can also contain genetic elements at which regulatory proteins and molecules can bind, such as RNA polymerase and other transcription factors. In some embodiments of the aspects, a promoter can drive the expression of a transcription factor that regulates the expression of the promoter itself, or that of another promoter used in another modular component of an engineered DNA methylation systemdescribed herein.

A promoter can be said to drive expression or drive transcription of the nucleic acid sequence that it regulates. The phrases "operably linked," "operatively positioned," "operatively linked," "under control," and "under transcriptional control" indicate that a promoter is in a correct functional location and/or orientation in relation to a nucleic acid sequence it regulates to control transcriptional initiation and/or expression of that sequence. An "inverted promoter," as used herein, refers to a promoter in which the nucleic acid sequence is in the reverse orientation, such that what was the coding strand is now the non-coding strand, and vice versa. Inverted promoter sequences can be used in various embodiments of the invention to regulate the state of a module or a system described herein. In addition, in various embodiments of the invention, a promoter can be used in conjunction with an "enhancer," which refers to a cis-acting regulatory sequence involved in the transcriptional activation of a nucleic acid sequence downstream of the promoter. The enhancer can be located at any functional location before or after the promoter, and/or the encoded nucleic acid.

A promoter can be one naturally associated with a gene or sequence, as can be obtained by isolating the 5' non-coding sequences located upstream of the coding segment and/or exon of a given gene or sequence. Such a promoter can be referred to as "endogenous." Similarly, in some embodiments, an enhancer can be one naturally associated with a nucleic acid sequence, located either downstream or upstream of that sequence.

Alternatively, certain advantages are gained by positioning a coding nucleic acid segment under the control of a "recombinant promoter" or "heterologous promoter," which refer to a promoter that is not normally associated with the encoded nucleic acid sequence it is operably linked to in its natural environment. A recombinant or heterologous enhancer refers to an enhancer not normally associated with a given nucleic acid sequence in its natural environment. Such promoters or enhancers can include promoters or enhancers of other genes; promoters or enhancers isolated from any other prokaryotic, viral, or eukaryotic cell; and synthetic promoters or enhancers that are not "naturally occurring," i.e., comprise different elements of different transcriptional regulatory regions, and/or mutations that alter expression through methods of genetic engineering that are known in the art. In addition to producing nucleic acid sequences of promoters and enhancers synthetically, promoter sequences can be produced using recombinant cloning and/or nucleic acid amplification technology, including PCR, in connection with the engineered DNA methylation systems and modules disclosed herein (see, e.g., U.S. Pat. No. 4,683,202, 5,928,906, each incorporated herein by reference). Furthermore, it is contemplated that control sequences that direct transcription and/or expression of sequences within non-nuclear organelles such as mitochondria, chloroplasts, and the like, can be employed as well.

As described herein, an "inducible promoter" is one that is characterized by initiating or enhancing transcriptional activity when in the presence of, influenced by, or contacted by an inducer or inducing agent. An "inducer" or "inducing agent," as defined herein, can be endogenous, or a normally exogenous compound or protein that is administered in such a way as to be active in inducing transcriptional activity from the inducible promoter. In some embodiments, the inducer or inducing agent, i.e., a chemical, a compound or a protein, can itself be the result of transcription or expression of a nucleic acid sequence (i.e., an inducer can be a transcriptional repressor protein expressed by another component or module), which itself can be under the control or an inducible promoter. In some embodiments, an inducible promoter is induced in the absence of certain agents, such as a repressor. Examples of inducible promoters include but are not limited to, tetracycline, metallothionine, ecdysone, mammalian viruses (e.g., the adenovirus late promoter; and the mouse mammary tumor virus long terminal repeat (MMTV-LTR)) and other steroid-responsive promoters, rapamycin responsive promoters and the like.

Inducible promoters useful in the engineered DNA methylation systems, and methods described herein are capable of functioning in both prokaryotic and eukaryotic host organisms. In some embodiments of the different aspects described herein, mammalian inducible promoters are included, although inducible promoters from other organisms, as well as synthetic promoters designed to function in a prokaryotic or eukaryotic host can be used. Exemplary environmental inducers include exposure to heat (i.e., thermal pulses or constant heat exposure), various steroidal compounds, divalent cations (including $Cu^{2-}$ and $Zn^{2+}$), galactose, tetracycline, IPTG (isopropyl-β-D thiogalactoside), as well as other naturally occurring and synthetic inducing agents and gratuitous inducers.

In some embodiments, the engineered DNA methylation systems and their component modules comprise suitable inducible promoters that can be dependent upon transcriptional activators that, in turn, are reliant upon an environmental inducer. In other embodiments, the inducible promoters can be repressed by a transcriptional repressor, which itself is rendered inactive by an environmental inducer, such as the product of a sequence driven by another promoter. Thus, unless specified otherwise, an inducible promoter can be one that is induced by an inducing agent that positively activates a transcriptional activator, or one which is derepressed by an inducing agent that negatively regulates a transcriptional repressor. In such embodiments of the various aspects described herein where it is required to distinguish between an activating and a repressing inducing agent, explicit distinction will be made.

Inducible promoters useful in the methods and systems described herein also include those that are repressed by "transcriptional repressors," which are subject to inactivation by the action of environmental, external agents, or the product of another gene. Such inducible promoters may also be termed "repressible promoters" where it is required to distinguish between other types of promoters in a given module or component of the engineered DNA methylation systems described herein. Examples include prokaryotic repressors molecules that can transcriptionally repress eukaryotic promoters that have been engineered to incorporate appropriate repressor-binding operator sequences. Preferred repressors for use in the modules and methods described herein are sensitive to inactivation by physiologically benign agent. Thus, where a lac repressor protein is used to control the expression of a promoter sequence that has been engineered to contain a lacO operator sequence, treatment of the host cell with IPTG will cause the dissociation of the lac repressor from the engineered promoter containing a lacO operator sequence and allow transcription to occur. Similarly, where a tet repressor is used to control the expression of a promoter sequence that has been engineered to contain a tetO operator sequence, treatment of the host cell with tetracycline will cause dissociation of the tet repressor from the engineered promoter and allow transcription of the sequence downstream of the engineered promoter to occur.

An inducible promoter useful in the methods and systems as described herein can be induced by one or more physiological conditions, such as changes in pH, temperature, radiation, osmotic pressure, saline gradients, cell surface binding, and the concentration of one or more extrinsic or intrinsic inducing agents. The extrinsic inducer or inducing agent can comprise amino acids and amino acid analogs, saccharides and polysaccharides, nucleic acids, protein transcriptional activators and repressors, cytokines, toxins, petroleum-based compounds, metal containing compounds, salts, ions, enzyme substrate analogs, hormones, and combinations thereof. In specific embodiments, the inducible promoter is activated or repressed in response to a change of an environmental condition, such as the change in concentration of a chemical, metal, temperature, radiation, nutrient or change in pH. Thus, an inducible promoter useful in the methods and systems as described herein can be a phage inducible promoter, nutrient inducible promoter, temperature inducible promoter, radiation inducible promoter, metal inducible promoter, hormone inducible promoter, steroid inducible promoter, and/or hybrids and combinations thereof.

The administration or removal of an inducer or repressor as described herein results in a switch between the "on" or "off" states of the transcription of the operably linked heterologous target gene. Thus, as defined herein, the "on" state of a promoter operably linked to a nucleic acid sequence, refers to the state when the promoter is actively driving transcription of the operably linked nucleic acid sequence, i.e., the linked nucleic acid sequence is expressed.

In some embodiments of the engineered DNA methylation systems described herein, ribosome binding sites (RBSs) can be added to one or more modules. RBSs are sequences that promote efficient and accurate translation of mRNAs for protein synthesis, and are also provided for use in the modules and engineered DNA methylation systems described herein to enable modulation of the efficiency and rates of synthesis of the proteins encoded by the engineered DNA methylation system. An RBS affects the translation rate of an open reading frame in two main ways—i) the rate at which ribosomes are recruited to the mRNA and initiate translation is dependent on the sequence of the RBS, and ii) the RBS can also affect the stability of the mRNA, thereby affecting the number of proteins made over the lifetime of the mRNA. Accordingly, one or more ribosome binding site (RBS) can be added to the modules and engineered DNA methylation systems described herein to control expression of proteins.

Thus, a "ribosome binding site" ("RBS"), as defined herein, is a segment of the 5' (upstream) part of an mRNA molecule that binds to the ribosome to position the message correctly for the initiation of translation. The RBS controls the accuracy and efficiency with which the translation of mRNA begins. In prokaryotes (such as $E.\ coli$) the RBS typically lies about 7 nucleotides upstream from the start codon (i.e., the first AUG). The sequence itself in general is called the "Shine-Dalgarno" sequence after its discoverers, regardless of the exact identity of the bases. Strong Shine-Dalgarno sequences are rich in purines (A's,G's), and the "Shine-Dalgarno consensus" sequence—derived statistically from lining up many well-characterized strong ribosome binding sites—has the sequence AGGAGG. The complementary sequence (CCUCCU) occurs at the 3'-end of the structural RNA ("16S") of the small ribosomal subunit and it base-pairs with the Shine-Dalgarno sequence in the mRNA to facilitate proper initiation of protein synthesis. In some embodiments of the aspects described herein, a ribosome binding site (RBS) is added to a modoule or engineered DNA methylation system to regulate expression of a component of interest.

For protein synthesis in eukaryotes and eukaryotic cells, the 5' end of the mRNA has a modified chemical structure ("cap") recognized by the ribosome, which then binds the mRNA and moves along it ("scans") until it finds the first AUG codon. A characteristic pattern of bases (called a "Kozak sequence") is sometimes found around that codon and assists in positioning the mRNA correctly in a manner reminiscent of the Shine-Dalgarno sequence, but does not involve base pairing with the ribosomal RNA.

RBSs can include only a portion of the Shine-Dalgarno sequence. When looking at the spacing between the RBS and the start codon, the aligned spacing rather than just the absolute spacing is important. In essence, if only a portion of the Shine-Dalgarno sequence is included in the RBS, the spacing that matters is between wherever the center of the full Shine-Dalgarno sequence would be and the start codon rather than between the included portion of the Shine-Dalgarno sequence and the start codon.

While the Shine-Dalgarno portion of the RBS is critical to the strength of the RBS, the sequence upstream of the Shine-Dalgarno sequence is also important. One of the ribosomal proteins, S1, is known to bind to adenine bases upstream from the Shine-Dalgarno sequence. As a result, in some embodiments of the modules and engineered DNA methylation systems described herein, an RBS can be made stronger by adding more adenines to the sequence upstream of the RBS. A promoter may add some bases onto the start of the mRNA that may affect the strength of the RBS by affecting S1 binding.

In addition, the degree of secondary structure can affect the translation initiation rate. This fact can be used to produce regulated translation initiation rates, as described in Isaacs F J et al., Nat Biotechnol 2004 July; 22(7) 841-7.

In addition to affecting the translation rate per unit time, an RBS can affect the level of protein synthesis in a second way. That is because the stability of the mRNA affects the steady state level of mRNA, i.e., a stable mRNA will have a higher steady state level than an unstable mRNA that is being produced as an identical rate. Since the primary sequence and the secondary structure of an RBS (for example, the RBS could introduce an RNase site) can affect the stability of the mRNA, the RBS can affect the amount of mRNA and hence the amount of protein that is synthesized.

A "regulated RBS" is an RBS for which the binding affinity of the RBS and the ribosome can be controlled, thereby changing the RBS strength. One strategy for regulating the strength of prokaryotic RBSs is to control the accessibility of the RBS to the ribosome. By occluding the RBS in RNA secondary structure, translation initiation can be significantly reduced. By contrast, by reducing secondary structure and revealing the RBS, translation initiation rate can be increased. Isaacs and coworkers engineered mRNA sequences with an upstream sequence partially complementary to the RBS. Base-pairing between the upstream sequence and the RBS 'locks' the RBS off. A 'key' RNA molecule that disrupts the mRNA secondary structure by preferentially base-pairing with the upstream sequence can be used to expose the RBS and increase translation initiation rate.

Terminators are sequences that usually occur at the end of a gene or operon and cause transcription to stop, and are also provided for use in the modules engineered DNA methylation systems described herein to regulate transcription and prevent transcription from occurring in an unregulated fashion, i.e., a terminator sequence prevents activation of downstream modules by upstream promoters. A "terminator" or "termination signal", as described herein, is comprised of the DNA sequences involved in specific termination of an RNA transcript by an RNA polymerase. Thus, in certain embodiments a terminator that ends the production of an RNA transcript is contemplated. A terminator can be necessary in vivo to achieve desirable message levels.

The most commonly used type of terminator is a forward terminator. When placed downstream of a nucleic acid sequence that is usually transcribed, a forward transcriptional terminator will cause transcription to abort. In some embodiments, bidirectional transcriptional terminators are provided. Such terminators will usually cause transcription to terminate on both the forward and reverse strand. Finally, in some embodiments, reverse transcriptional terminators are provided that terminate transcription on the reverse strand only.

In eukaryotic systems, the terminator region can also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in those embodiments involving eukaryotes, it is preferred that a terminator comprises a signal for the cleavage of the RNA, and it is more preferred that the terminator signal promotes polyadenylation of the message.

The terminator and/or polyadenylation site elements can serve to enhance message levels and/or to minimize read through between modules of the engineered DNA methylation systems. As disclosed herein, terminators contemplated for use in the modules, engineered DNA methylation systems, and methods of use thereof can include any known terminator of transcription described herein or known to one of ordinary skill in the art. Such terminators include, but are not limited to, the termination sequences of genes, such as for example, the bovine growth hormone terminator, or viral termination sequences, such as for example, the SV40 terminator. In certain embodiments, the termination signal encompasses a lack of transcribable or translatable sequence, such as due to a sequence truncation. The terminator used can be unidirectional or bidirectional.

In some embodiments of the aspects described herein, a nucleic sequence encoding a protein degradation tag can be added to the modules and engineered DNA methylation systems described herein to enhance protein degradation of a protein. As defined herein, a "degradation tag" is a genetic addition to the end of a nucleic acid sequence that modifies the protein that is expressed from that sequence, such that the protein undergoes faster degradation by cellular degradation mechanisms. Thus, such protein degradation tags 'mark' a protein for degradation, thus decreasing a protein's half-life.

One of the useful aspects of degradation tags is the ability to detect and regulate gene activity in a time-sensitive manner. Such protein degradation tags can operate through the use of protein-degrading enzymes, such as proteases, within the cell. In some embodiments, the tags encode for a sequence of about eleven amino acids at the C-terminus of a protein, wherein said sequence is normally generated in *E. coli* when a ribosome gets stuck on a broken ("truncated") mRNA. Without a normal termination codon, the ribosome can't detach from the defective mRNA. A special type of RNA known as ssrA ("small stable RNA A") or tmRNA ("transfer-messenger RNA") rescues the ribosome by adding the degradation tag followed by a stop codon. This allows the ribosome to break free and continue functioning The tagged, incomplete protein can get degraded by the proteases ClpXP or ClpAP. Although the initial discovery of the number of amino acids encoding for an ssRA/tmRNA tag was eleven, the efficacy of mutating the last three amino acids of that system has been tested. Thus, the tags AAV, ASV, LVA, and LAA are classified by only three amino acids.

In some embodiments, the protein degradation tag is an ssrA tag. In some embodiments, the protein degradation tag is an LAA variant. In some embodiments, the protein degradation tag is an AAV variant. In some embodiments, the protein degradation tag is an ASV variant.

The terms "nucleic acids" and "nucleotides" refer to naturally occurring or synthetic or artificial nucleic acid or nucleotides and any combinations thereof. The terms "nucleic acids" and "nucleotides" comprise deoxyribonucleotides or ribonucleotides or any nucleotide analogue and polymers or hybrids thereof in either single- or doublestranded, sense or antisense form. As will also be appreciated by those in the art, many variants of a nucleic acid can be used for the same purpose as a given nucleic acid. Thus, a nucleic acid also encompasses substantially identical nucleic acids and complements thereof. Nucleotide analogues include nucleotides having modifications in the chemical structure of the base, sugar and/or phosphate, including, but not limited to, 5-position pyrimidine modifications, 8-position purine modifications, modifications at cytosine exocyclic amines, substitution of 5-bromo-uracil, and the like; and 2'-position sugar modifications, including but not limited to, sugar-modified ribonucleotides in which the 2'-OH is replaced by a group selected from H, OR, R, halo, SH, SR, NH2, NHR, NR2, or CN. shRNAs also can comprise non-natural elements such as non-natural bases, e.g., ionosin and xanthine, nonnatural sugars, e.g., 2'-methoxy ribose, or non-natural phosphodiester linkages, e.g., methylphosphonates, phosphorothioates and peptides.

The term "nucleic acid sequence" or "oligonucleotide" or "polynucleotide" are used interchangeably herein and refers to at least two nucleotides covalently linked together. The term "nucleic acid sequence" is also used inter-changeably herein with "gene", "cDNA", and "mRNA". As will be appreciated by those in the art, the depiction of a single nucleic acid sequence also defines the sequence of the complementary nucleic acid sequence. Thus, a nucleic acid sequence also encompasses the complementary strand of a depicted single strand. Unless otherwise indicated, a particular nucleic acid sequence also implicitly encompasses conservatively modified variants thereof (e.g., degenerate codon substitutions) and complementary sequences, as well as the sequence explicitly indicated. As will also be appreciated by those in the art, a single nucleic acid sequence provides a probe that can hybridize to the target sequence under stringent hybridization conditions. Thus, a nucleic acid sequence also encompasses a probe that hybridizes under stringent hybridization conditions. The term "nucleic acid sequence" refers to a single or double-stranded polymer of deoxyribonucleotide or ribonucleotide bases read from the 5'- to the 3'-end. It includes chromosomal DNA, self-replicating plasmids, infectious polymers of DNA or RNA and DNA or RNA that performs a primarily structural role. "Nucleic acid sequence" also refers to a consecutive list of abbreviations, letters, characters or words, which represent nucleotides. Nucleic acid sequences can be single stranded or double stranded, or can contain portions of both double stranded and single stranded sequence. The nucleic acid sequence can be DNA, both genomic and cDNA, RNA, or a hybrid, where the nucleic acid sequence can contain combinations of deoxyribo- and ribo-nucleotides, and combinations of bases including uracil, adenine, thymine, cytosine, guanine, inosine, xanthine hypoxanthine, isocytosine and isoguanine. Nucleic acid sequences can be obtained by chemical synthesis methods or by recombinant methods. A nucleic acid sequence will generally contain phosphodiester bonds, although nucleic acid analogs can be included that can have at least one different linkage, e.g., phosphoramidate, phosphorothioate, phosphorodithioate, or O-methyl-phosphoroamidite linkages and peptide nucleic acid backbones and linkages in the nucleic acid sequence. Other analog nucleic acids include those with positive backbones; non-ionic backbones, and non-ribose backbones, including those described in U.S. Pat. Nos. 5,235,033 and 5,034,506, which are incorporated by reference. Nucleic acid sequences containing one or more non-naturally occurring or modified nucleotides are also included within one definition of nucleic acid sequences. The modified nucleotide analog can be located for example at the 5'-end and/or the 3'-end of the nucleic acid sequence. Representative examples of nucleotide analogs can be selected from sugar- or backbone-modified ribonucleotides. It should be noted, however, that also nucleobase-modified ribonucleotides, i.e. ribonucleotides, containing a non naturally occurring nucleobase instead of a naturally occurring nucleobase such as uridines or cytidines modified at the 5-position, e.g. 5-(2-amino) propyl uridine, 5-bromo uridine; adenosines and guanosines modified at the 8-position, e.g. 8-bromo guanosine; deaza nucleotides, e. g. 7 deaza-adenosine; O- and N-alkylated nucleotides, e.g. N6-methyl adenosine are suitable. The 2' OH— group can be replaced by a group selected from H. OR, R. halo, SH, SR, NH2, NHR, NR2 or CN, wherein R is C—C6 alkyl, alkenyl or alkynyl and halo is F, Cl, Br or I. Modifications of the ribose-phosphate backbone can be done for a variety of reasons, e.g., to increase the stability and half-life of such molecules in physiological environments or as probes on a biochip. Mixtures of naturally occurring nucleic acids and analogs can be used; alternatively, mixtures of different nucleic acid analogs, and mixtures of naturally occurring nucleic acids and analogs can be used. Nucleic acid sequences include but are not limited to, nucleic acid sequence encoding proteins, for example that act as transcriptional repressors, antisense molecules, ribozymes, small inhibitory nucleic acid sequences, for example but not limited to RNAi, shRNAi, siRNA, micro RNAi (mRNAi), antisense oligonucleotides etc.

The term "oligonucleotide" as used herein refers to an oligomer or polymer of ribonucleic acid (RNA) or deoxyribonucleic acid (DNA) or mimetics thereof, as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases. An oligonucleotide preferably includes two or more nucleomonomers covalently coupled to each other by linkages (e.g., phosphodiesters) or substitute linkages.

The term "operable linkage" or "operably linked" are used interchangeably herein, are to be understood as meaning, for example, the sequential arrangement of a regulatory element (e.g. a promoter) with a nucleic acid sequence to be expressed and, if appropriate, further regulatory elements (such as, e.g., a terminator) in such a way that each of the regulatory elements can fulfill its intended function to allow, modify, facilitate or otherwise influence expression of the linked nucleic acid sequence. To this end, direct linkage in the chemical sense is not necessarily required. Genetic control sequences such as, for example, enhancer sequences, can also exert their function on the target sequence from positions which are further away, or indeed from other DNA molecules. In some embodiments, arrangements are those in which the nucleic acid sequence to be expressed recombinantly is positioned behind the sequence acting as promoter, so that the two sequences are linked covalently to each other. Operable linkage, and an expression construct, can be generated by means of customary recombination and cloning techniques as described and known in the art.

The terms "promoter," "promoter element," or "promoter sequence" are equivalents and as used herein, refers to a DNA sequence which when operatively linked to a nucleotide sequence of interest is capable of controlling the transcription of the nucleotide sequence of interest into mRNA. A promoter is typically, though not necessarily, located 5' (i.e., upstream) of a nucleotide sequence of interest (e.g., proximal to the transcriptional start site of a structural gene) whose transcription into mRNA it controls, and provides a site for specific binding by RNA polymerase and other transcription factors for initiation of transcription. A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is not naturally associated with the promoter (e.g. a genetically engineered coding sequence or an allele from a different ecotype or variety). Suitable promoters can be derived from genes of the host cells where expression should occur or from pathogens for the host cells (e.g., tissue promoters or pathogens like viruses).

If a promoter is an "inducible promoter", as defined herein, then the rate of transcription is modified in response to an inducing agent or inducer. In contrast, the rate of transcription is not regulated by an inducer if the promoter is a constitutive promoter. The term "constitutive" when made in reference to a promoter means that the promoter is capable of directing transcription of an operably linked nucleic acid sequence in the absence of a stimulus (e.g., heat shock, chemicals, agents, light, etc.). Typically, constitutive promoters are capable of directing expression of a nucleic acid sequence in substantially any cell and any tissue. In contrast, the term "regulateable" or "inducible" promoter referred to herein is one which is capable of directing a level of transcription of an operably linked nucleic acid sequence in the presence of a stimulus (e.g., heat shock, chemicals, light, agent etc.) which is different from the level of transcription of the operably linked nucleic acid sequence in the absence of the stimulus.

A promoter may be regulated in a tissue-specific or tissue preferred manner such that it is only active in transcribing the associated coding region in a specific tissue type(s). The term "tissue specific" as it applies to a promoter refers to a promoter that is capable of directing selective expression of a nucleotide sequence of interest to a specific type of tissue (e.g., liver) in the relative absence of expression of the same nucleotide sequence of interest in a different type of tissue (e.g., kidney). Tissue specificity of a promoter may be evaluated by, for example, operably linking a reporter gene to the promoter sequence to generate a reporter construct, introducing the reporter construct into the genome of an organism, e.g. an animal model such that the reporter construct is integrated into every tissue of the resulting transgenic animal, and detecting the expression of the reporter gene (e.g., detecting mRNA, protein, or the activity of a protein encoded by the reporter gene) in different tissues of the transgenic animal. The detection of a greater level of expression of the reporter gene in one or more tissues relative to the level of expression of the reporter gene in other tissues shows that the promoter is specific for the tissues in which greater levels of expression are detected. The term "cell type specific" as applied to a promoter refers to a promoter, which is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, e.g., GUS activity staining or immunohistochemical staining. The term "minimal promoter" as used herein refers to the minimal nucleic acid sequence comprising a promoter element while also maintaining a functional promoter. A minimal promoter can comprise an inducible, constitutive or tissue-specific promoter.

The term "expression" as used herein refers to the biosynthesis of a gene or nucleic acid sequence, preferably to the transcription and/or translation of a nucleotide sequence, for example an endogenous gene or a heterologous gene, in a cell. For example, in the case of a heterologous nucleic acid sequence, expression involves transcription of the heterologous nucleic acid sequence into an RNA sequence, such as an mRNA or gRNA, and, optionally, the subsequent translation of mRNA into one or more polypeptides. Expression also refers to biosynthesis of an RNA molecule, but does not require translation to polypeptide sequences. The term "expression construct" and "nucleic acid construct" as used herein are synonyms and refer to a nucleic acid sequence capable of directing the expression of a particular nucleotide sequence, such as the heterologous target gene sequence in an appropriate host cell (e.g., a prokaryotic cell, eukaryotic cell, or mammalian cell). If translation of the desired heterologous target gene is required, it also typically comprises sequences required for proper translation of the nucleotide sequence. The coding region may code for a protein of interest but may also code for a functional RNA of interest. The nucleic acid construct as disclosed herein can be chimeric, meaning that at least one of its components is heterologous with respect to at least one of its other components.

The term "enhancer" refers to a cis-acting regulatory sequence involved in the transcriptional activation of a nucleic acid sequence. An enhancer can function in either orientation and can be upstream or downstream of the promoter. As used herein, the term "gene product(s)" is used to refer to include RNA transcribed from a gene, or a polypeptide encoded by a gene or translated from RNA. A protein and/or peptide or fragment thereof can be any protein of interest, for example, but not limited to; mutated proteins; therapeutic proteins; truncated proteins, wherein the protein is normally absent or expressed at lower levels in the cell. Proteins can also be selected from a group comprising; mutated proteins, genetically engineered proteins, peptides, synthetic peptides, recombinant proteins, chimeric proteins, antibodies, midibodies, tribodies, humanized proteins, humanized antibodies, chimeric antibodies, modified proteins and fragments thereof.

The term "nucleic acid construct" as used herein refers to a nucleic acid at least partly created by recombinant methods. The term "DNA construct" refers to a polynucleotide construct consisting of deoxyribonucleotides. The construct can be single or double stranded. The construct can be circular or linear. A person of ordinary skill in the art is familiar with a variety of ways to obtain and generate a DNA construct. Constructs can be prepared by means of customary recombination and cloning techniques as are known to those of ordinary skill in the art.

The terms "polypeptide", "peptide", "oligopeptide", "polypeptide", "gene product", "expression product" and "protein" are used interchangeably herein to refer to a polymer or oligomer of consecutive amino acid residues.

Methods and Uses of Engineered DNA Methylation Systems

The engineered DNA methylation systems described herein are useful for engineering complex genome modifications in cellular systems, such as prokaryotic, eukaryotic, or synthetic cells, or in non-cellular systems, including test tubes, viruses and phages. The novel engineered DNA methylation systems described herein harness the power of nucleic acid-based engineering methods to initiate and propagate methylation. The engineered DNA methylation systems described herein can be used for a variety of applications and in many different types of methods, including, but not limited to, genome editing, biosensing, and biomedical therapeutics.

The methods and uses of the engineered DNA methylation systems described herein can involve in vivo, ex vivo, or in vitro systems. The term "in vivo" refers to assays or processes that occur in or within an organism, such as a multicellular animal. In some of the aspects described herein, a method or use can be said to occur "in vivo" when a unicellular organism, such as bacteria, is used. The term "ex vivo" refers to methods and uses that are performed using a living cell with an intact membrane that is outside of the body of a multicellular animal or plant, e.g., explants, cultured cells, including primary cells and cell lines, transformed cell lines, and extracted tissue or cells, including blood cells, among others. The term "in vitro" refers to assays and methods that do not require the presence of a cell with an intact membrane, such as cellular extracts, and can refer to the introducing a module or engineered DNA methylation systems into a non-cellular system, such as a media not comprising cells or cellular systems, such as cellular extracts.

A cell to be engineered for use with the engineered DNA methylation systems described herein can be any cell or host cell. As defined herein, a "cell" or "cellular system" is the basic structural and functional unit of all known independently living organisms. It is the smallest unit of life that is classified as a living thing, and is often called the building block of life. Some organisms, such as most bacteria, are unicellular (consist of a single cell). Other organisms, such as humans, are multicellular. A "natural cell," as defined herein, refers to any prokaryotic or eukaryotic cell found naturally. A "prokaryotic cell" can comprise a cell envelope and a cytoplasmic region that contains the cell genome (DNA) and ribosomes and various sorts of inclusions.

In some embodiments, the cell is a eukaryotic cell. A eukaryotic cell comprises membrane-bound compartments in which specific metabolic activities take place, such as a nucleus. In other embodiments, the cell or cellular system is an artificial or synthetic cell. As defined herein, an "artificial cell" or a "synthetic cell" is a minimal cell formed from artificial parts that can do many things a natural cell can do, such as transcribe and translate proteins and generate ATP.

Host cells of use in the aspects for transformation or transfection with the engineered DNA methylation systems described herein include any host cell that is capable of supporting the activation and expression of the engineered DNA methylation systems, which can be modified according to the cell type utilized accordingly, for example, by codon optimization.

Cells of use in the various aspects described herein upon transformation or transfection with the engineered DNA methylation systems described herein include any cell that is capable of supporting the activation and expression of the engineered DNA methylation systems and component modules. In some embodiments of the aspects described herein, a cell can be from any organism or multi-cell organism. Examples of eukaryotic cells that can be useful in aspects described herein include eukaryotic cells selected from, e.g., mammalian, insect, yeast, or plant cells. The engineered DNA methylation systems described herein can be introduced into a variety of cells including, e.g., fungal, plant, or animal (nematode, insect, plant, bird, reptile, or mammal (e.g., a mouse, rat, rabbit, hamster, gerbil, dog, cat, goat, pig, cow, horse, whale, monkey, or human)). The cells can be primary cells, immortalized cells, stem cells, or transformed cells. In some embodiments, the cells comprise stem cells. Expression vectors for the components of the engineered DNA methylation systems will generally have a promoter and/or an enhancer suitable for expression in a particular host cell of interest. In alternative embodiments, the cells can be any cell, for example mammalian cells, plant cells and chimeric cells. In some embodiments, the cells can be from any organism or multi-cell organism. Examples of eukaryotic cells that can be useful in aspects described herein include eukaryotic cells selected from, e.g., mammalian, insect, yeast, or plant cells. In some embodiments, the eukaryotic cells are from a vertebrate animal. The present invention contemplates the use of any such vertebrate cells for the engineered DNA methylation systems described herein, including, but not limited to, reproductive cells including sperm, ova and embryonic cells, and non-reproductive cells, such as kidney, lung, spleen, lymphoid, cardiac, gastric, intestinal, pancreatic, muscle, bone, neural, brain, and epithelial cells. Also contemplated for use with the engineered DNA methylation systems described herein are stem cells, including human embryonic stem cells, pluripotent stem cells, multipotent stem cells, and induced pluripotent stem cells (iPSCs), as those terms are understood by one of skill in the art.

In some embodiments of the aspects described herein, engineered DNA methylation systems are introduced into a cellular or non-cellular system using a vector or plasmid. As used herein, the term "vector" is used interchangeably with "plasmid" to refer to a nucleic acid molecule capable of transporting another nucleic acid to which it has been linked. Vectors capable of directing the expression of genes and/or nucleic acid sequence to which they are operatively linked are referred to herein as "expression vectors." In general, expression vectors of utility in the methods and engineered DNA methylation systems described herein are often in the form of "plasmids," which refer to circular double stranded DNA loops which, in their vector form are not bound to the chromosome.

For example, in regard to using sequences associated with CRISPR, one of skill in the art can insert a short DNA fragment containing the DNA binding domain target site into a guide RNA expression plasmid. The sgRNA expression plasmid contains the DNA binding domain target site (about 20 nucleotides), a form of the tracrRNA sequence (the scaffold) as well as a suitable promoter and necessary elements for proper processing in eukaryotic cells. Such vectors are commercially available (see, for example, Addgene). Many of the systems rely on custom, complementary oligos that are annealed to form a double stranded DNA and then cloned into the sgRNA expression plasmid. In some embodiments, co-expression of the sgRNA and the appropriate Cas enzyme or domain thereof can be achieved using the same or separate plasmids in transfected cells results.

Other expression vectors can be used in different embodiments, for example, but not limited to, plasmids, episomes, bacteriophages or viral vectors, and such vectors can integrate into the host's genome or replicate autonomously in the particular cellular system used. Other forms of expression vectors known by those skilled in the art which serve the equivalent functions can also be used. Expression vectors comprise expression vectors for stable or transient expression encoding the DNA. A vector can be either a self-replicating extrachromosomal vector or a vector which integrates into a host genome. One type of vector is a genomic integrated vector, or "integrated vector", which can become integrated into the chromosomal DNA or RNA of a host cell, cellular system, or non-cellular system. In some embodiments, the nucleic acid sequence or sequences encoding the engineered DNA methylation systems integrates into the chromosomal DNA or RNA of a host cell, cellular system, or non-cellular system along with components of the vector sequence. In other embodiments, the nucleic acid sequence encoding the engineered DNA methylation systems directly integrates into chromosomal DNA or RNA of a host cell, cellular system, or non-cellular system, in the absence of any components of the vector by which it was introduced. In such embodiments, the nucleic acid sequence(s) encoding the module or engineered DNA methylation systems can be integrated using targeted insertions, such as knock-in technologies or homologous recombination techniques, or by non-targeted insertions, such as gene trapping techniques or non-homologous recombination. The number of copies of an engineered DNA methylation system that integrate into the chromosomal DNA or RNA of a cellular or non-cellular system can impact the fidelity of the system, and thus it is preferred, in some embodiments, that only one copy is integrated per cellular system.

Another type of vector is an episomal vector, i.e., a nucleic acid capable of extra-chromosomal replication. Such plasmids or vectors can include plasmid sequences from bacteria, viruses or phages. Such vectors include chromosomal, episomal and virus-derived vectors e.g., vectors derived from bacterial plasmids, bacteriophages, yeast episomes, yeast chromosomal elements, and viruses, vectors derived from combinations thereof, such as those derived from plasmid and bacteriophage genetic elements, cosmids and phagemids. A vector can be a plasmid, bacteriophage, bacterial artificial chromosome (BAC) or yeast artificial chromosome (YAC). A vector can be a single or double-stranded DNA, RNA, or phage vector. In some embodiments, the engineered DNA methylation systems are introduced into a cellular system using a BAC vector.

The vectors comprising the engineered DNA methylation systems described herein can be "introduced" into cells as polynucleotides, preferably DNA, by techniques well-known in the art for introducing DNA and RNA into cells. The term "transduction" refers to any method whereby a nucleic acid sequence is introduced into a cell, e.g., by transfection, lipofection, electroporation, biolistics, passive uptake, lipid:nucleic acid complexes, viral vector transduction, injection, contacting with naked DNA, gene gun, and the like. The vectors, in the case of phage and viral vectors can also be introduced into cells as packaged or encapsidated virus by well-known techniques for infection and transduction. Viral vectors can be replication competent or replication defective. In the latter case, viral propagation generally occurs only in complementing host cells. In some embodiments, the modules or engineered DNA methylation systems are introduced into a cell using other mechanisms known to one of skill in the art, such as a liposome, microspheres, gene gun, fusion proteins, such as a fusion of an antibody moiety with a nucleic acid binding moiety, or other such delivery vehicle.

The engineered DNA methylation systems or the vectors comprising the engineered DNA methylation systems described herein can be introduced into a cell using any method known to one of skill in the art. The term "transformation" as used herein refers to the introduction of genetic material (e.g., a vector comprising one or more modules of an engineered DNA methylation system) comprising one or more modules or engineered DNA methylation systems described herein into a cell, tissue or organism. Transformation of a cell can be stable or transient. The term "transient transformation" or "transiently transformed" refers to the introduction of one or more transgenes into a cell in the absence of integration of the transgene into the host cell's genome. Transient transformation can be detected by, for example, enzyme linked immunosorbent assay (ELISA), which detects the presence of a polypeptide encoded by one or more of the transgenes. Alternatively, transient transformation can be detected by detecting the activity of the protein encoded by the transgene. The term "transient transformant" refers to a cell which has transiently incorporated one or more transgenes.

In contrast, the term "stable transformation" or "stably transformed" refers to the introduction and integration of one or more transgenes into the genome of a cell or cellular system, preferably resulting in chromosomal integration and stable heritability through meiosis. Stable transformation of a cell can be detected by Southern blot hybridization of genomic DNA of the cell with nucleic acid sequences, which are capable of binding to one or more of the transgenes. Alternatively, stable transformation of a cell can also be detected by the polymerase chain reaction of genomic DNA of the cell to amplify transgene sequences. The term "stable transformant" refers to a cell or cellular, which has stably integrated one or more transgenes into the genomic DNA. Thus, a stable transformant is distinguished from a transient transformant in that, whereas genomic DNA from the stable transformant contains one or more transgenes, genomic DNA from the transient transformant does not contain a transgene. Transformation also includes introduction of genetic material into plant cells in the form of plant viral vectors involving epichromosomal replication and gene expression, which may exhibit variable properties with respect to meiotic stability. Transformed cells, tissues, or plants are understood to encompass not only the end product of a transformation process, but also transgenic progeny thereof.

As used herein, the term "comprising" means that other elements can also be present in addition to the defined elements presented. The use of "comprising" indicates inclusion rather than limitation. Accordingly, the terms "comprising" means "including principally, but not necessary solely". Furthermore, variation of the word "comprising", such as "comprise" and "comprises", have correspondingly the same meanings. The term "consisting essentially of" means "including principally, but not necessary solely at least one", and as such, is intended to mean a "selection of one or more, and in any combination". Stated another way, the term "consisting essentially of" means that an element can be added, subtracted or substituted without materially affecting the novel characteristics of the invention. This applies equally to steps within a described method as well as compositions and components therein. In other embodiments, the inventions, compositions, methods, and respective components thereof, described herein are intended to be exclusive of any element not deemed an essential element to the component, composition or method ("consisting of"). For example, module that comprises a sequence encoding a mutatnt DNA adenine methyltransferase and a DNA binding domain sequence encompasses both the mutatnt DNA adenine methyltransferase and a DNA binding domain sequence of a larger sequence. By way of further example, a composition that comprises elements A and B also encompasses a composition consisting of A, B and C.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, publications, and websites identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

EXAMPLES

Example 1

Experimental Assays and Supporting Data
Establishment and Enrichment of Adenine Methylation (m6A) at Target DNA Sites in Mammalian Cells
Cell Culture and Transfection HEK293FT (American Type Culture Collection, ATCC) cells were cultured in DMEM supplemented with 10% FBS, 1% glutamax, 1% Non-essential amino acids solution and 1% penicillin-streptomycin. Unless otherwise specified, plasmids encoding Reporter, Writer, Reader-Effector, and Reader-Writer constructs were transfected into HEK293FT cells by PEI. 60K HEK293FT cells were seeded into 48-well plates and transfected the following day with total of 300 ng of DNA (with equal ratio of testing constructs including IR fluorescent protein). Flow cytometry analysis showed ~80-90% of transfected cells are IRFP$^+$ under these conditions.
m6A-qPCR Assay A previously described qPCR-based assay to quantitatively measure adenine methylation at specific DNA sequences and loci was adopted. In this assay, genomic DNA of HEK293FT cells and/or transfected plasmids are isolated using DNEASY Blood and Tissue Kit (Qiagen) according to manufacturer's protocol, and then digested using DpnII (NEB) (16 hrs, 37° C.). The DpnII restriction enzyme specifically cleaves un-methylated GATC sequences, but not methylated GATC. Therefore, GATC sequences that are adenine-methylated (e.g. by a Writer protein) are protected from DpnII digestion, and will be PCR-amplified in an amount that is proportional to the adenine methylation frequency. qPCR was performed with LIGHTCYCLER® 480 SYBR Green I Master mix (Roche) using a LIGHTCYCLER 480 Instrument II (Roche).
Specific Enrichment of Adenine Methylation at Target Sites The m6A-qPCR assay was used to determine the methylation frequencies of GATC sequences at target sites in a transiently transfected reporter plasmid ([8XZF_14XGATC_interspersed] min CMV promoter) and at various off-target, endogenous GATC sites throughout the genome (IL7R, TNFRSF19, TNFBR3). Since local differences in chromatin accessibility affect the methylation frequency of individual GATCs, for each GATC site the ratio of methylation by ZF-Dam Writers (targeting DBD sites in the above reporter) and methylation by a mCherry-Dam (control non-targeting Dam) was calculated.

As shown herein, co-transfection of Writers utilizing mutant Dams (R116A and N132A) with the reporter led to significant and specific enrichment in the deposition of adenine methylation at target sites versus non-specific sites. These residues are predicted to make non-specific contact with the flanking DNA phosphate groups; alanine mutagenesis of the residues is aimed at lowering the intrinsic affinity of Dam for GATC, thus making the enzyme's activity more dependent on the ZF DNA binding activity. In particular, the mutant N132A showed ~6-fold enrichment in methylation at the target site.

The activities of Writers of various mutant Dams with singly integrated reporter cell line were also screened. ([5XZF 63XGATC] min CMV promoter (1.5-kb; 20-bps spacer); AAVS1 locus; HEK cells). This reporter module has a unique "barcoded" spacer sequence of 20 bps between adjacent GATC sites, which enables the measurement of m6A enrichment with single GATC site resolution. The data described herein shows the specific adenine methylation rate at the single GATC target site 140 bps downstream of the ZF10-1 nucleation site by various Dam mutants directly fused to ZF10-1 with GGGGSGGGGS linker (SEQ ID NO: 54). The overall trend of transiently transfected mutant Dam Writers activity in integrated reporter remains similar as in transiently transfected reporter. Specifically, the mutant N132A showed ~10-fold enrichment in methylation at the target site.

Spatial Footprinting of m6A

Next, using the transiently transfected [5XZF_63XGATC] min CMV promoter (1.5-kb; 20-bps spacer) reporter, the spatial footprint of m6A upon transient induction of Writers (using the ABA-inducible Writer constructs) was probed. This was performed by inducing cells with ABA for 0 hr (green), 5 hr (blue), and 49 hr (red), and subsequently using the m6A-qPCR assay and the "barcoded" reporter to measure methylation frequencies across the length of the reporter. A significant enrichment of m6A at the ZF DBD nucleation site was observed, and a concomitant decrease in methylation along the length of the reporter. Additionally, the profiles showed a dependency on the temporal duration of Writer induction, whereby longer recruitment of the Writer generally resulted in higher levels of m6A. As negative controls, the corresponding m6A footprints for ZF-VP64 (grey) and DpnI-VP64 (pink), in place of inducible Writers was measured, and observed no enrichment of m6A across the entire reporter.

The spatial footprint of m6A upon transient induction of Writers (using the ABA-inducible Writer constructs or constitutive expression of minCMV-ZF10-1-Dam (N132A) Writer construct) into integrated reporter cell line ([5XZF_63XGATC] min CMV promoter (1.5-kb; 20-bps spacer); AAVS1 locus; HEK cells) was also probed. This was performed by inducing cells with ABA for 0 hour (light blue), 6 hours (medium blue), and 2 days (dark blue), followed by the m6A-qPCR assay. For ABA inducible Writer with NES (minCMV-NLS-ABI1-ZF10-1-<P2A>-Dam (N132A)-PYL1-NES), significant specific (i.e., % methylation by Writer with ZF DBD over % methylation by Writer with mCh is greater than 1) enrichment of m6A at the ZF DBD nucleation site, and a concomitant decrease in methylation along the length of the reporter was observed. Additionally, the profiles showed a similar dependency on the temporal duration of Writer induction as in transiently transfected reporter assay. However, for ABA inducible Writer with no NES (minCMV-NLS-ABI1-ZF10-1-<P2A>-Dam (N132A)-PYL1), any specific enrichment of m6A at any site along the length of the reporter was not observed. This piece of data supports that actively localizing Dam protein with nuclear export signal (NES) to the cytoplasm in the absence of ABA is much more effective than passive cytoplasmic localization with no NES, in minimizing the basal non-targeted activity of Dam (N132A). As a negative control, the corresponding m6A footprints for ZF11-1-Dam (R116A) (grey), which has non-cognate ZF, was measured and no specific enrichment of m6A across the entire reporter was observed. For comparison, the corresponding m6A footprints for constitutively expressed direct fusion Writer (minCMV-ZF10-1-Dam (N132A)) was also measured, in place of inducible Writers, and again significant specific enrichment near the ZF nucleation site and a concomitant decrease in methylation along the length of the reporter was observed.

Adenine Methylation-Based Recruitment of Gene Regulatory Functions

Trans-Activation of GFP on Plasmid Reporter by Combination of Writer (ZF-Dam (WT)) and Reader-Effector (DpnI-VP64)

The cell culture and transfection methods described herein were used. Reporter plasmid was co-transfected with Writer and Reader-Effector constructs, and single-cell GFP levels were measured with flow cytometry two days post-transfection. The data provided herein shows fold-change of GFP over the basal (reporter only) level. Co-transfection of both the Writer and Reader-Effector constructs resulted in greater than 100-fold increase in GFP, as compared with negative controls (Writer only, Reader-Effector only).

Enhanced Trans-Activation of GFP on Plasmid Reporter by Combination of Writer (ZF-Dam Mutants) and Reader-Effector (DpnI-VP64)

Next, we tested Writer proteins incorporating the Dam mutants that were found to have more specific adenine methylation at target sites were tested. As shown herein, Writers incorporating mutant Dam (with exception for Y199A and R137A) led to an additional 3-4 fold increase in GFP trans-activation compared with Writers using wild type Dam.

Trans-Activation of GFP on Plasmid Reporter by Combination of Writer (dCas9-Dam (N132A)) and Reader-Effector (DpnI-VP64)

Next, Writer proteins that use an alternative DNA targeting platform were tested. Specifically, the ability of dCas9-Dam Writers to drive adenine methylation-based transcriptional activation of reporters was tested. As shown in the data herein, dCas9-Dam Writers that are recruited to the reporter DBD sites (via gRNA3 or gRNA10) led to more greater than 100-fold increase in GFP levels as compared with negative control (no gRNA, empty gRNA, and non-specific gRNAs target the VEGF-A gene or EGFP).

Repression of GFP on Plasmid Reporter by Combination of Writer (ZF-Dam (N132A)) and Reader-Effectors (DpnI-KRAB and DpnI-HP1 alpha)

It was next tested whether the effector domain in a Reader-Effector module could be replaced to incorporate other regulatory functionalities. Specifically Reader-Effector modules that utilize fusions to repressive domains (e.g., KRAB and Hp1 alpha chromoshadow domain) were constructed to investigate whether the mechanism of adenine methylation-based effector recruitment described herein could be used to silence a strong, full length CMV promoter on transfected plasmids. As shown herein, Reader-Effector module constructs utilizing KRAB or Hp1 alpha domains led to robust silencing of the full length CMV promoter driving expression of a GFP reporter.

Trans-Activation of GFP from Stably Integrated Reporter Cell Lines by Combination of Writer (ZF-Dam (N132A)) and Reader-Effector (DpnI-VP64)

It was next investigated whether adenine methylation-dependent transcriptional modulation could be translated from transient and episomal plasmids to genomically integrated contexts. Stable cell lines were created that harbor one of our Reporter module constructs ([8XZF_14XGATC_interspersed] minimal CMV promoter) with FLP-IN™ Integration using FLP-IN™ 293 cells (Invitrogen) and 1:9 ratio of Reporter donor plasmid:Flp recombinase expression plasmid (pOG44).

The stable reporter cell line was then transfected with equal ratios of Writer (ZF-Dam (N132A)), Reader-Effector (DpnI-VP64), and IRFP transfection marker using lipofectamine 2000. As shown in the data herein, the combination of Writer and Reader-Effector led to ~3-fold activation of GFP from the genomically integrated reporter.

Other stable cell lines were created with CRISPR/Cas9 tool that singly integrates Reporter constructs into AAVS1 locus of HEK293T cell lines. The stable reporter cell lines were then transfected with equal ratios of Writer (ZF-Dam (N132A)), Reader-Effector (DpnI-VP64), and IRFP transfection marker using PEI. As shown in the data herein, the combination of Writer and Reader-Effector led to ~30-fold activation of GFP (and 80% of population being GFP activated) from the genomically integrated [8XZF_14XGATC_interspersed] minimal CMV promoter Reporter cell line.

Repression of GFP from Stably Integrated reporter cell line by combination of Writer (ZF-Dam (N132A)) and Reader-Effectors (DpnI-KRAB and DpnI-HP1 alpha)

Using the above-described [8XZF_14XGATC_interspersed] full length CMV promoter AAVS1 locus integrated Reporter cell line, it was next investigated whether a mechanism of adenine methylation-based effector recruitment could be used to silence a strong, full length CMV promoter on an integrated reporter. As shown in the data herein, Reader-Effector constructs utilizing KRAB or HP1 alpha domains led to robust silencing of the full length CMV promoter driving expression of a GFP reporter.

Characterization of Methylation-Dependent Transcriptional Modulation by Inducible Writers Adenine methylation-dependent transcriptional modulation with the inducible Writer constructs described above was next characterized. Specifically, the leakiness, dynamic range, and dosage response of these systems in the context of the GFP trans-activation plasmid experiments were characterized. As shown in the co-transfection data provided herein, both inducible Writer systems led to robust trans-activation of GFP in the presence of ABA (+ABA), with the second inducible Writer (incorporating a NES) showing less leaky expression in the—ABA case. In these experiments, plasmids were co-transfected into HEK293FT cells. 200 μM ABA was added 6 hr post-transfection, and the cells were analyzed using flow cytometry 2 days post-transfection.

In a second set of experiments, the dosage response of GFP activation by the two inducible Writers was measured. These experiments were performed as above, except that different concentrations of ABA were added to cells and cells were at 36 hr.

Design and Development of Reader-Writer Systems for Propagation and Stable Maintenance of Adenine Methylation-Dependent Functions Enhancement of GFP Activation by Engineered Reader-Writer Module The objective was to develop an engineered Reader-Writer fusion protein capable of propagating methyl modification over long DNA/genomic distances and/or sustaining the modifications over extended periods of time (time periods beyond when a Writer is removed). In proof-of-concept experiments that build on the results described herein under "Spatial footprinting of m6A" the same plasmids described therein were co-transfected with an additional Reader-Writer construct plasmid (UBC-DpnI DBD-Dam (R95A)) or an impaired Reader-Writer construct plasmid (UBC-mCh-Dam-(R95A)). Cells were constantly induced with 400 μM ABA and analyzed using flow cytometry 2 days post-transfection. As shown herein, GFP activation levels increased by approximately 2-fold with Reader-Writer as compared to without Reader-Writer, while impaired Reader-Writer did not increase the GFP activation. These data indicate the Reader-Writer fusion protein can increase adenine methylation-dependent expression from a distant minimal CMV promoter by propagating m6A modifications from the nucleation site to the transcription start site (TSS) and/or by maintaining m6A modifications.

Example 2

Construction of a Synthetic, Chromatin-Based Epigenetic System in Human Cells

The chromatin landscape of DNA and histone modifications represents a fundamental layer of cellular regulation. These modifications are implicated in gene regulation[1,2], disease processes[3,4], and complex properties such as epigenetic programs that are remembered and heritably transmitted[5,6]. Despite its richness, the ability to manipulate or engineer this landscape in living cells is in its infancy Recent advances in "epigenetic editing" have focused on creating single-function editing tools that rely on often unknown interactions with endogenous chromatin systems[7-10].

To overcome these deficiencies, a fully synthetic, chromatin-based system with complex epigenetic properties was constructed that has no reliance on native chromatin machinery. This allows a unique platform to program a fuller set of operations on chromatin—writing, reading, propagating modifications—and unprecedented exploration of integrated circuitry and behaviors that can be de novo engineered from these basic operations. As described herein, DNA adenine methylation (m6A), a modification rarely found in metazoan genomes[11], was exploited to construct a synthetic chromatin system in human cells. The systems described herein comprise three functional modules that mediate m6A operations: (1) a synthetic initiator module to place m6A at specific genomic sites; (2) a synthetic readout module to program m6A recognition and m6A-dependent transcriptional logic; and (3) propagation module that implements "read-write," a mechanism proposed to underlie chromatin spreading and epigenetic maintenance across cellular systems[6,12]. Together with a quantitative model, these modules are used to construct regulatory circuits that drive spatial m6A propagation to regulate distal genes, and enable epigenetic memory of transcriptional states. These epigenetic functions do not make use of endogenous mechanisms, providing evidence that complex behaviors like memory can be programmed using specific molecular mechanisms at the chromatin level. The work described herein establishes a synthetic, chromatin 'programming language' to expand the regulatory potential of the genome and engineer epigenetic functions in mammalian cells.

Chromatin is a substrate for a complex assortment of chemical modifications made to DNA and histone proteins. These modifications influence genome structure and can orchestrate the ordered recruitment of effector protein complexes, thereby playing essential roles in regulating gene transcription and other critical biological processes[1-4]. Additionally, certain modifications have been implicated as carriers of epigenetic information by contributing to mechanisms for the transmission of heritable transcriptional states independent of DNA sequence[5,6]. The previously undescribed ability to synthetically manipulate this critical layer of information, on top of genome sequence, could provide new tools for interrogating and controlling the function of eukaryotic genomes, and would offer powerful new capabilities for synthetic biology1[13-15].

Toward this goal, recent advances in the development of "epigenome editing" tools have enabled one form of manipulation[7-10]. However, an integrated toolkit that allows programming a wider, defined set of operations common to diverse chromatin modification—e.g. writing, reading, and propagating—does not currently exist. With such a toolkit, various operations can be combined to systematically explore and engineer an array of higher-order, chromatin regulatory behaviors, and to enable new modes of gene expression and epigenetic control in cells. Additionally, these operations could be used as a means for synthetically recording and reading out information in the mammalian genome.

A key challenge to establishing a multi-part toolkit is creating well-defined interactions that minimize or avoid the natural cross-interference between modifications and their regulators[16,17]. To address this, as described herein, DNA N6-methyladenine (m6A) was exploited. In contrast to cytosine methylation, which is abundant in animals and typically acts to repress genes[3], m6A is rarely found in metazoan genomes and to date has no established function in the human genome[11,18]. The 'orthogonal' properties of adenine methylation were previously harnessed to develop technology for mapping chromatin-associated proteins in eukaryotic genomes[19,20]. By transplanting this modification into human cells, defined chromatin interactions were established that minimized cross-interference with pre-existing systems, and enables rapid construction of regulatory circuits that encode new functions. Analogously, in natural evolution, it has been proposed that the recent emergence of the phosphotyrosine modification presented similar opportunities for rapidly evolving signal transduction systems with new functions critical to metazoan biology[17]. As described herein, a synthetic chromatin system was developed in human cells, built from a toolkit of distinct operations on m6A. Critically, epigenetic functions engineered with this system are truly constructed de novo and do not make use of endogenous regulators or mechanisms, thus providing a minimal platform for exploring and tuning these higher-order behaviors.

Figures 8A, 8B, 8C, 8D:
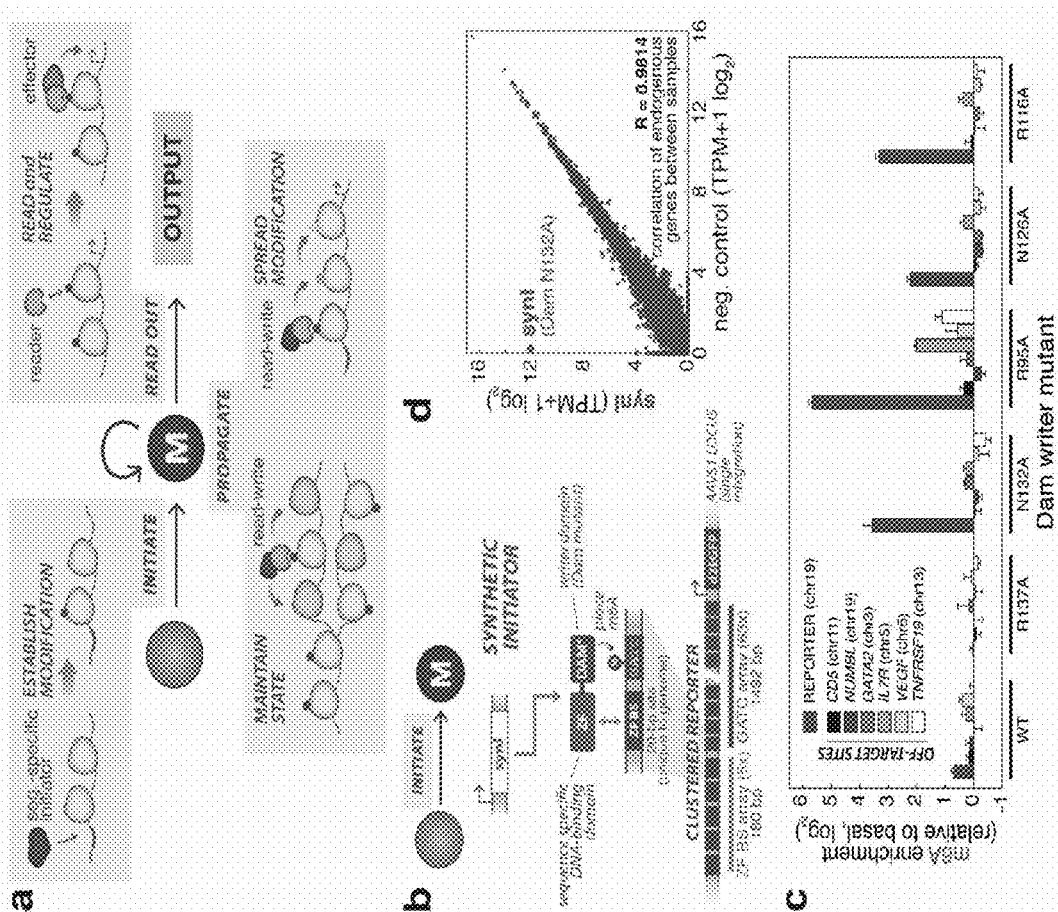
FIGS. 8A-8D demonstrate that a synthetic initiator module enables sequence-specific placement of DNA adenine methylation (m6A) in the human genome.

As described herein, three operational modules were defined, common to diverse chromatin modifications, that would represent basic requirements of an epigenetic system[6,21]: (1) Sequence-specific placement of the modification; (2) recruitment of protein effectors to the modification to mediate transcriptional changes; and (3) a module for self-propagation in the absence of an initial stimulus (FIG. 8A). Combined together, these modules drive complex chromatin-related phenomena, such as the formation of heterochromatin-like, silent domains in organisms, ranging from diverse yeasts to mammals[6, 22-24]. Here, a propagation mechanism is used to spread histone modifications along the chromatin template away from a nucleation site to create an altered domain. Once established, these domains and their transcriptional states can be maintained through cell division. While propagation mechanisms across chromatin and organismal systems vary greatly in molecular detail and have yet to be fully elucidated, a common theme is the presence of "read-write" motifs. Exemplified by regulators such as Clr4 in *S. pombe*[25] and Hpla/Suv39h in mammals[26], these function to recognize specific modifications and mediate the placement of the same modification on a nearby or adjacent template (e.g. in re-establishment after cell division)[12]. Interestingly, despite differences in molecular details, these mechanisms are similar to how DNA cytosine methylation patterns are thought to be re-established following cell division[6].

Figures 9A, 9B, 9C:
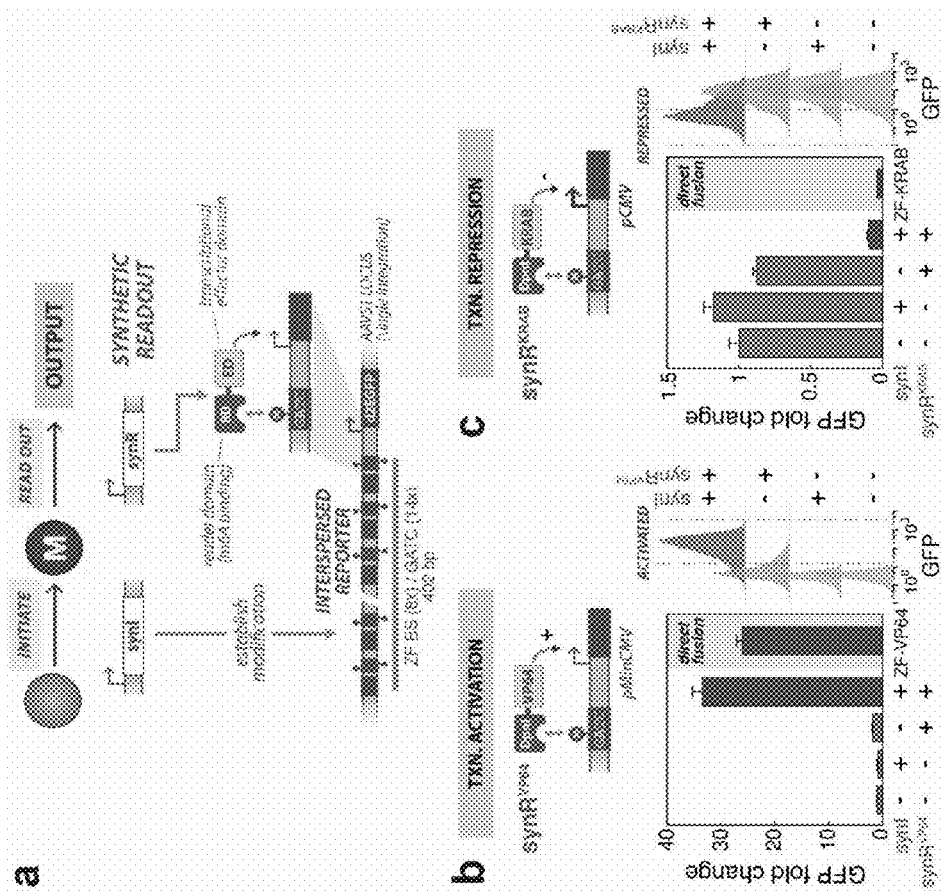
FIGS. 9A-9C demonstrate constructing a synthetic readout module to program recognition and m6A-dependent transcriptional regulation.

A synthetic initiator module (synI) was first designed to carry out sequence-specific, de novo placement of m6A at designer reporter loci in the human genome. The general design of the module is a fusion of a Dam (*E. coli* DNA adenine methyltransferase) writer domain, which catalyzes methylation of adenines in GATC motifs, and an engineered zinc finger protein (ZF), which specifically binds a 20-bp synthetic binding sequence (BS) (FIG. 8A, FIG. 12). Two types of reporters were used in the studies described herein—the Clustered Reporter and Interspersed Reporter (FIGS. 8B, 9A)—and generated respective reporter cell lines by singly-integrating these constructs into the HEK293FT genome (see Methods, FIG. 12). The two reporters feature different arrangements of BS and GATC arrays placed upstream of a promoter driving expression of a destabilized EGFP (d2EGFP).

To identify a synI that specifically nucleates our reporter locus, a library of Dam writer mutants (DAM*, FIGS. 9B, 12) was generated. By lowering intrinsic Dam activity, an allele whose activity is highly dependent on ZF binding could be identified. Two expression constructs were generated for each mutant: fusion to ZF (synI, targeted) and mCherry (synI$^{NT}$, non-targeted) (FIGS. 24A, 24B). Each construct was then transfected into the Clustered Reporter cell line, and an adapted m6A-qPCR assay was used to measure adenine methylation frequency at the reporter (see Methods, FIGS. 13A-14D). It was found that single mutations to residues that mediate DNA phosphate group contact, which are known to affect the biochemical activity of Dam[27,28], generally showed an enrichment in reporter m6A levels. Here, m6A enrichment is defined as targeted methylation (by synI) normalized to basal methylation, induced by the same Dam (synI$^{NT}$, non-targeted) (FIGS. 14A-14D). With these mutants, m6A enrichment was then compared at the reporter (red) to off-target, GATC-containing endogenous loci (greys), chosen to represent different chromosomal locations, to identify a factor with minimal off-target activity (FIG. 8C). The ZF-Dam N132A fusion was selected (also referred to as synI). SynI expression was found to have minimal effect on the 293FT transcriptome (FIGS. 8D, 25A, 25B), cell cycle and viability (FIGS. 15C, 15D). These results provide a synthetic tool for orthogonally and specifically placing m6A in the genome.

Figures 16A, 16B, 16C, 16D, 16E, 16F:
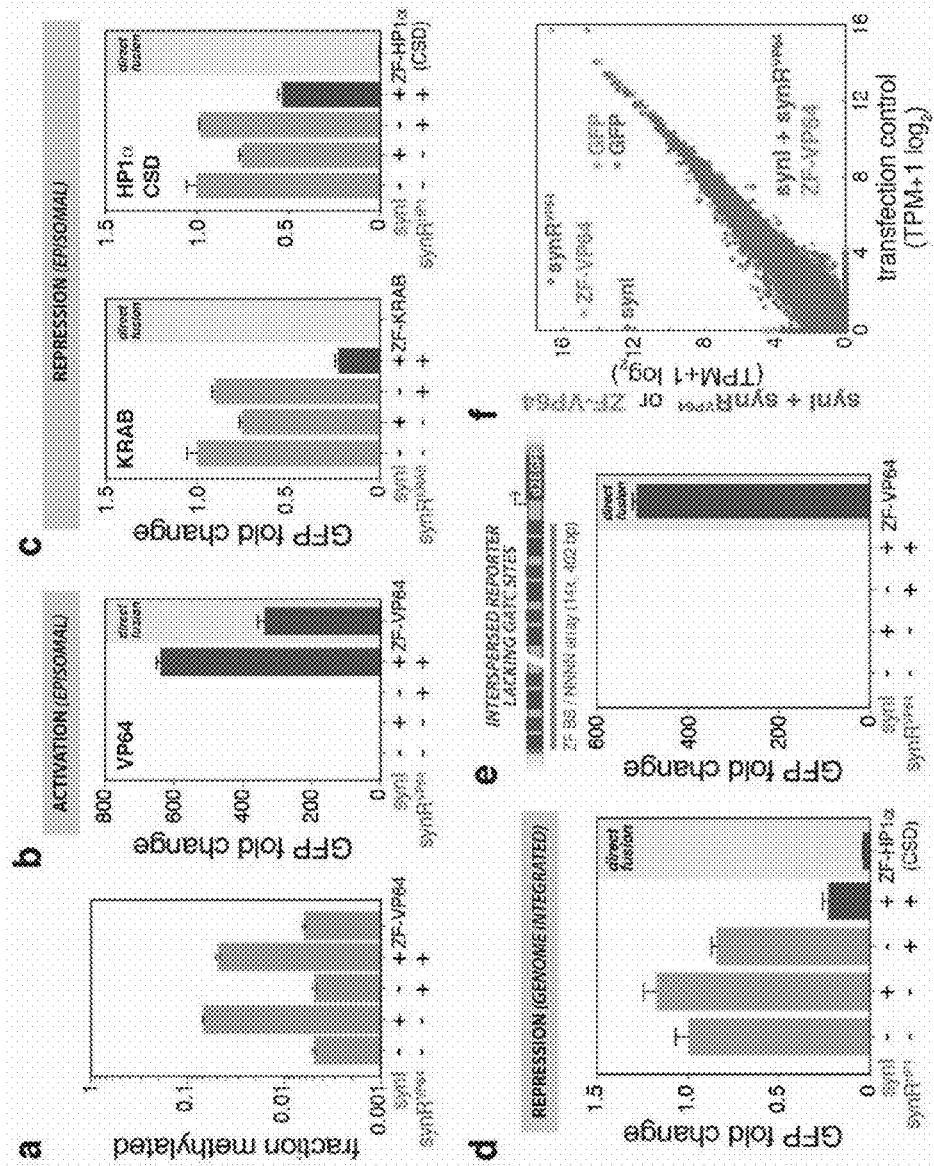
FIGS. 16A-16F demonstrate characterizing m6A-mediated transcriptional regulation by synI and synR modules.

Chromatin modifications can modulate gene transcription through several mechanisms, including through reader proteins that recognize specific, or combinations of, marks and recruit transcriptional effector functions[1,2,21]. Armed with the ability to nucleate orthogonal m6A marks, a mechanism for reading[29] and translating these modifications into defined transcriptional outputs was sought. A synthetic readout module (synR) was designed, comprising fusions of an m6A reader domain (RD, binding domain of *S. pneumoniae* DpnI), which selectively recognizes methylated GATC[19,30], and modular transcriptional effector domains (EDs) (FIG. 12). Expression constructs for synR modules were generated harboring different transcriptional effectors: synR$^{VP64}$ (VP64 activation domain), synR$^{KRAB}$ (KRAB repressive domain), and synR$^{HP1}$ (HP1α chromo shadow domain). Combinations of the constructs were then transfected into Interspersed Reporter cell lines (harboring either minimal CMV promoter for synR activators or full-length CMV for synR repressors), and measured GFP reporter output (see Methods). The synR modules drove significant gene activation or repression, only when expressed in combination with synI. Moreover, these transcriptional changes were similar in levels to those induced by a direct transcriptional regulator (direct fusion of ZF to EDs) (FIGS. 9B, 9C, 16A-16F). It was further confirmed that reporter m6A levels were enriched only in cells expressing synI (FIG. 16A), and that the presence of GATC motifs was required for transcriptional regulation by synI and synR (FIG. 16E). Finally, this two-module (synI/synR) system functioned on both integrated and episomal reporters (FIGS. 9B, 9C, 16B-16D), and was found to be highly specific genome-wide based on whole transcriptome measurements (FIG. 16F). Taken together, these results establish a specific, two-module system for programming m6A-dependent transcriptional logic states.

Cells have mechanisms for propagating chromatin modifications in space and time, such as those governing spreading across chromatin domains and their maintenance across cell division. These self-perpetuating behaviors are broadly thought to be driven by "read-write" systems[12]. A minimal read-write (RW) module was next constructed and used to construct regulatory systems that drive propagation of m6A. To enable these studies, a small molecule inducible initiator (synI$^{IND}$) was developed, which uses abscisic acid (ABA)-induced dimerization to trigger and temporally control initiation[31] (FIGS. 17A-17F). A synthetic RW module (synRW) was then designed composed of a direct fusion of m6A RD (binding domain of DpnI) and a Dam writer domain (DAM*) (FIG. 10A).

Figures 18A, 18B:
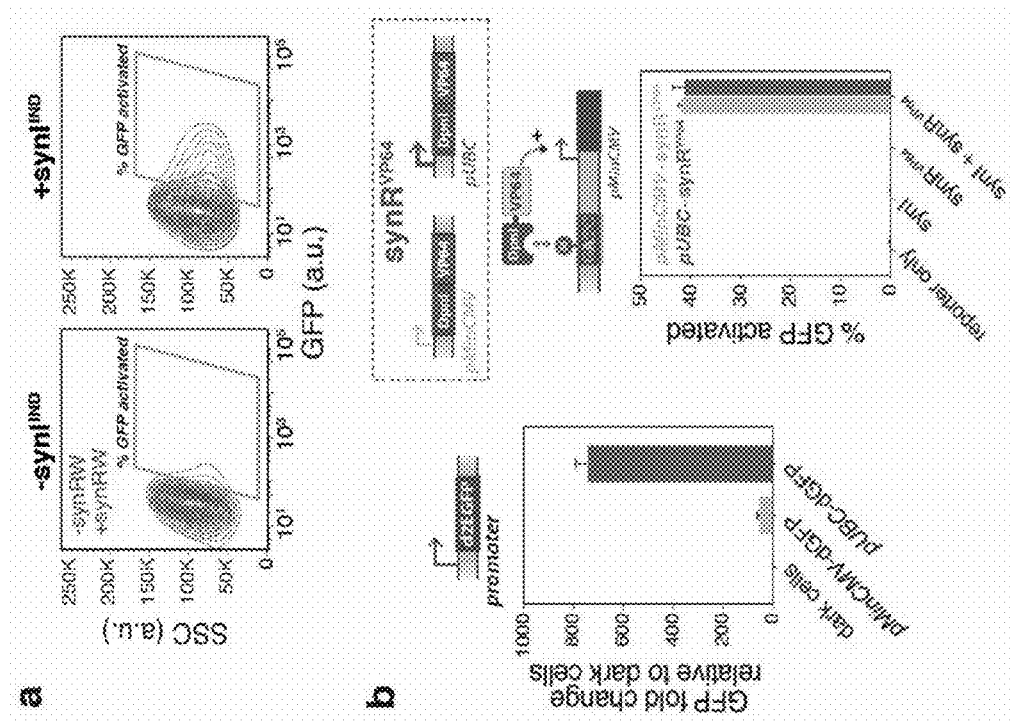
FIGS. 18A-18B demonstrate a spatial propagation screen.

The first objective was to identify RW circuit designs that can drive spatial propagation. Specifically, it was sought to identify synRW constructs that, when combined with synI$^{IND}$ and synR modules, could propagate m6A along a domain away from a nucleation site. To do this, a synRW library was generated (varying synRW expression levels and Dam writer mutants), and a simple, phenotypic screen for spatial propagation behavior was devised (FIG. 10B). A full description of the library, screen, and analysis is described herein. Briefly, the screen leverages the Clustered Reporter's long GATC domain separating the nucleation site from the reporter gene. Devoid of a propagation mechanism, reporter cells stably expressing the two-module (synI$^{IND}$/synR$^{VP64}$) system are not activated (FIG. 18A). As a result, the synRW library can be screened in these cells for candidates that lead to reporter activation (+synI$^{IND}$, FIG. 10B), as well as in cells lacking synI$^{IND}$ to screen out spurious cases for which downstream reporter activation is independent of m6A nucleation (−synI$^{IND}$, FIG. 10B). synRW constructs emerging from this screen provide promising candidates as the basis of a three-module (synI$^{IND}$/synR$^{VP64}$/synRW) system that enables nucleation-induced spatial propagation leading to reporter activation.

Figures 10A, 10B, 10C, 10D:
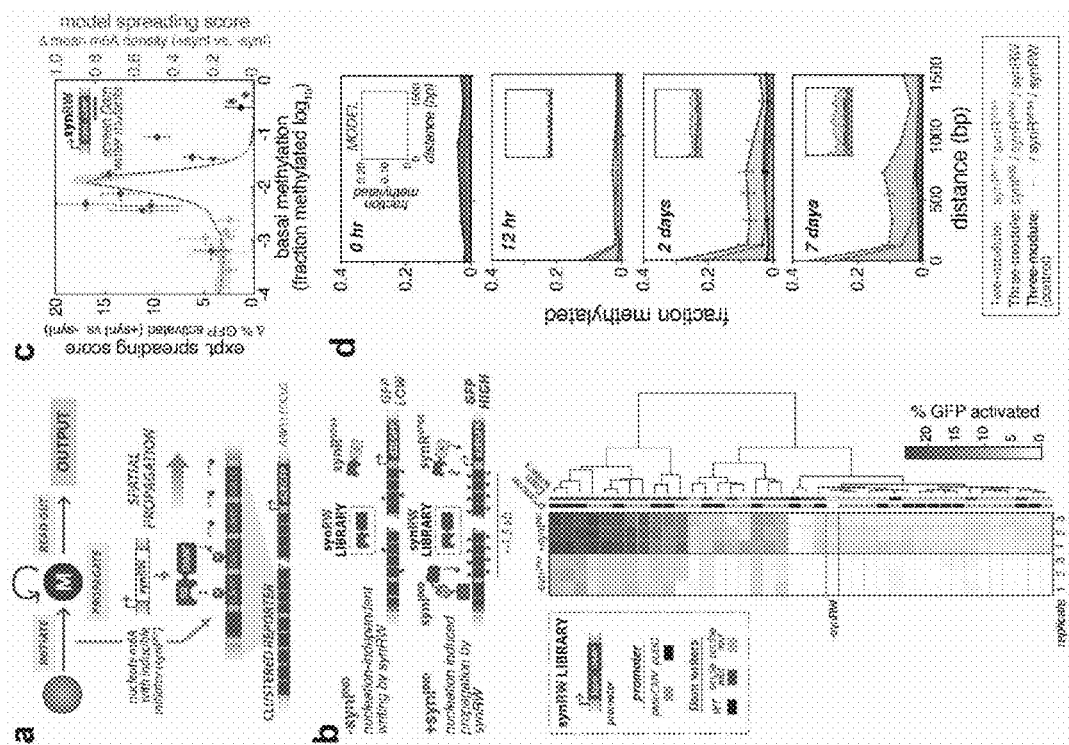
FIGS. 10A-10D demonstrate engineering spatial propagation of m6A with three-module, synthetic read-write circuits.

Clustering analysis of screen results based on GFP expression revealed a strong clustering by synRW Dam mutants (FIG. 10B). More specifically, a relationship was observed between the methylation activity of the synRW module and propagation, quantified by a "spreading score" metric developed herein to score the phenotypic outcomes of the propagation screen (FIG. 10C). This indicated that intermediate levels of writer activity can be an important property for the synRW module in driving these propagation phenotypes. To explore the generality of this result, quantitative modeling was used, adapting a previously described model of spreading dynamics[32] that captures the essential features of the systems described herein (see FIGS. 29A-29C). The model was used to interrogate how synRW properties, including writer activity, affect simulated spatial m6A profiles, and revealed a similar relationship to that observed from experimental screening described herein (FIG. 10C). Supported by these screen and simulation results, a high-scoring, intermediate-activity synRW (pUBC: DpnI-Dam R95A) was selected, and this construct was integrated to generate cells stably expressing a full "propagation circuit" (+synI$^{IND}$, +synR$^{VP64}$, +synRW). Upon triggering nucleation, cells expressing this circuit exhibited a growing m6A domain over time, in contrast to a control circuit lacking synRW (FIGS. 10D, 20A-20C). Interestingly, and consistent with recent studies measuring the dynamics of heterochromatin formation in mammalian cells[14], establishment of the m6A domain occurred over relatively slow time-scales (~days). Moreover, as designed, propagation was dependent on a priori nucleation by synI$^{IND}$ (−synI$^{IND}$). These results demonstrate the development of a three-module chromatin regulatory circuit that can drive spatial m6A propagation to modify a domain and regionally control the expression of genes.

Figures 11A, 11B, 11C, 11D, 11E:
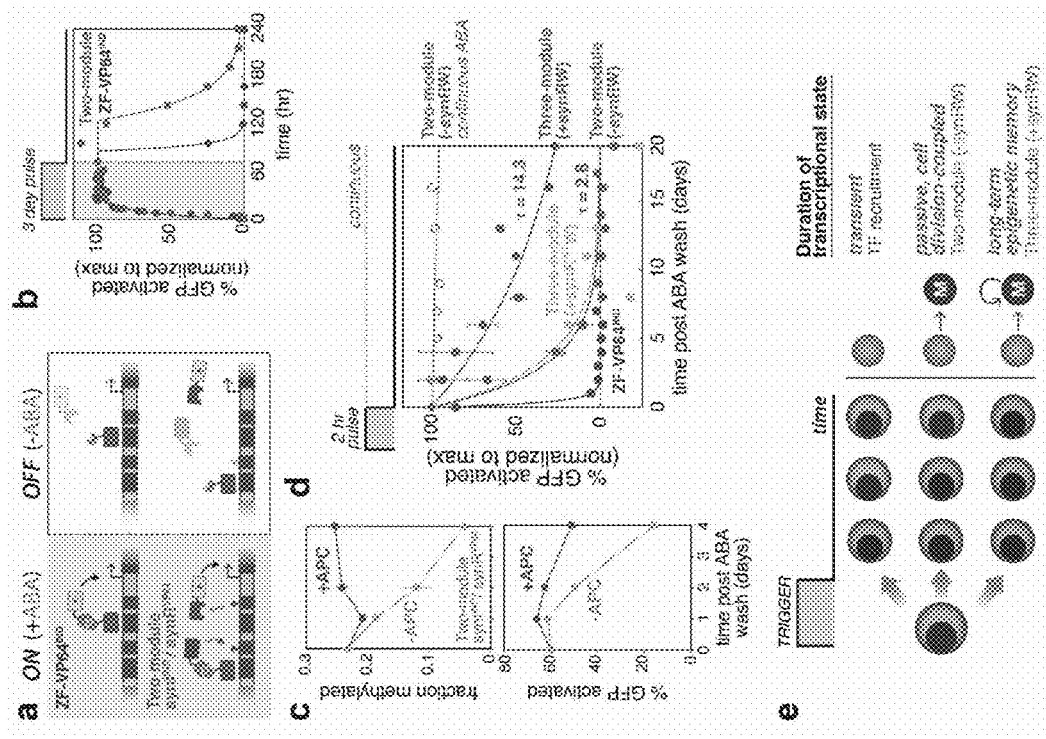
FIGS. 11A-11E demonstrate engineering epigenetic memory with three-module, synthetic read-write circuits.

As demonstrated herein, the self-propagating property of the synRW module described herein can additionally be used to engineer epigenetic memory in cells. Specifically, as compared with the transient states induced by a canonical transcriptional regulator, it was tested whether the propagation circuit described herein could mediate the maintenance and transmission of an induced transcriptional state through cell division. The response of Interspersed Reporter cells, stably expressing either an inducible ZF-VP64$^{IND}$ or the two-module (synI$^{IND}$/synR$^{VP64}$) system, to a transient pulse of ABA, was first followed (FIG. 11A). Both exhibited rapid reporter activation followed by deactivation upon removal of ABA, yet the m6A system exhibited a delay in the time-scale of deactivation (FIG. 11B). In contrast to canonical transcription factor (TF) regulation, these decay dynamics depend on the lifetime of the modified m6A state, which in the absence of an active removal mechanism is largely governed by passive dilution through semiconservative replication. This was tested by blocking DNA replication using Aphidicolin (APC). Without APC, m6A levels roughly halved every two days with a concomitant loss of GFP activated cells, whereas blocking DNA replication led to persistence of m6A and corresponding GFP states (FIGS. 11C, 31A).

Figures 21A, 21B, 21C, 21D, 21E:
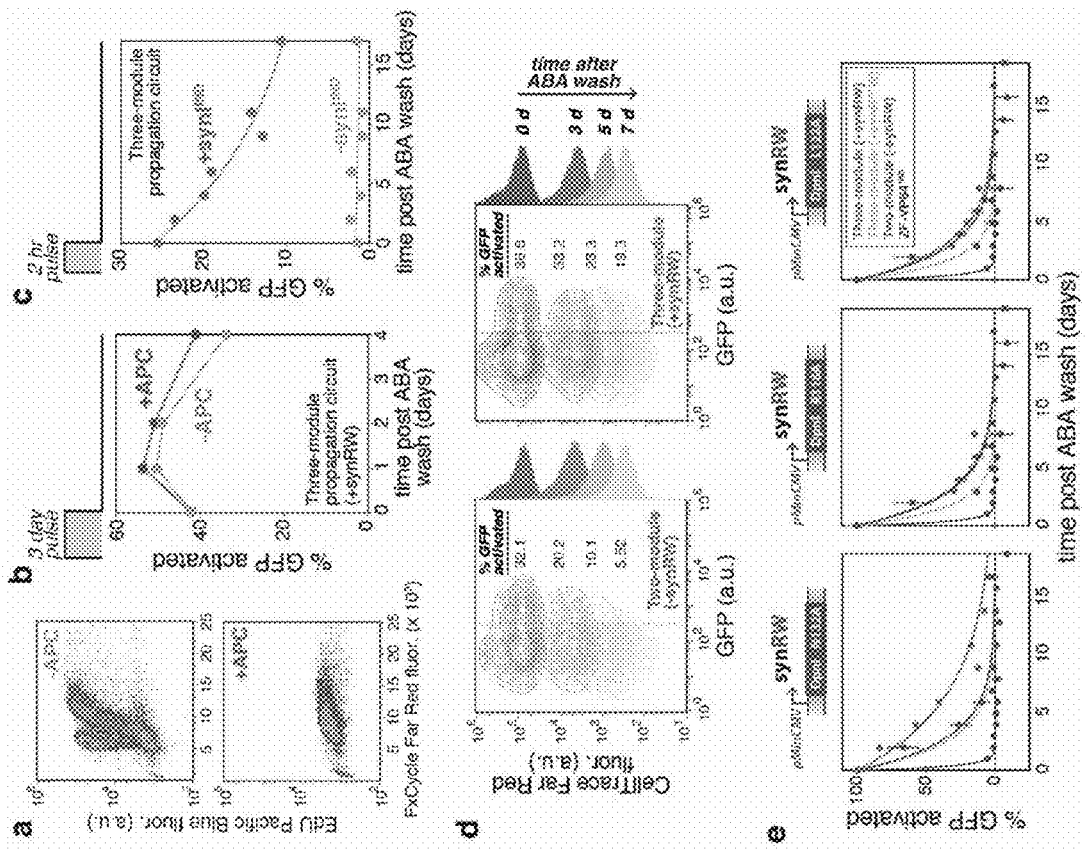
FIGS. 21A-21E demonstrate characterization of epigenetic memory by three-module, synthetic read-write circuits.

It was next explored whether the three-module propagation circuit described herein could transform this 'passive', cell division-coupled persistence into a more durable memory. Cells were subjected to a short pulse of ABA and the percentage of activated cells following removal of ABA was tracked for a total of 20 days (FIG. 11D). The propagation circuit described herein led to higher levels of maintenance of GFP activated cells (dark purple), extending the decay time significantly beyond ZF-VP64$^{IND}$ (grey) and the two-module circuit lacking synRW (green), which was fully lost by 8 days. Notably, with the three-module circuit, approximately half of the cellular population remained GFP-active for ~10 generations. To ensure this was not simply the result of a Dam dosage effect (by addition of synRW module), but indeed dependent on the RW mechanism, a control circuit in which the synRW RD was replaced with mCherry (synR$^{NT}$W) was also tested. This abolished memory, returning the deactivation phase to two-module circuit levels (−synRW, light purple). Memory conferred by the circuit described herein was able to match GFP maintenance resulting from blocking DNA replication with APC, and circuit function was dependent on initiation by the synI$^{IND}$ module (FIGS. 21B, 21C). Additionally, cells stably expressing the propagation circuit were actively dividing and transmitting the epigenetic state to progeny, not simply slowing/halting cell growth (FIG. 21D). Taken together, as demonstrated herein, the duration of a transcriptional state can be synthetically tuned by combining m6A-based operations. These ranged from (1) highly transient states driven by canonical TF recruitment, to (2) passive, cell division-coupled persistence by a two-module circuit that deposits and recognizes m6A, and finally (3) long-term epigenetic memory induced by a three-module propagation circuit (FIG. 11E).

Accordingly, as described herein, an integrated toolkit for programming a set of distinct chromatin operations using the m6A modification in human cells has been developed. These modules can be combined to engineer and explore an array of complex, chromatin-based regulatory behaviors, such as transcriptional logic, spatial propagation and epigenetic memory. As shown herein, self-perpetuating epigenetic functions can be engineered de novo, without reliance on endogenous mechanisms, using regulatory circuits that operate at the level of chromatin. These and other tools for manipulating chromatin expand the synthetic biology toolkit, and provide new means for engineering control of cellular memory states[33], beyond using canonical TF-based feedback[34]. Moreover, these tools provide powerful ways to record and readout information, such as lineage information and event histories[35], in mammalian systems, but without making irreversible changes to the genomic sequence. To that end, these synthetic operations can also be applied at endogenous genomic loci and used to modify and regulate their function. Finally, the toolkit described herein can include other operations, such as erasing, and other modifications to create a larger, more complex chromatin language with which to engineer biological systems.

Materials and Methods
Cloning and Plasmid Construction

Plasmid constructs used herein are listed in Table 1 and their designs described in FIG. 12. All constructs were constructed using standard molecular biology techniques and Gibson isothermal assembly. Donor plasmids for CRISPR/Cas9-induced reporter knock-in were constructed by PCR and subsequent Gibson assembly of components into the pCAGEN mammalian expression vector (Addgene 1160), digested with SalI/HindIII. Donor plasmids for lentiviral integration were constructed by PCR and subsequent Gibson assembly of components into pFUGW (Addgene 14883), digested with PacI/XhoI. During cloning, plasmids were transformed and prepped in *E. coli* TOP10 (Thermo Fisher Scientific). After sequence-verification, final reporter vectors were transformed and propagated in the dam-Idcm-strain, *E. coli* K12 ER2925 (NEB).

Cell Culture and Transfection

The background cell line for all experiments in the studies described herein was the 293FT cell line (Thermo Fisher Scientific). Cells were cultured in Dulbecco's modified Eagle's medium with L-Glutamine, 4.5 g/L Glucose and Sodium Pyruvate (DMEM, Thermo Fisher Scientific) supplemented with 10% Tet-system approved fetal bovine serum (FBS, Clontech), 1% GlutaMAX supplement (Thermo Fisher Scientific), 1% MEM Non-Essential Amino Acids (NEAA, Thermo Fisher Scientific) solution and 1% penicillin-streptomycin (Thermo Fisher Scientific). Cells were split every 3 days, and maintained at 37° C. and 5% $CO_2$ in a humidified incubator.

For all transient transfection experiments, plasmid constructs (FIG. 12) were transfected into indicated stable cell lines using polyethylenimine (PEI, 7.5 mM linear PEI stock, nitrogen/phosophorus ratio of 20, Polysciences). 60,000 cells were plated in 48-well plates and transfected the following day with a total of 200-300 ng DNA, including a pCAG-iRFP720 (Table 1) transfection control plasmid. Cells were collected and prepared for either flow cytometry or qPCR analysis 3 days after transfection, unless otherwise noted.

Cell Line Generation

Cell lines used in the studies described herein are listed in Table 2, and were generated by genome-integrating constructs into the 293FT cell line. Reporter lines were generated by site-specific integration of reporter constructs (FIG. 12) using CRISPR/Cas9-mediated homologous recombination into the AAVS1 (PPP1R2C) locus as follows: 60,000 cells were plated in a 48-well plate and co-transfected the following day with 70 ng of gRNA_AAVS1-T2 plasmid (Addgene 41820), 70 ng of VP12 humanSpCas9-Hf1 plasmid (Addgene 72247), and 175 ng of donor reporter plasmid using PEI. Donor reporter plasmids contain flanking arms homologous to the AAVS1 locus, a puromycin resistance cassette, and constitutive mCherry expression (FIG. 12). After transfection, cells were cultured in 2 μg/mL puromycin selection for at least 2 weeks with splitting 1:10 every 3 days, then monoclonal populations for each reporter cell line were isolated by limiting dilution in 96-well plates.

All other stable lines were generated by lentiviral integration of indicated constructs (encoding synI, synR, synRW modules and/or respective controls) into specific reporter lines. Lentivirus was produced by PEI co-transfection of 293FT cells with the donor plasmid, along with packaging vectors pCMVR8.74 (Addgene 22036), pAdVAntage (Promega), and pMD2.G (Addgene 12259). Virus was harvested with centrifugation (300 g, 5 min) and was added/incubated into specific reporter lines for three days, followed by selection in appropriate selection media: blasticidin (10 μg/ml), zeocin (100 μg/ml), and/or hygromycin (200 μg/ml).

m6A-qPCR Assay for Measuring Adenine Methylation

Figures 13A, 13B, 13C:
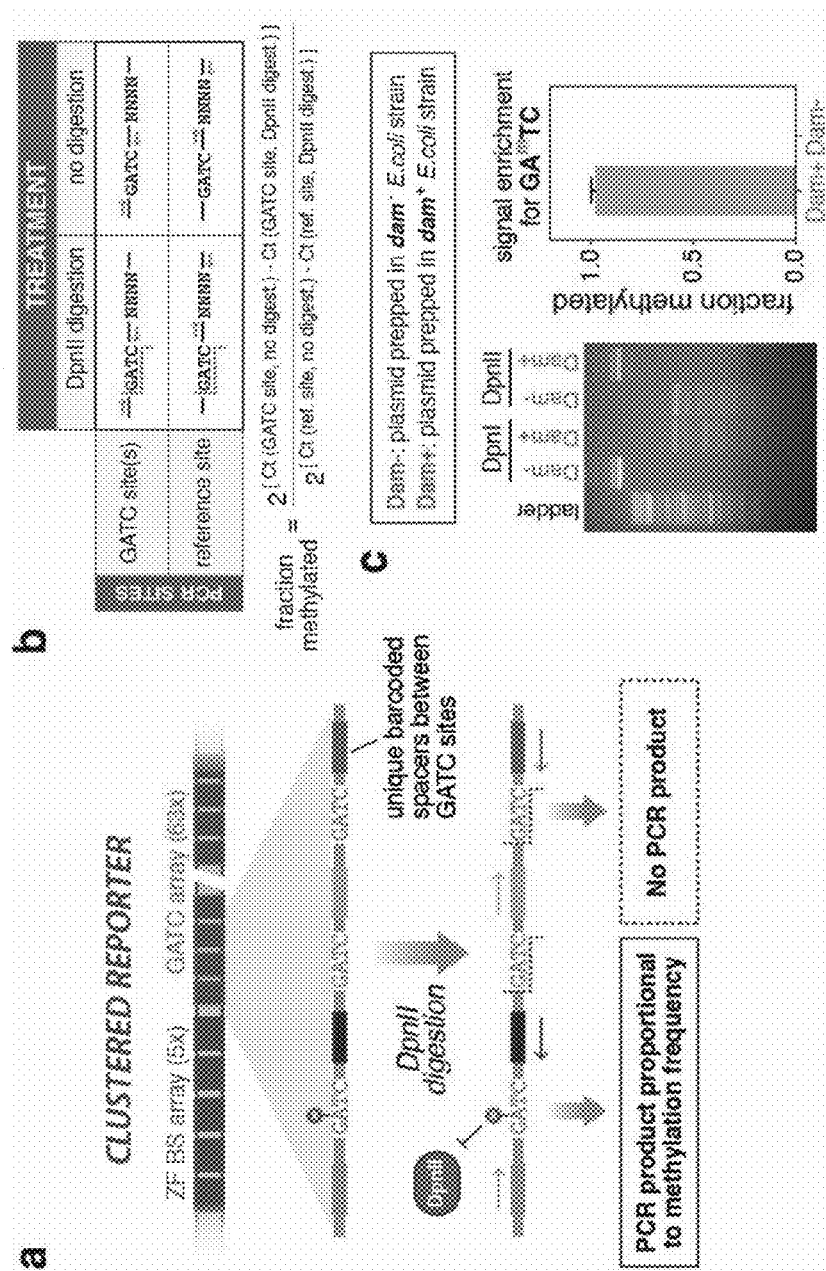
FIGS. 13A-13C demonstrate methods for quantifying DNA adenine methylation (m6A).

A previously described qPCR-based assay was adapted to quantitatively measure adenine methylation at specific genomic sequences/loci[20]. To obtain fraction methylated values at a GATC site(s) (reported throughout this paper), the assay was used to calculate the ratio of amplified DNA, protected from DpnII digestion, for a GATC site(s) of interest relative to a non-GATC reference site, which serves as an internal control to account for variation in DNA amount in each sample (FIGS. 13A-13C). First, total genomic DNA (gDNA) was isolated using a DNeasy Blood and Tissue Kit (Qiagen) according to the manufacturer's instructions (with addition of 4 μL of 100 mg/mL RNase A), eluting in 300 μL elution buffer. A 35 μL aliquot of the resulting gDNA was incubated for 16 hr at 37° C. with or without 2 units of DpnII (NEB), followed by a 20 min heat inactivation at 65° C. Next, four qPCR reactions were prepared to amplify: (1) DpnII-digested GATC site(s), (2) undigested GATC site(s), (3) DpnII-digested reference site, (4) undigested reference site (FIG. 23B). Specifically, qPCR reactions using a 1:10 dilution of the digested gDNA samples were prepared using LightCycler 480 SYBR Green I Master Kit (Roche) according to the manufacturer's instruction. qPCR reactions were performed on a LightCycler 480 instrument II (Roche) with a total reaction volume of 20 µL (5 µL of DNA, 0.5 µM of forward primer, 0.5 µM of reverse primer, 10 µL of 2×SYBR Green Master Mix), using the following cycle conditions: (i) pre-incubation: 95° C. for 10 min; (ii) amplification (45 cycles): 95° C. for 10 s, [annealing temperature] for 20 s, 72° C. for [extension time]; (iii) melting curve: 95° C. for 5 s, 65° C. for 1 min, 97° C. at ramp rate 0.11° C./s; (iv) cooling: 40° C. for 10 s. PCR primer sequences (listed in Table 3) were designed to flank the GATC site of interest or reference site. Annealing temperatures and extension times for specific primer sets are also listed in Table 3. Fraction methylated is then computed from the resulting qPCR Ct values using the ΔΔCt method/ equation shown in FIG. 23B.

Figures 14A, 14B, 14C, 14D:
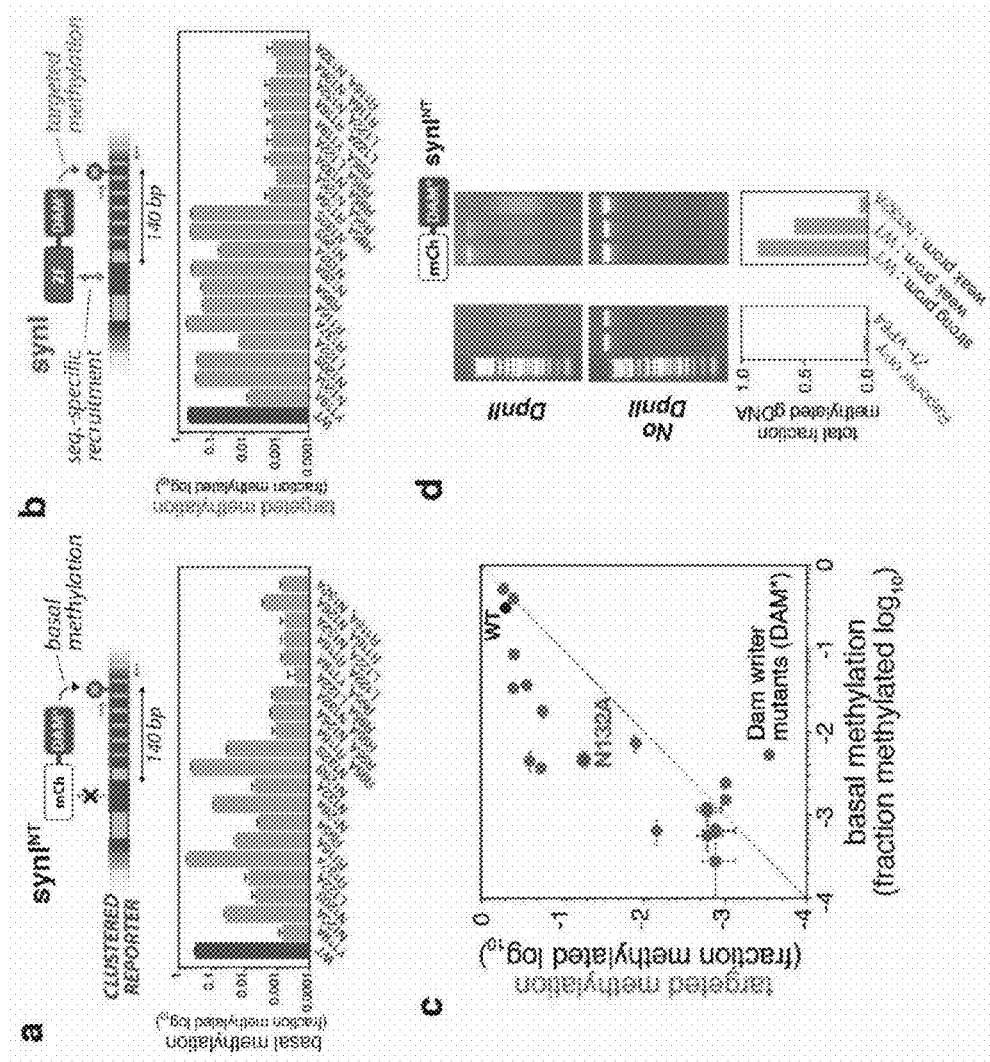
FIGS. 14A-14D demonstrate characterization of de novo m6A establishment by library of synI factors.
Figures 15A, 15B, 15C, 15D:
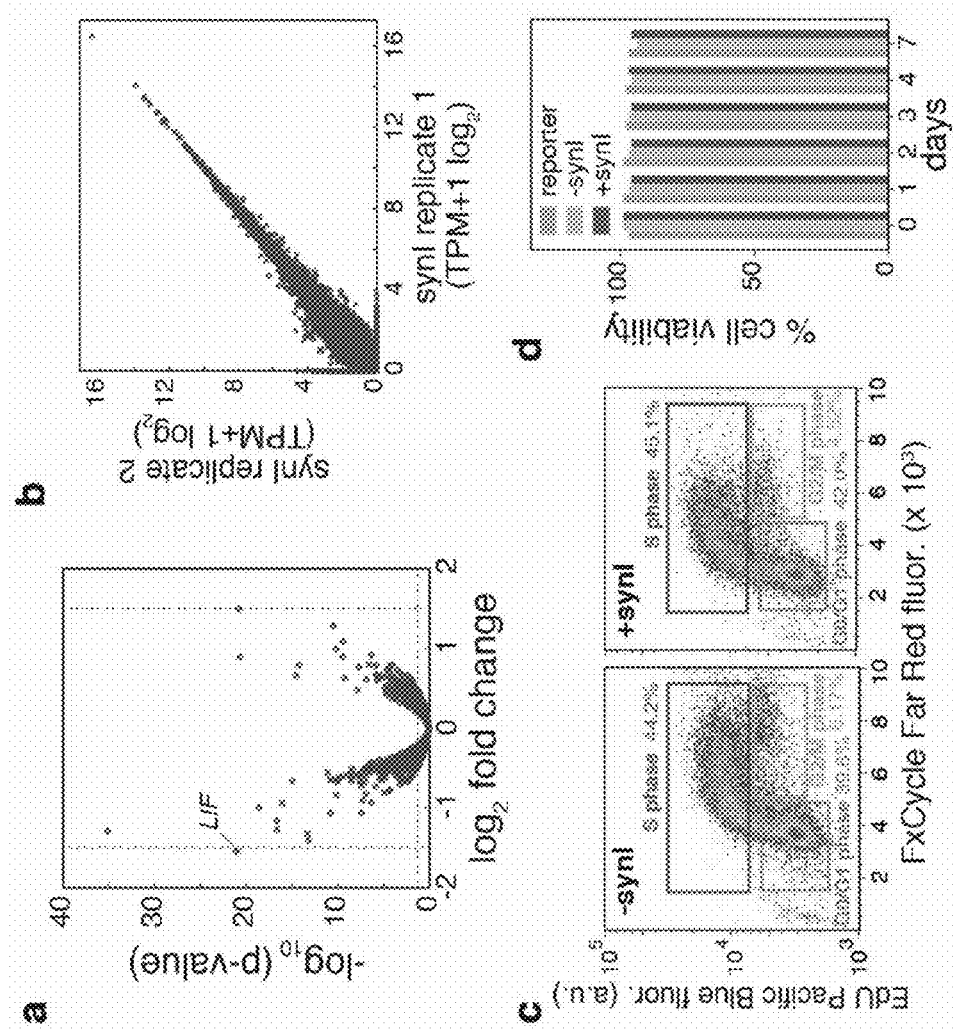
FIGS. 15A-15D demonstrate expression of synI has minimal effect on the transcriptome, cell cycle, and cell viability.

To obtain the level of ZF-specific enrichment in m6A ("m6A enrichment" in FIG. 8C), fraction methylation induced by synI at a GATC site in the locus of interest was measured using the m6A-qPCR assay, and normalized to basal methylation induced by Dam mutant not fused to the ZF (synI$^{IND}$, mCherry-Dam fusion) (FIGS. 14A, 14B).

Flow Cytometry

Figures 17A, 17B, 17C, 17D, 17E, 17F:
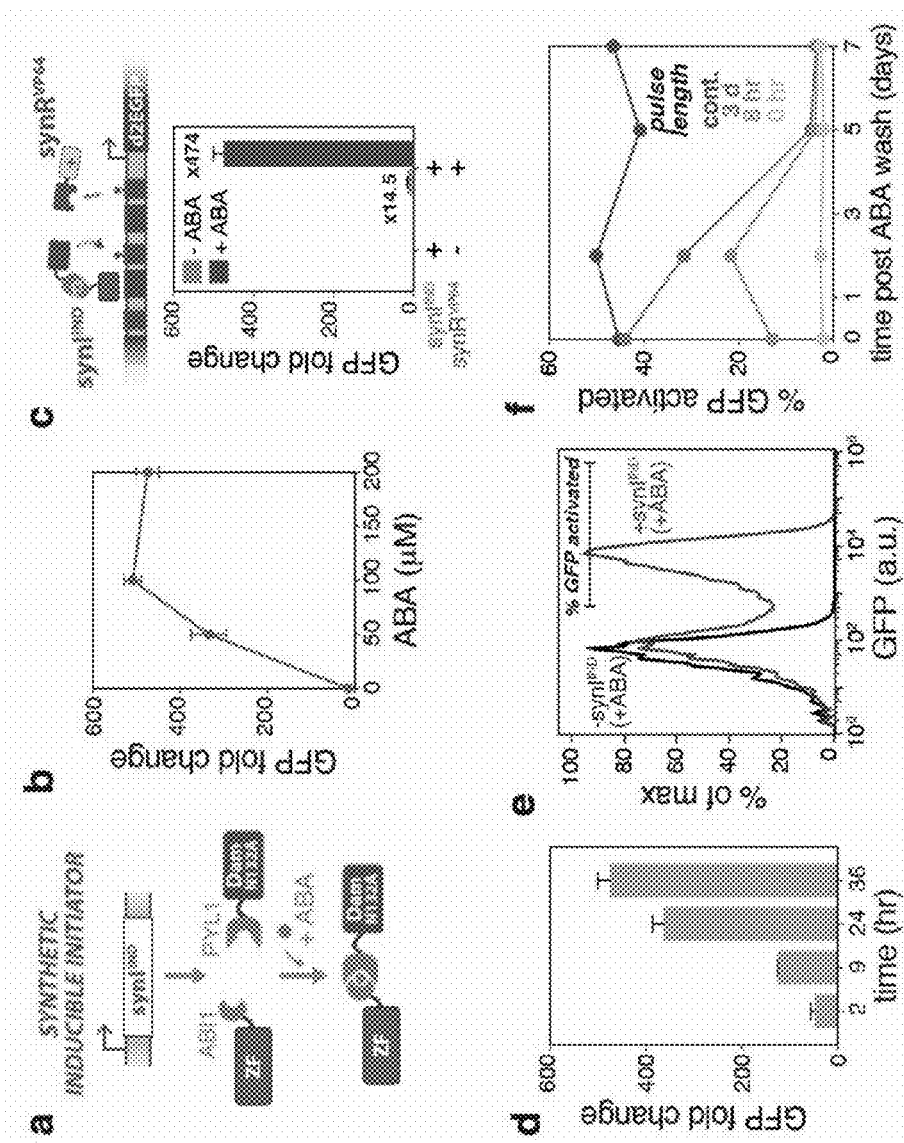
FIGS. 17A-17F demonstrate design and characterization of a small molecule inducible synI (synI$^{IND}$).

Flow cytometry measurements were performed using an Attune NxT Flow Cytometer (Thermo Fisher Scientific) equipped with a high-throughput auto-sampler. Typically, 50,000 or 70,000 events were acquired for transient transfection or stable cell line experiments, respectively. Cells were gated by forward (FSC) and side scatter (SSC) distributions, and either iRFP or mCherry expression for transfection- or integration-positive populations, respectively. For experiments with transient transfection of synI/synR modules (FIGS. 9A-9C), geometric means of the GFP fluorescence distributions were calculated using FLOWJO (Treestar Software). GFP fold change was then calculated by normalizing mean GFP intensity to reporter-only controls, unless otherwise noted. For spreading and memory experiments (with integrated constructs), the percentage of GFP activated cells was quantified using a GFP+gate that contains ~0.5-1% of negative control cells (FIG. 17E). Flow cytometer laser/filter configurations used in this study were: Click-iT Plus Edu Pacific Blue (405 nm laser, 440/50 emission filter), EGFP (488 nm, 510/10), mCherry (561 nm, 615/25), FxCycle Far Red or CellTrace Far Red (638 nm, 670/14), iRFP-720 (638 nm, 720/30).

Cell Cycle Assay

Cells cultured for 3 days with or without 200 µM abscisic acid (ABA, Sigma Aldrich) were labeled with Click-iT EdU Pacific Blue (Click-iT Plus EdU Pacific Blue Flow Cytometry Assay Kit, Thermo Fisher Scientific) to monitor DNA replication and FxCycle Far Red Stain (Thermo Fisher Scientific) to measure DNA content. Labeling was performed according to the manufacturers' instructions, with a 1.5 hr incubation in 10 µM EdU, and 30 min additional incubation with 200 nM FxCycle Far Red Stain and µL of RNaseA (100 mg/mL). Cells were analyzed using flow cytometry.

RNA Sequencing

RNA-seq measurements were performed on two biological replicates per experimental condition. Total RNA was purified from ~1 million cells using the RNEASY PLUS Mini Kit (Qiagen) and QIASHREDDER (Qiagen), according to manufacturer's instructions, three days following transfection. Sequencing libraries were prepared at the Tufts University Core Facility (TUCF Genomics) using the TRUSEQ Stranded mRNA Library Prep Kit (Illumina). 50-bp single-end reads were sequenced on an Illumina HiSeq 2500.

DNA sequences for synthetic constructs (reporter, synI, synR, ZF-VP64) were appended to the human UCSC genome (version hg19), and genome indices were built using the Bowtie 2 software (found on the world wide web at bowtie-bio.sourceforge.net/bowtie2/index.shtml). Sequencing reads were aligned to this indexed genome using the TopHat software (found on the world wide web at ccb.jhu.edu/software/tophat/index.shtml), and the mapped reads were counted for genomic features using featureCounts (found on the worldwide web at bioinf.wehi.edu.au/featureCounts/). Differential expression analysis was performed in R using the DESeq2 analysis package. Multiple hypothesis correction was performed using the Benjamini-Hochberg procedure with a FDR of <1%.

Screen for Spatial Propagation

A phenotypic screen was designed that allows for identification of three-module, read-write (RW) circuit designs that mediate spatial propagation behaviors. Specifically, synRW constructs were identified that, when coupled with synI$^{IND}$ and synR modules, can propagate m6A modifications across a domain in a manner that is dependent on m6A nucleation.

Generation of synRW Module Library

A synRW module library was created by varying two biochemical properties: expression level and Dam writer activity. To vary expression level, synRW expression was placed under the control of two promoters of different strength: pMinCMV (weak) and pUBC (strong) (FIG. 18B). To vary writer activity, we used a series of Dam mutants, comprising a range of methylation activity (FIGS. 10B, 12). Most of these mutations target residues responsible for mediating DNA phosphate group contact, either within or flanking the GATC sequence, which are known to affect the biochemical activity of the molecule[1,2]. In total, this collection represented 11 single residue mutants and 9 double residue mutants, along with WT Dam. The DpnI reader domain affinity represents another potential, tunable biochemical property of the module; however, it was chosen to keep this reader domain fixed across the library because (1) less has been done to identify mutants and characterize their biochemical properties (relative to Dam) and (2) it was desired to maintain a manageable library size to transform, culture, and assay in arrayed format.

Gibson isothermal assembly was used to construct the library, and then cloned the collection into a lentiviral vector (FIG. 12).

Screen Design

To identify three-module synRW circuits that can drive spatial propagation, a phenotypic screen in Clustered Reporter cell lines was devised. The screen leverages the long GATC domain (~1.5 kb) that separates the nucleation site (ZF BS array) from the reporter gene (FIG. 10B). Devoid of a mechanism for propagating m6A across this domain, reporter cells stably expressing the two-module (synI$^{IND}$/synR$^{VP64}$) system do not activate the reporter (FIG. 18A), as marks nucleated at the ZF BS array are too distal from the promoter to allow synR transcriptional regulation. The synRW library in these cells was therefore screened for candidates that lead to reporter activation (+synI$^{IND}$, FIG. 10B), as well as in cells lacking synI$^{IND}$ to screen out spurious cases for which downstream reporter activation is independent of m6A nucleation (−synI$^{IND}$, FIG. 10B). synRW constructs emerging from this screen represent promising candidates as the basis of a three-module system that enables nucleation-induced spatial propagation.

To perform the screen, 100 ng of each synRW construct was transfected (and 50 ng of pCAG-iRFP720 transfection marker) into two cell lines (60,000 cells, in triplicates): (1) Clustered Reporter cells stably expressing the two-module (synI$^{IND}$/synR$^{VP64}$) system, and (2) Clustered Reporter cells stably expressing only synR$^{VP64}$. Cells triggered at the same time (6 hr after transfection) and induced continuously thereafter with 200 µM of ABA were harvested 4 days after transfection, whereupon half of the cells were assayed for GFP activation by flow cytometry (FIG. 10B) and the remaining half collected for potential m6A-qPCR analysis of methylation profiles.

Screen Analysis

To examine screen results, define thresholds and guide circuit designs, hierarchical cluster analysis was performed on the GFP expression patterns (similarity in % GFP activated data, treating each replicate individually; heatmap.2 function in R). The unbiased analysis distinguished −synI$^{IND}$ from +synI$^{IND}$ cells (vertical dendrogram not shown in FIG. 10B). The analysis also revealed a number of interesting features. Library members divided into two parental clusters: one with strong GFP activation in the +synI$^{IND}$ case (top) and the other with weak or no GFP activation (bottom) (FIG. 10B). These clusters were used to define a threshold of circuits exhibiting functional (top) vs. non-functional (bottom) propagation phenotypes, with the −synRW control circuit occupying the latter.

Examining molecular components within these clusters, it was founf that the non-functional cluster possessed all the Dam double mutants (as well as WT Dam), whereas the functional cluster was composed entirely of Dam single mutants. These results indicate that methylation activity of the synRW is a key factor in the design of synthetic propagation circuits. The two tested promoters were scattered across parental and sub clusters. The lack of significant promoter clustering indicates that synRW expression level differences (at least among those tested here) do not significantly affect phenotypic outcomes. If this were the case, then reader-mediated activation of the reporter by synR$^{VP64}$ would also be insensitive to promoter expression levels. To test this, a separate experiment was performed with the two-module system, in which expression of the synR$^{VP64}$ module was placed under the control of two promoters: weak pMinCMV and strong pUBC. Similar levels of GFP activated cells were found for both synR$^{VP64}$ expression constructs (FIG. 18B).

The unbiased analysis of the propagation screen revealed a strong clustering of circuits based on synRW Dam writer mutants (FIG. 10B). To further examine the relationship between writer methylation activity and the results of the screen, a quantitative metric ws defined to score propagation propensity for synRW candidates: "expt. spreading score" is computed as the difference (A) in % GFP activated for cells with and without synI$^{IND}$ (FIGS. 10B, 10C). Larger spreading scores correspond to synRW members that are dependent on synI$^{IND}$ nucleation to drive high levels of reporter activation. In FIG. 10C, the spreading score for each synRW library member is plotted as a function of its Dam basal methylation activity, as previously measured (FIGS. 14A, 14C). Note that in FIG. 10C, the average of both pMinCMV and pUBC-driven synRW modules for respective Dam mutants are plotted, since results were generally insensitive to promoter (the full library can be found in FIG. 19D). From this analysis, it was found that intermediate methylation activity is an important design feature for a synRW module in enabling nucleation-dependent spreading phenotypes by these circuits.

Figures 19A, 19B, 19C:
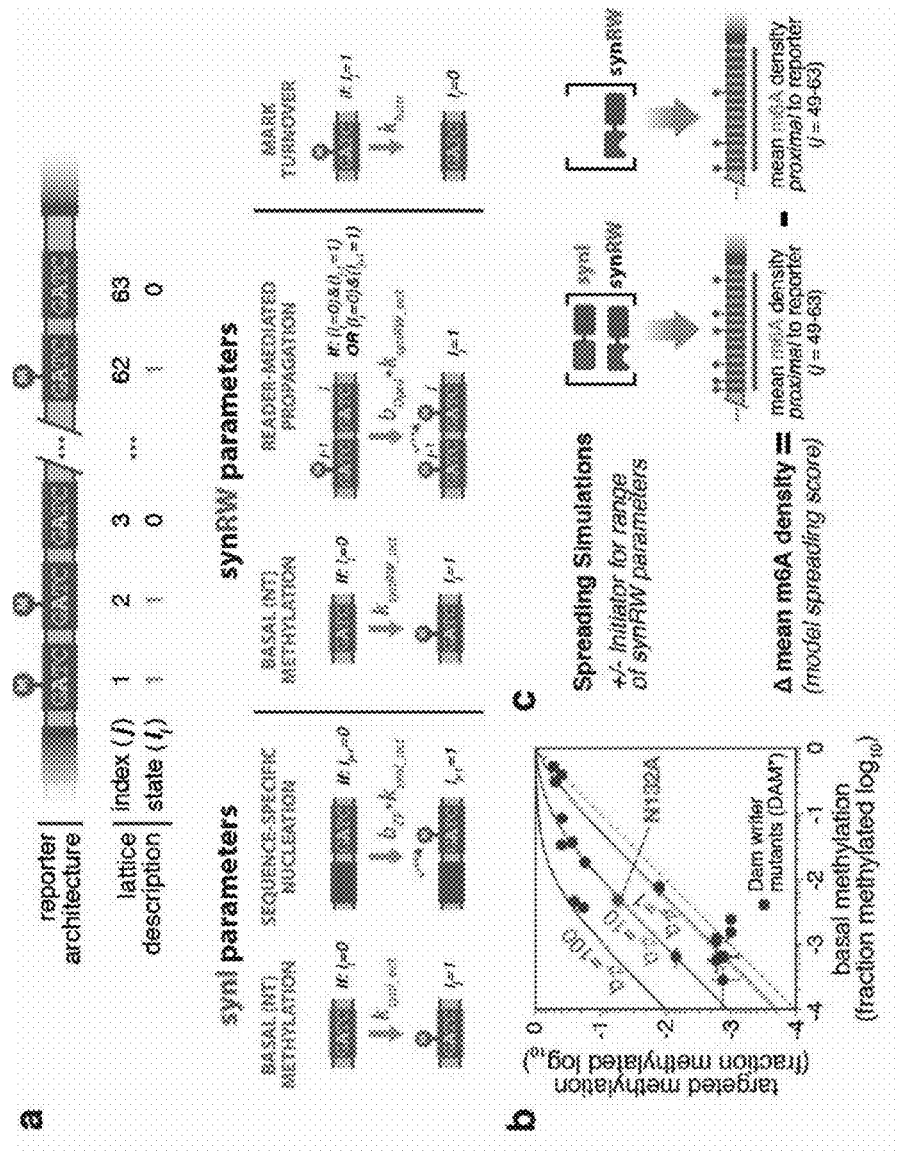
FIGS. 19A-19G demonstrate a model of m6A spatial dynamics.
Figures 19D, 19E, 19F, 19G:
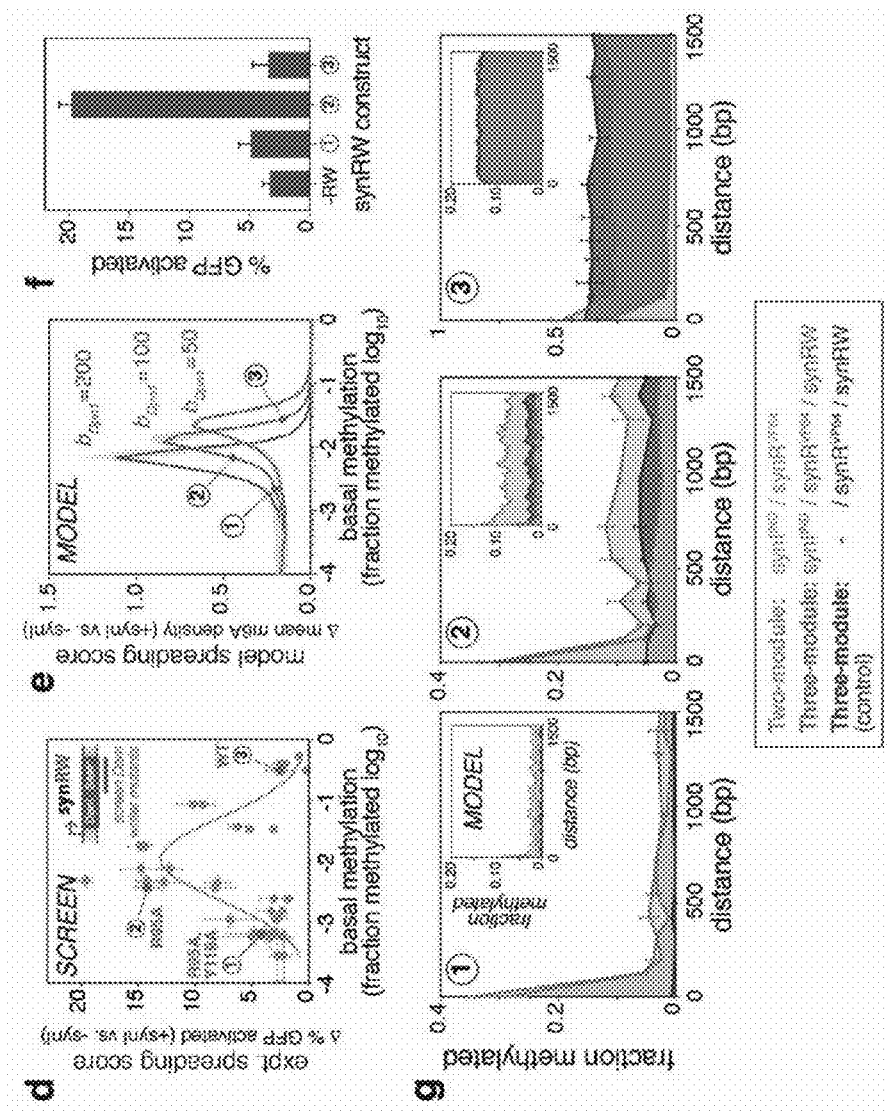
Figures 20A, 20B, 20C:
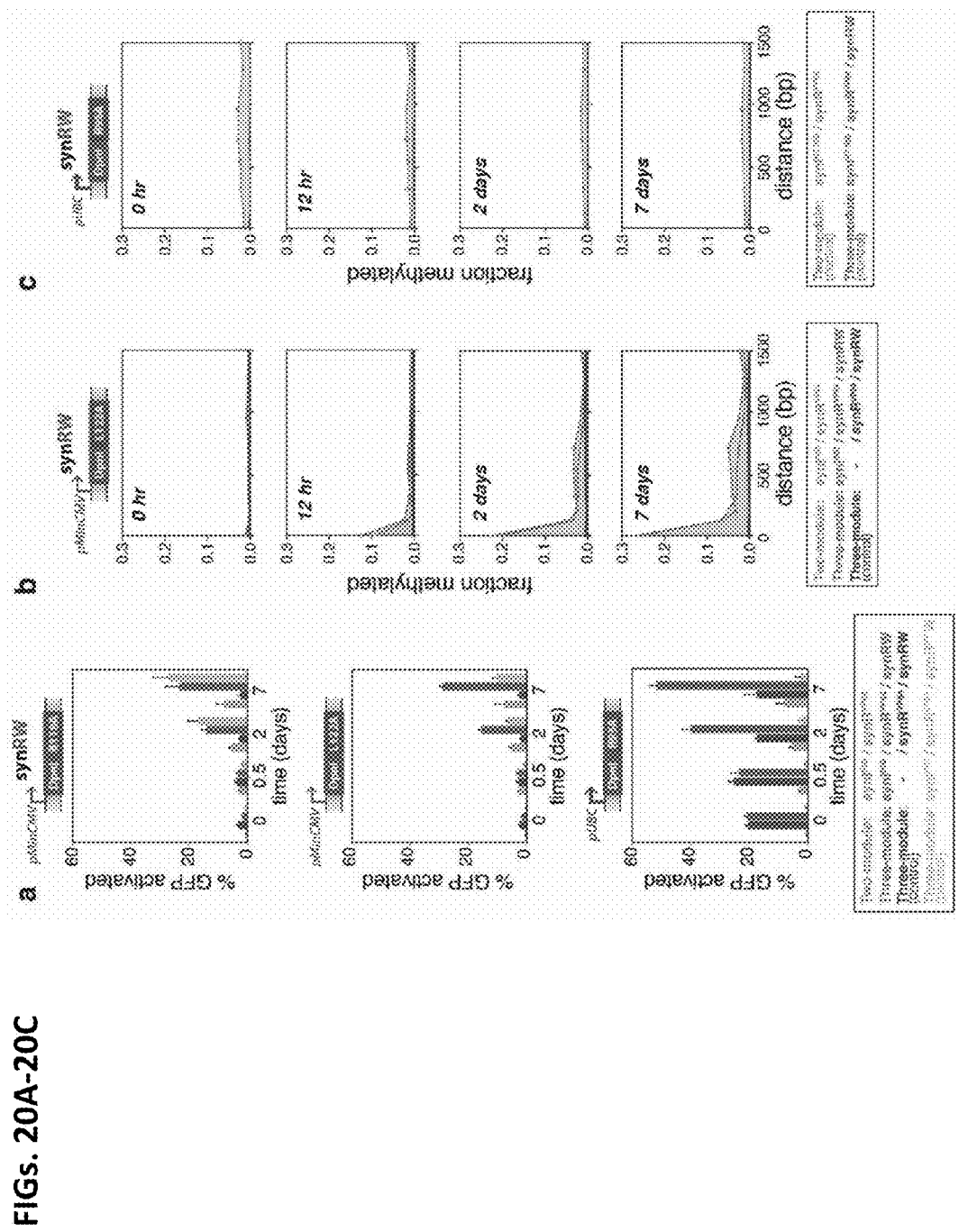
FIGS. 20A-20C demonstrate characterization and controls for propagation by three-module, synthetic read-write circuits.

Three synRW constructs were selected, representing low, intermediate and high Dam writer activity, to further investigate (FIGS. 19D-19G). The corresponding m6A profiles generated at the Clustered Reporter in cells that were transfected with or without the synRW module were measured (see Methods). A low-activity synRW module produced no enrichment in m6A across the promoter over control cells lacking synRW (FIG. 19G, left). A high-activity synRW module, on the other hand, led to significantly higher levels of m6A over the −synRW case; however, this high basal writer activity came at a cost, as m6A levels were enriched in cells with or without initiation (FIG. 19G, right). It was thought that the corresponding low percentage of reporter-activated cells (FIG. 19F) is likely a result of global, off-target m6A enrichment by the high-activity synRW module, similar to what was observed with high-activity synI factors, which could serve to titrate synR factors away from the reporter. Finally, profiles measured for the intermediate-activity synRW module showed evidence for an enlarged m6A domain in cells expressing both synI$^{IND}$ and synRW (FIG. 19G, middle). These results further validate the "spreading score" metric described herein as a useful phenotypic surrogate for identifying spatial propagation behaviors.

Model of m6A Spatial Dynamics

Despite the molecular complexities inherent in chromatin regulatory systems, previous studies have shown that behaviors like nucleation and propagation of histone modifications along a chromosome can be captured by simple, general models. It was therefore determined whether such models can also be used to capture the spatial propagation of m6A by synthetic RW circuits, providing a general guide for their design and construction.

A previously described chromatin spreading model[4] was adapted in order to explore how the properties of synI and synRW affect m6A spatial dynamics. The array of GATC sites in the Clustered Reporter was modeled as a discrete, one-dimensional lattice with 63 sites (FIGS. 19A-19G). Each position (j) on the lattice ($I_j$) corresponds to a GATC site on the promoter, where methylated and unmethylated states are denoted by values of $I_j=1$ and $I_j=0$, respectively (FIG. 19A). Four reactions govern this model: basal (non-targeted) methylation, sequence-specific nucleation, reader-mediated propagation, and mark turnover. These reactions were implemented with the following rules:

(1) Basal methylation by synI or synRW occurs at a rate $k_{synI\_act}$ or $k_{syncRW\_act}$, respectively, to convert any unmethylated GATC site ($I_j=0$) to methylated ($I_j=1$).

(2) Sequence-specific nucleation by synI occurs at a rate $b_{ZF} \cdot k_{synI\_act}$ to convert the first lattice site from unmethylated ($I_j=0$) to methylated ($I_j=1$). $k_{synI\_act}$ is the basal methylation rate of the synI Dam writer domain, while $b_{ZF}$ serves as a specificity multiplier to increase the methylation frequency by synI at the nucleation site.

(3) Reader-mediated propagation by synRW occurs at a rate $b_{Dpnl} \cdot k_{synRW\_act}$ to convert unmarked sites ($I_j=0$) to methylated, if any neighboring GATC sites are marked ($I_{j-1}=1$ or $I_{j-1}=1$). $k_{synRW\_act}$ is the basal methylation rate of the synRW Dam writer domain, while $b_{Dpnl}$ serves as a specificity multiplier to increase the methylation frequency of unmarked sites adjacent to marked ones.

(4) Mark turnover occurs at rate $k_{turn}$ during which any methylated GATC site ($I_j=1$) can be converted to unmethylated ($I_j=0$).

Model Parameterization

For all simulations, $k_{turn}$ was set to 0.05 hr$^{-1}$ to approximate dilution of m6A modifications by cell division (~20 hr doubling time). In the model, synI activity is described by the non-specific methylation ($k_{synI\_act}$) of each Dam mutant as well as the specificity ($b_{ZF}$) conferred by the ZF domain at the nucleation site ($I_j$). To approximate the range of non-specific methylation activity ($k_{synI\_act}$) values across the Dam library, the following relationship was used:

$$f_{meth\_basal} = \frac{k_{synI\_act}}{k_{turn} + k_{synI\_act}}$$

where $f_{meth\_target}$ is the experimentally obtained values of basal methylation for each Dam mutant (FIG. 14A) and $k_{turn}=0.05$ hr$^{-1}$. It was found that non-specific activity values ranged from $k_{synI\_act}=10^{-6}$ to $10^1$ hr$^{-1}$. Subsequently, to parameterize the ZF specificity multiplier ($b_{ZF}$) for each synI in the library steady-state methylation ($f_{meth}$) was calculated by synI across a range of $k_{synI\_act}$ and $b_{ZF}$ values with the following relationship:

$$f_{meth\_targ} = \frac{k_{synI\_act} + b_{ZF} \cdot k_{synI\_act}}{k_{turn} + k_{synI\_act} + b_{ZF} \cdot k_{synI\_act}}$$

where $f_{meth\_target}$ is the experimentally obtained values of targeted methylation for each Dam mutant (FIG. 14B) and $k_{turn}=0.05$ hr$^{-1}$. It was found that a synI module library is captured by specificity multiplier values, ranging between $b_{ZF}=1-100$ (FIG. 19B). The values of $k_{synI\_act}=5 \cdot 10^{-4}$ hr$^{-1}$ and $b_{ZF}=10$ were chosen, which closely approximated the behavior of the selected synI (Dam N132A) featured in the three-module propagation circuit described herein.

Stochastic Simulations of Spatial Propagation

To model the synRW library screen in FIG. 10B, stochastic simulations of synRW activity were run for a range of $k_{synRW\_act}$ ($10^{-6}$ to $10^1$ hr$^{-1}$ as obtained above for $k_{synI\_act}$) and $b_{Dpn1}$ values, with and without synI. A "model spreading score" was defined to assess m6A propagation from the nucleation site (j=1) for each synRW library member. This was defined as the difference in mean m6A density at the 15 most downstream GATC sites (j=49 to j=63), with and without synI (FIG. 19C). All stochastic simulations were implemented using the Gillespie algorithm and were run to steady-state (t=5000 hr).

It was found that the model spreading score distribution closely resembled the experimental spreading score distribution for $b_{Dpn1}$ values ranging between 50 and 200 (FIGS. 19D, 19E, see also FIG. 10C with $b_{Dpn1}=100$). Moreover, the model results showed a similar relationship between methylation activity of synRW and propagation propensity, where intermediate methylation levels were predicted to yield the highest propensity for propagation. Interestingly, the model also predicted that, if reader specificity could be increased (higher $b_{Dpn1}$), then one could generate synRW factors that drive high levels of propagation with lower writer activity (FIG. 19E).

In general, model-generated m6A spatial profiles agreed well the experimentally measured profiles for the range of synRW constructs demonstrated herein, representing low, intermediate and high Dam writer activity (FIG. 19G). For example, high-activity synRW was predicted to lead to nucleation-independent methylation, while low-activity synRW was predicted to yield weak spreading from the nucleation site. Furthermore, the model captured the dynamics of the growing m6A domain induced by a three-module "propagation circuit" (with $b_{Dpn1}=100$, $k_{synRW\_act}=3.4 \cdot 10^{-4}$ hr$^{-1}$) (FIG. 10D). Taken together, this simple, four-parameter model can effectively capture the essential features of synthetic m6A propagation systems described herein.

In order to increase the predictive power of this model, additional iterations include off-target methylation by synI and synRW (at other genomic loci), as well as incorporating the effect of synR on transcriptional output. Describing these properties can be necessary for predicting targeted reporter activity from the distribution of methylation across the genome.

TABLE 1

Plasmids used herein

| Plasmid | Content | Bacterial selection | Mammalian selection | Plasmid type | Integration | Reference |
|---|---|---|---|---|---|---|
| pCAGEN | Mammalian expression vector for cloning | Amp | | Transient | | pCAGEN; Addgene #11160 |
| pMP15 (pFUGW) | pUBC-EGFP-WPRE | Amp | | Integrating | Lenti | Lois et al., Science 2002; Addgene #14883 |
| pMP56 (pCMVR8.74) | pCMV gag pol tat rev | Amp | | Integrating | Lenti | Addgene #22036 |
| pMP57 | pAdVAntage™ Vector | Amp | | Integrating | Lenti | Promega |
| pMP58 (pMD2.G) | pCMV VSVG | Amp | | Integrating | Lenti | Addgene #12259 |
| pMP73 | pCLPIT-NLS-mCh-Dam (WT) | Amp | Puromycin | Integrating | Retroviral | This study |
| pMP258 | pUBC ZF-VP64 | Amp | | Transient | | This study |
| pMP286 | pMinCMV-EGFP | Amp | | Transient | | This study |
| pMP315 | pUBC-KRAB-NLS-DpnI(aa146-254) | Amp | | Transient | | This study |
| pMP328 | pUBC-HP1aCSD (aa.104-185)-NLS-DpnI(aa146-254) | Amp | | Transient | | This study |

TABLE 1-continued

Plasmids used herein

| Plasmid | Content | Bacterial selection | Mammalian selection | Plasmid type | Integration | Reference |
|---|---|---|---|---|---|---|
| pMP330 | pUBC-KRAB-NLS-ZF | Amp | | Transient | | This study |
| pMP332 | pUBC-HP1aCSD(aa.104-185)-NLS-ZF | Amp | | Transient | | This study |
| pMP380 | pMinCMV-NLS-ZF-Dam (N132A) | Amp | | Transient | | This study |
| pMP461 | gRNA_AAVS1-T2 | Amp | | Integrating | CRISPR; AAVS1 | Mali et al., Science 2013 |
| pMP462 (VP12) | CMV-T7-humanSpCas9-HF1(N497A, R661A, Q695A, Q926A)-NLS-3xFLAG | Amp | | Integrating | CRISPR; AAVS1 | Kleinstiver et al., Nature 2016 |
| pMP472 | Inters. (8XZFBS 14XGATC)-pMinCMV-GFPd2-RbGpA pGK-PuroR-T2A-mCh-BGHpA AAVS1 donor | Amp | Puromycin | Integrating | CRISPR; AAVS1 | This study |
| pMP498 | Clust. (5XZFBS 63XGATC)-pMinCMV-GFPd2-RbGpA pGK-PuroR-T2A-mCh-BGHpA AAVS1 donor | Amp | Puromycin | Integrating | CRISPR; AAVS1 | This study |
| pMP506 | Inters. (8XZFBS 14XGATC)-pCMV-GFPd2-RbGpA pGK-PuroR-T2A-mCh-BGHpA AAVS1 donor | Amp | Puromycin | Integrating | CRISPR; AAVS1 | This study |
| pMP538 | pMinCMV-NLS-ZF-Dam (Y119A) | Amp | | Transient | | This study |
| pMP539 | pMinCMV-NLS-ZF-Dam (N120A) | Amp | | Transient | | This study |
| pMP540 | pMinCMV-NLS-ZF-Dam (N120S) | Amp | | Transient | | This study |
| pMP541 | pMinCMV-NLS-ZF-Dam (L122A) | Amp | | Transient | | This study |
| pMP542 | pMinCMV-NLS-ZF-Dam (R137A) | Amp | | Transient | | This study |
| pMP543 | pMinCMV-NLS-ZF-Dam (R116A) | Amp | | Transient | | This study |
| pMP544 | pMinCMV-NLS-ZF-Dam (R95A) | Amp | | Transient | | This study |
| pMP545 | pMinCMV-NLS-ZF-Dam (N126A) | Amp | | Transient | | This study |
| pMP547 | pMinCMV-NLS-ZF-Dam (N126S) | Amp | | Transient | | This study |
| pMP548 | pMinCMV-NLS-ZF-Dam (N132S) | Amp | | Transient | | This study |
| pMP549 | pMinCMV-NLS-ZF-Dam (R95A, R116A) | Amp | | Transient | | This study |
| pMP550 | pMinCMV-NLS-ZF-Dam (R95A, N126A) | Amp | | Transient | | This study |
| pMP551 | pMinCMV-NLS-ZF-Dam (R95A, N132A) | Amp | | Transient | | This study |
| pMP552 | pMinCMV-NLS-ZF-Dam (R95A, L122A) | Amp | | Transient | | This study |
| pMP553 | pMinCMV-NLS-ZF-Dam (R95A, Y119A) | Amp | | Transient | | This study |
| pMP554 | pMinCMV-NLS-ZF-Dam (L122A, R116A) | Amp | | Transient | | This study |
| pMP555 | pMinCMV-NLS-ZF-Dam (L122A, N132A) | Amp | | Transient | | This study |
| pMP556 | pMinCMV-NLS-ZF-Dam (R116A, N126A) | Amp | | Transient | | This study |
| pMP557 | pMinCMV-NLS-ZF-Dam (R116A, N132A) | Amp | | Transient | | This study |
| pMP558 | pMinCMV-NLS-mCh-Dam (WT) | Amp | | Transient | | This study |
| pMP559 | pMinCMV-NLS-mCh-Dam (Y119A) | Amp | | Transient | | This study |
| pMP560 | pMinCMV-NLS-mCh-Dam (N120A) | Amp | | Transient | | This study |
| pMP561 | pMinCMV-NLS-mCh-Dam (N120S) | Amp | | Transient | | This study |
| pMP562 | pMinCMV-NLS-mCh-Dam (L122A) | Amp | | Transient | | This study |
| pMP563 | pMinCMV-NLS-mCh-Dam (R137A) | Amp | | Transient | | This study |
| pMP564 | pMinCMV-NLS-mCh-Dam (R116A) | Amp | | Transient | | This study |
| pMP565 | pMinCMV-NLS-mCh-Dam (R95A) | Amp | | Transient | | This study |
| pMP566 | pMinCMV-NLS-mCh-Dam (N126A) | Amp | | Transient | | This study |
| pMP567 | pMinCMV-NLS-mCh-Dam (N132A) | Amp | | Transient | | This study |
| pMP568 | pMinCMV-NLS-mCh-Dam (N126S) | Amp | | Transient | | This study |
| pMP569 | pMinCMV-NLS-mCh-Dam (N132S) | Amp | | Transient | | This study |
| pMP570 | pMinCMV-NLS-mCh-Dam (R95A, R116A) | Amp | | Transient | | This study |
| pMP571 | pMinCMV-NLS-mCh-Dam (R95A, N126A) | Amp | | Transient | | This study |
| pMP572 | pMinCMV-NLS-mCh-Dam (R95A, N132A) | Amp | | Transient | | This study |
| pMP573 | pMinCMV-NLS-mCh-Dam (R95A, L122A) | Amp | | Transient | | This study |
| pMP574 | pMinCMV-NLS-mCh-Dam (R95A, Y119A) | Amp | | Transient | | This study |
| pMP575 | pMinCMV-NLS-mCh-Dam (L122A, R116A) | Amp | | Transient | | This study |

TABLE 1-continued

Plasmids used herein

| Plasmid | Content | Bacterial selection | Mammalian selection | Plasmid type | Integration | Reference |
|---|---|---|---|---|---|---|
| pMP576 | pMinCMV-NLS-mCh-Dam (L122A, N132A) | Amp | | Transient | | This study |
| pMP577 | pMinCMV-NLS-mCh-Dam (R116A, N126A) | Amp | | Transient | | This study |
| pMP578 | pMinCMV-NLS-mCh-Dam (R116A, N132A) | Amp | | Transient | | This study |
| pMP596 | pMinCMV-NLS-ZF-Dam (WT) | Amp | | Transient | | This study |
| pMP597 | pMinCMV-NLS-ABI1cs-ZF-NLS-P2A-Dam(N132A)-PYL1cs-HA pGK-BlastR | Amp | Blasticidin | Integrating | Lenti | This study |
| pMP650 | pUBC-DpnI(aa146-254)-VP64-V5 pGK-ZeoR | Amp | Zeocin | Integrating | Lenti | This study |
| pMP696 | pMinCMV-NLS-ABI1cs-mCh-NLS-P2A-Dam(N132A)-PYL1cs-HA pGK-BlastR | Amp | Blasticidin | Integrating | Lenti | This study |
| pMP700 | pMinCMV-DpnI(aa146-254)-VP64-V5 pGK-ZeoR | Amp | Zeocin | Integrating | Lenti | This study |
| pMP710 | pUBC-NLS-ABI1cs-ZF-NLS-P2A-VP64-PYL1cs-HA pGK-BlastR | Amp | Blasticidin | Integrating | Lenti | This study |
| pMP711 | Inters. (8XZFBS 0XGATC)-pMinCMV-GFPd2-RbGpA pGK-PuroR-T2A-mCh-BGHpA AAVS1 donor | Amp | Puromycin | Integrating | CRISPR; AAVS1 | This study |
| pMP900 | pMinCMV-DpnI(aa146-254)-3XFLAG-Dam(WT) pGK-HygroR | Amp | Hygromycin | Integrating | Lenti | This study |
| pMP901 | pMinCMV-DpnI(aa146-254)-3XFLAG-Dam(Y119A) pGK-HygroR | Amp | Hygromycin | Integrating | Lenti | This study |
| pMP902 | pMinCMV-DpnI(aa146-254)-3XFLAG-Dam(N120S) pGK-HygroR | Amp | Hygromycin | Integrating | Lenti | This study |
| pMP903 | pMinCMV-DpnI(aa146-254)-3XFLAG-Dam(L122A) pGK-HygroR | Amp | Hygromycin | Integrating | Lenti | This study |
| pMP904 | pMinCMV-DpnI(aa146-254)-3XFLAG-Dam(R137A) pGK-HygroR | Amp | Hygromycin | Integrating | Lenti | This study |
| pMP905 | pMinCMV-DpnI(aa146-254)-3XFLAG-Dam(R116A) pGK-HygroR | Amp | Hygromycin | Integrating | Lenti | This study |
| pMP906 | pMinCMV-DpnI(aa146-254)-3XFLAG-Dam(R95A) pGK-HygroR | Amp | Hygromycin | Integrating | Lenti | This study |
| pMP907 | pMinCMV-DpnI(aa146-254)-3XFLAG-Dam(N126A) pGK-HygroR | Amp | Hygromycin | Integrating | Lenti | This study |
| pMP908 | pMinCMV-DpnI(aa146-254)-3XFLAG-Dam(N132A) pGK-HygroR | Amp | Hygromycin | Integrating | Lenti | This study |
| pMP909 | pMinCMV-DpnI(aa146-254)-3XFLAG-Dam(N126S) pGK-HygroR | Amp | Hygromycin | Integrating | Lenti | This study |
| pMP910 | pMinCMV-DpnI(aa146-254)-3XFLAG-Dam(N132S) pGK-HygroR | Amp | Hygromycin | Integrating | Lenti | This study |
| pMP911 | pMinCMV-DpnI(aa146-254)-3XFLAG-Dam(R95A, R116A) pGK-HygroR | Amp | Hygromycin | Integrating | Lenti | This study |
| pMP912 | pMinCMV-DpnI(aa146-254)-3XFLAG-Dam(R95A, N126A) pGK-HygroR | Amp | Hygromycin | Integrating | Lenti | This study |
| pMP913 | pMinCMV-DpnI(aa146-254)-3XFLAG-Dam(R95A, N132A) pGK-HygroR | Amp | Hygromycin | Integrating | Lenti | This study |
| pMP914 | pMinCMV-DpnI(aa146-254)-3XFLAG-Dam(R95A, L122A) pGK-HygroR | Amp | Hygromycin | Integrating | Lenti | This study |
| pMP915 | pMinCMV-DpnI(aa146-254)-3XFLAG-Dam(R95A, Y119A) pGK-HygroR | Amp | Hygromycin | Integrating | Lenti | This study |
| pMP916 | pMinCMV-DpnI(aa146-254)-3XFLAG-Dam(L122A, R116A) pGK-HygroR | Amp | Hygromycin | Integrating | Lenti | This study |
| pMP917 | pMinCMV-DpnI(aa146-254)-3XFLAG-Dam(L122A, N132A) pGK-HygroR | Amp | Hygromycin | Integrating | Lenti | This study |

TABLE 1-continued

Plasmids used herein

| Plasmid | Content | Bacterial selection | Mammalian selection | Plasmid type | Integration | Reference |
|---|---|---|---|---|---|---|
| pMP918 | pMinCMV-DpnI(aa146-254)-3XFLAG-Dam(R116A, N126A) pGK-HygroR | Amp | Hygromycin | Integrating | Lenti | This study |
| pMP919 | pMinCMV-DpnI(aa146-254)-3XFLAG-Dam(R116A, N132A) pGK-HygroR | Amp | Hygromycin | Integrating | Lenti | This study |
| pMP920 | pUBC-DpnI(aa146-254)-3XFLAG-Dam(WT) pGK-HygroR | Amp | Hygromycin | Integrating | Lenti | This study |
| pMP921 | pUBC-DpnI(aa146-254)-3XFLAG-Dam(Y119A) pGK-HygroR | Amp | Hygromycin | Integrating | Lenti | This study |
| pMP922 | pUBC-DpnI(aa146-254)-3XFLAG-Dam(N120A) pGK-HygroR | Amp | Hygromycin | Integrating | Lenti | This study |
| pMP923 | pUBC-DpnI(aa146-254)-3XFLAG-Dam(N120S)pGK-HygroR | Amp | Hygromycin | Integrating | Lenti | This study |
| pMP924 | pUBC-DpnI(aa146-254)-3XFLAG-Dam(L122A) pGK-HygroR | Amp | Hygromycin | Integrating | Lenti | This study |
| pMP925 | pUBC-DpnI(aa146-254)-3XFLAG-Dam(R116A) pGK-HygroR | Amp | Hygromycin | Integrating | Lenti | This study |
| pMP926 | pUBC-DpnI(aa146-254)-3XFLAG-Dam(R95A) pGK-HygroR | Amp | Hygromycin | Integrating | Lenti | This study |
| pMP927 | pUBC-DpnI(aa146-254)-3XFLAG-Dam(N126A) pGK-HygroR | Amp | Hygromycin | Integrating | Lenti | This study |
| pMP928 | pUBC-DpnI(aa146-254)-3XFLAG-Dam(N132A) pGK-HygroR | Amp | Hygromycin | Integrating | Lenti | This study |
| pMP929 | pUBC-DpnI(aa146-254)-3XFLAG-Dam(N126S) pGK-HygroR | Amp | Hygromycin | Integrating | Lenti | This study |
| pMP930 | pUBC-DpnI(aa146-254)-3XFLAG-Dam(N132S)pGK-HygroR | Amp | Hygromycin | Integrating | Lenti | This study |
| pMP931 | pUBC-DpnI(aa146-254)-3XFLAG-Dam(R95A, R116A) pGK-HygroR | Amp | Hygromycin | Integrating | Lenti | This study |
| pMP932 | pUBC-DpnI(aa146-254)-3XFLAG-Dam(R95A, N126A) pGK-HygroR | Amp | Hygromycin | Integrating | Lenti | This study |
| pMP933 | pUBC-DpnI(aa146-254)-3XFLAG-Dam(R95A, N132A) pGK-HygroR | Amp | Hygromycin | Integrating | Lenti | This study |
| pMP934 | pUBC-DpnI(aa146-254)-3XFLAG-Dam(R95A, L122A) pGK-HygroR | Amp | Hygromycin | Integrating | Lenti | This study |
| pMP935 | pUBC-DpnI(aa146-254)-3XFLAG-Dam(R95A, Y119A) pGK-HygroR | Amp | Hygromycin | Integrating | Lenti | This study |
| pMP936 | pUBC-DpnI(aa146-254)-3XFLAG-Dam(L122A, R116A) pGK-HygroR | Amp | Hygromycin | Integrating | Lenti | This study |
| pMP937 | pUBC-DpnI(aa146-254)-3XFLAG-Dam(R116A, N126A) pGK-HygroR | Amp | Hygromycin | Integrating | Lenti | This study |
| pMP938 | pUBC-DpnI(aa146-254)-3XFLAG-Dam(R116A, N132A) pGK-HygroR | Amp | Hygromycin | Integrating | Lenti | This study |
| pMP939 | pMinCMV-mCh-3XFLAG-Dam(WT) pGK-HygroR | Amp | Hygromycin | Integrating | Lenti | This study |
| pMP940 | pMinCMV-mCh-3XFLAG-Dam(Y119A) pGK-HygroR | Amp | Hygromycin | Integrating | Lenti | This study |
| pMP941 | pMinCMV-mCh-3XFLAG-Dam(N120A) pGK-HygroR | Amp | Hygromycin | Integrating | Lenti | This study |
| pMP943 | pMinCMV-mCh-3XFLAG-Dam(L122A)pGK-HygroR | Amp | Hygromycin | Integrating | Lenti | This study |
| pMP944 | pMinCMV-mCh-3XFLAG-Dam(R137A) pGK-HygroR | Amp | Hygromycin | Integrating | Lenti | This study |
| pMP945 | pMinCMV-mCh-3XFLAG-Dam(R116A) pGK-HygroR | Amp | Hygromycin | Integrating | Lenti | This study |
| pMP946 | pMinCMV-mCh-3XFLAG-Dam(R95A) pGK-HygroR | Amp | Hygromycin | Integrating | Lenti | This study |
| pMP948 | pMinCMV-mCh-3XFLAG-Dam(N132A) pGK-HygroR | Amp | Hygromycin | Integrating | Lenti | This study |
| pMP949 | pMinCMV-mCh-3XFLAG-Dam(N126S) pGK-HygroR | Amp | Hygromycin | Integrating | Lenti | This study |
| pMP950 | pMinCMV-mCh-3XFLAG-Dam(N132S) pGK-HygroR | Amp | Hygromycin | Integrating | Lenti | This study |
| pMP951 | pMinCMV-mCh-3XFLAG-Dam(R95A, R116A) pGK-HygroR | Amp | Hygromycin | Integrating | Lenti | This study |
| pMP952 | pMinCMV-mCh-3XFLAG-Dam(R95A, N126A) pGK-HygroR | Amp | Hygromycin | Integrating | Lenti | This study |
| pMP953 | pMinCMV-mCh-3XFLAG-Dam(R95A, N132A) pGK-HygroR | Amp | Hygromycin | Integrating | Lenti | This study |
| pMP955 | pMinCMV-mCh-3XFLAG-Dam(R95A, Y119A) pGK-HygroR | Amp | Hygromycin | Integrating | Lenti | This study |
| pMP956 | pMinCMV-mCh-3XFLAG-Dam(L122A, R116A) pGK-HygroR | Amp | Hygromycin | Integrating | Lenti | This study |

TABLE 1-continued

Plasmids used herein

| Plasmid | Content | Bacterial selection | Mammalian selection | Plasmid type | Integration | Reference |
|---|---|---|---|---|---|---|
| pMP957 | pMinCMV-mCh-3XFLAG-Dam(L122A, N132A) pGK-HygroR | Amp | Hygromycin | Integrating | Lenti | This study |
| pMP958 | pMinCMV-mCh-3XFLAG-Dam(R116A, N126A) pGK-HygroR | Amp | Hygromycin | Integrating | Lenti | This study |
| pMP959 | pMinCMV-mCh-3XFLAG-Dam(R116A, N132A) pGK-HygroR | Amp | Hygromycin | Integrating | Lenti | This study |
| pMP961 | pUBC-mCh-3XFLAG-Dam(Y119A) pGK-HygroR | Amp | Hygromycin | Integrating | Lenti | This study |
| pMP966 | pUBC-mCh-3XFLAG-Dam(R116A) pGK-HygroR | Amp | Hygromycin | Integrating | Lenti | This study |
| pMP967 | pUBC-mCh-3XFLAG-Dam(R95A) pGK-HygroR | Amp | Hygromycin | Integrating | Lenti | This study |
| pMP968 | pUBC-mCh-3XFLAG-Dam(N126A) pGK-HygroR | Amp | Hygromycin | Integrating | Lenti | This study |
| pMP969 | pUBC-mCh-3XFLAG-Dam(N132A) pGK-HygroR | Amp | Hygromycin | Integrating | Lenti | This study |
| pMP970 | pUBC-mCh-3XFLAG-Dam(N126S) pGK-HygroR | Amp | Hygromycin | Integrating | Lenti | This study |
| pMP972 | pUBC-mCh-3XFLAG-Dam(R95A, R116A) pGK-HygroR | Amp | Hygromycin | Integrating | Lenti | This study |
| pMP973 | pUBC-mCh-3XFLAG-Dam(R95A, N126A) pGK-HygroR | Amp | Hygromycin | Integrating | Lenti | This study |
| pMP974 | pUBC-mCh-3XFLAG-Dam(R95A, N132A) pGK-HygroR | Amp | Hygromycin | Integrating | Lenti | This study |
| pMP977 | pUBC-mCh-3XFLAG-Dam(L122A, R116A) pGK-HygroR | Amp | Hygromycin | Integrating | Lenti | This study |
| pMP978 | pUBC-mCh-3XFLAG-Dam(L122A, N132A) pGK-HygroR | Amp | Hygromycin | Integrating | Lenti | This study |
| pMP980 | pUBC-mCh-3XFLAG-Dam(R116A, N132A) pGK-HygroR | Amp | Hygromycin | Integrating | Lenti | This study |

TABLE 2

Cell lines used herein

| Cell line | Description | Parental line | Modification | Selection | Integration |
|---|---|---|---|---|---|
| MP151 | Inters. pCMV-GFPd2-RbGpA pGK-PuroR-T2A-mCh-BGHpA (clone #11) | 293FT | pMP506 | Puromycin | AAVS1/CRISPR |
| MP153 | Inters. pMinCMV-GFPd2-RbGpA pGK-PuroR-T2A-mCh-BGHpA (clone #40) | 293FT | pMP472 | Puromycin | AAVS1/CRISPR |
| MP175 | Clust. pMinCMV-GFPd2-RbGpA pGK-PuroR-T2A-mCh-BGHpA (clone #13) | 293FT | pMP498 | Puromycin | AAVS1/CRISPR |
| MP231 | Intrs. pMinCMV Reporter + synI$^{IND}$ | MP153 | pMP597 | Puromycin + Blasticidin | Lenti |
| MP236 | Clust. pMinCMV Reporter + synI$^{IND}$ | MP175 | pMP597 | Puromycin + Blasticidin | Lenti |
| MP243 | Intrs. pMinCMV Reporter + synR$^{VP64}$ | MP153 | pMP650 | Puromycin + Zeocin | Lenti |
| MP244 | Intrs. pMinCMV Reporter + synI$^{IND}$ + synR$^{VP64}$ | MP231 | pMP650 | Puromycin + Blasticidin + Zeocin | Lenti |
| MP252 | Clust. pMinCMV Reporter + synR$^{VP64}$ | MP175 | pMP650 | Puromycin + Zeocin | Lenti |
| MP253 | Clust. pMinCMV Reporter + synI$^{IND}$ + synR$^{VP64}$ | MP236 | pMP650 | Puromycin + Blasticidin + Zeocin | Lenti |
| MP263 | Intrs. pMinCMV Reporter + synI$^{IND\ NT}$ + synR$^{VP64}$ | MP153 | pMP696, pMP650 | Puromycin + Blasticidin + Zeocin | Lenti |
| MP267 | Clust. pMinCMV Reporter + synI$^{IND\ NT}$ + synR$^{VP64}$ | MP175 | pMP696, pMP650 | Puromycin + Blasticidin + Zeocin | Lenti |
| MP422 | Intrs. pMinCMV Reporter + synR$^{VP64}$ + synRW(pUBC-DpnI-Dam(R95A)) | MP243 | pMP926 | Puromycin + Zeocin + Hygromycin | Lenti |
| MP423 | Intrs. pMinCMV Reporter + synI$^{IND}$ + synR$^{VP64}$ + synRW(pUBC-DpnI-Dam(R95A)) | MP244 | pMP926 | Puromycin + Blasticidin + Zeocin + Hygromycin | Lenti |

TABLE 2-continued

Cell lines used herein

| Cell line | Description | Parental line | Modification | Selection | Integration |
|---|---|---|---|---|---|
| MP425 | Intrs. pMinCMV Reporter + synI$^{IND\ NT}$ + synR$^{VP64}$ + synRW(pUBC-Dpnl-Dam(R95A)) | MP263 | pMP926 | Puromycin + Blasticidin + Zeocin + Hygromycin | Lenti |
| MP427 | Clust. pMinCMV Reporter + synR$^{VP64}$ + synRW(pUBC-Dpnl-Dam(R95A)) | MP252 | pMP926 | Puromycin + Zeocin + Hygromycin | Lenti |
| MP428 | Clust. pMinCMV Reporter + synI$^{IND}$ + synR$^{VP64}$ + synRW(pUBC-Dpnl-Dam(R95A)) | MP253 | pMP926 | Puromycin + Blasticidin + Zeocin + Hygromycin | Lenti |
| MP430 | Clust. pMinCMV Reporter + synI$^{IND\ NT}$ + synR$^{VP64}$ + synRW(pUBC-Dpnl-Dam(R95A)) | MP267 | pMP926 | Puromycin + Blasticidin + Zeocin + Hygromycin | Lenti |
| MP440 | Intrs. pMinCMV Reporter + synR$^{VP64}$ + synRW(pUBC-mCh-Dam(R95A)) | MP243 | pMP967 | Puromycin + Zeocin + Hygromycin | Lenti |
| MP441 | Intrs. pMinCMV Reporter + synI$^{IND}$ + synR$^{VP64}$ + synRW(pUBC-mCh-Dam(R95A)) | MP244 | pMP967 | Puromycin + Blasticidin + Zeocin + Hygromycin | Lenti |
| MP443 | Intrs. pMinCMV Reporter + synI$^{IND\ NT}$ + synR$^{VP64}$ + synRW(pUBC-mCh-Dam(R95A)) | MP263 | pMP967 | Puromycin + Blasticidin + Zeocin + Hygromycin | Lenti |
| MP445 | Clust. pMinCMV Reporter + synR$^{VP64}$ + synRW(pUBC-mCh-Dam(R95A)) | MP252 | pMP967 | Puromycin + Zeocin + Hygromycin | Lenti |
| MP446 | Clust. pMinCMV Reporter + synI$^{IND}$ + synR$^{VP64}$ + synRW(pUBC-mCh-Dam(R95A)) | MP253 | pMP967 | Puromycin + Blasticidin + Zeocin + Hygromycin | Lenti |
| MP448 | Clust. pMinCMV Reporter + synI$^{IND\ NT}$ + synR$^{VP64}$ + synRW(pUBC-mCh-Dam(R95A)) | MP267 | pMP967 | Puromycin + Blasticidin + Zeocin + Hygromycin | Lenti |
| MP449 | Intrs. pMinCMV Reporter + synR$^{VP64}$ + synRW(empty) | MP243 | pMP626 | Puromycin + Zeocin + Hygromycin | Lenti |
| MP450 | Intrs. pMinCMV Reporter + synI$^{IND}$ + synR$^{VP64}$ + synRW(empty) | MP244 | pMP626 | Puromycin + Blasticidin + Zeocin + Hygromycin | Lenti |
| MP452 | Intrs. pMinCMV Reporter + synI$^{IND\ NT}$ + synRvP64 + synRW(empty) | MP263 | pMP626 | Puromycin + Blasticidin + Zeocin + Hygromycin | Lenti |
| MP454 | Clust. pMinCMV Reporter + synR$^{VP64}$ + synRW(empty) | MP252 | pMP626 | Puromycin + Zeocin + Hygromycin | Lenti |
| MP455 | Clust. pMinCMV Reporter + synI$^{IND}$ + synR$^{VP64}$ + synRW(empty) | MP253 | pMP626 | Puromycin + Blasticidin + Zeocin + Hygromycin | Lenti |
| MP457 | Clust. pMinCMV Reporter + synI$^{IND\ NT}$ + synRvP64 + synRW(empty) | MP267 | pMP626 | Puromycin + Blasticidin + Zeocin + Hygromycin | Lenti |
| MP466 | Intrs. pMinCMV Reporter + synR$^{VP64}$ + synRW(pMinCMV-Dpnl-Dam(R116A)) | MP243 | pMP905 | Puromycin + Zeocin + Hygromycin | Lenti |
| MP467 | Intrs. pMinCMV Reporter + synI$^{IND}$ + synR$^{VP64}$ + synRW(pMinCMV-Dpnl-Dam(R116A)) | MP244 | pMP905 | Puromycin + Blasticidin + Zeocin + Hygromycin | Lenti |
| MP469 | Intrs. pMinCMV Reporter + synI$^{IND\ NT}$ + synR$^{VP64}$ + synRW(pMinCMV-Dpnl-Dam(R116A)) | MP263 | pMP905 | Puromycin + Blasticidin + Zeocin + Hygromycin | Lenti |
| MP471 | Clust. pMinCMV Reporter + synR$^{VP64}$ + synRW(pMinCMV-Dpnl-Dam(R116A)) | MP252 | pMP905 | Puromycin + Zeocin + Hygromycin | Lenti |

TABLE 2-continued

Cell lines used herein

| Cell line | Description | Parental line | Modification | Selection | Integration |
|---|---|---|---|---|---|
| MP472 | Clust. pMinCMV Reporter + synI$^{IND}$ + synR$^{VP64}$ + synRW(pMinCMV-Dpnl-Dam(R116A)) | MP253 | pMP905 | Puromycin + Blasticidin + Zeocin + Hygromycin | Lenti |
| MP474 | Clust. pMinCMV Reporter + synI$^{IND\ NT}$ + synR$^{VP64}$ + synRW(pMinCMV-Dpnl-Dam(R116A)) | MP267 | pMP905 | Puromycin + Blasticidin + Zeocin + Hygromycin | Lenti |
| MP484 | Intrs. pMinCMV Reporter + synR$^{VP64}$ + synRW(pMinCMV-mCh-Dam(R116A)) | MP243 | pMP945 | Puromycin + Zeocin + Hygromycin | Lenti |
| MP485 | Intrs. pMinCMV Reporter + synI$^{IND}$ + synR$^{VP64}$ + synRW(pMinCMV-mCh-Dam(R116A)) | MP244 | pMP945 | Puromycin + Blasticidin + Zeocin + Hygromycin | Lenti |
| MP487 | Intrs. pMinCMV Reporter + synI$^{IND\ NT}$ + synR$^{VP64}$ + synRW(pMinCMV-mCh-Dam(R116A)) | MP263 | pMP945 | Puromycin + Blasticidin + Zeocin + Hygromycin | Lenti |
| MP489 | Clust. pMinCMV Reporter + synR$^{VP64}$ + synRW(pMinCMV-mCh-Dam(R116A)) | MP252 | pMP945 | Puromycin + Zeocin + Hygromycin | Lenti |
| MP490 | Clust. pMinCMV Reporter + synI$^{IND}$ + synR$^{VP64}$ + synRW(pMinCMV-mCh-Dam(R116A)) | MP253 | pMP945 | Puromycin + Blasticidin + Zeocin + Hygromycin | Lenti |
| MP492 | Clust. pMinCMV Reporter + synI$^{IND\ NT}$ + synR$^{VP64}$ + synRW(pMinCMV-mCh-Dam(R116A)) | MP267 | pMP945 | Puromycin + Blasticidin + Zeocin + Hygromycin | Lenti |
| MP493 | Intrs. pMinCMV Reporter + synR$^{VP64}$ + synRW(pMinCMV-Dpnl-Dam(L122A)) | MP243 | pMP903 | Puromycin + Zeocin + Hygromycin | Lenti |
| MP494 | Intrs. pMinCMV Reporter + synI$^{IND}$ + synR$^{VP64}$ + synRW(pMinCMV-Dpnl-Dam(L122A)) | MP244 | pMP903 | Puromycin + Blasticidin + Zeocin + Hygromycin | Lenti |
| MP496 | Intrs. pMinCMV Reporter + synI$^{IND\ NT}$ + synR$^{VP64}$ + synRW(pMinCMV-Dpnl-Dam(L122A)) | MP263 | pMP903 | Puromycin + Blasticidin + Zeocin + Hygromycin | Lenti |
| MP498 | Clust. pMinCMV Reporter + synR$^{VP64}$ + synRW(pMinCMV-Dpnl-Dam(L122A)) | MP252 | pMP903 | Puromycin + Zeocin + Hygromycin | Lenti |
| MP499 | Clust. pMinCMV Reporter + synI$^{IND}$ + synR$^{VP64}$ + synRW(pMinCMV-Dpnl-Dam(L122A)) | MP253 | pMP903 | Puromycin + Blasticidin + Zeocin + Hygromycin | Lenti |
| MP501 | Clust. pMinCMV Reporter + synI$^{IND\ NT}$ + synR$^{VP64}$ + synRW(pMinCMV-Dpnl-Dam(L122A)) | MP267 | pMP903 | Puromycin + Blasticidin + Zeocin + Hygromycin | Lenti |
| MP510 | Intrs. pMinCMV Reporter + synR$^{VP64}$ + synRW(pMinCMV-mCh-Dam(L122A)) | MP243 | pMP943 | Puromycin + Zeocin + Hygromycin | Lenti |
| MP511 | Intrs. pMinCMV Reporter + synI$^{IND}$ + synR$^{VP64}$ + synRW(pMinCMV-mCh-Dam(L122A)) | MP244 | pMP943 | Puromycin + Blasticidin + Zeocin + Hygromycin | Lenti |
| MP513 | Intrs. pMinCMV Reporter + synI$^{IND\ NT}$ + synR$^{VP64}$ + synRW(pMinCMV-mCh-Dam(L122A)) | MP263 | pMP943 | Puromycin + Blasticidin + Zeocin + Hygromycin | Lenti |
| MP515 | Clust. pMinCMV Reporter + synR$^{VP64}$ + synRW(pMinCMV-mCh-Dam(L122A)) | MP252 | pMP943 | Puromycin + Zeocin + Hygromycin | Lenti |
| MP516 | Clust. pMinCMV Reporter + synI$^{IND}$ + synR$^{VP64}$ + synRW(pMinCMV-mCh-Dam(L122A)) | MP253 | pMP943 | Puromycin + Blasticidin + Zeocin + Hygromycin | Lenti |
| MP518 | Clust. pMinCMV Reporter + synI$^{IND\ NT}$ + synR$^{VP64}$ + synRW(pMinCMV-mCh-Dam(L122A)) | MP267 | pMP943 | Puromycin + Blasticidin + Zeocin + Hygromycin | Lenti |

TABLE 2-continued

Cell lines used herein

| Cell line | Description | Parental line | Modification | Selection | Integration |
|---|---|---|---|---|---|
| MP639 | Intrs. pMinCMV Reporter + synR$^{VP64}$ + synRW(pMinCMV-Dpnl-Dam(N132A)) | MP243 | pMP908 | Puromycin + Zeocin + Hygromycin | Lenti |
| MP640 | Intrs. pMinCMV Reporter + synI$^{IND}$ + synR$^{VP64}$ + synRW(pMinCMV-Dpnl-Dam(N132A)) | MP244 | pMP908 | Puromycin + Blasticidin + Zeocin + Hygromycin | Lenti |
| MP641 | Intrs. pMinCMV Reporter + synI$^{IND\ NT}$ + synR$^{VP64}$ + synRW(pMinCMV-Dpnl-Dam(N132A)) | MP263 | pMP908 | Puromycin + Blasticidin + Zeocin + Hygromycin | Lenti |
| MP642 | Clust. pMinCMV Reporter + synR$^{VP64}$ + synRW(pMinCMV-Dpnl-Dam(N132A)) | MP252 | pMP908 | Puromycin + Zeocin + Hygromycin | Lenti |
| MP643 | Clust. pMinCMV Reporter + synI$^{IND}$ + synR$^{VP64}$ + synRW(pMinCMV-Dpnl-Dam(N132A)) | MP253 | pMP908 | Puromycin + Blasticidin + Zeocin + Hygromycin | Lenti |
| MP644 | Clust. pMinCMV Reporter + synI$^{IND\ NT}$ + synR$^{VP64}$ + synRW(pMinCMV-Dpnl-Dam(N132A)) | MP267 | pMP908 | Puromycin + Blasticidin + Zeocin + Hygromycin | Lenti |
| MP645 | Intrs. pMinCMV Reporter + synR$^{VP64}$ + synRW(pMinCMV-mCh-Dam(N132A)) | MP243 | pMP948 | Puromycin + Zeocin + Hygromycin | Lenti |
| MP646 | Intrs. pMinCMV Reporter + synI$^{IND}$ + synR$^{VP64}$ + synRW(pMinCMV-mCh-Dam(N132A)) | MP244 | pMP948 | Puromycin + Blasticidin + Zeocin + Hygromycin | Lenti |
| MP647 | Intrs. pMinCMV Reporter + synI$^{IND\ NT}$ + synR$^{VP64}$ + synRW(pMinCMV-mCh-Dam(N132A)) | MP263 | pMP948 | Puromycin + Blasticidin + Zeocin + Hygromycin | Lenti |
| MP648 | Clust. pMinCMV Reporter + synR$^{VP64}$ + synRW(pMinCMV-mCh-Dam(N132A)) | MP252 | pMP948 | Puromycin + Zeocin + Hygromycin | Lenti |
| MP649 | Clust. pMinCMV Reporter + synI$^{IND}$ + synR$^{VP64}$ + synRW(pMinCMV-mCh-Dam(N132A)) | MP253 | pMP948 | Puromycin + Blasticidin + Zeocin + Hygromycin | Lenti |
| MP650 | Clust. pMinCMV Reporter + synI$^{IND\ NT}$ + synR$^{VP64}$ + synRW(pMinCMV-mCh-Dam(N132A)) | MP267 | pMP948 | Puromycin + Blasticidin + Zeocin + Hygromycin | Lenti |
| MP674 | Intrs. pMinCMV Reporter + ZF-VP64$^{IND}$ | MP153 | pMP710 | Puromycin + Blasticidin | Lenti |

TABLE 3

Primers used for m6A-qPCR

| Locus | Forward primer | Reverse primer | Anneal. temp (° C.) | Extens. time (sec) |
|---|---|---|---|---|
| ON-REPORTER GATC sites Clustered reporter | | | | |
| no GATC reference | GTGAACCGCATCGAGCTGAAG (SEQ ID NO: 55) | TGTTGCCGTCCTCCTTGAAGTC (SEQ ID NO: 67) | 58 | 3 |
| GATC (20bp from ZF BS) | TAAAGGCTTACTGAGCACTA (SEQ ID NO: 56) | TGTGATTCAGAGACAACTTC (SEQ ID NO: 68) | 58 | 3 |
| GATC (140bp) | AATCGTTGCGTAATCTACAA (SEQ ID NO: 57) | TTGCGAAAGTTGGAGAAATA (SEQ ID NO: 69) | 58 | 3 |
| GATC (212bp) | TCTGGAGGATAATCTCAGTC (SEQ ID NO: 58) | CAGGAGCCAGGTTTATTATC (SEQ ID NO: 70) | 58 | 3 |
| GATC (332bp) | GAACTTTCTCTGCGTCTATT (SEQ ID NO: 59) | GTAAGCAATAGGTCTTCAGG (SEQ ID NO: 71) | 58 | 3 |

TABLE 3-continued

Primers used for m6A-qPCR

| Locus | Forward primer | Reverse primer | Anneal. temp (° C.) | Extens. time (sec) |
|---|---|---|---|---|
| GATC (548bp) | AAATAATACTGTGCCAGAGC (SEQ ID NO: 60) | TATTCACAGGGTGTTATCCT (SEQ ID NO: 72) | 58 | 3 |
| GATC (716bp) | CCTTCTGTATTTCTACTGGC (SEQ ID NO: 61) | TAACTCAGGTATTGGTGGAT (SEQ ID NO: 73) | 58 | 3 |
| GATC (956 bp) | GATACTATTCCGAGGATTGC (SEQ ID NO: 62) | GAGTTCCTGGTAGCAATAAG (SEQ ID NO: 74) | 58 | 3 |
| GATC (1268bp) | TTTATTCAACCTTCTGCGAA (SEQ ID NO: 63) | CTATCAGGACTGGTAAAAGC (SEQ ID NO: 75) | 58 | 3 |
| GATC (1484bp) | GGATAAACTTCTACCAGCAG (SEQ ID NO: 64) | TGTCCAGATAATCACGGATA (SEQ ID NO: 76) | 58 | 3 |
| Interspersed reporter | | | | |
| no GATC reference | GTGAACCGCATCGAGCTGAAG (SEQ ID NO: 65) | TGTTGCCGTCCTCCTTGAAGTC (SEQ ID NO: 77) | 58 | 3 |
| GATC 260bp upstream from promoter | GCGCGTGTCGCACGTATCACTT (SEQ ID NO: 66) | GCCGGAGGAAGCAAGCGC (SEQ ID NO: 78) | 60 | 3 |
| OFF-TARGET GATC sites | | | | |
| CD5 | TCTGGAGCGTTGTGGAGATTTGG (SEQ ID NO: 79) | AGGACAGAGGGCCAAGCTGC (SEQ ID NO: 85) | 58 | 4 |
| NUMBL | GCGACAGTGACAGCATCAACG (SEQ ID NO: 80) | CCTGTTGTGGCAGGTGGTGG (SEQ ID NO: 86) | 58 | 4 |
| GATA2 | TGACGGCAGGACTGTGTGTTTC (SEQ ID NO: 81) | GGTGATGTTCAACAGGCTGTGC (SEQ ID NO: 87) | 58 | 4 |
| IL7R | AGTCAAGAAGGGAAGAGAGCATTGG (SEQ ID NO: 82) | GCCCAGAGCATCTGCCACTTG (SEQ ID NO: 88) | 58 | 4 |
| VEGFA | GAAACTGTCTCTACCCTGGTCTCC (SEQ ID NO: 83) | CTGCCACTGTAGCCACGAAAC (SEQ ID NO: 89) | 58 | 4 |
| TNFRSF19 | TGCTTTGGAGTTGTCCTGGACG (SEQ ID NO: 84) | TTCAGTGCTCACCCACCAGG (SEQ ID NO: 90) | 58 | 4 |

REFERENCES

Coffin, S. R. & Reich, N. O. *Escherichia coli* DNA adenine methyltransferase: the structural basis of processive catalysis and indirect read-out. *J Biol Chem* 284, 18390-18400 (2009).

Horton, J. R., Liebert, K., Bekes, M., Jeltsch, A. & Cheng, X. Structure and substrate recognition of the *Escherichia coli* DNA adenine methyltransferase. *J Mol Biol* 358, 559-570 (2006).

Hathaway, N. A. et al. Dynamics and memory of heterochromatin in living cells. *Cell* 149, 1447-1460 (2012).

Hodges, C. & Crabtree, G. R. Dynamics of inherently bounded histone modification domains. *Proc Natl Acad Sci USA* 109, 13296-13301 (2012).

Epigenetic Memory Experiments

~120,000 cells were initially plated in multiple wells of a 6-well plate, and incubated either with or without 200 µM ABA. ABA was washed out at indicated times by aspirating out ABA-containing media and adding back fresh media. At indicated time points following ABA washout, approximately half of the cells were re-plated and continued in culture, while the rest were harvested for downstream analysis. For Aphidicolin (APC) experiments, re-plated cells were continued in culture with or without 5 µg/mL Aphidicolin (APC).

Cell Proliferation Assay

~120,000 cells were initially plated in multiple wells of a 6-well plate, and incubated either with or without 200 µM ABA. ABA was washed out after 3 days by aspirating out ABA-containing media and adding back fresh media. Cells were harvested with trypsin and brought to suspension. Cells were then stained with 5 µM CellTrace Far Red, according to manufacturer's instructions for labeling cells in suspension (CellTrace Far Red Cell Proliferation Kit, Thermo Fisher Scientific). About half of the stained cells were analyzed with flow cytometry (Day 0), while the rest were re-plated for continued culture. Thereafter at indicated time points following ABA washout, approximately half of the cells were re-plated and continued in culture, while the rest were resuspended in media for flow cytometry analysis.

The invention claimed is:

1. An engineered DNA methylation system comprising:
   a. a reporter module comprising a nucleic acid sequence comprising one or more DNA binding domain target sites, one or more GATC nucleic acid sequences, a promoter nucleic acid sequence, and a nucleic acid sequence encoding a reporter molecule;
   b. a writer module comprising a promoter sequence operably linked to a nucleic acid sequence encoding a writer fusion protein comprising: a DNA binding protein or domain thereof and a DNA adenine methyltransferase comprising the amino acid sequence of any one of SEQ ID NOs: 12-31;
   c. a reader-effector module comprising a promoter sequence operably linked to a nucleic acid sequence encoding a reader-effector fusion protein comprising: a methyl-adenine DNA binding domain of DpnI endonuclease and one or more transcriptional effector domains, wherein the one or more transcriptional effector domains are repressive transcriptional domains or activating transcriptional domains; and
   d. a reader-writer module comprising a promoter sequence operably linked to a nucleic acid sequence encoding a reader-writer fusion protein comprising: a DNA adenine methyltransferase comprising the amino acid sequence of any one of SEQ ID NOs: 12-31 and a methyl-adenine DNA binding domain of DpnI endonuclease.

2. An engineered DNA methylation system comprising:
   a. a reporter module comprising a nucleic acid sequence comprising one or more DNA binding domain target sites, one or more GATC nucleic acid sequences, a promoter nucleic acid sequence, and a nucleic acid sequence encoding a reporter molecule;
   b. a writer module comprising a promoter sequence operably linked to a nucleic acid sequence encoding a writer fusion protein comprising: a DNA binding protein or domain thereof and a DNA adenine methyltransferase comprising the amino acid sequence of any one of SEQ ID NOs: 12-31, wherein the writer module binds to the one or more DNA binding domain target sites and methylates adenines (A) of the one or more GATC nucleic acid sequences of the reporter molecule, thereby initiating adenine methylation;
   c. a reader-effector module comprising a promoter sequence operably linked to a nucleic acid sequence encoding a reader-effector fusion protein comprising: a methyl-adenine DNA binding domain of DpnI endonuclease and one or more transcriptional effector domains, wherein the one or more transcriptional effector domains are repressive transcriptional domains or activating transcriptional domains, and wherein the reader-effector module recognizes methylated adenines and can recruit one or more regulatory factors to the reporter molecule; and
   d. a reader-writer module comprising a promoter sequence operably linked to a nucleic acid sequence encoding a reader-writer fusion protein comprising: a DNA adenine methyltransferase comprising the amino acid sequence of any one of SEQ ID NOs: 12-31 and a methyl-adenine DNA binding domain of DpnI endonuclease, wherein the reader-writer fusion protein propagates the adenine methylation initiated by the writer fusion protein module.

3. The engineered DNA methylation system of claim 1, wherein the one or more DNA binding domain target sites of the reporter module are zinc finger DNA binding domain target sites.

4. The engineered DNA methylation system of claim 3, wherein the zinc finger DNA binding domain target site comprises SEQ ID NO: 1.

5. The engineered DNA methylation system of claim 1, wherein the one or more DNA binding domain target sites of the reporter module are CRISPR DNA binding domain target sites.

6. The engineered DNA methylation system of claim 5, wherein the one or more CRISPR DNA binding domain target sites comprise a sequence complementary or identical to SEQ ID NO: 36 or SEQ ID NOs: 37.

7. The engineered DNA methylation system of of claim 1, wherein the reporter module comprises a spacer nucleic acid sequence between the one or more GATC nucleic acid sequences.

8. The engineered DNA methylation system of claim 7, wherein the spacer sequence is at least 20 bp.

9. The engineered DNA methylation system of claim 1, wherein the nucleic acid sequence encoding the DNA adenine methyltransferase of the writer fusion protein encodes SEQ ID NO: 20.

10. The engineered DNA methylation system of claim 1, wherein the nucleic acid sequence encoding the DNA binding protein or domain thereof of the writer fusion protein encodes a zinc finger binding protein or domain thereof.

11. The engineered DNA methylation system of claim 10, wherein the zinc finger binding protein or domain thereof comprises SEQ ID NO: 9.

12. The engineered DNA methylation system of claim 1, wherein the nucleic acid sequence encoding the DNA binding protein or domain thereof of the writer fusion protein encodes a Cas enzyme or domain thereof, and wherein the system further comprises a guide module comprising a promoter sequence operably linked to a target sequence and a sequence encoding a guide RNA.

13. The engineered DNA methylation system of claim 12, wherein the Cas enzyme or domain thereof comprises SEQ ID NO: 10.

14. The engineered DNA methylation system of claim 12, wherein the sequence encoding a guide RNA comprises SEQ ID NO: 45.

15. The engineered DNA methylation system of claim 12, wherein the target sequence comprises SEQ ID NO: 36 or SEQ ID NO: 37.

16. The engineered DNA methylation system of claim 1, wherein the nucleic acid sequence encoding the writer fusion protein comprises a nuclear export signal.

17. The engineered DNA methylation system of claim 1, wherein the writer fusion protein further comprises a linker sequence between the DNA binding protein or domain thereof and the DNA adenine methyltransferase.

18. The engineered DNA methylation system of claim 1, wherein the nucleic acid sequence encoding the methyl-adenine DNA binding domain of DpnI endonuclease of the reader-effector fusion protein encodes SEQ ID NO: 40.

19. The engineered DNA methylation system of claim 1, wherein at least one of the one or more transcriptional effector domains of the reader-effector fusion protein is a repressive transcriptional domain.

20. The engineered DNA methylation system of claim 1, wherein at least one of the one or more transcriptional effector domains of the reader-effector fusion protein is an activating transcriptional domain.

21. The engineered DNA methylation system of claim 1, wherein the nucleic acid sequence encoding the DNA adenine methyltransferase of the reader-writer fusion protein encodes SEQ ID NO: 20.

22. The engineered DNA methylation system of claim 1, wherein the nucleic acid sequence encoding the methyl-adenine DNA binding domain of DpnI endonuclease of the reader-writer fusion protein encodes SEQ ID NO: 40.

23. A set of vectors or a single vector comprising the engineered DNA methylation system of claim 1.

24. A cell comprising the engineered DNA methylation system of claim 1.

25. The cell of claim 24, wherein at least the reporter module of the engineered DNA methylation system is integrated at a target genomic locus of the cell.

26. The cell of claim 24, wherein the reporter module, writer module, reader-effector module, and reader-writer module are all integrated at a target genomic locus of the cell.

27. A method of modulating the adenine methylation status of a target sequence in a cell, wherein said method comprises introducing the engineered DNA methylation system of claim 1 into a cell.

* * * * *

SEQUENCE LISTING

<160> NUMBER OF SEQ ID NOS: 94

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
cggcgtagcc gatgtcgcgc                                                    20

<210> SEQ ID NO 2

<400> SEQUENCE: 2

000

<210> SEQ ID NO 3
<211> LENGTH: 513
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
gtcgacgaac ggcgtagccg atgtcgcgcc ctttccacga tcatgtgccg gcgtagccga        60
tgtcgcgcag taataccacc actgcgaccc tagatcggag atccaattag atccatgatc       120
cgaaaccggc gtagccgatg tcgcgcgtgt cgcacgtatc acttgatcgg caaacggcgt       180
agccgatgtc gcgcttgctt cctccggcgt agccgatgtc gcgcgaggta gatcaggcca       240
cggcgtagcc gatgtcgcgc ttgcgctgcc tagatcatcg ttggccggcg tagccgatgt       300
cgcgcacaga tcgagatctt tggtcggcgt agccgatgtc gcgctccata gtgagttctg       360
atcgtgtcac ggctagccga tgtcgcgcta ggatcgagga tcatctctga tctgttttag       420
gactagttag gcgtgtacgg tgggaggcct atataagcag agctcgttta gtgaaccgtc       480
agatcgcctg gaacgcgtac cggtgtcgcc acc                                    513

<210> SEQ ID NO 4
<211> LENGTH: 1116
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
gtcgacgaac ggcgtagccg atgtcgcgcc ctttccacga tcatgtgccg gcgtagccga        60
tgtcgcgcag taataccacc actgcgaccc tagatcggag atccaattag atccatgatc       120
cgaaaccggc gtagccgatg tcgcgcgtgt cgcacgtatc acttgatcgg caaacggcgt       180
agccgatgtc gcgcttgctt cctccggcgt agccgatgtc gcgcgaggta gatcaggcca       240
cggcgtagcc gatgtcgcgc ttgcgctgcc tagatcatcg ttggccggcg tagccgatgt       300
cgcgcacaga tcgagatctt tggtcggcgt agccgatgtc gcgctccata gtgagttctg       360
atcgtgtcac ggctagccga tgtcgcgcta ggatcgagga tcatctctga tctgttttag       420
gactagtgca tgcgcgttga cattgattat tgactagtta ttaatagtaa tcaattacgg       480
ggtcattagt tcatagccca tatatggagt tccgcgttac ataacttacg gtaaatggcc       540

| | |
|---|---|
| cgcctggctg accgcccaac gaccccgcc cattgacgtc aataatgacg tatgttccca | 600 |
| tagtaacgcc aatagggact ttccattgac gtcaatgggt ggagtattta cggtaaactg | 660 |
| cccacttggc agtacatcaa gtgtatcata tgccaagtac gccccctatt gacgtcaatg | 720 |
| acggtaaatg gcccgcctgg cattatgccc agtacatgac cttatgggac tttcctactt | 780 |
| ggcagtacat ctacgtatta gtcatcgcta ttaccatggt gatgcggttt tggcagtaca | 840 |
| tcaatgggcg tggatagcgg tttgactcac ggggatttcc aagtctccac cccattgacg | 900 |
| tcaatgggag tttgttttgg caccaaaatc aacgggactt tccaaaatgt cgtaacaact | 960 |
| ccgcccatt gacgcaaatg gcggtaggc gtgtacggtg gaggtctat ataagcagag | 1020 |
| ctctctggct aactagagaa cccactgctt actggcttat cgaaattaat acgactcact | 1080 |
| atagggagac ccaagctgac gcgtaccggt gccacc | 1116 |

<210> SEQ ID NO 5
<211> LENGTH: 1810
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

| | |
|---|---|
| caattggaaa agtgccacct gggtcgaccg gcgtagccga tgtcgcgcaa ccaccagtaa | 60 |
| gtatctcacg gcgtagccga tgtcgcgcca gtaaaggctt ctctacaccg gcgtagccga | 120 |
| tgtcgcgcct ccttcgggat aaaatctccg gcgtagccga tgtcgcgcag gtggtagac | 180 |
| tatctctgcg gcgtagccga tgtcgcgcta aaggcttact gagcactaga tcgaagttgt | 240 |
| ctctgaatca cagatcgtta cgatacttta cacggtgatc gtggtattgt tgtgacacta | 300 |
| gatcagatag ggtgtgattg gttagatcaa tcgttgcgta atctacaaga tctatttctc | 360 |
| caactttcgc aagatccttt ctgagtaagt agcaccgatc tctggaggat aatctcagtc | 420 |
| gatcgataat aaacctggct cctggatcga ttactgagga tacgcttcga tcgtttccaa | 480 |
| ctactggctt tagatcgaga ttcgtaaaag gctgatgatc gaactttctc tgcgtctatt | 540 |
| gatccctgaa gacctattgc ttacgatcaa taatactatc gggcgagaga tcagtaggtg | 600 |
| aggattacac aagatccgaa tctctggctt caataagatc tgtggttatt actcagggat | 660 |
| gatcggcgaa acaatcttct ctatgatccg attgcgagat actattgtga tccagtgtgc | 720 |
| caataagttt tcgatcaaat aatactgtgc cagagcgatc aggataacac cctgtgaata | 780 |
| gatcatcaga cagtcggatt ctatgatcga aagtctgagc gatttactga tcagcgacaa | 840 |
| ctatttactg acgatcatca acgatagagg tgagatgatc taaaccgata cgggtaacta | 900 |
| gatcccttct gtatttctac tggcgatcat ccaccaatac ctgagttaga tcgaatcagc | 960 |
| ctttacagta gggatccagt cctactatca ccagatgatc gctctcagtt tctatttcgt | 1020 |
| gatcacagta gtgagaacca gttagatcat aagtgttgat acctcccaga tcctctgaaa | 1080 |
| taggcagtta ccgatccagg gcttacaata gaactcgatc tacaccacaa tagaagggat | 1140 |
| gatcgatact attccgagga ttgcgatcct tattgctacc aggaactcga tcctggaata | 1200 |
| agaaggtgct acgatccgag aatcacgata gtaagggatc agcacgattc tccttttatc | 1260 |
| gatcaacttt cctattacca acggggatct gaagaataga tttcctgcgg atctattttc | 1320 |
| cgtcgtaact caggatcgaa taagaatcgc tctggttgat cgctttatca ctgggtaaga | 1380 |
| ggatcagttg aatactgtgg gtagagatcg agtaaaaccc gttcacttag atcctctcaa | 1440 |

```
taaccgatag acggatcttt attcaacctt ctgcgaagat cgcttttacc agtcctgata    1500
ggatcgaaac agaaccgaaa atcaggatcg gaggctattg ctactctatg atctgatact    1560
caatcgtcag gtagatcaaa tagtccgtaa gtaggctgat cccagttgaa tagtaagagc    1620
cgatctactc aactggtggg ataatgatct tttattgagt tcagccgaag atcggataaa    1680
cttctaccag caggatctat ccgtgattat ctggacagat cactagttag gcgtgtacgg    1740
tgggaggcct atataagcag agctcgttta gtgaaccgtc agatcgcctg aacgcgtac     1800 cggtgccacc                                                           1810
```

<210> SEQ ID NO 6
<211> LENGTH: 4452
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

```
caattggaaa agtgccacct gggtcgaccg gcgtagccga tgtcgcgcaa ccaccagtaa      60
gtatctcacg gcgtagccga tgtcgcgcca gtaaaggctt ctctacaccg gcgtagccga    120
tgtcgcgcct ccttcgggat aaaatctccg gcgtagccga tgtcgcgcag tgtggtagac    180
tatctctgcg gcgtagccga tgtcgcgcta aaggcttact gagcactagc tagcgatcat    240
tctgtggatt caataccagc gagatttaga cggaggctca cttttacaga tcatcccttg    300
tagagtattt gagataaccg ctaactgata ggactttccg aggatctaag cgaggttatt    360
accacaaaac gatagattct ggctacttga ctgctggatc tttcagattt cgtttacaa     420 gacgccgttc aacagtggaa gagtatcgca gatcctcaag cagtaaaacg acgagtattc    480
tattggagcc ttcttagtgc ctatgatcgt ctgacagtaa agggatttcc taagattcaa    540
ccgcagtttg ttctacaggg atcgcaaact ccttagccgt ggttctacaa taggtcttcg    600
taaaataatc ggagatcagg tgcctttaga agtcactgag acgattgttt attactccac    660
tacgaaggat cgaataaata gggtctcact gtgtaatcag atacgaactc cgcttccttt    720
ggatctattc accctatttc ttcagttgag gagtcacgca gcaaagttac aaggagatct    780
tctgcgtcta ttttggatac ggaaacttga atctcaggcg actaagcaag atcataggag    840
taactgttca cacgctgata cacaatcgtt taggtctgtc actgatcagc acggattctg    900
ataaacgact atttggctgg acctgtctac aagtaatgat ctaacgggag gcagtaacaa    960
tctcactacg actttatttt agaccgaggt tgatcaagtc aacggctatt tcttgggatt   1020
accgagataa actactgtgt cctacgatct attagtaacc ttcttcaggg cgaaagtatt   1080
caccacacgg gtaagttctg atcctccctt ccagttgtaa gacgcaagta ttattttagg   1140
tgataggacg acagatcttg agttcttgga tagtgcgttc cgtcctacga caaccagatt   1200
gaaaatagat cacaccgtag cgttcttgct caaaggaaac aacttctatt gggtaactgt   1260
agatcaccga cgcttagaat agagttccta ccctgattag tttgaaagta tcgctgatca   1320
agcccacgaa aggtcaccgt tttgtctgta aatagtaagt cttgagtcag atcggctcaa   1380
acctatccaa gtgtagtatc aggagattct attattcagt ggcgatcatt cttgaggcgg   1440
tctaaataaa acttggctta ccttcgcaac gagtatcgat ctactaaatc aaagtgtctg   1500
aaagggcgtg aatctcccag ttggttacct agatcgttgg gtaacgccga tttagtagaa   1560
aacacctttg aacctattga ctcaggatca caaagcgtag aaaatcagta gggtttatcc   1620
```

```
ttggtagtct tcctccagtg atccacgagg cttgtgttgt attgacttta tccgtagaca    1680
gcaaaatcac caagatcatc agataacctc ccagaataaa ccgattggtg ttccgttcgt    1740
ggtaatagat cattacctaa gcgtctaact tgcgactaca gcagtgactc tattgagatt    1800
ggatccttta gggcaaactg tgatagcaat ccgctgttag tcaaatctac gcttagatcg    1860
ctgaaccaca gtatttgttt tagaaggaag taagcctatc tggcaactcg atcacactta    1920
cttggaacta ttttcaaacg atacgactga taacgctggg tgcgatcgtg gtcctcaaat    1980
cttctcgtgc cgtagtgata ataagcagca acaatagat  ccgtcgttca gttggataac    2040
agcgaaaagt ttgatacccct ctcagattgt agatctgtcc tgactctgaa taccgtctgt   2100
gaaataactg tttgtaagcg aacgagatcg cggaatctgt aaagggagt  ccaataatac    2160 gctatcctgt tctacttagg atcgagtaga gttatccctt agactgtatc ttcacccgta    2220
ggcaaagtat tgagatccca cgggattact aaacctgatt tgttgccgaa gagatacttg    2280
tgataacgat catctcacta ttggtcaagg aagagtagag cactttctcc cgtaacgatt    2340
tgatcattgc gtcagcgttg gctctcggtt attactattg aaacaaggac ctaaagatca    2400
tacctgggag aacgatttta gtgacttatt tacgctatca gccctacgag atcatcaatc    2460
cttagggtgc gaagtcagtt tgtcttattc cagcgataca aagatctta  tcgtagattt    2520 ccgacacctg agactgtgaa gacccacttt gagtaatgat ctttagaaag ttgacaaggc    2580
tgtattttgc tgaatccaga ccctgactcc agatctgcct cgtaacggct tggtcttagt    2640
caatctgaac cgatagtaaa atacagatct tccaactgct tcaaaagtaa tctatcaagg    2700
tggttctgtg ggctaaacgg atcttcacct attagagcag tgtcgtcagt agtcggtaag    2760
ataaagtaac ctcgatcctc tactgtgtaa atcgtaacaa taaacgggct ggtgtggcta    2820
tccaaatgat ctgcctatcc tcccttgttg gaaatcacta aaactgagta agagtcggaa    2880
tgatcagtgt cggcttctta ttcctcgcaa ccgtcagagt aaaacagtag tattagatcg    2940
ttgagccaaa taactgactc ggaatagagg ttttacgcct aatactgctg atccaatagg    3000
tgagggtcct tatcggaaaa tcgtcgcaaa acttactctt agtgatcatt tcaacagtat    3060
cggttagcaa ctacctacgc cagtgtaagg attttcggat cagtaagatt tgtttagttg    3120
acactgcgag tctatttccc tccaagaagg cgatctagaa tcgttgaaac ctgtggctaa    3180
aatagttgtg cgtaatccct tccgagatcg aagaagttcc ctacgagtta cgctgccttt    3240
attagagatt accccttgaag atcaagagat tattgatttg ctatttgtg  acaccgaaag    3300 tccacctggc acggatctcg gctcactaca gattgataat aacgactaag gtaaactctt    3360
cgggtctgat cgtcactgtt acaactaata aaataggtgg acgactccct tgaatctgtg    3420
cgatcgtttc agggcaacgg ttcaacactt acaaggtatc tgtgctaatc aatctgatcg    3480
agacaatcgc tgtattagat aaaccgtgta gttgaatcag ttacctcccg atcaggcttt    3540
acacaataga cttagattag caactcttac gggattcctg gacgatcatt accctgatac    3600
gacctggata acaaggctaa ataagtggtg tctcttcgat cttgtgattc gtgtaaaact    3660
atcctgaaga gcaccgttcc tccaaaagta ggatctaccg ttttatcctt agaagcagag    3720
gttagttcac gagcaagcgt caaatgatca actattagag gattgtgcct acactttatt    3780
tgactcagcc agcagcgatg atccagccgt ttcccgtcct caatagttag aagatttagg    3840
taataagcga agtgatctaa aatctattag caatcgtaag tcccttttgag gagaccttct    3900 accgtgggat caacgaactt ctaactctac cgtaaggtca aaccagtgta ttgtggctga    3960
```

```
tgatctaaac ccaagaggga ccgtgattat tctgtattac ctgttagcaa gtagcgatct    4020
tctctggtta caaaagtgag tgccttacct cgtcaggaat aaacacagtg atccaaaata    4080
atagaggctt ggagattcct gtgaaaagtc ctactcggtc ttcgatcttg cgaagaataa    4140
tctgtctaaa gtccgaactg ctgaaactcg tgttacggat ctgttaccac gctatttgtc    4200
ttgtgaaagc cagtccgaga atcgttagaa agatcttcgc aggattctac agtttccgtg    4260
ttctcggcaa atagcaataa aaggtgatcg cttcaaacac ggagaactac gatttcctca    4320
ggctatttat tacagggtag atctatccgt gattatctgg acaactagtt aggcgtgtac    4380
ggtgggaggc ctatataagc agagctcgtt tagtgaaccg tcagatcgcc tggaacgcgt    4440
accggtgcca cc                                                       4452

<210> SEQ ID NO 7
<211> LENGTH: 4451
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
caattggaaa agtgccacct gggtcgaccg gcgtagccga tgtcgcgcaa ccaccagtaa      60
gtatctcacg gcgtagccga tgtcgcgcca gtaaaggctt ctctacaccg gcgtagccga    120
tgtcgcgcct ccttcgggat aaaatctccg gcgtagccga tgtcgcgcag tgtggtagac    180
tatctctgcg gcgtagccga tgtcgcgcta aaggcttact gagcactagc tagcgatcat    240
tctgtggatt caataccagc gagatttaga cggaggctca cttttacaag taatcccttg    300
tagagtattt gagataaccg ctaactgata ggactttccg agcgtataag cgaggttatt    360
accacaaaac gatagattct ggctacttga ctgctggcat tttcagattt tcgtttacaa    420
gacgccgttc aacagtggaa gagtatcgca gatcctcaag cagtaaaacg acgagtattc    480
tattggagcc ttcttagtgc ctatggtcgt ctgacagtaa agggatttcc taagattcaa    540
ccgcagtttg ttctacagac acgcaaactc cttagccgtg gttctacaat aggtcttcgt    600
aaaataatcg gaacagaggt gcctttagaa gtcactgaga cgattgttta ttactccact    660
acgaaggatc gaataaatag ggtctcactg tgtaatcaga tacgaactcc gcttcctttg    720
tagatattca ccctatttct tcagttgagg agtcacgcag caaagttaca aggaatgctt    780
ctgcgtctat tttggatacg gaaacttgaa tctcaggcga ctaagcaaat ccataggagt    840
aactgttcac acgctgatac acaatcgttt aggtctgtca ctgatcagca cggattctga    900
taaacgacta tttggctgga cctgtctaca gtaataagt  taacgggagg cagtaacaat    960
ctcactacga ctttatttta gaccgaggtt ctaaagtca  acggctattt cttgggatta   1020
ccgagataaa ctactgtgtc ctacatggta ttagtaacct tcttcagggc gaaagtattc   1080
accacacggg taagttctga tcctcccttc cagttgtaag acgcaagtat tatttttaggt  1140 gataggacga cacgatttga gttcttggat agtgcgttcc gtcctacgac aaccagattg   1200
aaaatatgtg acaccgtagc gttcttgctc aaaggaaaca acttctattg ggtaactgta   1260
gatgaccgac gcttagaata gagttcctac cctgattagt ttgaaagtat cgctgatcaa   1320
gcccacgaaa ggtcaccgtt ttgtctgtaa atagtaagtc ttgagtcagg caggctcaaa   1380
cctatccaag tgtagtatca ggagattcta ttattcagtg gcttgtattc ttgaggcggt   1440
ctaaataaaa cttggcttac cttcgcaacg agtatctaca tactaaatca aagtgtctga   1500
```

```
aagggcgtga atctcccagt tggttaccta gatcgttggg taacgccgat ttagtagaaa   1560
acacctttga acctattgac tcagtaccac aaagcgtaga aaatcagtag ggtttatcct   1620
tggtagtctt cctccagttg ctcacgaggc ttgtgttgta ttgactttat ccgtagacag   1680
caaaatcacc aagaatatca gataacctcc cagaataaac cgattggtgt tccgttcgtg   1740
gtaatagatc attacctaag cgtctaactt gcgactacag cagtgactct attgagattg   1800
agtgctttag ggcaaactgt gatagcaatc cgctgttagt caaatctacg cttagcgagc   1860
tgaaccacag tatttgtttt agaaggaagt aagcctatct ggcaactcta tgacacttac   1920
ttggaactat tttcaaacga tacgactgat aacgctgggt gcgatcgtgg tcctcaaatc   1980
ttctcgtgcc gtagtgataa taagcagcaa acaatagcgt cgtcgttcag ttggataaca   2040
gcgaaaagtt tgatacccctc tcagattgta gtgatgtcct gactctgaat ccgtctgtg    2100 aaataactgt ttgtaagcga acgagctcgc ggaatctgta aaagggagtc caataatacg   2160
ctatcctgtt ctacttagga tcgagtagag ttatcccta gactgtatct tcacccgtag   2220
gcaaagtatt gacagtccac gggattacta aacctgattt gttgccgaag agatacttgt   2280
gataactgct atctcactat tggtcaagga agagtagagc actttctccc gtaacgattt   2340
tcagattgcg tcagcgttgg ctctcggtta ttactattga aacaaggacc taaagatcat   2400
acctgggaga acgattttag tgacttattt acgctatcag ccctacgaca caatcaatcc   2460
ttagggtgcg aagtcagttt gtcttattcc agcgatacag aatgcattat cgtagatttc   2520
cgacacctga gactgtgaag acccactttg agtaatagta tttagaaagt tgacaaggct   2580
gtattttgct gaatccagac cctgactcca gatctgcctc gtaacggctt ggtcttagtc   2640
aatctgaacc gatagtaaaa tacagtcgtt ccaactgctt caaaagtaat ctatcaaggt   2700
ggttctgtgg gctaaacgat tgttcaccta ttagagcagt gtcgtcagta gtcggtaaga   2760
taaagtaacc tcgtcactct actgtgtaaa tcgtaacaat aaacgggctg gtgtggctat   2820
ccaaatgatc tgcctatcct cccttgttgg aaatcactaa aactgagtaa gagtcggaat   2880
ccgaagtgtc ggcttcttat tcctcgcaac cgtcagagta aaacagtagt attagtgagt   2940
tgagccaaat aactgactcg gaatagaggt tttacgccta atactgctgc gtcaataggt   3000
gagggtcctt atcggaaaat cgtcgcaaaa cttactctta gtgatcattt caacagtatc   3060
ggttagcaac tacctacgcc agtgtaagga ttttcggaca agtaagattt gtttagttga   3120
cactgcgagt ctatttccct ccaagaaggc gaactagaat cgttgaaacc tgtggctaaa   3180
atagttgtgc gtaatccctt ccgaccatga agaagttccc tacgagttac gctgcccttta  3240 ttagagatta cccttgaaga tcaagagatt attgatttgc tattttgtga caccgaaagt   3300
ccacctggca cgttcctcgg ctcactacag attgataata acgactaagg taaactcttc   3360
gggtcttagt gtcactgtta caactaataa aataggtgga cgactcccctt gaatctgtgc   3420 ccatgtttca gggcaacggt tcaacactta caaggtatct gtgctaatca atctgatcga   3480
gacaatcgct gtattagata aaccgtgtag ttgaatcagt tacctccccc gaaggcttta   3540
cacaatagac ttagattagc aactcttacg ggattcctgg actcgtatta ccctgatacg   3600
acctggataa caaggctaaa taagtggtgt ctcttcacat ttgtgattcg tgtaaaacta   3660
tcctgaagag caccgttcct ccaaaagtag gatctaccgt tttatcctta aagcagagg    3720 ttagttcacg agcaagcgtc aaatgttcaa ctattagagg attgtgccta cactttatttt  3780 gactcagcca gcagcgatac tccagccgtt tcccgtcctc aatagttaga agatttaggt   3840
aataagcgaa gtatgataaa atctattagc aatcgtaagt cccctttgagg agaccttcta   3900
```

```
ccgtgggatc aacgaacttc taactctacc gtaaggtcaa accagtgtat tgtggctgat    3960
accttaaacc caagagggac cgtgattatt ctgtattacc tgttagcaag tagctaagtt    4020
ctctggttac aaaagtgagt gccttacctc gtcaggaata acacagtga accaaaataa    4080 tagaggcttg gagattcctg tgaaaagtcc tactcggtct tcgatcttgc gaagaataat    4140
ctgtctaaag tccgaactgc tgaaactcgt gttacgcaca tgttaccacg ctatttgtct    4200
tgtgaaagcc agtccgagaa tcgttagaaa agagttcgca ggattctaca gtttccgtgt    4260
tctcggcaaa tagcaataaa aggtttccgc ttcaaacacg gagaactacg atttcctcag    4320
gctatttatt acagggtaga tctatccgtg attatctgga caactagtta ggcgtgtacg    4380
gtgggaggcc tatataagca gagctcgttt agtgaaccgt cagatcgcct ggaacgcgta    4440
ccggtgccac c                                                          4451

<210> SEQ ID NO 8
<211> LENGTH: 4451
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
caattggaaa agtgccacct gggtcgaccg gcgtagccga tgtcgcgcaa ccaccagtaa      60
gtatctcacg gcgtagccga tgtcgcgcca gtaaaggctt ctctacaccg gcgtagccga    120
tgtcgcgcct ccttcgggat aaaatctccg gcgtagccga tgtcgcgcag gtggtagac    180 tatctctgcg gcgtagccga tgtcgcgcta aaggcttact gagcactagc tagcgatcat    240
tctgtggatt caataccagc gagatttaga cggaggctca cttttacaag taatcccttg    300
tagagtattt gagataaccg ctaactgata ggactttccg agcgtataag cgaggttatt    360
accacaaaac gatagattct ggctacttga ctgctggcat tttcagattt tcgtttacaa    420
gacgccgttc aacagtggaa gagtatcgca tgcactcaag cagtaaaacg acgagtattc    480
tattggagcc ttcttagtgc ctatggtcgt ctgacagtaa agggatttcc taagattcaa    540
ccgcagtttg ttctacagac acgcaaactc cttagccgtg gttctacaat aggtcttcgt    600
aaaataatcg gaacagaggt gcctttagaa gtcactgaga cgattgttta ttactccact    660
acgaagcttg gaataaatag ggtctcactg tgtaatcaga tacgaactcc gcttcctttg    720
tagatattca ccctatttct tcagttgagg agtcacgcag caaagttaca aggaatgctt    780
ctgcgtctat tttggatacg gaaacttgaa tctcaggcga ctaagcaaat ccataggagt    840
aactgttcac acgctgatac acaatcgttt aggtctgtca ctaggaagca cggattctga    900
taaacgacta tttggctgga cctgtctaca agtaataagt taacgggagg cagtaacaat    960
ctcactacga ctttatttta gaccgaggtt tctaaagtca acggctattt cttgggatta   1020
ccgagataaa ctactgtgtc ctacgatcta ttagtaacct tcttcagggc gaaagtattc   1080
accacacggg taagttctct tcctcccttc cagttgtaag acgcaagtat tattttaggt   1140
gataggacga cacgatttga gttcttggat agtgcgttcc gtcctacgac aaccagattg   1200
aaaatatgtg acaccgtagc gttcttgctc aaaggaaaca acttctattg ggtaactgta   1260
gatgaccgac gcttagaata gagttcctac cctgattagt ttgaaagtat cgctgtagaa   1320
gcccacgaaa ggtcaccgtt ttgtctgtaa atagtaagtc ttgagtcagg caggctcaaa   1380
cctatccaag tgtagtatca ggagattcta ttattcagtg gcttgtattc ttgaggcggt   1440
```

```
ctaaataaaa cttggcttac cttcgcaacg agtatctaca tactaaatca aagtgtctga    1500
aagggcgtga atctcccagt tggttaccta gatggttggg taacgccgat ttagtagaaa    1560
acacctttga acctattgac tcagtaccac aaagcgtaga aaatcagtag ggtttatcct    1620
tggtagtctt cctccagttg ctcacgaggc ttgtgttgta ttgactttat ccgtagacag    1680
caaaatcacc aagaatatca gataacctcc cagaataaac cgattggtgt tccgttcgtg    1740
gtaatattgc attacctaag cgtctaactt gcgactacag cagtgactct attgagattg    1800
agtgctttag ggcaaactgt gatagcaatc cgctgttagt caaatctacg cttagatcgc    1860
tgaaccacag tatttgtttt agaaggaagt aagcctatct ggcaactcta tgacacttac    1920
ttggaactat tttcaaacga tacgactgat aacgctgggt gcgcgagtgg tcctcaaatc    1980
ttctcgtgcc gtagtgataa taagcagcaa acaatagcgt cgtcgttcag ttggataaca    2040
gcgaaaagtt tgataccctc tcagattgta gtgatgtcct gactctgaat accgtctgtg    2100
aaataactgt ttgtaagcga acgagctcgc ggaatctgta aaagggagtc caataatacg    2160
ctatcctgtt ctacttagtg gtgagtagag ttatccctta gactgtatct tcacccgtag    2220
gcaaagtatt gacagtccac gggattacta aacctgattt gttgccgaag agatacttgt    2280
gataactgct atctcactat tggtcaagga agagtagagc actttctccc gtaacgattt    2340
tcagattgcg tcagcgttgg ctctcggtta ttactattga acaaggacc  taaaatggat    2400 acctgggaga acgattttag tgacttattt acgctatcag ccctacgaca caatcaatcc    2460
ttagggtgcg aagtcagttt gtcttattcc agcgatacag aatgcattat cgtagatttc    2520
cgacacctga gactgtgaag acccactttg agtaatagta tttagaaagt tgacaaggct    2580
gtattttgct gaatccagac cctgactcca aagctgcctc gtaacggctt ggtcttagtc    2640
aatctgaacc gatagtaaaa tacagatctt ccaactgctt caaaagtaat ctatcaaggt    2700
ggttctgtgg gctaaacgat tgttcaccta ttagagcagt gtcgtcagta gtcggtaaga    2760
taaagtaacc tcgtcactct actgtgtaaa tcgtaacaat aaacgggctg gtgtggctat    2820
ccaaatgtcg tgcctatcct cccttgttgg aaatcactaa aactgagtaa gagtcggaat    2880
ccgaagtgtc ggcttcttat tcctcgcaac cgtcagagta aaacagtagt attagtgagt    2940
tgagccaaat aactgactcg gaatagaggt tttacgccta atactgctgc gtcaataggt    3000
gagggtcctt atcggaaaat cgtcgcaaaa cttactctta gtagcaattt caacagtatc    3060
ggttagcaac tacctacgcc agtgtaagga ttttcggaca agtaagattt gtttagttga    3120
cactgcgagt ctatttccct ccaagaaggc gaactagaat cgttgaaacc tgtggctaaa    3180
atagttgtgc gtaatccctt ccgaccatga agaagttccc tacgagttac gctgccttta    3240
ttagagatta cccttgaatc caaagagatt attgatttgc tattttgtga caccgaaagt    3300
ccacctggca cgttcctcgg ctcactacag attgataata acgactaagg taaactcttc    3360
gggtcttagt gtcactgtta caactaataa aataggtgga cgactcccct gaatctgtgc    3420
ccatgtttca gggcaacggt tcaacactta caaggtatct gtgctaatca atctgatcga    3480
gacaatcgct gtattagata aaccgtgtag ttgaatcagt tacctccccc gaaggcttta    3540
cacaatagac ttagattagc aactcttacg ggattcctgg actcgtatta ccctgatacg    3600
acctggataa caaggctaaa taagtggtgt ctcttcacat ttgtgattcg tgtaaaacta    3660
tcctgaagag caccgttcct ccaaaagtag ccaataccgt tttatcctta gaagcagagg    3720
ttagttcacg agcaagcgtc aaatgttcaa ctattagagg attgtgccta cactttattt    3780
```

```
gactcagcca gcagcgatac tccagccgtt tcccgtcctc aatagttaga agatttaggt    3840
aataagcgaa gtatgataaa atctattagc aatcgtaagt ccctttgagg agaccttcta    3900
ccgtggcaca aacgaacttc taactctacc gtaaggtcaa accagtgtat tgtggctgat    3960
accttaaacc caagagggac cgtgattatt ctgtattacc tgttagcaag tagctaagtt    4020
ctctggttac aaaagtgagt gccttacctc gtcaggaata aacacagtga accaaaataa    4080
tagaggcttg gagattcctg tgaaaagtcc tactcggtct tccgtattgc gaagaataat    4140
ctgtctaaag tccgaactgc tgaaactcgt gttacgcaca tgttaccacg ctatttgtct    4200
tgtgaaagcc agtccgagaa tcgttagaaa agagttcgca ggattctaca gtttccgtgt    4260
tctcggcaaa tagcaataaa aggtgatcgc ttcaaacacg gagaactacg atttcctcag    4320
gctatttatt acagggtatt cctatccgtg attatctgga caactagtta ggcgtgtacg    4380
gtgggaggcc tatataagca gagctcgttt agtgaaccgt cagatcgcct ggaacgcgta    4440
ccggtgccac c                                                        4451
```

<210> SEQ ID NO 9
<211> LENGTH: 176
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

```
Ser Arg Pro Gly Glu Arg Pro Phe Gln Cys Arg Ile Cys Met Arg Asn
1               5                   10                  15

Phe Ser Arg Arg His Gly Leu Asp Arg His Thr Arg Thr His Thr Gly
            20                  25                  30

Glu Lys Pro Phe Gln Cys Arg Ile Cys Met Arg Asn Phe Ser Asp His
        35                  40                  45

Ser Ser Leu Lys Arg His Leu Arg Thr His Thr Gly Ser Gln Lys Pro
    50                  55                  60

Phe Gln Cys Arg Ile Cys Met Arg Asn Phe Ser Val Arg His Asn Leu
65                  70                  75                  80

Thr Arg His Leu Arg Thr His Thr Gly Glu Lys Pro Phe Gln Cys Arg
                85                  90                  95

Ile Cys Met Arg Asn Phe Ser Asp His Ser Asn Leu Ser Arg His Leu
            100                 105                 110

Lys Thr His Thr Gly Ser Gln Lys Pro Phe Gln Cys Arg Ile Cys Met
        115                 120                 125

Arg Asn Phe Ser Gln Arg Ser Ser Leu Val Arg His Leu Arg Thr His
    130                 135                 140

Thr Gly Glu Lys Pro Phe Gln Cys Arg Ile Cys Met Arg Asn Phe Ser
145                 150                 155                 160

Glu Ser Gly His Leu Lys Arg His Leu Arg Thr His Leu Arg Gly Ser
                165                 170                 175
```

<210> SEQ ID NO 10
<211> LENGTH: 1368
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
            35                  40                  45

Gly Ala Leu Leu Phe Asp Ser Gly Glu Thr Ala Glu Ala Thr Arg Leu
        50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
                100                 105                 110

His Glu Arg His Pro Ile Phe Gly Asn Ile Val Asp Glu Val Ala Tyr
                115                 120                 125

His Glu Lys Tyr Pro Thr Ile Tyr His Leu Arg Lys Lys Leu Val Asp
                130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
                180                 185                 190

Asn Gln Leu Phe Glu Glu Asn Pro Ile Asn Ala Ser Gly Val Asp Ala
                195                 200                 205

Lys Ala Ile Leu Ser Ala Arg Leu Ser Lys Ser Arg Arg Leu Glu Asn
        210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
                260                 265                 270

Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
        290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
        370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
```

```
            420             425             430
Leu Lys Asp Asn Arg Glu Lys Ile Glu Lys Ile Leu Thr Phe Arg Ile
            435             440             445
Pro Tyr Tyr Val Gly Pro Leu Ala Arg Gly Asn Ser Arg Phe Ala Trp
            450             455             460
Met Thr Arg Lys Ser Glu Glu Thr Ile Thr Pro Trp Asn Phe Glu Glu
465             470             475             480
Val Val Asp Lys Gly Ala Ser Ala Gln Ser Phe Ile Glu Arg Met Thr
            485             490             495
Asn Phe Asp Lys Asn Leu Pro Asn Glu Lys Val Leu Pro Lys His Ser
            500             505             510
Leu Leu Tyr Glu Tyr Phe Thr Val Tyr Asn Glu Leu Thr Lys Val Lys
            515             520             525
Tyr Val Thr Glu Gly Met Arg Lys Pro Ala Phe Leu Ser Gly Glu Gln
            530             535             540
Lys Lys Ala Ile Val Asp Leu Leu Phe Lys Thr Asn Arg Lys Val Thr
545             550             555             560
Val Lys Gln Leu Lys Glu Asp Tyr Phe Lys Lys Ile Glu Cys Phe Asp
            565             570             575
Ser Val Glu Ile Ser Gly Val Glu Asp Arg Phe Asn Ala Ser Leu Gly
            580             585             590
Thr Tyr His Asp Leu Leu Lys Ile Ile Lys Asp Lys Asp Phe Leu Asp
            595             600             605
Asn Glu Glu Asn Glu Asp Ile Leu Glu Asp Ile Val Leu Thr Leu Thr
            610             615             620
Leu Phe Glu Asp Arg Glu Met Ile Glu Glu Arg Leu Lys Thr Tyr Ala
625             630             635             640
His Leu Phe Asp Asp Lys Val Met Lys Gln Leu Lys Arg Arg Arg Tyr
            645             650             655
Thr Gly Trp Gly Arg Leu Ser Arg Lys Leu Ile Asn Gly Ile Arg Asp
            660             665             670
Lys Gln Ser Gly Lys Thr Ile Leu Asp Phe Leu Lys Ser Asp Gly Phe
            675             680             685
Ala Asn Arg Asn Phe Met Gln Leu Ile His Asp Asp Ser Leu Thr Phe
            690             695             700
Lys Glu Asp Ile Gln Lys Ala Gln Val Ser Gly Gln Gly Asp Ser Leu
705             710             715             720
His Glu His Ile Ala Asn Leu Ala Gly Ser Pro Ala Ile Lys Lys Gly
            725             730             735
Ile Leu Gln Thr Val Lys Val Val Asp Glu Leu Val Lys Val Met Gly
            740             745             750
Arg His Lys Pro Glu Asn Ile Val Ile Glu Met Ala Arg Glu Asn Gln
            755             760             765
Thr Thr Gln Lys Gly Gln Lys Asn Ser Arg Glu Arg Met Lys Arg Ile
            770             775             780
Glu Glu Gly Ile Lys Glu Leu Gly Ser Gln Ile Leu Lys Glu His Pro
785             790             795             800
Val Glu Asn Thr Gln Leu Gln Asn Glu Lys Leu Tyr Leu Tyr Tyr Leu
            805             810             815
Gln Asn Gly Arg Asp Met Tyr Val Asp Gln Glu Leu Asp Ile Asn Arg
            820             825             830
Leu Ser Asp Tyr Asp Val Asp Ala Ile Val Pro Gln Ser Phe Leu Lys
            835             840             845
```

-continued

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

```
Pro Glu  Asp Asn Glu Gln Lys Gln Leu Phe Val Glu  Gln His Lys
    1250             1255                1260

His Tyr  Leu Asp Glu Ile Ile Glu Gln Ile Ser Glu  Phe Ser Lys
    1265             1270                1275

Arg Val  Ile Leu Ala Asp Ala Asn Leu Asp Lys Val  Leu Ser Ala
    1280             1285                1290

Tyr Asn  Lys His Arg Asp Lys Pro Ile Arg Glu Gln  Ala Glu Asn
    1295             1300                1305

Ile Ile  His Leu Phe Thr Leu Thr Asn Leu Gly Ala  Pro Ala Ala
    1310             1315                1320

Phe Lys  Tyr Phe Asp Thr Thr Ile Asp Arg Lys Arg  Tyr Thr Ser
    1325             1330                1335

Thr Lys  Glu Val Leu Asp Ala Thr Leu Ile His Gln  Ser Ile Thr
    1340             1345                1350

Gly Leu  Tyr Glu Thr Arg Ile Asp Leu Ser Gln Leu  Gly Gly Asp
    1355             1360                1365

<210> SEQ ID NO 11
<211> LENGTH: 277
<212> TYPE: PRT
<213> ORGANISM: Escherichia coli

<400> SEQUENCE: 11

Lys Lys Asn Arg Ala Phe Leu Lys Trp Ala Gly Gly Lys Tyr Pro Leu
1               5                   10                  15

Leu Asp Asp Ile Lys Arg His Leu Pro Lys Gly Glu Cys Leu Val Glu
            20                  25                  30

Pro Phe Val Gly Ala Gly Ser Val Phe Leu Asn Thr Asp Phe Ser Arg
        35                  40                  45

Tyr Ile Leu Ala Asp Ile Asn Ser Asp Leu Ile Ser Leu Tyr Asn Ile
    50                  55                  60

Val Lys Met Arg Thr Asp Glu Tyr Val Gln Ala Ala Arg Glu Leu Phe
65              70                  75                  80

Val Pro Glu Thr Asn Cys Ala Glu Val Tyr Tyr Gln Phe Arg Glu Glu
            85                  90                  95

Phe Asn Lys Ser Gln Asp Pro Phe Arg Arg Ala Val Leu Phe Leu Tyr
            100                 105                 110

Leu Asn Arg Tyr Gly Tyr Asn Gly Leu Cys Arg Tyr Asn Leu Arg Gly
        115                 120                 125

Glu Phe Asn Val Pro Phe Gly Arg Tyr Lys Lys Pro Tyr Phe Pro Glu
    130                 135                 140

Ala Glu Leu Tyr His Phe Ala Glu Lys Ala Gln Asn Ala Phe Phe Tyr
145             150                 155                 160

Cys Glu Ser Tyr Ala Asp Ser Met Ala Arg Ala Asp Asp Ala Ser Val
            165                 170                 175

Val Tyr Cys Asp Pro Pro Tyr Ala Pro Leu Ser Ala Thr Ala Asn Phe
            180                 185                 190

Thr Ala Tyr His Thr Asn Ser Phe Thr Leu Glu Gln Gln Ala His Leu
        195                 200                 205

Ala Glu Ile Ala Glu Gly Leu Val Glu Arg His Ile Pro Val Leu Ile
    210                 215                 220

Ser Asn His Asp Thr Met Leu Thr Arg Glu Trp Tyr Gln Arg Ala Lys
225             230                 235                 240

Leu His Val Val Lys Val Arg Arg Ser Ile Ser Ser Asn Gly Gly Thr
            245                 250                 255
```

```
Arg Lys Lys Val Asp Glu Leu Leu Ala Leu Tyr Lys Pro Gly Val Val
            260                 265                 270

Ser Pro Ala Lys Lys
            275

<210> SEQ ID NO 12
<211> LENGTH: 277
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Lys Lys Asn Arg Ala Phe Leu Lys Trp Ala Gly Gly Lys Tyr Pro Leu
1               5                   10                  15

Leu Asp Asp Ile Lys Arg His Leu Pro Lys Gly Glu Cys Leu Val Glu
            20                  25                  30

Pro Phe Val Gly Ala Gly Ser Val Phe Leu Asn Thr Asp Phe Ser Arg
        35                  40                  45

Tyr Ile Leu Ala Asp Ile Asn Ser Asp Leu Ile Ser Leu Tyr Asn Ile
50                  55                  60

Val Lys Met Arg Thr Asp Glu Tyr Val Gln Ala Ala Arg Glu Leu Phe
65                  70                  75                  80

Val Pro Glu Thr Asn Cys Ala Glu Val Tyr Tyr Gln Phe Arg Glu Glu
            85                  90                  95

Phe Asn Lys Ser Gln Asp Pro Phe Arg Arg Ala Val Leu Phe Leu Tyr
            100                 105                 110

Leu Asn Arg Tyr Gly Ala Asn Gly Leu Cys Arg Tyr Asn Leu Arg Gly
        115                 120                 125

Glu Phe Asn Val Pro Phe Gly Arg Tyr Lys Lys Pro Tyr Phe Pro Glu
130                 135                 140

Ala Glu Leu Tyr His Phe Ala Glu Lys Ala Gln Asn Ala Phe Phe Tyr
145                 150                 155                 160

Cys Glu Ser Tyr Ala Asp Ser Met Ala Arg Ala Asp Asp Ala Ser Val
            165                 170                 175

Val Tyr Cys Asp Pro Pro Tyr Ala Pro Leu Ser Ala Thr Ala Asn Phe
            180                 185                 190

Thr Ala Tyr His Thr Asn Ser Phe Thr Leu Glu Gln Gln Ala His Leu
        195                 200                 205

Ala Glu Ile Ala Glu Gly Leu Val Glu Arg His Ile Pro Val Leu Ile
    210                 215                 220

Ser Asn His Asp Thr Met Leu Thr Arg Glu Trp Tyr Gln Arg Ala Lys
225                 230                 235                 240

Leu His Val Val Lys Val Arg Arg Ser Ile Ser Ser Asn Gly Gly Thr
            245                 250                 255

Arg Lys Lys Val Asp Glu Leu Leu Ala Leu Tyr Lys Pro Gly Val Val
            260                 265                 270

Ser Pro Ala Lys Lys
            275

<210> SEQ ID NO 13
<211> LENGTH: 277
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 13

```
Lys Lys Asn Arg Ala Phe Leu Lys Trp Ala Gly Gly Lys Tyr Pro Leu
1               5                   10                  15

Leu Asp Asp Ile Lys Arg His Leu Pro Lys Gly Glu Cys Leu Val Glu
            20                  25                  30

Pro Phe Val Gly Ala Gly Ser Val Phe Leu Asn Thr Asp Phe Ser Arg
        35                  40                  45

Tyr Ile Leu Ala Asp Ile Asn Ser Asp Leu Ile Ser Leu Tyr Asn Ile
    50                  55                  60

Val Lys Met Arg Thr Asp Glu Tyr Val Gln Ala Arg Glu Leu Phe
65                  70                  75                  80

Val Pro Glu Thr Asn Cys Ala Glu Val Tyr Tyr Gln Phe Arg Glu Glu
                85                  90                  95

Phe Asn Lys Ser Gln Asp Pro Phe Arg Arg Ala Val Leu Phe Leu Tyr
            100                 105                 110

Leu Asn Arg Tyr Gly Tyr Ala Gly Leu Cys Arg Tyr Asn Leu Arg Gly
        115                 120                 125

Glu Phe Asn Val Pro Phe Gly Arg Tyr Lys Lys Pro Tyr Phe Pro Glu
    130                 135                 140

Ala Glu Leu Tyr His Phe Ala Glu Lys Ala Gln Asn Ala Phe Tyr
145                 150                 155                 160

Cys Glu Ser Tyr Ala Asp Ser Met Ala Arg Ala Asp Asp Ala Ser Val
                165                 170                 175

Val Tyr Cys Asp Pro Pro Tyr Ala Pro Leu Ser Ala Thr Ala Asn Phe
            180                 185                 190

Thr Ala Tyr His Thr Asn Ser Phe Thr Leu Glu Gln Gln Ala His Leu
        195                 200                 205

Ala Glu Ile Ala Glu Gly Leu Val Glu Arg His Ile Pro Val Leu Ile
    210                 215                 220

Ser Asn His Asp Thr Met Leu Thr Arg Glu Trp Tyr Gln Arg Ala Lys
225                 230                 235                 240

Leu His Val Val Lys Val Arg Arg Ser Ile Ser Ser Asn Gly Gly Thr
                245                 250                 255

Arg Lys Lys Val Asp Glu Leu Leu Ala Leu Tyr Lys Pro Gly Val Val
            260                 265                 270

Ser Pro Ala Lys Lys
        275
```

<210> SEQ ID NO 14
<211> LENGTH: 277
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 14

```
Lys Lys Asn Arg Ala Phe Leu Lys Trp Ala Gly Gly Lys Tyr Pro Leu
1               5                   10                  15

Leu Asp Asp Ile Lys Arg His Leu Pro Lys Gly Glu Cys Leu Val Glu
            20                  25                  30

Pro Phe Val Gly Ala Gly Ser Val Phe Leu Asn Thr Asp Phe Ser Arg
        35                  40                  45

Tyr Ile Leu Ala Asp Ile Asn Ser Asp Leu Ile Ser Leu Tyr Asn Ile
```

```
            50                  55                  60
Val Lys Met Arg Thr Asp Glu Tyr Val Gln Ala Ala Arg Glu Leu Phe
 65                  70                  75                  80

Val Pro Glu Thr Asn Cys Ala Glu Val Tyr Tyr Gln Phe Arg Glu Glu
                 85                  90                  95

Phe Asn Lys Ser Gln Asp Pro Phe Arg Arg Ala Val Leu Phe Leu Tyr
            100                 105                 110

Leu Asn Arg Tyr Gly Tyr Ser Gly Leu Cys Arg Tyr Asn Leu Arg Gly
            115                 120                 125

Glu Phe Asn Val Pro Phe Gly Arg Tyr Lys Lys Pro Tyr Phe Pro Glu
            130                 135                 140

Ala Glu Leu Tyr His Phe Ala Glu Lys Ala Gln Asn Ala Phe Phe Tyr
145                 150                 155                 160

Cys Glu Ser Tyr Ala Asp Ser Met Ala Arg Ala Asp Asp Ala Ser Val
                165                 170                 175

Val Tyr Cys Asp Pro Pro Tyr Ala Pro Leu Ser Ala Thr Ala Asn Phe
                180                 185                 190

Thr Ala Tyr His Thr Asn Ser Phe Thr Leu Glu Gln Gln Ala His Leu
                195                 200                 205

Ala Glu Ile Ala Glu Gly Leu Val Glu Arg His Ile Pro Val Leu Ile
            210                 215                 220

Ser Asn His Asp Thr Met Leu Thr Arg Glu Trp Tyr Gln Arg Ala Lys
225                 230                 235                 240

Leu His Val Val Lys Val Arg Arg Ser Ile Ser Ser Asn Gly Gly Thr
                245                 250                 255

Arg Lys Lys Val Asp Glu Leu Leu Ala Leu Tyr Lys Pro Gly Val Val
                260                 265                 270

Ser Pro Ala Lys Lys
            275

<210> SEQ ID NO 15
<211> LENGTH: 277
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Lys Lys Asn Arg Ala Phe Leu Lys Trp Ala Gly Gly Lys Tyr Pro Leu
 1                   5                  10                  15

Leu Asp Asp Ile Lys Arg His Leu Pro Lys Gly Glu Cys Leu Val Glu
                 20                  25                  30

Pro Phe Val Gly Ala Gly Ser Val Phe Leu Asn Thr Asp Phe Ser Arg
             35                  40                  45

Tyr Ile Leu Ala Asp Ile Asn Ser Asp Leu Ile Ser Leu Tyr Asn Ile
         50                  55                  60

Val Lys Met Arg Thr Asp Glu Tyr Val Gln Ala Ala Arg Glu Leu Phe
 65                  70                  75                  80

Val Pro Glu Thr Asn Cys Ala Glu Val Tyr Tyr Gln Phe Arg Glu Glu
                 85                  90                  95

Phe Asn Lys Ser Gln Asp Pro Phe Arg Arg Ala Val Leu Phe Leu Tyr
            100                 105                 110

Leu Asn Arg Tyr Gly Tyr Asn Gly Ala Cys Arg Tyr Asn Leu Arg Gly
            115                 120                 125
```

```
Glu Phe Asn Val Pro Phe Gly Arg Tyr Lys Lys Pro Tyr Phe Pro Glu
    130                 135                 140

Ala Glu Leu Tyr His Phe Ala Glu Lys Ala Gln Asn Ala Phe Phe Tyr
145                 150                 155                 160

Cys Glu Ser Tyr Ala Asp Ser Met Ala Arg Ala Asp Asp Ala Ser Val
                165                 170                 175

Val Tyr Cys Asp Pro Pro Tyr Ala Pro Leu Ser Ala Thr Ala Asn Phe
                180                 185                 190

Thr Ala Tyr His Thr Asn Ser Phe Thr Leu Glu Gln Gln Ala His Leu
                195                 200                 205

Ala Glu Ile Ala Glu Gly Leu Val Glu Arg His Ile Pro Val Leu Ile
210                 215                 220

Ser Asn His Asp Thr Met Leu Thr Arg Glu Trp Tyr Gln Arg Ala Lys
225                 230                 235                 240

Leu His Val Val Lys Val Arg Arg Ser Ile Ser Ser Asn Gly Gly Thr
                245                 250                 255

Arg Lys Lys Val Asp Glu Leu Leu Ala Leu Tyr Lys Pro Gly Val Val
                260                 265                 270

Ser Pro Ala Lys Lys
            275

<210> SEQ ID NO 16
<211> LENGTH: 277
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Lys Lys Asn Arg Ala Phe Leu Lys Trp Ala Gly Gly Lys Tyr Pro Leu
1               5                   10                  15

Leu Asp Asp Ile Lys Arg His Leu Pro Lys Gly Glu Cys Leu Val Glu
                20                  25                  30

Pro Phe Val Gly Ala Gly Ser Val Phe Leu Asn Thr Asp Phe Ser Arg
            35                  40                  45

Tyr Ile Leu Ala Asp Ile Asn Ser Asp Leu Ile Ser Leu Tyr Asn Ile
50                  55                  60

Val Lys Met Arg Thr Asp Glu Tyr Val Gln Ala Ala Arg Glu Leu Phe
65                  70                  75                  80

Val Pro Glu Thr Asn Cys Ala Glu Val Tyr Tyr Gln Phe Arg Glu Glu
                85                  90                  95

Phe Asn Lys Ser Gln Asp Pro Phe Arg Arg Ala Val Leu Phe Leu Tyr
                100                 105                 110

Leu Asn Arg Tyr Gly Tyr Asn Gly Leu Cys Arg Tyr Asn Leu Arg Gly
            115                 120                 125

Glu Phe Asn Val Pro Phe Gly Ala Tyr Lys Lys Pro Tyr Phe Pro Glu
    130                 135                 140

Ala Glu Leu Tyr His Phe Ala Glu Lys Ala Gln Asn Ala Phe Phe Tyr
145                 150                 155                 160

Cys Glu Ser Tyr Ala Asp Ser Met Ala Arg Ala Asp Asp Ala Ser Val
                165                 170                 175

Val Tyr Cys Asp Pro Pro Tyr Ala Pro Leu Ser Ala Thr Ala Asn Phe
                180                 185                 190

Thr Ala Tyr His Thr Asn Ser Phe Thr Leu Glu Gln Gln Ala His Leu
                195                 200                 205
```

```
Ala Glu Ile Ala Glu Gly Leu Val Glu Arg His Ile Pro Val Leu Ile
        210                 215                 220

Ser Asn His Asp Thr Met Leu Thr Arg Glu Trp Tyr Gln Arg Ala Lys
225                 230                 235                 240

Leu His Val Val Lys Val Arg Arg Ser Ile Ser Ser Asn Gly Gly Thr
                245                 250                 255

Arg Lys Lys Val Asp Glu Leu Leu Ala Leu Tyr Lys Pro Gly Val Val
            260                 265                 270

Ser Pro Ala Lys Lys
        275

<210> SEQ ID NO 17
<211> LENGTH: 277
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Lys Lys Asn Arg Ala Phe Leu Lys Trp Ala Gly Gly Lys Tyr Pro Leu
1               5                   10                  15

Leu Asp Asp Ile Lys Arg His Leu Pro Lys Gly Glu Cys Leu Val Glu
            20                  25                  30

Pro Phe Val Gly Ala Gly Ser Val Phe Leu Asn Thr Asp Phe Ser Arg
        35                  40                  45

Tyr Ile Leu Ala Asp Ile Asn Ser Asp Leu Ile Ser Leu Tyr Asn Ile
50                  55                  60

Val Lys Met Arg Thr Asp Glu Tyr Val Gln Ala Ala Arg Glu Leu Phe
65                  70                  75                  80

Val Pro Glu Thr Asn Cys Ala Glu Val Tyr Tyr Gln Phe Arg Glu Glu
                85                  90                  95

Phe Asn Lys Ser Gln Asp Pro Phe Arg Arg Ala Val Leu Phe Leu Tyr
            100                 105                 110

Leu Asn Ala Tyr Gly Tyr Asn Gly Leu Cys Arg Tyr Asn Leu Arg Gly
        115                 120                 125

Glu Phe Asn Val Pro Phe Gly Arg Tyr Lys Lys Pro Tyr Phe Pro Glu
130                 135                 140

Ala Glu Leu Tyr His Phe Ala Glu Lys Ala Gln Asn Ala Phe Phe Tyr
145                 150                 155                 160

Cys Glu Ser Tyr Ala Asp Ser Met Ala Arg Ala Asp Asp Ala Ser Val
                165                 170                 175

Val Tyr Cys Asp Pro Pro Tyr Ala Pro Leu Ser Ala Thr Ala Asn Phe
            180                 185                 190

Thr Ala Tyr His Thr Asn Ser Phe Thr Leu Glu Gln Gln Ala His Leu
        195                 200                 205

Ala Glu Ile Ala Glu Gly Leu Val Glu Arg His Ile Pro Val Leu Ile
        210                 215                 220

Ser Asn His Asp Thr Met Leu Thr Arg Glu Trp Tyr Gln Arg Ala Lys
225                 230                 235                 240

Leu His Val Val Lys Val Arg Arg Ser Ile Ser Ser Asn Gly Gly Thr
                245                 250                 255

Arg Lys Lys Val Asp Glu Leu Leu Ala Leu Tyr Lys Pro Gly Val Val
            260                 265                 270

Ser Pro Ala Lys Lys
```

<210> SEQ ID NO 18
<211> LENGTH: 277
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 18

Lys Lys Asn Arg Ala Phe Leu Lys Trp Ala Gly Gly Lys Tyr Pro Leu
1               5                   10                  15

Leu Asp Asp Ile Lys Arg His Leu Pro Lys Gly Glu Cys Leu Val Glu
            20                  25                  30

Pro Phe Val Gly Ala Gly Ser Val Phe Leu Asn Thr Asp Phe Ser Arg
        35                  40                  45

Tyr Ile Leu Ala Asp Ile Asn Ser Asp Leu Ile Ser Leu Tyr Asn Ile
    50                  55                  60

Val Lys Met Arg Thr Asp Glu Tyr Val Gln Ala Ala Arg Glu Leu Phe
65                  70                  75                  80

Val Pro Glu Thr Asn Cys Ala Glu Val Tyr Tyr Gln Phe Ala Glu Glu
                85                  90                  95

Phe Asn Lys Ser Gln Asp Pro Phe Arg Arg Ala Val Leu Phe Leu Tyr
            100                 105                 110

Leu Asn Arg Tyr Gly Tyr Asn Gly Leu Cys Arg Tyr Asn Leu Arg Gly
        115                 120                 125

Glu Phe Asn Val Pro Phe Gly Arg Tyr Lys Lys Pro Tyr Phe Pro Glu
    130                 135                 140

Ala Glu Leu Tyr His Phe Ala Glu Lys Ala Gln Asn Ala Phe Phe Tyr
145                 150                 155                 160

Cys Glu Ser Tyr Ala Asp Ser Met Ala Arg Ala Asp Ala Ser Val
                165                 170                 175

Val Tyr Cys Asp Pro Pro Tyr Ala Pro Leu Ser Ala Thr Ala Asn Phe
            180                 185                 190

Thr Ala Tyr His Thr Asn Ser Phe Thr Leu Glu Gln Gln Ala His Leu
        195                 200                 205

Ala Glu Ile Ala Glu Gly Leu Val Glu Arg His Ile Pro Val Leu Ile
    210                 215                 220

Ser Asn His Asp Thr Met Leu Thr Arg Glu Trp Tyr Gln Arg Ala Lys
225                 230                 235                 240

Leu His Val Val Lys Val Arg Arg Ser Ile Ser Ser Asn Gly Gly Thr
                245                 250                 255

Arg Lys Lys Val Asp Glu Leu Leu Ala Leu Tyr Lys Pro Gly Val Val
            260                 265                 270

Ser Pro Ala Lys Lys
        275

<210> SEQ ID NO 19
<211> LENGTH: 277
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 19

Lys Lys Asn Arg Ala Phe Leu Lys Trp Ala Gly Gly Lys Tyr Pro Leu

```
                1               5                   10                  15
            Leu Asp Asp Ile Lys Arg His Leu Pro Lys Gly Glu Cys Leu Val Glu
                            20                  25                  30

Pro Phe Val Gly Ala Gly Ser Val Phe Leu Asn Thr Asp Phe Ser Arg
                            35                  40                  45

Tyr Ile Leu Ala Asp Ile Asn Ser Asp Leu Ile Ser Leu Tyr Asn Ile
                        50                  55                  60

Val Lys Met Arg Thr Asp Glu Tyr Val Gln Ala Ala Arg Glu Leu Phe
            65                  70                  75                  80

Val Pro Glu Thr Asn Cys Ala Glu Val Tyr Tyr Gln Phe Arg Glu Glu
                            85                  90                  95

Phe Asn Lys Ser Gln Asp Pro Phe Arg Arg Ala Val Leu Phe Leu Tyr
                            100                 105                 110

Leu Asn Arg Tyr Gly Tyr Asn Gly Leu Cys Arg Tyr Ala Leu Arg Gly
                            115                 120                 125

Glu Phe Asn Val Pro Phe Gly Arg Tyr Lys Lys Pro Tyr Phe Pro Glu
                        130                 135                 140

Ala Glu Leu Tyr His Phe Ala Glu Lys Ala Gln Asn Ala Phe Phe Tyr
            145                 150                 155                 160

Cys Glu Ser Tyr Ala Asp Ser Met Ala Arg Ala Asp Ala Ser Val
                            165                 170                 175

Val Tyr Cys Asp Pro Pro Tyr Ala Pro Leu Ser Ala Thr Ala Asn Phe
                        180                 185                 190

Thr Ala Tyr His Thr Asn Ser Phe Thr Leu Glu Gln Gln Ala His Leu
                        195                 200                 205

Ala Glu Ile Ala Glu Gly Leu Val Glu Arg His Ile Pro Val Leu Ile
            210                 215                 220

Ser Asn His Asp Thr Met Leu Thr Arg Glu Trp Tyr Gln Arg Ala Lys
            225                 230                 235                 240

Leu His Val Val Lys Val Arg Arg Ser Ile Ser Ser Asn Gly Gly Thr
                            245                 250                 255

Arg Lys Lys Val Asp Glu Leu Leu Ala Leu Tyr Lys Pro Gly Val Val
                        260                 265                 270

Ser Pro Ala Lys Lys
                    275

<210> SEQ ID NO 20
<211> LENGTH: 277
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Lys Lys Asn Arg Ala Phe Leu Lys Trp Ala Gly Gly Lys Tyr Pro Leu
            1               5                   10                  15

Leu Asp Asp Ile Lys Arg His Leu Pro Lys Gly Glu Cys Leu Val Glu
                            20                  25                  30

Pro Phe Val Gly Ala Gly Ser Val Phe Leu Asn Thr Asp Phe Ser Arg
                            35                  40                  45

Tyr Ile Leu Ala Asp Ile Asn Ser Asp Leu Ile Ser Leu Tyr Asn Ile
                        50                  55                  60

Val Lys Met Arg Thr Asp Glu Tyr Val Gln Ala Ala Arg Glu Leu Phe
            65                  70                  75                  80
```

```
Val Pro Glu Thr Asn Cys Ala Glu Val Tyr Tyr Gln Phe Arg Glu Glu
                85                  90                  95

Phe Asn Lys Ser Gln Asp Pro Phe Arg Arg Ala Val Leu Phe Leu Tyr
            100                 105                 110

Leu Asn Arg Tyr Gly Tyr Asn Gly Leu Cys Arg Tyr Asn Leu Arg Gly
        115                 120                 125

Glu Phe Ala Val Pro Phe Gly Arg Tyr Lys Pro Tyr Phe Pro Glu
    130                 135                 140

Ala Glu Leu Tyr His Phe Ala Glu Lys Ala Gln Asn Ala Phe Phe Tyr
145                 150                 155                 160

Cys Glu Ser Tyr Ala Asp Ser Met Ala Arg Ala Asp Asp Ala Ser Val
                165                 170                 175

Val Tyr Cys Asp Pro Pro Tyr Ala Pro Leu Ser Ala Thr Ala Asn Phe
            180                 185                 190

Thr Ala Tyr His Thr Asn Ser Phe Thr Leu Glu Gln Gln Ala His Leu
        195                 200                 205

Ala Glu Ile Ala Glu Gly Leu Val Glu Arg His Ile Pro Val Leu Ile
    210                 215                 220

Ser Asn His Asp Thr Met Leu Thr Arg Glu Trp Tyr Gln Arg Ala Lys
225                 230                 235                 240

Leu His Val Val Lys Val Arg Arg Ser Ile Ser Ser Asn Gly Gly Thr
                245                 250                 255

Arg Lys Lys Val Asp Glu Leu Leu Ala Leu Tyr Lys Pro Gly Val Val
            260                 265                 270

Ser Pro Ala Lys Lys
        275

<210> SEQ ID NO 21
<211> LENGTH: 277
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Lys Lys Asn Arg Ala Phe Leu Lys Trp Ala Gly Gly Lys Tyr Pro Leu
1               5                   10                  15

Leu Asp Asp Ile Lys Arg His Leu Pro Lys Gly Glu Cys Leu Val Glu
            20                  25                  30

Pro Phe Val Gly Ala Gly Ser Val Phe Leu Asn Thr Asp Phe Ser Arg
        35                  40                  45

Tyr Ile Leu Ala Asp Ile Asn Ser Asp Leu Ile Ser Leu Tyr Asn Ile
    50                  55                  60

Val Lys Met Arg Thr Asp Glu Tyr Val Gln Ala Arg Glu Leu Phe
65                  70                  75                  80

Val Pro Glu Thr Asn Cys Ala Glu Val Tyr Tyr Gln Phe Arg Glu Glu
                85                  90                  95

Phe Asn Lys Ser Gln Asp Pro Phe Arg Arg Ala Val Leu Phe Leu Tyr
            100                 105                 110

Leu Asn Arg Tyr Gly Tyr Asn Gly Leu Cys Arg Tyr Ser Leu Arg Gly
        115                 120                 125

Glu Phe Asn Val Pro Phe Gly Arg Tyr Lys Lys Pro Tyr Phe Pro Glu
    130                 135                 140

Ala Glu Leu Tyr His Phe Ala Glu Lys Ala Gln Asn Ala Phe Phe Tyr
145                 150                 155                 160
```

```
Cys Glu Ser Tyr Ala Asp Ser Met Ala Arg Ala Asp Ala Ser Val
                165                 170                 175

Val Tyr Cys Asp Pro Pro Tyr Ala Pro Leu Ser Ala Thr Ala Asn Phe
            180                 185                 190

Thr Ala Tyr His Thr Asn Ser Phe Thr Leu Glu Gln Gln Ala His Leu
            195                 200                 205

Ala Glu Ile Ala Glu Gly Leu Val Glu Arg His Ile Pro Val Leu Ile
            210                 215                 220

Ser Asn His Asp Thr Met Leu Thr Arg Glu Trp Tyr Gln Arg Ala Lys
225                 230                 235                 240

Leu His Val Val Lys Val Arg Arg Ser Ile Ser Ser Asn Gly Gly Thr
                245                 250                 255

Arg Lys Lys Val Asp Glu Leu Leu Ala Leu Tyr Lys Pro Gly Val Val
            260                 265                 270

Ser Pro Ala Lys Lys
            275

<210> SEQ ID NO 22
<211> LENGTH: 277
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Lys Lys Asn Arg Ala Phe Leu Lys Trp Ala Gly Gly Lys Tyr Pro Leu
1               5                   10                  15

Leu Asp Asp Ile Lys Arg His Leu Pro Lys Gly Glu Cys Leu Val Glu
            20                  25                  30

Pro Phe Val Gly Ala Gly Ser Val Phe Leu Asn Thr Asp Phe Ser Arg
        35                  40                  45

Tyr Ile Leu Ala Asp Ile Asn Ser Asp Leu Ile Ser Leu Tyr Asn Ile
50                  55                  60

Val Lys Met Arg Thr Asp Glu Tyr Val Gln Ala Ala Arg Glu Leu Phe
65                  70                  75                  80

Val Pro Glu Thr Asn Cys Ala Glu Val Tyr Tyr Gln Phe Arg Glu Glu
                85                  90                  95

Phe Asn Lys Ser Gln Asp Pro Phe Arg Arg Ala Val Leu Phe Leu Tyr
            100                 105                 110

Leu Asn Arg Tyr Gly Tyr Asn Gly Leu Cys Arg Tyr Asn Leu Arg Gly
            115                 120                 125

Glu Phe Ser Val Pro Phe Gly Arg Tyr Lys Lys Pro Tyr Phe Pro Glu
        130                 135                 140

Ala Glu Leu Tyr His Phe Ala Glu Lys Ala Gln Asn Ala Phe Phe Tyr
145                 150                 155                 160

Cys Glu Ser Tyr Ala Asp Ser Met Ala Arg Ala Asp Ala Ser Val
                165                 170                 175

Val Tyr Cys Asp Pro Pro Tyr Ala Pro Leu Ser Ala Thr Ala Asn Phe
            180                 185                 190

Thr Ala Tyr His Thr Asn Ser Phe Thr Leu Glu Gln Gln Ala His Leu
            195                 200                 205

Ala Glu Ile Ala Glu Gly Leu Val Glu Arg His Ile Pro Val Leu Ile
            210                 215                 220

Ser Asn His Asp Thr Met Leu Thr Arg Glu Trp Tyr Gln Arg Ala Lys
```

```
                225                 230                 235                 240

Leu His Val Val Lys Val Arg Arg Ser Ile Ser Ser Asn Gly Gly Thr
                245                 250                 255

Arg Lys Lys Val Asp Glu Leu Leu Ala Leu Tyr Lys Pro Gly Val Val
                260                 265                 270

Ser Pro Ala Lys Lys
                275

<210> SEQ ID NO 23
<211> LENGTH: 276
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Lys Lys Asn Arg Ala Phe Leu Lys Trp Ala Gly Gly Lys Tyr Pro Leu
1               5                   10                  15

Leu Asp Asp Ile Lys Arg His Leu Pro Lys Gly Glu Cys Leu Val Glu
                20                  25                  30

Pro Phe Val Gly Ala Gly Ser Val Phe Leu Asn Thr Asp Phe Ser Arg
            35                  40                  45

Tyr Ile Leu Ala Asp Ile Asn Ser Asp Leu Ile Ser Leu Tyr Asn Ile
        50                  55                  60

Val Lys Met Arg Thr Asp Glu Tyr Val Gln Ala Ala Arg Glu Leu Phe
65                  70                  75                  80

Val Pro Glu Thr Asn Cys Ala Glu Val Tyr Tyr Gln Phe Ala Glu Glu
                85                  90                  95

Phe Asn Lys Ser Gln Asp Pro Phe Arg Arg Ala Val Leu Phe Leu Tyr
            100                 105                 110

Leu Asn Arg Tyr Gly Tyr Asn Gly Leu Cys Arg Tyr Ala Leu Arg Gly
        115                 120                 125

Glu Phe Asn Val Pro Phe Gly Arg Tyr Lys Lys Pro Tyr Phe Pro Glu
130                 135                 140

Ala Glu Leu Tyr His Phe Ala Glu Lys Ala Gln Asn Ala Phe Phe Tyr
145                 150                 155                 160

Cys Glu Ser Tyr Ala Asp Ser Met Ala Arg Ala Asp Asp Ala Ser Val
                165                 170                 175

Val Cys Asp Pro Pro Tyr Ala Pro Leu Ser Ala Thr Ala Asn Phe Thr
            180                 185                 190

Ala Tyr His Thr Asn Ser Phe Thr Leu Glu Gln Gln Ala His Leu Ala
        195                 200                 205

Glu Ile Ala Glu Gly Leu Val Glu Arg His Ile Pro Val Leu Ile Ser
210                 215                 220

Asn His Asp Thr Met Leu Thr Arg Glu Trp Tyr Gln Arg Ala Lys Leu
225                 230                 235                 240

His Val Val Lys Val Arg Arg Ser Ile Ser Ser Asn Gly Gly Thr Arg
                245                 250                 255

Lys Lys Val Asp Glu Leu Leu Ala Leu Tyr Lys Pro Gly Val Val Ser
            260                 265                 270

Pro Ala Lys Lys
        275

<210> SEQ ID NO 24
<211> LENGTH: 277
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Lys Lys Asn Arg Ala Phe Leu Lys Trp Ala Gly Gly Lys Tyr Pro Leu
1               5                   10                  15

Leu Asp Asp Ile Lys Arg His Leu Pro Lys Gly Glu Cys Leu Val Glu
            20                  25                  30

Pro Phe Val Gly Ala Gly Ser Val Phe Leu Asn Thr Asp Phe Ser Arg
        35                  40                  45

Tyr Ile Leu Ala Asp Ile Asn Ser Asp Leu Ile Ser Leu Tyr Asn Ile
    50                  55                  60

Val Lys Met Arg Thr Asp Glu Tyr Val Gln Ala Ala Arg Glu Leu Phe
65                  70                  75                  80

Val Pro Glu Thr Asn Cys Ala Glu Val Tyr Tyr Gln Phe Ala Glu Glu
                85                  90                  95

Phe Asn Lys Ser Gln Asp Pro Phe Arg Arg Ala Val Leu Phe Leu Tyr
            100                 105                 110

Leu Asn Ala Tyr Gly Tyr Asn Gly Leu Cys Arg Tyr Asn Leu Arg Gly
        115                 120                 125

Glu Phe Asn Val Pro Phe Gly Arg Tyr Lys Lys Pro Tyr Phe Pro Glu
130                 135                 140

Ala Glu Leu Tyr His Phe Ala Glu Lys Ala Gln Asn Ala Phe Phe Tyr
145                 150                 155                 160

Cys Glu Ser Tyr Ala Asp Ser Met Ala Arg Ala Asp Asp Ala Ser Val
                165                 170                 175

Val Tyr Cys Asp Pro Pro Tyr Ala Pro Leu Ser Ala Thr Ala Asn Phe
            180                 185                 190

Thr Ala Tyr His Thr Asn Ser Phe Thr Leu Glu Gln Gln Ala His Leu
        195                 200                 205

Ala Glu Ile Ala Glu Gly Leu Val Glu Arg His Ile Pro Val Leu Ile
210                 215                 220

Ser Asn His Asp Thr Met Leu Thr Arg Glu Trp Tyr Gln Arg Ala Lys
225                 230                 235                 240

Leu His Val Val Lys Val Arg Arg Ser Ile Ser Ser Asn Gly Gly Thr
                245                 250                 255

Arg Lys Lys Val Asp Glu Leu Leu Ala Leu Tyr Lys Pro Gly Val Val
            260                 265                 270

Ser Pro Ala Lys Lys
        275

<210> SEQ ID NO 25
<211> LENGTH: 277
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Lys Lys Asn Arg Ala Phe Leu Lys Trp Ala Gly Gly Lys Tyr Pro Leu
1               5                   10                  15

Leu Asp Asp Ile Lys Arg His Leu Pro Lys Gly Glu Cys Leu Val Glu
            20                  25                  30

Pro Phe Val Gly Ala Gly Ser Val Phe Leu Asn Thr Asp Phe Ser Arg
            35                  40                  45

Tyr Ile Leu Ala Asp Ile Asn Ser Asp Leu Ile Ser Leu Tyr Asn Ile
 50                  55                  60

Val Lys Met Arg Thr Asp Glu Tyr Val Gln Ala Ala Arg Glu Leu Phe
 65                  70                  75                  80

Val Pro Glu Thr Asn Cys Ala Glu Val Tyr Tyr Gln Phe Ala Glu Glu
                 85                  90                  95

Phe Asn Lys Ser Gln Asp Pro Phe Arg Arg Ala Val Leu Phe Leu Tyr
            100                 105                 110

Leu Asn Arg Tyr Gly Tyr Asn Gly Leu Cys Arg Tyr Asn Leu Arg Gly
            115                 120                 125

Glu Phe Ala Val Pro Phe Gly Arg Tyr Lys Lys Pro Tyr Phe Pro Glu
130                 135                 140

Ala Glu Leu Tyr His Phe Ala Glu Lys Ala Gln Asn Ala Phe Phe Tyr
145                 150                 155                 160

Cys Glu Ser Tyr Ala Asp Ser Met Ala Arg Ala Asp Asp Ala Ser Val
                165                 170                 175

Val Tyr Cys Asp Pro Pro Tyr Ala Pro Leu Ser Ala Thr Ala Asn Phe
            180                 185                 190

Thr Ala Tyr His Thr Asn Ser Phe Thr Leu Glu Gln Gln Ala His Leu
            195                 200                 205

Ala Glu Ile Ala Glu Gly Leu Val Glu Arg His Ile Pro Val Leu Ile
210                 215                 220

Ser Asn His Asp Thr Met Leu Thr Arg Glu Trp Tyr Gln Arg Ala Lys
225                 230                 235                 240

Leu His Val Val Lys Val Arg Arg Ser Ile Ser Ser Asn Gly Gly Thr
                245                 250                 255

Arg Lys Lys Val Asp Glu Leu Leu Ala Leu Tyr Lys Pro Gly Val Val
            260                 265                 270

Ser Pro Ala Lys Lys
            275

<210> SEQ ID NO 26
<211> LENGTH: 277
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Lys Lys Asn Arg Ala Phe Leu Lys Trp Ala Gly Gly Lys Tyr Pro Leu
1               5                   10                  15

Leu Asp Asp Ile Lys Arg His Leu Pro Lys Gly Glu Cys Leu Val Glu
            20                  25                  30

Pro Phe Val Gly Ala Gly Ser Val Phe Leu Asn Thr Asp Phe Ser Arg
            35                  40                  45

Tyr Ile Leu Ala Asp Ile Asn Ser Asp Leu Ile Ser Leu Tyr Asn Ile
 50                  55                  60

Val Lys Met Arg Thr Asp Glu Tyr Val Gln Ala Ala Arg Glu Leu Phe
 65                  70                  75                  80

Val Pro Glu Thr Asn Cys Ala Glu Val Tyr Tyr Gln Phe Ala Glu Glu
                 85                  90                  95

Phe Asn Lys Ser Gln Asp Pro Phe Arg Arg Ala Val Leu Phe Leu Tyr
            100                 105                 110

```
Leu Asn Arg Tyr Gly Tyr Asn Gly Ala Cys Arg Tyr Asn Leu Arg Gly
            115                 120                 125

Glu Phe Asn Val Pro Phe Gly Arg Tyr Lys Lys Pro Tyr Phe Pro Glu
        130                 135                 140

Ala Glu Leu Tyr His Phe Ala Glu Lys Ala Gln Asn Ala Phe Phe Tyr
145                 150                 155                 160

Cys Glu Ser Tyr Ala Asp Ser Met Ala Arg Ala Asp Asp Ala Ser Val
                165                 170                 175

Val Tyr Cys Asp Pro Pro Tyr Ala Pro Leu Ser Ala Thr Ala Asn Phe
            180                 185                 190

Thr Ala Tyr His Thr Asn Ser Phe Thr Leu Glu Gln Gln Ala His Leu
            195                 200                 205

Ala Glu Ile Ala Glu Gly Leu Val Glu Arg His Ile Pro Val Leu Ile
        210                 215                 220

Ser Asn His Asp Thr Met Leu Thr Arg Glu Trp Tyr Gln Arg Ala Lys
225                 230                 235                 240

Leu His Val Val Lys Val Arg Arg Ser Ile Ser Ser Asn Gly Gly Thr
                245                 250                 255

Arg Lys Lys Val Asp Glu Leu Leu Ala Leu Tyr Lys Pro Gly Val Val
            260                 265                 270

Ser Pro Ala Lys Lys
            275

<210> SEQ ID NO 27
<211> LENGTH: 277
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Lys Lys Asn Arg Ala Phe Leu Lys Trp Ala Gly Gly Lys Tyr Pro Leu
1               5                   10                  15

Leu Asp Asp Ile Lys Arg His Leu Pro Lys Gly Glu Cys Leu Val Glu
            20                  25                  30

Pro Phe Val Gly Ala Gly Ser Val Phe Leu Asn Thr Asp Phe Ser Arg
        35                  40                  45

Tyr Ile Leu Ala Asp Ile Asn Ser Asp Leu Ile Ser Leu Tyr Asn Ile
    50                  55                  60

Val Lys Met Arg Thr Asp Glu Tyr Val Gln Ala Ala Arg Glu Leu Phe
65                  70                  75                  80

Val Pro Glu Thr Asn Cys Ala Glu Val Tyr Tyr Gln Phe Ala Glu Glu
                85                  90                  95

Phe Asn Lys Ser Gln Asp Pro Phe Arg Arg Ala Val Leu Phe Leu Tyr
            100                 105                 110

Leu Asn Arg Tyr Gly Ala Asn Gly Leu Cys Arg Tyr Asn Leu Arg Gly
            115                 120                 125

Glu Phe Asn Val Pro Phe Gly Arg Tyr Lys Lys Pro Tyr Phe Pro Glu
        130                 135                 140

Ala Glu Leu Tyr His Phe Ala Glu Lys Ala Gln Asn Ala Phe Phe Tyr
145                 150                 155                 160

Cys Glu Ser Tyr Ala Asp Ser Met Ala Arg Ala Asp Asp Ala Ser Val
                165                 170                 175

Val Tyr Cys Asp Pro Pro Tyr Ala Pro Leu Ser Ala Thr Ala Asn Phe
```

```
            180                 185                 190
Thr Ala Tyr His Thr Asn Ser Phe Thr Leu Glu Gln Gln Ala His Leu
            195                 200                 205

Ala Glu Ile Ala Glu Gly Leu Val Glu Arg His Ile Pro Val Leu Ile
            210                 215                 220

Ser Asn His Asp Thr Met Leu Thr Arg Glu Trp Tyr Gln Arg Ala Lys
225                 230                 235                 240

Leu His Val Val Lys Val Arg Arg Ser Ile Ser Ser Asn Gly Gly Thr
                245                 250                 255

Arg Lys Lys Val Asp Glu Leu Leu Ala Leu Tyr Lys Pro Gly Val Val
            260                 265                 270

Ser Pro Ala Lys Lys
            275

<210> SEQ ID NO 28
<211> LENGTH: 277
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Lys Lys Asn Arg Ala Phe Leu Lys Trp Ala Gly Gly Lys Tyr Pro Leu
1               5                   10                  15

Leu Asp Asp Ile Lys Arg His Leu Pro Lys Gly Glu Cys Leu Val Glu
            20                  25                  30

Pro Phe Val Gly Ala Gly Ser Val Phe Leu Asn Thr Asp Phe Ser Arg
        35                  40                  45

Tyr Ile Leu Ala Asp Ile Asn Ser Asp Leu Ile Ser Leu Tyr Asn Ile
    50                  55                  60

Val Lys Met Arg Thr Asp Glu Tyr Val Gln Ala Ala Arg Glu Leu Phe
65              70                  75                  80

Val Pro Glu Thr Asn Cys Ala Glu Val Tyr Tyr Gln Phe Arg Glu Glu
            85                  90                  95

Phe Asn Lys Ser Gln Asp Pro Phe Arg Arg Ala Val Leu Phe Leu Tyr
            100                 105                 110

Leu Asn Ala Tyr Gly Tyr Asn Gly Ala Cys Arg Tyr Asn Leu Arg Gly
            115                 120                 125

Glu Phe Asn Val Pro Phe Gly Arg Tyr Lys Lys Pro Tyr Phe Pro Glu
130                 135                 140

Ala Glu Leu Tyr His Phe Ala Glu Lys Ala Gln Asn Ala Phe Phe Tyr
145                 150                 155                 160

Cys Glu Ser Tyr Ala Asp Ser Met Ala Arg Ala Asp Asp Ala Ser Val
                165                 170                 175

Val Tyr Cys Asp Pro Pro Tyr Ala Pro Leu Ser Ala Thr Ala Asn Phe
            180                 185                 190

Thr Ala Tyr His Thr Asn Ser Phe Thr Leu Glu Gln Gln Ala His Leu
            195                 200                 205

Ala Glu Ile Ala Glu Gly Leu Val Glu Arg His Ile Pro Val Leu Ile
            210                 215                 220

Ser Asn His Asp Thr Met Leu Thr Arg Glu Trp Tyr Gln Arg Ala Lys
225                 230                 235                 240

Leu His Val Val Lys Val Arg Arg Ser Ile Ser Ser Asn Gly Gly Thr
                245                 250                 255
```

Arg Lys Lys Val Asp Glu Leu Leu Ala Leu Tyr Lys Pro Gly Val Val
            260                 265                 270

Ser Pro Ala Lys Lys
        275

<210> SEQ ID NO 29
<211> LENGTH: 277
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Lys Lys Asn Arg Ala Phe Leu Lys Trp Ala Gly Gly Lys Tyr Pro Leu
1               5                   10                  15

Leu Asp Asp Ile Lys Arg His Leu Pro Lys Gly Glu Cys Leu Val Glu
            20                  25                  30

Pro Phe Val Gly Ala Gly Ser Val Phe Leu Asn Thr Asp Phe Ser Arg
        35                  40                  45

Tyr Ile Leu Ala Asp Ile Asn Ser Asp Leu Ile Ser Leu Tyr Asn Ile
    50                  55                  60

Val Lys Met Arg Thr Asp Glu Tyr Val Gln Ala Ala Arg Glu Leu Phe
65                  70                  75                  80

Val Pro Glu Thr Asn Cys Ala Glu Val Tyr Tyr Gln Phe Arg Glu Glu
                85                  90                  95

Phe Asn Lys Ser Gln Asp Pro Phe Arg Arg Ala Val Leu Phe Leu Tyr
            100                 105                 110

Leu Asn Arg Tyr Gly Tyr Asn Gly Ala Cys Arg Tyr Asn Leu Arg Gly
        115                 120                 125

Glu Phe Ala Val Pro Phe Gly Arg Tyr Lys Lys Pro Tyr Phe Pro Glu
    130                 135                 140

Ala Glu Leu Tyr His Phe Ala Glu Lys Ala Gln Asn Ala Phe Phe Tyr
145                 150                 155                 160

Cys Glu Ser Tyr Ala Asp Ser Met Ala Arg Ala Asp Asp Ala Ser Val
                165                 170                 175

Val Tyr Cys Asp Pro Pro Tyr Ala Pro Leu Ser Ala Thr Ala Asn Phe
            180                 185                 190

Thr Ala Tyr His Thr Asn Ser Phe Thr Leu Glu Gln Gln Ala His Leu
        195                 200                 205

Ala Glu Ile Ala Glu Gly Leu Val Glu Arg His Ile Pro Val Leu Ile
    210                 215                 220

Ser Asn His Asp Thr Met Leu Thr Arg Glu Trp Tyr Gln Arg Ala Lys
225                 230                 235                 240

Leu His Val Val Lys Val Arg Arg Ser Ile Ser Ser Asn Gly Gly Thr
                245                 250                 255

Arg Lys Lys Val Asp Glu Leu Leu Ala Leu Tyr Lys Pro Gly Val Val
            260                 265                 270

Ser Pro Ala Lys Lys
        275

<210> SEQ ID NO 30
<211> LENGTH: 277
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Lys Lys Asn Arg Ala Phe Leu Lys Trp Ala Gly Gly Lys Tyr Pro Leu
1               5                   10                  15

Leu Asp Asp Ile Lys Arg His Leu Pro Lys Gly Glu Cys Leu Val Glu
            20                  25                  30

Pro Phe Val Gly Ala Gly Ser Val Phe Leu Asn Thr Asp Phe Ser Arg
        35                  40                  45

Tyr Ile Leu Ala Asp Ile Asn Ser Asp Leu Ile Ser Leu Tyr Asn Ile
    50                  55                  60

Val Lys Met Arg Thr Asp Glu Tyr Val Gln Ala Ala Arg Glu Leu Phe
65                  70                  75                  80

Val Pro Glu Thr Asn Cys Ala Glu Val Tyr Tyr Gln Phe Arg Glu Glu
            85                  90                  95

Phe Asn Lys Ser Gln Asp Pro Phe Arg Arg Ala Val Leu Phe Leu Tyr
        100                 105                 110

Leu Asn Ala Tyr Gly Tyr Asn Gly Leu Cys Arg Tyr Ala Leu Arg Gly
    115                 120                 125

Glu Phe Asn Val Pro Phe Gly Arg Tyr Lys Lys Pro Tyr Phe Pro Glu
130                 135                 140

Ala Glu Leu Tyr His Phe Ala Glu Lys Ala Gln Asn Ala Phe Phe Tyr
145                 150                 155                 160

Cys Glu Ser Tyr Ala Asp Ser Met Ala Arg Ala Asp Ala Ser Val
            165                 170                 175

Val Tyr Cys Asp Pro Pro Tyr Ala Pro Leu Ser Ala Thr Ala Asn Phe
        180                 185                 190

Thr Ala Tyr His Thr Asn Ser Phe Thr Leu Glu Gln Gln Ala His Leu
    195                 200                 205

Ala Glu Ile Ala Glu Gly Leu Val Glu Arg His Ile Pro Val Leu Ile
210                 215                 220

Ser Asn His Asp Thr Met Leu Thr Arg Glu Trp Tyr Gln Arg Ala Lys
225                 230                 235                 240

Leu His Val Val Lys Val Arg Arg Ser Ile Ser Ser Asn Gly Gly Thr
            245                 250                 255

Arg Lys Lys Val Asp Glu Leu Leu Ala Leu Tyr Lys Pro Gly Val Val
        260                 265                 270

Ser Pro Ala Lys Lys
        275

<210> SEQ ID NO 31
<211> LENGTH: 277
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Lys Lys Asn Arg Ala Phe Leu Lys Trp Ala Gly Gly Lys Tyr Pro Leu
1               5                   10                  15

Leu Asp Asp Ile Lys Arg His Leu Pro Lys Gly Glu Cys Leu Val Glu
            20                  25                  30

Pro Phe Val Gly Ala Gly Ser Val Phe Leu Asn Thr Asp Phe Ser Arg
        35                  40                  45

Tyr Ile Leu Ala Asp Ile Asn Ser Asp Leu Ile Ser Leu Tyr Asn Ile
    50                  55                  60

```
Val Lys Met Arg Thr Asp Glu Tyr Val Gln Ala Ala Arg Glu Leu Phe
 65                  70                  75                  80

Val Pro Glu Thr Asn Cys Ala Glu Val Tyr Tyr Gln Phe Arg Glu Glu
                 85                  90                  95

Phe Asn Lys Ser Gln Asp Pro Phe Arg Arg Ala Val Leu Phe Leu Tyr
            100                 105                 110

Leu Asn Ala Tyr Gly Tyr Asn Gly Leu Cys Arg Tyr Asn Leu Arg Gly
        115                 120                 125

Glu Phe Ala Val Pro Phe Gly Arg Tyr Lys Pro Tyr Phe Pro Glu
130                 135                 140

Ala Glu Leu Tyr His Phe Ala Glu Lys Ala Gln Asn Ala Phe Phe Tyr
145                 150                 155                 160

Cys Glu Ser Tyr Ala Asp Ser Met Ala Arg Ala Asp Asp Ala Ser Val
                165                 170                 175

Val Tyr Cys Asp Pro Pro Tyr Ala Pro Leu Ser Ala Thr Ala Asn Phe
            180                 185                 190

Thr Ala Tyr His Thr Asn Ser Phe Thr Leu Glu Gln Gln Ala His Leu
        195                 200                 205

Ala Glu Ile Ala Glu Gly Leu Val Glu Arg His Ile Pro Val Leu Ile
210                 215                 220

Ser Asn His Asp Thr Met Leu Thr Arg Glu Trp Tyr Gln Arg Ala Lys
225                 230                 235                 240

Leu His Val Val Lys Val Arg Arg Ser Ile Ser Ser Asn Gly Gly Thr
                245                 250                 255

Arg Lys Lys Val Asp Glu Leu Leu Ala Leu Tyr Lys Pro Gly Val Val
            260                 265                 270

Ser Pro Ala Lys Lys
            275

<210> SEQ ID NO 32
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
taggcgtgta cggtgggagg cctatataag cagagctcgt ttagtgaacc gtcagatcgc    60
ctggaacgcg tttaattaag ccgccacc                                      88

<210> SEQ ID NO 33
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
taggcgtgta cggtgggagg cctatataag cagagctcgt ttagtgaacc gtcagatcgc    60
ctggaacgcg tttaattaag ccgccacc                                      88

<210> SEQ ID NO 34
<211> LENGTH: 85
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 34
taggcgtgta cggtgggagg cctatataag cagagctcgt ttagtgaacc gtcagatcgc    60
ctggaacgcg tttaattaag ccacc                                         85

<210> SEQ ID NO 35
<211> LENGTH: 320
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
tgtacaaaaa agcaggcttt aaaggaacca attcagtcga ctggatccgg taccaaggtc    60
gggcaggaag agggcctatt tcccatgatt ccttcatatt tgcatatacg atacaaggct   120
gttagagaga taattagaat taatttgact gtaaacacaa agatattagt acaaaatacg   180
tgacgtagaa agtaataatt tcttgggtag tttgcagttt taaaattatg ttttaaaatg   240
gactatcata tgcttaccgt aacttgaaag tatttcgatt tcttggcttt atatatcttg   300
tggaaaggac gaaacaccgg                                              320

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
acgcgcgaca tcggctacgc                                               20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
cggctagccg atgtcgcgct                                               20

<210> SEQ ID NO 38
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
taggcgtgta cggtgggagg cctatataag cagagctcgt ttagtgaacc gtcagatcgc    60
ctggaacgcg tttaattaag ccgccacc                                      88

<210> SEQ ID NO 39
<211> LENGTH: 88
<212> TYPE: DNA
<213> ORGANISM: Artificial Sequence
<220> FEATURE:

<223> OTHER INFORMATION: Description of Artificial Sequence: Synthetic
oligonucleotide

<400> SEQUENCE: 39
taggcgtgta cggtgggagg cctatataag cagagctcgt ttagtgaacc gtcagatcgc    60
ctggaacgcg tttaattaag ccgccacc    88

<210> SEQ ID NO 40
<211> LENGTH: 109
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 40

Ser Gln Val Pro Ser Lys Gly Arg Ile Phe Leu Val Gln Asp Gly Gln
1               5                   10                  15

Val Arg Asp Pro Glu Lys Val Thr Lys Glu Phe Lys Gln Gly Leu Phe
            20                  25                  30

Leu Arg Lys Ser Ser Leu Ser Ser Arg Gly Trp Thr Ile Glu Ile Leu
        35                  40                  45

Asn Cys Ile Asp Lys Ile Glu Gly Ser Glu Phe Thr Leu Glu Asp Met
    50                  55                  60

Tyr Arg Phe Glu Ser Asp Leu Lys Asn Ile Phe Val Lys Asn Asn His
65                  70                  75                  80

Ile Lys Glu Lys Ile Arg Gln Gln Leu Gln Ile Leu Arg Asp Lys Glu
                85                  90                  95

Ile Ile Glu Phe Lys Gly Arg Gly Lys Tyr Arg Lys Leu
            100                 105

<210> SEQ ID NO 41
<211> LENGTH: 1254
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 41
gcgccgggtt ttggcgcctc ccgcgggcgc ccccctcctc acggcgagcg ctgccacgtc    60
agacgaaggg cgcaggagcg ttcctgatcc ttccgcccgg acgctcagga cagcggcccg   120
ctgctcataa gactcggcct tagaaccccca gtatcagcag aaggacattt taggacggga   180
cttgggtgac tctagggcac tggttttctt tccagagagc ggaacaggcg aggaaaagta   240
gtcccttctc ggcgattctg cggagggatc tccgtgggc ggtgaacgcc gatgattata   300
taaggacgcg ccggggtgtgg cacagctagt tccgtcgcag ccgggatttg ggtcgcggtt   360
cttgtttgtg gatcgctgtg atcgtcactt ggtgagttgc gggctgctgg gctggccggg   420
gctttcgtgg ccgccgggcc gctcggtggg acgaagcgt gtggagagac cgccaagggc   480
tgtagtctgg gtccgcgagc aaggttgccc tgaactgggg gttgggggga gcgcacaaaa   540
tggcggctgt tcccgagtct tgaatggaag acgcttgtaa ggcgggctgt gaggtcgttg   600
aaacaaggtg gggggcatgg tgggcggcaa gaacccaagg tcttgaggcc ttcgctaatg   660
cgggaaagct cttattcggg tgagatgggc tggggcacca tctggggacc ctgacgtgaa   720
gtttgtcact gactgagaa ctcgggtttg tcgtctggtt gcggggcgg cagttatgcg   780 gtgccgttgg gcagtgcacc cgtacctttg ggagcgcgcg cctcgtcgtg tcgtgacgtc   840

```
acccgttctg ttggcttata atgcagggtg gggccacctg ccggtaggtg tgcggtaggc        900
ttttctccgt cgcaggacgc agggttcggg cctagggtag gctctcctga atcgacaggc        960
gccggacctc tggtgagggg agggataagt gaggcgtcag tttctttggt cggttttatg       1020
tacctatctt cttaagtagc tgaagctccg gttttgaact atgcgctcgg ggttggcgag       1080
tgtgttttgt gaagtttttt aggcaccttt tgaaatgtaa tcatttgggt caatatgtaa       1140
ttttcagtgt tagactagta aagcttctgc aggtcgactc tagaaaattg tccgctaaat       1200
tctggccgtt tttggctttt ttgttagaca ggatccccgg gtaccggtgc cacc             1254
```

<210> SEQ ID NO 42
<211> LENGTH: 1227
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42

```
gcgccgggtt ttggcgcctc ccgcgggcgc cccctcctc acggcgagcg ctgccacgtc          60
agacgaaggg cgcagcgagc gtcctgatcc ttccgcccgg acgctcagga cagcggcccg        120
ctgctcataa gactcggcct tagaaccccca gtatcagcag aaggacattt taggacggga       180
cttgggtgac tctagggcac tggttttctt tccagagagc ggaacaggcg aggaaaagta       240
gtcccttctc ggcgattctg cggagggatc tccgtggggc ggtgaacgcc gatgattata       300
taaggacgcg ccgggtgtgg cacagctagt tccgtcgcag ccgggatttg ggtcgcggtt       360
cttgtttgtg gatcgctgtg atcgtcactt ggtgagtagc gggctgctgg gctggccggg       420
gctttcgtgg ccgccgggcc gctcggtggg acggaagcgt gtggagagac cgccaagggc       480
tgtagtctgg gtccgcgagc aaggttgccc tgaactgggg gttgggggga gcgcacaaaa       540
tggcggctgt tcccgagtct tgaatggaag acgcttgtaa ggcgggctgt gaggtcgttg       600
aaacaaggtg gggggcatgg tgggcggcaa gaacccaagg tcttgaggcc ttcgctaatg       660
cgggaaagct cttattcggg tgagatgggc tggggcacca tctggggacc ctgacgtgaa       720
gtttgtcact gactggagaa ctcggtttgt cgtctgttgc ggggggcggca gttatggcgg       780 tgccgttggg cagtgcaccc gtaccttttgg gagcgcgcgc cctcgtcgtg tcgtgacgtc       840
acccgttctg ttggcttata atgcagggtg gggccacctg ccggtaggtg tgcggtaggc        900
ttttctccgt cgcaggacgc agggttcggg cctagggtag gctctcctga atcgacaggc        960
gccggacctc tggtgagggg agggataagt gaggcgtcag tttctttggt cggttttatg       1020
tacctatctt cttaagtagc tgaagctccg gttttgaact atgcgctcgg ggttggcgag       1080
tgtgttttgt gaagtttttt aggcaccttt tgaaatgtaa tcatttgggt caatatgtaa       1140
ttttcagtgt tagactagta aattgtccgc taaattctgg ccgttttggg cttttttgtt       1200
agacacgcgt ttaattaagc cgccacc                                          1227
```

<210> SEQ ID NO 43
<211> LENGTH: 1227
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43

```
gcgccgggtt ttggcgcctc ccgcgggcgc ccccctcctc acggcgagcg ctgccacgtc    60
agacgaaggg cgcagcgagc gtcctgatcc ttccgcccgg acgctcagga cagcggcccg   120
ctgctcataa gactcggcct tagaaccccca gtatcagcag aaggacattt taggacggga   180
cttgggtgac tctagggcac tggttttctt tccagagagc ggaacaggcg aggaaaagta   240
gtcccttctc ggcgattctg cggagggatc tccgtggggc ggtgaacgcc gatgattata   300
taaggacgcg ccgggtgtgg cacagctagt tccgtcgcag ccgggatttg ggtcgcggtt   360
cttgtttgtg gatcgctgtg atcgtcactt ggtgagtagc gggctgctgg gctggccggg   420
gctttcgtgg ccgccgggcc gctcggtggg acggaagcgt gtggagagac cgccaagggc   480
tgtagtctgg gtccgcgagc aaggttgccc tgaactgggg gttgggggga gcgcacaaaa   540
tggcggctgt tcccgagtct tgaatggaag acgcttgtaa ggcgggctgt gaggtcgttg   600
aaacaaggtg gggggcatgg tgggcggcaa gaacccaagg tcttgaggcc ttcgctaatg   660
cgggaaagct cttattcggg tgagatgggc tggggcacca tctggggacc ctgacgtgaa   720
gtttgtcact gactggagaa ctcggtttgt cgtctgttgc gggggcggca gttatggcgg   780
tgccgttggg cagtgcaccc gtacctttgg gagcgcgcgc cctcgtcgtg tcgtgacgtc   840
acccgttctg ttggcttata atgcaggtg gggccacctg ccggtaggtg tgcggtaggc   900
ttttctccgt cgcaggacgc agggttcggg cctagggtag gctctcctga atcgacaggc   960
gccggacctc tggtgagggg agggataagt gaggcgtcag tttctttggt cggtttttatg  1020 tacctatctt cttaagtagc tgaagctccg gttttgaact atgcgctcgg ggttggcgag  1080
tgtgttttgt gaagttttttt aggcacccttt tgaaatgtaa tcatttgggt caatatgtaa  1140
ttttcagtgt tagactagta aattgtccgc taaattctgg ccgttttttgg ctttttttgtt  1200 agacacgcgt ttaattaagc cgccacc                                      1227
```

<210> SEQ ID NO 44
<211> LENGTH: 1227
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44

```
gcgccgggtt ttggcgcctc ccgcgggcgc ccccctcctc acggcgagcg ctgccacgtc    60
agacgaaggg cgcagcgagc gtcctgatcc ttccgcccgg acgctcagga cagcggcccg   120
ctgctcataa gactcggcct tagaaccccca gtatcagcag aaggacattt taggacggga   180
cttgggtgac tctagggcac tggttttctt tccagagagc ggaacaggcg aggaaaagta   240
gtcccttctc ggcgattctg cggagggatc tccgtggggc ggtgaacgcc gatgattata   300
taaggacgcg ccgggtgtgg cacagctagt tccgtcgcag ccgggatttg ggtcgcggtt   360
cttgtttgtg gatcgctgtg atcgtcactt ggtgagtagc gggctgctgg gctggccggg   420
gctttcgtgg ccgccgggcc gctcggtggg acggaagcgt gtggagagac cgccaagggc   480
tgtagtctgg gtccgcgagc aaggttgccc tgaactgggg gttgggggga gcgcacaaaa   540
tggcggctgt tcccgagtct tgaatggaag acgcttgtaa ggcgggctgt gaggtcgttg   600
aaacaaggtg gggggcatgg tgggcggcaa gaacccaagg tcttgaggcc ttcgctaatg   660
cgggaaagct cttattcggg tgagatgggc tggggcacca tctggggacc ctgacgtgaa   720
gtttgtcact gactggagaa ctcggtttgt cgtctgttgc gggggcggca gttatggcgg   780
```

```
tgccgttggg cagtgcaccc gtacctttgg gagcgcgcgc cctcgtcgtg tcgtgacgtc    840
acccgttctg ttggcttata atgcagggtg gggccacctg ccggtaggtg tgcggtaggc    900
ttttctccgt cgcaggacgc agggttcggg cctagggtag gctctcctga atcgacaggc    960
gccggacctc tggtgagggg agggataagt gaggcgtcag tttctttggt cggttttatg   1020
tacctatctt cttaagtagc tgaagctccg gttttgaact atgcgctcgg ggttggcgag   1080
tgtgttttgt gaagttttt aggcaccttt tgaaatgtaa tcatttgggt caatatgtaa   1140
ttttcagtgt tagactagta aattgtccgc taaattctgg ccgttttggg ctttttttgtt   1200 agacacgcgt ttaattaagc cgccacc                                       1227

<210> SEQ ID NO 45
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
gttttagagc tagaaatagc aagttaaaat aaggctagtc cgttatcaac ttgaaaaagt     60
ggcaccgagt cggtgctttt ttt                                            83

<210> SEQ ID NO 46
<211> LENGTH: 472
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46
```

Met Phe Glu Pro Lys Lys Lys Arg Lys Val Phe Glu Gly Thr Ala Ser
1               5                   10                  15

Ser Arg Pro Gly Glu Arg Pro Phe Gln Cys Arg Ile Cys Met Arg Asn
            20                  25                  30

Phe Ser Arg Arg His Gly Leu Asp Arg His Thr Arg Thr His Thr Gly
        35                  40                  45

Glu Lys Pro Phe Gln Cys Arg Ile Cys Met Arg Asn Phe Ser Asp His
    50                  55                  60

Ser Ser Leu Lys Arg His Leu Arg Thr His Thr Gly Ser Gln Lys Pro
65                  70                  75                  80

Phe Gln Cys Arg Ile Cys Met Arg Asn Phe Ser Val Arg His Asn Leu
                85                  90                  95

Thr Arg His Leu Arg Thr His Thr Gly Glu Lys Pro Phe Gln Cys Arg
            100                 105                 110

Ile Cys Met Arg Asn Phe Ser Asp His Ser Asn Leu Ser Arg His Leu
        115                 120                 125

Lys Thr His Thr Gly Ser Gln Lys Pro Phe Gln Cys Arg Ile Cys Met
    130                 135                 140

Arg Asn Phe Ser Gln Arg Ser Ser Leu Val Arg His Leu Arg Thr His
145                 150                 155                 160

Thr Gly Glu Lys Pro Phe Gln Cys Arg Ile Cys Met Arg Asn Phe Ser
                165                 170                 175

Glu Ser Gly His Leu Lys Arg His Leu Arg Thr His Leu Arg Gly Ser
            180                 185                 190

Thr Cys Arg Lys Lys Asn Arg Ala Phe Leu Lys Trp Ala Gly Gly Lys

```
            195                 200                 205
Tyr Pro Leu Leu Asp Asp Ile Lys Arg His Leu Pro Lys Gly Glu Cys
    210                 215                 220

Leu Val Glu Pro Phe Val Gly Ala Gly Ser Val Phe Leu Asn Thr Asp
225                 230                 235                 240

Phe Ser Arg Tyr Ile Leu Ala Asp Ile Asn Ser Asp Leu Ile Ser Leu
            245                 250                 255

Tyr Asn Ile Val Lys Met Arg Thr Asp Glu Tyr Val Gln Ala Ala Arg
        260                 265                 270

Glu Leu Phe Val Pro Glu Thr Asn Cys Ala Glu Val Tyr Tyr Gln Phe
    275                 280                 285

Arg Glu Glu Phe Asn Lys Ser Gln Asp Pro Phe Arg Arg Ala Val Leu
290                 295                 300

Phe Leu Tyr Leu Asn Arg Tyr Gly Tyr Asn Gly Leu Cys Arg Tyr Asn
305                 310                 315                 320

Leu Arg Gly Glu Phe Ala Val Pro Phe Gly Arg Tyr Lys Lys Pro Tyr
            325                 330                 335

Phe Pro Glu Ala Glu Leu Tyr His Phe Ala Glu Lys Ala Gln Asn Ala
        340                 345                 350

Phe Phe Tyr Cys Glu Ser Tyr Ala Asp Ser Met Ala Arg Ala Asp Asp
    355                 360                 365

Ala Ser Val Val Tyr Cys Asp Pro Pro Tyr Ala Pro Leu Ser Ala Thr
370                 375                 380

Ala Asn Phe Thr Ala Tyr His Thr Asn Ser Phe Thr Leu Glu Gln Gln
385                 390                 395                 400

Ala His Leu Ala Glu Ile Ala Glu Gly Leu Val Glu Arg His Ile Pro
            405                 410                 415

Val Leu Ile Ser Asn His Asp Thr Met Leu Thr Arg Glu Trp Tyr Gln
        420                 425                 430

Arg Ala Lys Leu His Val Val Lys Val Arg Arg Ser Ile Ser Ser Asn
    435                 440                 445

Gly Gly Thr Arg Lys Lys Val Asp Glu Leu Leu Ala Leu Tyr Lys Pro
450                 455                 460

Gly Val Val Ser Pro Ala Lys Lys
465                 470

<210> SEQ ID NO 47
<211> LENGTH: 1719
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80
```

```
Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
        100                 105                 110

His Glu Arg His Pro Ile Phe Gly Asn Ile Val Asp Glu Val Ala Tyr
            115                 120                 125

His Glu Lys Tyr Pro Thr Ile Tyr His Leu Arg Lys Lys Leu Val Asp
        130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
```

```
                500             505             510
Leu Leu Tyr Glu Tyr Phe Thr Val Tyr Asn Glu Leu Thr Lys Val Lys
            515             520             525
Tyr Val Thr Glu Gly Met Arg Lys Pro Ala Phe Leu Ser Gly Glu Gln
            530             535             540
Lys Lys Ala Ile Val Asp Leu Leu Phe Lys Thr Asn Arg Lys Val Thr
545             550             555             560
Val Lys Gln Leu Lys Glu Asp Tyr Phe Lys Lys Ile Glu Cys Phe Asp
            565             570             575
Ser Val Glu Ile Ser Gly Val Glu Asp Arg Phe Asn Ala Ser Leu Gly
            580             585             590
Thr Tyr His Asp Leu Leu Lys Ile Ile Lys Asp Lys Asp Phe Leu Asp
            595             600             605
Asn Glu Glu Asn Glu Asp Ile Leu Glu Asp Ile Val Leu Thr Leu Thr
            610             615             620
Leu Phe Glu Asp Arg Glu Met Ile Glu Arg Leu Lys Thr Tyr Ala
625             630             635             640
His Leu Phe Asp Asp Lys Val Met Lys Gln Leu Lys Arg Arg Arg Tyr
            645             650             655
Thr Gly Trp Gly Arg Leu Ser Arg Lys Leu Ile Asn Gly Ile Arg Asp
            660             665             670
Lys Gln Ser Gly Lys Thr Ile Leu Asp Phe Leu Lys Ser Asp Gly Phe
            675             680             685
Ala Asn Arg Asn Phe Met Gln Leu Ile His Asp Asp Ser Leu Thr Phe
            690             695             700
Lys Glu Asp Ile Gln Lys Ala Gln Val Ser Gly Gln Gly Asp Ser Leu
705             710             715             720
His Glu His Ile Ala Asn Leu Ala Gly Ser Pro Ala Ile Lys Lys Gly
            725             730             735
Ile Leu Gln Thr Val Lys Val Val Asp Glu Leu Val Lys Val Met Gly
            740             745             750
Arg His Lys Pro Glu Asn Ile Val Ile Glu Met Ala Arg Glu Asn Gln
            755             760             765
Thr Thr Gln Lys Gly Gln Lys Asn Ser Arg Glu Arg Met Lys Arg Ile
            770             775             780
Glu Glu Gly Ile Lys Glu Leu Gly Ser Gln Ile Leu Lys Glu His Pro
785             790             795             800
Val Glu Asn Thr Gln Leu Gln Asn Glu Lys Leu Tyr Leu Tyr Tyr Leu
            805             810             815
Gln Asn Gly Arg Asp Met Tyr Val Asp Gln Glu Leu Asp Ile Asn Arg
            820             825             830
Leu Ser Asp Tyr Asp Val Asp Ala Ile Val Pro Gln Ser Phe Leu Lys
            835             840             845
Asp Asp Ser Ile Asp Asn Lys Val Leu Thr Arg Ser Asp Lys Asn Arg
850             855             860
Gly Lys Ser Asp Asn Val Pro Ser Glu Glu Val Val Lys Lys Met Lys
865             870             875             880
Asn Tyr Trp Arg Gln Leu Leu Asn Ala Lys Leu Ile Thr Gln Arg Lys
            885             890             895
Phe Asp Asn Leu Thr Lys Ala Glu Arg Gly Gly Leu Ser Glu Leu Asp
            900             905             910
Lys Ala Gly Phe Ile Lys Arg Gln Leu Val Glu Thr Arg Gln Ile Thr
            915             920             925
```

```
Lys His Val Ala Gln Ile Leu Asp Ser Arg Met Asn Thr Lys Tyr Asp
        930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
            995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320
```

```
Phe Lys Tyr Phe Asp Thr Thr Ile Asp Arg Lys Arg Tyr Thr Ser
    1325             1330                1335

Thr Lys Glu Val Leu Asp Ala Thr Leu Ile His Gln Ser Ile Thr
    1340             1345                1350

Gly Leu Tyr Glu Thr Arg Ile Asp Leu Ser Gln Leu Gly Gly Asp
    1355             1360                1365

Gly Ser Pro Lys Lys Arg Lys Val Ser Ser Asp Tyr Lys Asp
    1370             1375                1380

His Asp Gly Asp Tyr Lys Asp His Asp Ile Asp Tyr Lys Asp Asp
    1385             1390                1395

Asp Asp Lys Ala Ala Gly Gly Gly Ser Gly Gly Glu Leu Ser
    1400             1405                1410

Ser Gly Asn Ser Asn Ala Asn Ser Arg Gly Pro Ser Phe Ser Ser
    1415             1420                1425

Gly Leu Val Pro Leu Ser Leu Arg Gly Ser His Ala Cys Arg Lys
    1430             1435                1440

Lys Asn Arg Ala Phe Leu Lys Trp Ala Gly Gly Lys Tyr Pro Leu
    1445             1450                1455

Leu Asp Asp Ile Lys Arg His Leu Pro Lys Gly Glu Cys Leu Val
    1460             1465                1470

Glu Pro Phe Val Gly Ala Gly Ser Val Phe Leu Asn Thr Asp Phe
    1475             1480                1485

Ser Arg Tyr Ile Leu Ala Asp Ile Asn Ser Asp Leu Ile Ser Leu
    1490             1495                1500

Tyr Asn Ile Val Lys Met Arg Thr Asp Glu Tyr Val Gln Ala Ala
    1505             1510                1515

Arg Glu Leu Phe Val Pro Glu Thr Asn Cys Ala Glu Val Tyr Tyr
    1520             1525                1530

Gln Phe Arg Glu Glu Phe Asn Lys Ser Gln Asp Pro Phe Arg Arg
    1535             1540                1545

Ala Val Leu Phe Leu Tyr Leu Asn Arg Tyr Gly Tyr Asn Gly Leu
    1550             1555                1560

Cys Arg Tyr Asn Leu Arg Gly Glu Phe Ala Val Pro Phe Gly Arg
    1565             1570                1575

Tyr Lys Lys Pro Tyr Phe Pro Glu Ala Glu Leu Tyr His Phe Ala
    1580             1585                1590

Glu Lys Ala Gln Asn Ala Phe Phe Tyr Cys Glu Ser Tyr Ala Asp
    1595             1600                1605

Ser Met Ala Arg Ala Asp Asp Ala Ser Val Val Tyr Cys Asp Pro
    1610             1615                1620

Pro Tyr Ala Pro Leu Ser Ala Thr Ala Asn Phe Thr Ala Tyr His
    1625             1630                1635

Thr Asn Ser Phe Thr Leu Glu Gln Gln Ala His Leu Ala Glu Ile
    1640             1645                1650

Ala Glu Gly Leu Val Glu Arg His Ile Pro Val Leu Ile Ser Asn
    1655             1660                1665

His Asp Thr Met Leu Thr Arg Glu Trp Tyr Gln Arg Ala Lys Leu
    1670             1675                1680

His Val Val Lys Val Arg Arg Ser Ile Ser Ser Asn Gly Gly Thr
    1685             1690                1695

Arg Lys Lys Val Asp Glu Leu Leu Ala Leu Tyr Lys Pro Gly Val
    1700             1705                1710

Val Ser Pro Ala Lys Lys
```

1715

<210> SEQ ID NO 48
<211> LENGTH: 989
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

```
Met Phe Glu Pro Lys Lys Arg Lys Val Phe Thr Ser Val Pro
1               5                   10                  15

Leu Tyr Gly Phe Thr Ser Ile Cys Gly Arg Arg Pro Glu Met Glu Ala
            20                  25                  30

Ala Val Ser Thr Ile Pro Arg Phe Leu Gln Ser Ser Ser Gly Ser Met
        35                  40                  45

Leu Asp Gly Arg Phe Asp Pro Gln Ser Ala Ala His Phe Phe Gly Val
    50                  55                  60

Tyr Asp Gly His Gly Gly Ser Gln Val Ala Asn Tyr Cys Arg Glu Arg
65                  70                  75                  80

Met His Leu Ala Leu Ala Glu Glu Ile Ala Lys Glu Lys Pro Met Leu
                85                  90                  95

Cys Asp Gly Asp Thr Trp Leu Glu Lys Trp Lys Lys Ala Leu Phe Asn
            100                 105                 110

Ser Phe Leu Arg Val Asp Ser Glu Ile Glu Ser Val Ala Pro Glu Thr
        115                 120                 125

Val Gly Ser Thr Ser Val Val Ala Val Phe Pro Ser His Ile Phe
    130                 135                 140

Val Ala Asn Cys Gly Asp Ser Arg Ala Val Leu Cys Arg Gly Lys Thr
145                 150                 155                 160

Ala Leu Pro Leu Ser Val Asp His Lys Pro Asp Arg Glu Asp Glu Ala
                165                 170                 175

Ala Arg Ile Glu Ala Ala Gly Gly Lys Val Ile Gln Trp Asn Gly Ala
            180                 185                 190

Arg Val Phe Gly Val Leu Ala Met Ser Arg Ser Ile Gly Asp Arg Tyr
        195                 200                 205

Leu Lys Pro Ser Ile Ile Pro Asp Pro Glu Val Thr Ala Val Lys Arg
    210                 215                 220

Val Lys Glu Asp Asp Cys Leu Ile Leu Ala Ser Asp Gly Val Trp Asp
225                 230                 235                 240

Val Met Thr Asp Glu Glu Ala Cys Glu Met Ala Arg Lys Arg Ile Leu
                245                 250                 255

Leu Trp His Lys Lys Asn Ala Val Ala Gly Asp Ala Ser Leu Leu Ala
            260                 265                 270

Asp Glu Arg Arg Lys Glu Gly Lys Asp Pro Ala Ala Met Ser Ala Ala
        275                 280                 285

Glu Tyr Leu Ser Lys Leu Ala Ile Gln Arg Gly Ser Lys Asp Asn Ile
    290                 295                 300

Ser Val Val Val Asp Leu Lys Gly Gly Ser Gly Gly Ser Arg Pro
305                 310                 315                 320

Gly Glu Arg Pro Phe Gln Cys Arg Ile Cys Met Arg Asn Phe Ser Arg
                325                 330                 335

Arg His Gly Leu Asp Arg His Thr Arg Thr His Thr Gly Glu Lys Pro
            340                 345                 350
```

```
Phe Gln Cys Arg Ile Cys Met Arg Asn Phe Ser Asp His Ser Ser Leu
            355                 360                 365

Lys Arg His Leu Arg Thr His Thr Gly Ser Gln Lys Pro Phe Gln Cys
370                 375                 380

Arg Ile Cys Met Arg Asn Phe Ser Val Arg His Asn Leu Thr Arg His
385                 390                 395                 400

Leu Arg Thr His Thr Gly Glu Lys Pro Phe Gln Cys Arg Ile Cys Met
                405                 410                 415

Arg Asn Phe Ser Asp His Ser Asn Leu Ser Arg His Leu Lys Thr His
                420                 425                 430

Thr Gly Ser Gln Lys Pro Phe Gln Cys Arg Ile Cys Met Arg Asn Phe
            435                 440                 445

Ser Gln Arg Ser Ser Leu Val Arg His Leu Arg Thr His Thr Gly Glu
            450                 455                 460

Lys Pro Phe Gln Cys Arg Ile Cys Met Arg Asn Phe Ser Glu Ser Gly
465                 470                 475                 480

His Leu Lys Arg His Leu Arg Thr His Leu Arg Gly Ser Pro Lys Lys
                485                 490                 495

Lys Arg Lys Val Thr Cys Arg Gly Ser Gly Ala Thr Asn Phe Ser Leu
            500                 505                 510

Leu Lys Gln Ala Gly Asp Val Glu Glu Asn Pro Gly Pro Gly His His
            515                 520                 525

Lys Lys Asn Arg Ala Phe Leu Lys Trp Ala Gly Gly Lys Tyr Pro Leu
530                 535                 540

Leu Asp Asp Ile Lys Arg His Leu Pro Lys Gly Glu Cys Leu Val Glu
545                 550                 555                 560

Pro Phe Val Gly Ala Gly Ser Val Phe Leu Asn Thr Asp Phe Ser Arg
                565                 570                 575

Tyr Ile Leu Ala Asp Ile Asn Ser Asp Leu Ile Ser Leu Tyr Asn Ile
                580                 585                 590

Val Lys Met Arg Thr Asp Glu Tyr Val Gln Ala Ala Arg Glu Leu Phe
            595                 600                 605

Val Pro Glu Thr Asn Cys Ala Glu Val Tyr Tyr Gln Phe Arg Glu Glu
610                 615                 620

Phe Asn Lys Ser Gln Asp Pro Phe Arg Arg Ala Val Leu Phe Leu Tyr
625                 630                 635                 640

Leu Asn Arg Tyr Gly Tyr Asn Gly Leu Cys Arg Tyr Asn Leu Arg Gly
                645                 650                 655

Glu Phe Ala Val Pro Phe Gly Arg Tyr Lys Lys Pro Tyr Phe Pro Glu
                660                 665                 670

Ala Glu Leu Tyr His Phe Ala Glu Lys Ala Gln Asn Ala Phe Phe Tyr
                675                 680                 685

Cys Glu Ser Tyr Ala Asp Ser Met Ala Arg Ala Asp Asp Ala Ser Val
            690                 695                 700

Val Tyr Cys Asp Pro Pro Tyr Ala Pro Leu Ser Ala Thr Ala Asn Phe
705                 710                 715                 720

Thr Ala Tyr His Thr Asn Ser Phe Thr Leu Glu Gln Gln Ala His Leu
                725                 730                 735

Ala Glu Ile Ala Glu Gly Leu Val Glu Arg His Ile Pro Val Leu Ile
                740                 745                 750

Ser Asn His Asp Thr Met Leu Thr Arg Glu Trp Tyr Gln Arg Ala Lys
            755                 760                 765

Leu His Val Val Lys Val Arg Arg Ser Ile Ser Ser Asn Gly Gly Thr
```

```
              770                 775                 780
Arg Lys Lys Val Asp Glu Leu Leu Ala Leu Tyr Lys Pro Gly Val Val
785                 790                 795                 800

Ser Pro Ala Lys Lys Gly Gly Ser Gly Gln Leu Thr Gln Asp Glu
                805                 810                 815

Phe Thr Gln Leu Ser Gln Ser Ile Ala Glu Phe His Thr Tyr Gln Leu
                820                 825                 830

Gly Asn Gly Arg Cys Ser Ser Leu Leu Ala Gln Arg Ile His Ala Pro
                835                 840                 845

Pro Glu Thr Val Trp Ser Val Val Arg Arg Phe Asp Arg Pro Gln Ile
            850                 855                 860

Tyr Lys His Phe Ile Lys Ser Cys Asn Val Ser Glu Asp Phe Glu Met
865                 870                 875                 880

Arg Val Gly Cys Thr Arg Asp Val Asn Val Ile Ser Gly Leu Pro Ala
                885                 890                 895

Asn Thr Ser Arg Glu Arg Leu Asp Leu Leu Asp Asp Arg Arg Val
                900                 905                 910

Thr Gly Phe Ser Ile Thr Gly Gly Glu His Arg Leu Arg Asn Tyr Lys
            915                 920                 925

Ser Val Thr Thr Val His Arg Phe Glu Lys Glu Glu Glu Glu Arg
            930                 935                 940

Ile Trp Thr Val Val Leu Glu Ser Tyr Val Val Asp Val Pro Glu Gly
945                 950                 955                 960

Asn Ser Glu Glu Asp Thr Arg Leu Phe Ala Asp Thr Val Ile Arg Leu
                965                 970                 975

Asn Leu Gln Lys Leu Ala Ser Ile Thr Glu Ala Met Asn
                980                 985

<210> SEQ ID NO 49
<211> LENGTH: 1008
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Met Phe Glu Pro Lys Lys Arg Lys Val Phe Glu Thr Ser Val Pro
1               5                   10                  15

Leu Tyr Gly Phe Thr Ser Ile Cys Gly Arg Arg Pro Glu Met Glu Ala
                20                  25                  30

Ala Val Ser Thr Ile Pro Arg Phe Leu Gln Ser Ser Gly Ser Met
                35                  40                  45

Leu Asp Gly Arg Phe Asp Pro Gln Ser Ala Ala His Phe Phe Gly Val
    50                  55                  60

Tyr Asp Gly His Gly Gly Ser Gln Val Ala Asn Tyr Cys Arg Glu Arg
65                  70                  75                  80

Met His Leu Ala Leu Ala Glu Glu Ile Ala Lys Glu Lys Pro Met Leu
                85                  90                  95

Cys Asp Gly Asp Thr Trp Leu Glu Lys Trp Lys Lys Ala Leu Phe Asn
                100                 105                 110

Ser Phe Leu Arg Val Asp Ser Glu Ile Glu Ser Val Ala Pro Glu Thr
            115                 120                 125

Val Gly Ser Thr Ser Val Val Ala Val Val Phe Pro Ser His Ile Phe
        130                 135                 140
```

-continued

| | | | | | | | | | | | | |
|---|---|---|---|---|---|---|---|---|---|---|---|---|
|Val|Ala|Asn|Cys|Gly|Asp|Ser|Arg|Ala|Val|Leu|Cys|Arg|Gly|Lys|Thr|
|145| | | | |150| | | | |155| | | | |160|

Val Ala Asn Cys Gly Asp Ser Arg Ala Val Leu Cys Arg Gly Lys Thr
145                 150                 155                 160

Ala Leu Pro Leu Ser Val Asp His Lys Pro Asp Arg Glu Asp Glu Ala
                165                 170                 175

Ala Arg Ile Glu Ala Ala Gly Gly Lys Val Ile Gln Trp Asn Gly Ala
            180                 185                 190

Arg Val Phe Gly Val Leu Ala Met Ser Arg Ser Ile Gly Asp Arg Tyr
        195                 200                 205

Leu Lys Pro Ser Ile Ile Pro Asp Pro Glu Val Thr Ala Val Lys Arg
    210                 215                 220

Val Lys Glu Asp Asp Cys Leu Ile Leu Ala Ser Asp Gly Val Trp Asp
225                 230                 235                 240

Val Met Thr Asp Glu Glu Ala Cys Glu Met Ala Arg Lys Arg Ile Leu
                245                 250                 255

Leu Trp His Lys Lys Asn Ala Val Ala Gly Asp Ala Ser Leu Leu Ala
                260                 265                 270

Asp Glu Arg Arg Lys Glu Gly Lys Asp Pro Ala Ala Met Ser Ala Ala
                275                 280                 285

Glu Tyr Leu Ser Lys Leu Ala Ile Gln Arg Gly Ser Lys Asp Asn Ile
            290                 295                 300

Ser Val Val Val Asp Leu Lys Gly Gly Ser Gly Gly Ser Arg Pro
305                 310                 315                 320

Gly Glu Arg Pro Phe Gln Cys Arg Ile Cys Met Arg Asn Phe Ser Arg
                325                 330                 335

Arg His Gly Leu Asp Arg His Thr Arg Thr His Thr Gly Glu Lys Pro
            340                 345                 350

Phe Gln Cys Arg Ile Cys Met Arg Asn Phe Ser Asp His Ser Ser Leu
            355                 360                 365

Lys Arg His Leu Arg Thr His Thr Gly Ser Gln Lys Pro Phe Gln Cys
    370                 375                 380

Arg Ile Cys Met Arg Asn Phe Ser Val Arg His Asn Leu Thr Arg His
385                 390                 395                 400

Leu Arg Thr His Thr Gly Glu Lys Pro Phe Gln Cys Arg Ile Cys Met
                405                 410                 415

Arg Asn Phe Ser Asp His Ser Asn Leu Ser Arg His Leu Lys Thr His
                420                 425                 430

Thr Gly Ser Gln Lys Pro Phe Gln Cys Arg Ile Cys Met Arg Asn Phe
            435                 440                 445

Ser Gln Arg Ser Ser Leu Val Arg His Leu Arg Thr His Thr Gly Glu
    450                 455                 460

Lys Pro Phe Gln Cys Arg Ile Cys Met Arg Asn Phe Ser Glu Ser Gly
465                 470                 475                 480

His Leu Lys Arg His Leu Arg Thr His Leu Arg Gly Ser Pro Lys Lys
                485                 490                 495

Lys Arg Lys Val Thr Cys Arg Gly Ser Gly Ala Thr Asn Phe Ser Leu
            500                 505                 510

Leu Lys Gln Ala Gly Asp Val Glu Glu Asn Pro Gly Pro Gly His His
            515                 520                 525

Lys Lys Asn Arg Ala Phe Leu Lys Trp Ala Gly Gly Lys Tyr Pro Leu
    530                 535                 540

Leu Asp Asp Ile Lys Arg His Leu Pro Lys Gly Glu Cys Leu Val Glu
545                 550                 555                 560

Pro Phe Val Gly Ala Gly Ser Val Phe Leu Asn Thr Asp Phe Ser Arg

-continued

```
            565                 570                 575
Tyr Ile Leu Ala Asp Ile Asn Ser Asp Leu Ile Ser Leu Tyr Asn Ile
                580                 585                 590

Val Lys Met Arg Thr Asp Glu Tyr Val Gln Ala Ala Arg Glu Leu Phe
            595                 600                 605

Val Pro Glu Thr Asn Cys Ala Glu Val Tyr Tyr Gln Phe Arg Glu Glu
            610                 615                 620

Phe Asn Lys Ser Gln Asp Pro Phe Arg Arg Ala Val Leu Phe Leu Tyr
625                 630                 635                 640

Leu Asn Arg Tyr Gly Tyr Asn Gly Leu Cys Arg Tyr Asn Leu Arg Gly
                645                 650                 655

Glu Phe Ala Val Pro Phe Gly Arg Tyr Lys Lys Pro Tyr Phe Pro Glu
                660                 665                 670

Ala Glu Leu Tyr His Phe Ala Glu Lys Ala Gln Asn Ala Phe Phe Tyr
                675                 680                 685

Cys Glu Ser Tyr Ala Asp Ser Met Ala Arg Ala Asp Asp Ala Ser Val
                690                 695                 700

Val Tyr Cys Asp Pro Pro Tyr Ala Pro Leu Ser Ala Thr Ala Asn Phe
705                 710                 715                 720

Thr Ala Tyr His Thr Asn Ser Phe Thr Leu Glu Gln Gln Ala His Leu
                725                 730                 735

Ala Glu Ile Ala Glu Gly Leu Val Glu Arg His Ile Pro Val Leu Ile
                740                 745                 750

Ser Asn His Asp Thr Met Leu Thr Arg Glu Trp Tyr Gln Arg Ala Lys
                755                 760                 765

Leu His Val Val Lys Val Arg Arg Ser Ile Ser Ser Asn Gly Gly Thr
                770                 775                 780

Arg Lys Lys Val Asp Glu Leu Leu Ala Leu Tyr Lys Pro Gly Val Val
785                 790                 795                 800

Ser Pro Ala Lys Lys Gly Gly Gly Ser Gly Gln Leu Thr Gln Asp Glu
                805                 810                 815

Phe Thr Gln Leu Ser Gln Ser Ile Ala Glu Phe His Thr Tyr Gln Leu
                820                 825                 830

Gly Asn Gly Arg Cys Ser Ser Leu Leu Ala Gln Arg Ile His Ala Pro
                835                 840                 845

Pro Glu Thr Val Trp Ser Val Val Arg Arg Phe Asp Arg Pro Gln Ile
                850                 855                 860

Tyr Lys His Phe Ile Lys Ser Cys Asn Val Ser Glu Asp Phe Glu Met
865                 870                 875                 880

Arg Val Gly Cys Thr Arg Asp Val Asn Val Ile Ser Gly Leu Pro Ala
                885                 890                 895

Asn Thr Ser Arg Glu Arg Leu Asp Leu Leu Asp Asp Asp Arg Arg Val
                900                 905                 910

Thr Gly Phe Ser Ile Thr Gly Gly Glu His Arg Leu Arg Asn Tyr Lys
                915                 920                 925

Ser Val Thr Thr Val His Arg Phe Glu Lys Glu Glu Glu Glu Glu Arg
                930                 935                 940

Ile Trp Thr Val Val Leu Glu Ser Tyr Val Val Asp Val Pro Glu Gly
945                 950                 955                 960

Asn Ser Glu Glu Asp Thr Arg Leu Phe Ala Asp Thr Val Ile Arg Leu
                965                 970                 975

Asn Leu Gln Lys Leu Ala Ser Ile Thr Glu Ala Met Asn Cys Leu Asn
                980                 985                 990
```

Ile Gln Gln Gln Leu Gly Gln Leu Thr Leu Glu Asn Leu Gln Met Leu
        995                 1000                1005

<210> SEQ ID NO 50
<211> LENGTH: 183
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Met Val Asn Pro Lys Lys Arg Lys Val Val Asn Leu Glu Ser Gln
1               5                   10                  15

Val Pro Ser Lys Gly Arg Ile Phe Leu Val Gln Asp Gly Gln Val Arg
            20                  25                  30

Asp Pro Glu Lys Val Thr Lys Glu Phe Lys Gln Gly Leu Phe Leu Arg
        35                  40                  45

Lys Ser Ser Leu Ser Ser Arg Gly Trp Thr Ile Glu Ile Leu Asn Cys
    50                  55                  60

Ile Asp Lys Ile Glu Gly Ser Glu Phe Thr Leu Glu Asp Met Tyr Arg
65                  70                  75                  80

Phe Glu Ser Asp Leu Lys Asn Ile Phe Val Lys Asn Asn His Ile Lys
                85                  90                  95

Glu Lys Ile Arg Gln Gln Leu Gln Ile Leu Arg Asp Lys Glu Ile Ile
            100                 105                 110

Glu Phe Lys Gly Arg Gly Lys Tyr Arg Lys Leu Phe Glu Gly Gly Gly
        115                 120                 125

Gly Ser Gly Arg Ala Asp Ala Leu Asp Asp Phe Asp Leu Asp Met Leu
    130                 135                 140

Gly Ser Asp Ala Leu Asp Asp Phe Asp Leu Asp Met Leu Gly Ser Asp
145                 150                 155                 160

Ala Leu Asp Asp Phe Asp Leu Asp Met Leu Gly Ser Asp Ala Leu Asp
                165                 170                 175

Asp Phe Asp Leu Asp Met Leu
            180

<210> SEQ ID NO 51
<211> LENGTH: 224
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Met Asp Ala Lys Ser Leu Thr Ala Trp Ser Arg Thr Leu Val Thr Phe
1               5                   10                  15

Lys Asp Val Phe Val Asp Phe Thr Arg Glu Glu Trp Lys Leu Leu Asp
            20                  25                  30

Thr Ala Gln Gln Ile Leu Tyr Arg Asn Val Met Leu Glu Asn Tyr Lys
        35                  40                  45

Asn Leu Val Ser Leu Gly Tyr Gln Leu Thr Lys Pro Asp Val Ile Leu
    50                  55                  60

Arg Leu Glu Lys Gly Glu Glu Pro Trp Leu Val Glu Arg Glu Ile His
65                  70                  75                  80

Gln Glu Thr His Pro Asp Ser Glu Thr Ala Phe Glu Ile Lys Ser Ser
                85                  90                  95

```
Val Pro Lys Lys Arg Lys Val Leu Glu Gly Gly Gly Ser Gly
        100                 105                 110

Thr Cys Arg Ser Gln Val Pro Ser Lys Gly Arg Ile Phe Leu Val Gln
            115                 120                 125

Asp Gly Gln Val Arg Asp Pro Glu Lys Val Thr Lys Glu Phe Lys Gln
    130                 135                 140

Gly Leu Phe Leu Arg Lys Ser Ser Leu Ser Arg Gly Trp Thr Ile
145                 150                 155                 160

Glu Ile Leu Asn Cys Ile Asp Lys Ile Glu Gly Ser Glu Phe Thr Leu
                165                 170                 175

Glu Asp Met Tyr Arg Phe Glu Ser Asp Leu Lys Asn Ile Phe Val Lys
            180                 185                 190

Asn Asn His Ile Lys Glu Lys Ile Arg Gln Gln Leu Gln Ile Leu Arg
            195                 200                 205

Asp Lys Glu Ile Ile Glu Phe Lys Gly Arg Gly Lys Tyr Arg Lys Leu
    210                 215                 220
```

<210> SEQ ID NO 52
<211> LENGTH: 211
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 52

```
Lys Lys Arg Glu Gln Ser Asn Asp Ile Ala Arg Gly Phe Glu Arg Gly
1               5                   10                  15

Leu Glu Pro Glu Lys Ile Ile Gly Ala Thr Asp Ser Cys Gly Asp Leu
                20                  25                  30

Met Phe Leu Met Lys Trp Lys Asp Thr Asp Glu Ala Asp Leu Val Leu
            35                  40                  45

Ala Lys Glu Ala Asn Val Lys Cys Pro Gln Ile Val Ile Ala Phe Tyr
    50                  55                  60

Glu Glu Arg Leu Thr Trp His Ala Tyr Pro Glu Asp Ala Glu Asn Lys
65                  70                  75                  80

Glu Lys Ala Ser Pro Lys Lys Arg Lys Val Leu Glu Gly Gly Gly
                85                  90                  95

Gly Ser Gly Thr Cys Arg Ser Gln Val Pro Ser Lys Gly Arg Ile Phe
            100                 105                 110

Leu Val Gln Asp Gly Gln Val Arg Asp Pro Glu Lys Val Thr Lys Glu
        115                 120                 125

Phe Lys Gln Gly Leu Phe Leu Arg Lys Ser Ser Leu Ser Arg Gly
    130                 135                 140

Trp Thr Ile Glu Ile Leu Asn Cys Ile Asp Lys Ile Glu Gly Ser Glu
145                 150                 155                 160

Phe Thr Leu Glu Asp Met Tyr Arg Phe Glu Ser Asp Leu Lys Asn Ile
                165                 170                 175

Phe Val Lys Asn Asn His Ile Lys Glu Lys Ile Arg Gln Gln Leu Gln
            180                 185                 190

Ile Leu Arg Asp Lys Glu Ile Ile Glu Phe Lys Gly Arg Gly Lys Tyr
        195                 200                 205

Arg Lys Leu
    210
```

<210> SEQ ID NO 53
<211> LENGTH: 405
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 53

```
Met Phe Glu Pro Lys Lys Arg Lys Val Phe Glu Gly Thr Ala Ser
1               5                   10                  15

Ser Gln Val Pro Ser Lys Gly Arg Ile Phe Leu Val Gln Asp Gly Gln
                20                  25                  30

Val Arg Asp Pro Glu Lys Val Thr Lys Glu Phe Lys Gln Gly Leu Phe
            35                  40                  45

Leu Arg Lys Ser Ser Leu Ser Ser Arg Gly Trp Thr Ile Glu Ile Leu
        50                  55                  60

Asn Cys Ile Asp Lys Ile Glu Gly Ser Glu Phe Thr Leu Glu Asp Met
65                  70                  75                  80

Tyr Arg Phe Glu Ser Asp Leu Lys Asn Ile Phe Val Lys Asn Asn His
                85                  90                  95

Ile Lys Glu Lys Ile Arg Gln Gln Leu Gln Ile Leu Arg Asp Lys Glu
            100                 105                 110

Ile Ile Glu Phe Lys Gly Arg Gly Lys Tyr Arg Lys Leu Thr Cys Arg
        115                 120                 125

Lys Lys Asn Arg Ala Phe Leu Lys Trp Ala Gly Gly Lys Tyr Pro Leu
130                 135                 140

Leu Asp Asp Ile Lys Arg His Leu Pro Lys Gly Glu Cys Leu Val Glu
145                 150                 155                 160

Pro Phe Val Gly Ala Gly Ser Val Phe Leu Asn Thr Asp Phe Ser Arg
                165                 170                 175

Tyr Ile Leu Ala Asp Ile Asn Ser Asp Leu Ile Ser Leu Tyr Asn Ile
            180                 185                 190

Val Lys Met Arg Thr Asp Glu Tyr Val Gln Ala Ala Arg Glu Leu Phe
        195                 200                 205

Val Pro Glu Thr Asn Cys Ala Glu Val Tyr Gln Phe Ala Glu Glu
210                 215                 220

Phe Asn Lys Ser Gln Asp Pro Phe Arg Arg Ala Val Leu Phe Leu Tyr
225                 230                 235                 240

Leu Asn Arg Tyr Gly Tyr Asn Gly Leu Cys Arg Tyr Asn Leu Arg Gly
                245                 250                 255

Glu Phe Asn Val Pro Phe Gly Arg Tyr Lys Lys Pro Tyr Phe Pro Glu
            260                 265                 270

Ala Glu Leu Tyr His Phe Ala Glu Lys Ala Gln Asn Ala Phe Phe Tyr
        275                 280                 285

Cys Glu Ser Tyr Ala Asp Ser Met Ala Arg Ala Asp Asp Ala Ser Val
        290                 295                 300

Val Tyr Cys Asp Pro Pro Tyr Ala Pro Leu Ser Ala Thr Ala Asn Phe
305                 310                 315                 320

Thr Ala Tyr His Thr Asn Ser Phe Thr Leu Glu Gln Gln Ala His Leu
                325                 330                 335

Ala Glu Ile Ala Glu Gly Leu Val Glu Arg His Ile Pro Val Leu Ile
            340                 345                 350

Ser Asn His Asp Thr Met Leu Thr Arg Glu Trp Tyr Gln Arg Ala Lys
        355                 360                 365
```

```
Leu His Val Val Lys Val Arg Arg Ser Ile Ser Ser Asn Gly Gly Thr
        370                 375                 380

Arg Lys Lys Val Asp Glu Leu Leu Ala Leu Tyr Lys Pro Gly Val Val
385                 390                 395                 400

Ser Pro Ala Lys Lys
                405

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Gly Gly Gly Ser Gly Gly Gly Gly Ser
1               5                   10

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
gtgaaccgca tcgagctgaa g                                            21

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
taaaggctta ctgagcacta                                              20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
aatcgttgcg taatctacaa                                              20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
tctggaggat aatctcagtc                                              20

<210> SEQ ID NO 59
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 59
gaactttctc tgcgtctatt                                                     20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
aaataatact gtgccagagc                                                     20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
ccttctgtat ttctactggc                                                     20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
gatactattc cgaggattgc                                                     20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
tttattcaac cttctgcgaa                                                     20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
ggataaactt ctaccagcag                                                     20

<210> SEQ ID NO 65
<211> LENGTH: 21
<212> TYPE: DNA
<213> ORGANISM: Artificial Sequence
```

<220> FEATURE:
<223> OTHER INFORMATION: Description of Artificial Sequence: Synthetic
      primer

<400> SEQUENCE: 65
gtgaaccgca tcgagctgaa g                                              21

<210> SEQ ID NO 66
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
gcgcgtgtcg cacgtatcac tt                                             22

<210> SEQ ID NO 67
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
tgttgccgtc ctccttgaag tc                                             22

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
tgtgattcag agacaacttc                                                20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
ttgcgaaagt tggagaaata                                                20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
caggagccag gtttattatc                                                20

<210> SEQ ID NO 71
<211> LENGTH: 20
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 71
gtaagcaata ggtcttcagg                                               20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
tattcacagg gtgttatcct                                               20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
taactcaggt attggtggat                                               20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
gagttcctgg tagcaataag                                               20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
ctatcaggac tggtaaaagc                                               20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
tgtccagata atcacggata                                               20

<210> SEQ ID NO 77
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 77
tgttgccgtc ctccttgaag tc                                              22

<210> SEQ ID NO 78
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
gccggaggaa gcaagcgc                                                   18

<210> SEQ ID NO 79
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
tctggagcgt tgtggagatt tgg                                             23

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
gcgacagtga cagcatcaac g                                               21

<210> SEQ ID NO 81
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
tgacggcagg actgtgtgtt tc                                              22

<210> SEQ ID NO 82
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
agtcaagaag ggaagagagc attgg                                           25

<210> SEQ ID NO 83
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 83
gaaactgtct ctaccctggt ctcc                                          24

<210> SEQ ID NO 84
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
tgctttggag ttgtcctgga cg                                            22

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
aggacagagg gccaagctgc                                               20

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
cctgttgtgg caggtggtgg                                               20

<210> SEQ ID NO 87
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
ggtgatgttc aacaggctgt gc                                            22

<210> SEQ ID NO 88
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
gcccagagca tctgccactt g                                             21

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 89
ctgccactgt agccacgaaa c                                               21

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
ttcagtgctc acccaccagg                                                 20

<210> SEQ ID NO 91
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91
```

Gly Ser Gly Ser Gly Ser Gly Ser Gly Ser Gly Ser Gly Ser Gly Ser
1               5                   10                  15

Gly Ser Gly Ser
            20

```
<210> SEQ ID NO 92
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92
```

Gly Ser Gly Ser Gly Ser Gly Ser Gly Ser
1               5                   10

```
<210> SEQ ID NO 93
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93
```

Gly Ser Gly Ser Gly Ser Gly Ser Gly Ser Gly Ser
1               5                   10

```
<210> SEQ ID NO 94
<211> LENGTH: 472
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94
```

Met Phe Glu Pro Lys Lys Lys Arg Lys Val Phe Glu Gly Thr Ala Ser
1               5                   10                  15

Ser Arg Pro Gly Glu Arg Pro Phe Gln Cys Arg Ile Cys Met Arg Asn
            20                  25                  30

```
Phe Ser Arg Arg His Gly Leu Asp Arg His Thr Arg Thr His Thr Gly
            35                  40                  45
Glu Lys Pro Phe Gln Cys Arg Ile Cys Met Arg Asn Phe Ser Asp His
 50                  55                  60
Ser Ser Leu Lys Arg His Leu Arg Thr His Thr Gly Ser Gln Lys Pro
 65                  70                  75                  80
Phe Gln Cys Arg Ile Cys Met Arg Asn Phe Ser Val Arg His Asn Leu
                 85                  90                  95
Thr Arg His Leu Arg Thr His Thr Gly Glu Lys Pro Phe Gln Cys Arg
            100                 105                 110
Ile Cys Met Arg Asn Phe Ser Asp His Ser Asn Leu Ser Arg His Leu
            115                 120                 125
Lys Thr His Thr Gly Ser Gln Lys Pro Phe Gln Cys Arg Ile Cys Met
    130                 135                 140
Arg Asn Phe Ser Gln Arg Ser Ser Leu Val Arg His Leu Arg Thr His
145                 150                 155                 160
Thr Gly Glu Lys Pro Phe Gln Cys Arg Ile Cys Met Arg Asn Phe Ser
                165                 170                 175
Glu Ser Gly His Leu Lys Arg His Leu Arg Thr His Leu Arg Gly Ser
            180                 185                 190
Thr Cys Arg Lys Lys Asn Arg Ala Phe Leu Lys Trp Ala Gly Gly Lys
    195                 200                 205
Tyr Pro Leu Leu Asp Asp Ile Lys Arg His Leu Pro Lys Gly Glu Cys
    210                 215                 220
Leu Val Glu Pro Phe Val Gly Ala Gly Ser Val Phe Leu Asn Thr Asp
225                 230                 235                 240
Phe Ser Arg Tyr Ile Leu Ala Asp Ile Asn Ser Asp Leu Ile Ser Leu
                245                 250                 255
Tyr Asn Ile Val Lys Met Arg Thr Asp Glu Tyr Val Gln Ala Ala Arg
            260                 265                 270
Glu Leu Phe Val Pro Glu Thr Asn Cys Ala Glu Val Tyr Tyr Gln Phe
    275                 280                 285
Arg Glu Glu Phe Asn Lys Ser Gln Asp Pro Phe Arg Arg Ala Val Leu
    290                 295                 300
Phe Leu Tyr Leu Asn Arg Tyr Gly Tyr Asn Gly Leu Cys Arg Tyr Asn
305                 310                 315                 320
Leu Arg Gly Glu Phe Asn Val Pro Phe Gly Arg Tyr Lys Lys Pro Tyr
                325                 330                 335
Phe Pro Glu Ala Glu Leu Tyr His Phe Ala Glu Lys Ala Gln Asn Ala
            340                 345                 350
Phe Phe Tyr Cys Glu Ser Tyr Ala Asp Ser Met Ala Arg Ala Asp Asp
            355                 360                 365
Ala Ser Val Val Tyr Cys Asp Pro Pro Tyr Ala Pro Leu Ser Ala Thr
    370                 375                 380
Ala Asn Phe Thr Ala Tyr His Thr Asn Ser Phe Thr Leu Glu Gln Gln
385                 390                 395                 400
Ala His Leu Ala Glu Ile Ala Glu Gly Leu Val Glu Arg His Ile Pro
                405                 410                 415
Val Leu Ile Ser Asn His Asp Thr Met Leu Thr Arg Glu Trp Tyr Gln
            420                 425                 430
Arg Ala Lys Leu His Val Val Lys Val Arg Arg Ser Ile Ser Ser Asn
    435                 440                 445
```

```
Gly Gly Thr Arg Lys Lys Val Asp Glu Leu Leu Ala Leu Tyr Lys Pro
    450                 455                 460

Gly Val Val Ser Pro Ala Lys Lys
465                 470
```